US009689004B2

(12) United States Patent
Maggio-Hall

(10) Patent No.: US 9,689,004 B2
(45) Date of Patent: Jun. 27, 2017

(54) ACETATE SUPPLEMENTION OF MEDIUM FOR BUTANOLOGENS

(71) Applicant: BUTAMAX(TM) ADVANCED BIOFUELS LLC, Wilmington, DE (US)

(72) Inventor: Lori Ann Maggio-Hall, Wilmington, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 13/833,369

(22) Filed: Mar. 15, 2013

(65) Prior Publication Data

US 2013/0252296 A1 Sep. 26, 2013

Related U.S. Application Data

(60) Provisional application No. 61/615,174, filed on Mar. 23, 2012.

(51) Int. Cl.
*C12P 7/16* (2006.01)
*C12N 1/20* (2006.01)

(52) U.S. Cl.
CPC .................. *C12P 7/16* (2013.01); *C12N 1/20* (2013.01); *C12Y 101/01008* (2013.01); *C12Y 101/01086* (2013.01); *C12Y 102/01005* (2013.01); *C12Y 401/01001* (2013.01); *C12Y 402/01009* (2013.01); *Y02E 50/10* (2013.01)

(58) Field of Classification Search
CPC ............... C12P 7/16; C12Y 401/01001; C12Y 402/01009; C12N 1/20; C12N 9/0006; C12N 9/0008
See application file for complete search history.

(56) References Cited

U.S. PATENT DOCUMENTS 7,541,173 B2 6/2009 Bramucci et al.
7,659,104 B2 2/2010 Bramucci et al.
7,851,188 B2 * 12/2010 Donaldson et al. .......... 435/160
7,910,342 B2 3/2011 Liao et al.
7,932,063 B2 4/2011 Dunson, Jr. et al.
7,993,889 B1 * 8/2011 Donaldson et al. .......... 435/157
8,017,364 B2 9/2011 Bramucci et al.
8,071,358 B1 * 12/2011 Dundon .................. C12N 9/88 435/254.2
8,129,162 B2 3/2012 Li et al.
8,178,328 B2 5/2012 Donaldson et al.
8,188,250 B2 5/2012 Bramucci et al.
8,206,970 B2 6/2012 Eliot et al.
8,222,017 B2 7/2012 Li et al.
8,241,878 B2 8/2012 Anthony et al.
8,273,558 B2 9/2012 Donaldson et al.
8,283,144 B2 10/2012 Donaldson et al.
8,372,612 B2 2/2013 Larossa et al.
8,389,252 B2 3/2013 Larossa
8,409,834 B2 4/2013 Burlew et al.
8,426,173 B2 4/2013 Bramucci et al.
8,426,174 B2 4/2013 Bramucci et al.
8,455,224 B2 6/2013 Paul
8,455,225 B2 6/2013 Bramucci et al.
8,465,964 B2 6/2013 Anthony et al.
8,476,047 B2 7/2013 Burlew et al.
8,518,678 B2 8/2013 Flint et al.
8,557,562 B2 10/2013 Bramucci et al.
8,614,085 B2 12/2013 Van Dyk et al.
8,617,861 B2 12/2013 Grady et al.
8,637,281 B2 1/2014 Paul et al.
8,637,289 B2 1/2014 Anthony et al.
8,652,823 B2 2/2014 Flint et al.
8,669,094 B2 3/2014 Anthony et al.
8,691,540 B2 4/2014 Bramucci et al.
8,697,404 B2 4/2014 Anton et al.
8,735,114 B2 5/2014 Donaldson et al.
8,759,044 B2 6/2014 DiCosimo et al.
8,765,425 B2 7/2014 DiCosimo et al.
8,765,433 B2 7/2014 Gude et al.
8,785,166 B2 7/2014 Anthony et al.
8,795,992 B2 8/2014 Bramucci et al.
8,828,694 B2 9/2014 Anthony et al.
8,828,695 B2 9/2014 Grady et al.

(Continued)

FOREIGN PATENT DOCUMENTS

WO 2008052991 A1 5/2008
WO 2010151525 A1 12/2010

(Continued)

OTHER PUBLICATIONS

Kizer L et al. Application of Functional Genomics to Pathway Optimization for Increase Isoprenoid Production. 2008. Applied and Environmental Microbiology. vol. 74, No. 10. p. 3229-3241.*
Prather KLJ et al. De novo biosynthetic pathways: rational design of microbial chemical factories. 2008. Current Opinion in Biotechnology. 19:468-474.*
Sonderegger MS et al. Metabolic Engineering of a Phosphoketolase Pathway for Pentose Catabolism in *Saccharomyces cerevisiae*. 2004. Applied and Environmental Microbiology. vol. 70, No. 5. p. 2892-2897.*
Kumanovics A et al. Identification of FRA1 and FRA2 as Genes Involved in Regulating the Yeast Iron Regulon in Response to Decreased Mitochondrial Iron-Sulfur Cluster Synthesis. 2008. Journal of Biological Chemistry. 283:10276-10286.*
Aden et al., "Lignocellulosic Biomass to Ethanol Process Design and Economics Utilizing Co-Current Dilute Acid Prehydrolysis and Enzymatic Hydrolysis for Corn Stover", Report NREL/TP-510-32438, National Renewable Energy Laboratory, Jun. 2002.

(Continued)

*Primary Examiner* — Paul Holland

(57) ABSTRACT

The invention relates to the fields of industrial microbiology and alcohol production. More specifically, the invention relates to improved production of butanol isomers by recombinant microorganisms containing an engineered butanol pathway and disrupted activity of the genes in pathways for the production of by-products during the fermentation when the microorganisms are grown in a fermentation medium containing acetate. In embodiments, recombinant microorganisms have an increased growth rate in a fermentation medium containing acetate as a C2 supplement.

8 Claims, 2 Drawing Sheets

(56) References Cited

U.S. PATENT DOCUMENTS 8,828,704 B2 9/2014 Donaldson et al.
8,871,488 B2 10/2014 Dauner et al.
8,889,385 B2 11/2014 Donaldson et al.
8,895,307 B2 11/2014 Li et al.
8,906,666 B2 12/2014 Alsaker et al.
8,911,981 B2 12/2014 Li et al.
8,940,511 B2 1/2015 Larossa
8,945,859 B2 2/2015 Donaldson et al.
8,945,899 B2 2/2015 Li et al.
8,951,774 B2 2/2015 Donaldson et al.
8,951,937 B2 2/2015 Flint et al.
8,956,850 B2 2/2015 Anthony et al.
8,962,298 B2 2/2015 Donaldson et al.
8,969,065 B2 3/2015 Anthony et al.
8,980,612 B2 3/2015 Donaldson et al.
2008/0182308 A1 7/2008 Donaldson et al.
2008/0274526 A1 11/2008 Bramucci et al.
2008/0293086 A1* 11/2008 Contag .......................... 435/29
2009/0269823 A1 10/2009 Bramucci et al.
2009/0305363 A1 12/2009 Anthony et al.
2009/0305370 A1 12/2009 Grady et al.
2010/0081154 A1 4/2010 Flint et al.
2010/0081179 A1 4/2010 Anthony et al.
2010/0081182 A1 4/2010 Paul et al.
2010/0093020 A1 4/2010 Bramucci et al.
2010/0120105 A1 5/2010 Anthony et al.
2010/0197519 A1 8/2010 Li et al.
2011/0124060 A1 5/2011 Anthony et al.
2011/0136192 A1 6/2011 Paul et al.
2011/0136193 A1 6/2011 Grady et al.
2011/0195505 A1 8/2011 Euler et al.
2011/0244536 A1 10/2011 Nagarajan et al.
2011/0250610 A1 10/2011 Bramucci et al.
2011/0269199 A1 11/2011 Satagopan et al.
2011/0312043 A1 12/2011 Burlew et al.
2011/0312044 A1 12/2011 Anton et al.
2011/0312053 A1 12/2011 Burlew et al.
2012/0058541 A1 3/2012 Alsaker et al.
2012/0064561 A1 3/2012 Flint et al.
2012/0149080 A1 6/2012 Bramucci et al.
2012/0156735 A1 6/2012 Dauner et al.
2012/0196341 A1 8/2012 Donaldson et al.
2012/0208246 A1 8/2012 Anton et al.
2012/0237988 A1 9/2012 Anthony et al.
2012/0258873 A1 10/2012 Gibson et al.
2012/0323047 A1 12/2012 Dauner et al.
2013/0035515 A1 2/2013 Dobson et al.
2013/0071898 A1 3/2013 Anthony et al.
2013/0171706 A1 7/2013 Donaldson et al.
2013/0203138 A1 8/2013 McElvain et al.
2013/0316414 A1 11/2013 Paul et al.
2014/0004526 A1 1/2014 Dauner et al.
2014/0030782 A1 1/2014 Anthony et al.
2014/0030783 A1 1/2014 Anthony et al.
2014/0038263 A1 2/2014 Flint et al.
2014/0038268 A1 2/2014 Flint et al.
2014/0051133 A1 2/2014 Govindarajan et al.
2014/0051137 A1 2/2014 Flint et al.
2014/0057329 A1 2/2014 Li et al.
2014/0073021 A1 3/2014 Bazzana et al.
2014/0093930 A1 4/2014 Li et al.
2014/0093931 A1 4/2014 Dauner et al.
2014/0096439 A1 4/2014 Bramucci et al.
2014/0141479 A1 5/2014 Anthony et al.
2014/0170732 A1 6/2014 Bramucci et al.
2014/0186910 A1 7/2014 Rothman et al.
2014/0186911 A1 7/2014 Anthony et al.
2014/0273116 A1 9/2014 Kelly et al.
2014/0273129 A1 9/2014 Bhalla et al.
2014/0308735 A1 10/2014 Anthony et al.
2014/0335582 A1 11/2014 Donaldson et al.
2014/0349349 A1 11/2014 Dauner et al.
2014/0377824 A1 12/2014 Satagopan et al.
2015/0037855 A1 2/2015 Bhadra et al.
2015/0111269 A1 4/2015 Li et al.
2015/0119608 A1 4/2015 Donaldson et al.
2015/0125920 A1 5/2015 Anthony et al.

FOREIGN PATENT DOCUMENTS

WO 2011041415 A1 4/2011
WO 2011142865 A2 11/2011
WO 2011159853 A1 12/2011
WO 2012129555 A2 9/2012

OTHER PUBLICATIONS

Ausubel et al., "Current Protocols in Molecular Biology", published by Greene Publishing Assoc. and Wiley-Interscience, 1987.

Bellion et al., "Methylamine Utilization in Yeast and Bacteria: Studies Using in vivo NMR", Microbial Growth C1 Compounds [Int. Symp.], 7th ed., 415-32. Editor(s): Murrell, J. Collin; Kelly, Don P. Publisher: Intercept, Andover, UK.

Carlini et al., "Guerbet condensation of methanol with n-propanol to isobutyl alcohol over heterogeneous copper chromite/Mg-A1 mixed oxides catalysts" Journal of Molecular Catalysis A: Chemical 220 (2004) 215-220.

Deshpande, "Ethanol Production from Cellulose by Coupled Saccharification/Fermentation using *Saccharomyces cerevisiae* and Cellulase Complex from Sclerotium rolfsii UV-8 Mutant", Applied Biochemistry and Biotechnology 36:227 (1992).

Dickinson et al., "An Investigation of the Metabolism of Valine to Isobutyl Alcohol in *Saccharomyces cerevisiae*", Journal of Biological Chemistry, vol. 273, No. 40, Issue of Oct. 2, pp. 25752-25756, (1998).

Doherty and Malone, Conceptual Design of Distillation Systems, McGraw Hill, New York (2001).

Durre, "New insights and novel developments in clostridial acetone/butanol/isopropanol fermentation", Appl. Microbiol. Biotechnol. 49:639-648 (1998).

Flikweert et al., "Growth requirements of pyruvate-decarbosylase-negative *Saccharomyces cerevisiae*", FEMS Microbiology Letters, Wiley-blackwell Publishing Ltd. GB, vol. 174, No. 1, May 1, 1999, pp. 73-79.

Groot et al., "Technologies for butanol recovery integrated with fermentations", Process Biochemistry, vol. 27 (1992) pp. 61-75.

Guo et al., "Pervaporation study on the dehydration of aqueous butanol solutions: a comparison of flux vs. permeance, separation factor vs. selectivity", Journal of Membrane Science, 245:199-210 (2004).

Hazelwood et al., The ehrlich pathway for fusel alcohol production: a century of research on *Saccharomyces cerevisiae* metabolism: Applied and Environmental Microbiology, vol. 74, No. 8, Apr. 2008, pp. 2259-2266.

Navarro-Avino et al., "A Proposal for Nomenclature of Aldehyde Dehydrogenases in *Saccharomyces cerevisiae* and Characterization of the Stress-Inducible ALD2 and ALD3 Gnese", Yeast 15:829-42, 1999.

Saint-Prix et al., "Functional analysis of the ALD gene family of *Saccharomyces cerevisiae* during anaerobic growth on glucose: the NADP+-dependent ALD6p and ALD5p isoforms play a major role in acetate formation", Microbiology 150:2209-20, 2004.

Sambrook, J., Fritsch, E. F. and Maniatis, T. Molecular Cloning: A Laboratory Manual, 2nd ed., Cold Spring Harbor Laboratory: Cold Spring Harbor, NY (1989), particularly 9.50-9.51, 11.7-11.8 and Table 11.1.

Sulter et al., "Proliferation and metabolic significance of peroxisomes in candida boidinii during growth on D-alanine or oleic acid as the sole carbon source", Arch. Microbiol., vol. 153, pp. 485 489 (1990).

Ullmann's Encyclopedia of Industrial Chemistry, 6th edition, 2003, Wiley-VCH Verlag GmbH and Co., Weinheim, Germany, vol. 5, pp. 716-719.

Wang et al., Molecular Cloning, Characterization, and Potential Roles of Cytosolic and Mitochondrial Aldehyde Dehydrogenases in Ethanol Metabolism in *Saccharomyces cerevisiae*, Journal of Bacteriology, Feb. 1998, p. 822-830.

(56) References Cited

OTHER PUBLICATIONS

Silhavy, T.J., M. L. Berman, and L. W. Enquist Editors, Experiments with Gene Fusions Cold Spring Harbor Laboratory, Cold Spring Harbor, N. Y., 1984, 303 pp. Book Review.
Codon et al., "Factors which affect the frequency of sporulation and tetrad formation in *Saccharomyces cerevisiae* baker's yeast," Appl. Environ. Microbiol. (1995).
International Search Report and Written Opinion mailed on Jun. 6, 2014 in PCT/US2013/032159, filed on Mar. 15, 2013.

* cited by examiner

ACETATE SUPPLEMENTION OF MEDIUM FOR BUTANOLOGENS

CROSS-REFERENCE TO RELATED APPLICATIONS

This application claims priority under 35 U.S.C. §119(e) to U.S. Provisional Patent Application Ser. No. 61/615,174, filed on Mar. 23, 2012, and incorporated herein by reference in its entirety.

FIELD OF THE INVENTION

The invention relates to the fields of industrial microbiology and alcohol production. More specifically, the invention relates to improvements in fermentative production of butanol isomers by recombinant microorganisms containing an engineered butanol pathway when the microorganisms are grown in a fermentation medium containing acetate.

REFERENCE TO SEQUENCE LISTING SUBMITTED ELECTRONICALLY VIA EFS-WEB

The content of the electronically submitted Sequence Listing (20120315_CL5681USNP_SEQLIST_ST25; SIZE: 294,486; DATE OF CREATION: Mar. 14, 2013), filed herewith, is herein incorporated by reference in its entirety.

BACKGROUND OF THE INVENTION

Butanol is an important industrial chemical with a variety of applications, where its potential as a fuel or fuel additive is particularly significant. Butanol is favored as a fuel or fuel additive because it yields only $CO_2$ and little or no $SO_x$ or $NO_x$ when burned in the standard internal combustion engine. Although butanol is a four-carbon alcohol, it has an energy content similar to that of gasoline and can be blended with any fossil fuel. Additionally, butanol is less corrosive than ethanol, the most preferred fuel additive to date.

Butanol also has the potential of impacting hydrogen distribution problems in the fuel cell industry. Fuel cells today are plagued by safety concerns associated with hydrogen transport and distribution. Butanol, however, can be easily reformed for its hydrogen content and can be distributed through existing gas stations in the purity required for either fuel cells or vehicles. Butanol is also useful as a feedstock chemical in the plastics industry and as a food grade extractant in the food and flavor industry. Each year 10 to 12 billion pounds of butanol are produced by petrochemical means and the need for this commodity chemical will likely increase in the future.

Methods for the chemical synthesis of isobutanol are known, such as oxo synthesis, catalytic hydrogenation of carbon monoxide (*Ullmann's Encyclopedia of Industrial Chemistry,* 6th edition, Wiley-VCH Verlag GmbH and Co., Weinheim, Germany, Vol. 5, pp. 716-719 (2003)) and Guerbet condensation of methanol with n-propanol (Carlini et al., *J. Molec. Catal. A. Chem.,* 220:215-220 (2004)). These processes use starting materials derived from petrochemicals, are generally expensive and not environmentally friendly. The production of isobutanol from plant-derived raw materials could minimize the use of fossil fuels.

Isobutanol is produced biologically in minute quantities as a by-product of yeast fermentation. It is a minor component of "fusel oil" that forms as a result of the incomplete metabolism of amino acids by yeast. Isobutanol is specifically produced from catabolism of L-valine. After the amine group of L-valine is harvested as a nitrogen source, the resulting α-keto acid is decarboxylated and reduced to isobutanol by enzymes of the so-called Ehrlich pathway (Dickinson et al., *J. Biol. Chem.* 273:25752-25756, 1998) ("Dickinson"). Addition of exogenous L-valine to the fermentation medium increases the yield of isobutanol, as described by Dickinson, wherein it is reported that a yield of isobutanol of 3 g/L is obtained by providing L-valine at a concentration of 20 g/L in the fermentation broth. However, the use of valine as a feedstock would be cost prohibitive for industrial scale isobutanol production.

Microorganisms expressing engineered biosynthetic pathways for producing butanol, including isobutanol, directly from sugars have been described previously in, e.g., U.S. Pat. Nos. 7,851,188 and 7,993,889. Such butanologens may further include disruption of certain genes involved in the formation of by-products during fermentation in order to maximize the yield of butanol isomers. The genes involved in the by-product formation include the genes necessary for ethanol formation (see U.S. Patent Appl. Pub. No. 20090305363) and isobutyric acid formation. (see PCT Patent Appl. Pub. No. WO2012/129555). Microorganisms in which genes necessary for ethanol formation (e.g., PDC gene) are disrupted require an exogeneous C2 supplement for proper growth. This requirement for a C2 supplement is usually met by adding small amounts of ethanol to the culture medium. For example, U.S. Patent Application Publication No. 20090305363, incorporated herein by reference, describes PDC knockout yeast strains that were unable to grow in a medium containing 2% glucose as carbon source, but were found to grow very well in a medium containing glucose supplemented with a small amount of ethanol.

Under some circumstances, butanologens with disruptions in genes necessary for isobutyric acid production (e.g., ALD6) in addition to PDC gene disruptions may have altered ability to grow and produce butanol, even when ethanol is used as a C2 supplement. Although approaches to such challenges have been described in the art, for example by engineering the strain for reduced C2 dependence (see, for example, US App. Pub. No. 20120156735), alternative or supplemental methods to replace or supplement such strategies would represent an advance in the art.

SUMMARY OF THE INVENTION

Provided herein are methods for producing butanol comprising:

a. providing a recombinant host cell comprising:
   i. an engineered butanol biosynthetic pathway; and
b. contacting the host cell of a) with a fermentation medium comprising:
   i. a fermentable carbon substrate; and
   ii. acetate;

wherein said recombinant host cell has been engineered to reduce or eliminate pyruvate decarboxylase (PDC) activity and, optionally, aldehyde dehydrogenase activity; and whereby butanol is produced directly from the fermentable carbon substrate via the engineered butanol biosynthetic pathway. In embodiments, the acetate is added to the fermentation medium. In embodiments, the acetate is present in an amount sufficient for growth of the host cell. In embodiments, the acetate is present in an amount sufficient for improved butanol production. In embodiments, the acetate is added to the fermentation medium. In embodiments, the acetate is from a renewable feedstock source.

One embodiment of the invention is directed to a method for producing butanol comprising:

a. providing a recombinant host cell comprising:
   i. an engineered butanol biosynthetic pathway; and
b. contacting the host cell of a) with a fermentation medium comprising:
   i. a fermentable carbon substrate; and
   ii. acetate as C2 supplement in an amount sufficient for growth of the host cell of a) and for butanol production, wherein the acetate is added to the fermentation medium;

wherein said recombinant host cell has been engineered to reduce or eliminate pyruvate decarboxylase (PDC) activity and aldehyde dehydrogenase activity; and whereby butanol is produced directly from the fermentable carbon substrate via the engineered butanol biosynthetic pathway.

One embodiment of the invention is directed to a method for producing isobutanol comprising the following substrate to product conversions:

a) pyruvate to acetolactate (pathway step a);
b) the acetolactate from a) to 2,3-dihydroxyisovalerate (pathway step b);
c) the 2,3-dihydroxyisovalerate from b) to α-ketoisovalerate (pathway step c);
d) the α-ketoisovalerate from c) to isobutyraldehyde (pathway step d); and
e) the isobutyraldehyde from d) to isobutanol (pathway step e);

and wherein i) the substrate to product conversion of step a) is performed by an acetolactate synthase enzyme;
ii) the substrate to product conversion of step b) is performed by an acetohydroxy acid isomeroreductase enzyme;
iii) the substrate to product conversion of step c) is performed by a dihydroxyacid dehydratase dehydratase enzyme;
iv) the substrate to product conversion of step d) is performed by an α-ketoacid decarboxylase enzyme; and
v) the substrate to product conversion of step e) is performed by an alcohol dehydrogenase enzyme;

whereby isobutanol is produced directly from pyruvate via the engineered biosynthetic pathway.

One embodiment of the invention is directed to a method for producing isobutanol comprising the following substrate to product conversions:

a) pyruvate to acetolactate (pathway step a);
b) the acetolactate from a) to 2,3-dihydroxyisovalerate (pathway step b);
c) the 2,3-dihydroxyisovalerate from b) to α-ketoisovalerate (pathway step c);
d) the α-ketoisovalerate from c) to isobutyryl-CoA (pathway step f); and
e) the isobutyryl-CoA from d) to isobutyraldehyde (pathway step g);
f) the isobutyraldehyde from e) to isobutanol (pathway step e);

and wherein i) the substrate to product conversion of step a) is performed by an acetolactate synthase enzyme;
ii) the substrate to product conversion of step b) is performed by an acetohydroxy acid isomeroreductase enzyme;
iii) the substrate to product conversion of step c) is performed by a dihydroxyacid dehydratase dehydratase enzyme;
iv) the substrate to product conversion of step d) is performed by a branched-chain keto acid dehydrogenase enzyme;
v) the substrate to product conversion of step e) is performed by an acetylating aldehyde dehydrogenase enzyme; and
vi) the substrate to product conversion of step f) is performed by an alcohol dehydrogenase enzyme;

whereby isobutanol is produced directly from pyruvate via the engineered biosynthetic pathway.

One embodiment of the invention is directed to a composition comprising:

a) a recombinant host cell comprising:
   i) an engineered butanol biosynthetic pathway; and
b) a fermentation medium comprising:
   i) a fermentable carbon substrate; and
   ii) acetate in an amount sufficient for growth of the host cell of a) and for butanol production;

wherein said recombinant host cell has been engineered to reduce or eliminate pyruvate decarboxylase (PDC) activity and aldehyde dehydrogenase activity.

In embodiments, the acetate is added to the fermentation medium. In embodiments, the acetate is from a renewable feedstock source. In embodiments, both the acetate and carbon substrate are from a renewable feedstock source.

One embodiment of the invention is directed to a composition, wherein the fermentation medium further comprises butanol.

One embodiment of the invention is directed to a method for producing butanol comprising maintaining the composition above under conditions whereby butanol is produced directly from the fermentable carbon substrate via the engineered butanol biosynthetic pathway.

One embodiment of the invention is directed to butanol produced from the method disclosed herein.

In some embodiments, the polypeptide having pyruvate decarboxylase activity is PDC1, PDC5, PDC6 or combinations thereof. In some embodiments, the polypeptide having aldehyde dehydrogenase activity is ALD2, ALD3, ALD4, ALD5, ALD6 or combinations thereof.

In some embodiments, the host cell has been engineered or evolved to comprise a reduced or eliminated requirement for exogenous two-carbon substrate supplementation for their growth.

In some embodiments, the host cell comprises a heterologous polynucleotide encoding a polypeptide with phosphoketolase activity, a heterologous polynucleotide encoding a polypeptide with phosphotransacetylase activity, or both.

In some embodiments, the recombinant host cell is a bacteria or yeast.

In some embodiments, the recombinant host cell is a whole cell catalyst subjected to conditions for isobutanol production.

In some embodiments, the butanol produced is isobutanol. In some embodiments, the butanol produced is 1-butanol.

In some embodiments, the method further comprises recovering the butanol. In some embodiments, the recovery is by distillation, liquid-liquid extraction, adsorption, decantation, pervaporation or combinations thereof. In some embodiments, the method also comprises removing solids from the fermentation medium. In some embodiments, the removing step occurs before the recovery step. In some embodiments, the removing is by centrifugation, filtration or decantation.

DETAILED DESCRIPTION

Figure 1:
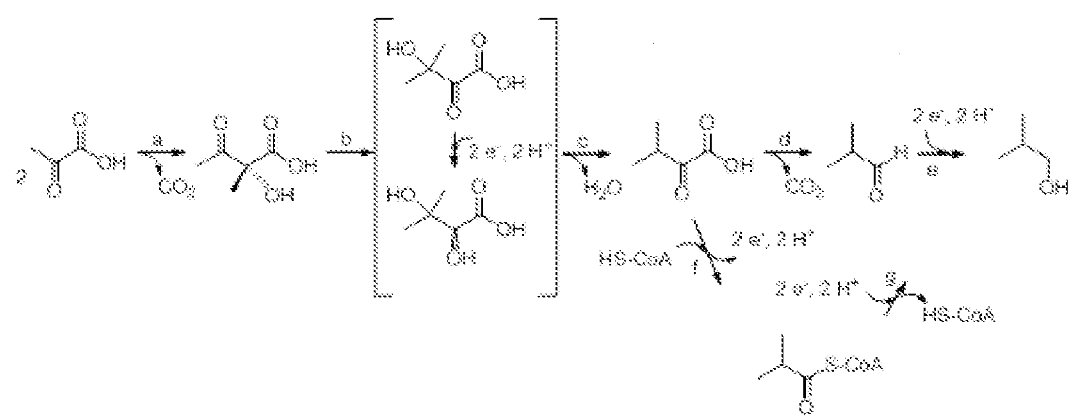
FIG. 1 depicts different isobutanol biosynthetic pathways. The steps labeled "a", "b", "c", "d", "e", "f" and "g" represent substrate to product conversions described below. Step "a" may be catalyzed, for example, by acetolactate synthase. Step "b" may be catalyzed, for example, by acetohydroxyacid reductoisomerase. Step "c" may be catalyzed, for example, by dihydroxyacid dehydratase. Step "d" may be catalyzed, for example, by branched-chain keto acid decarboxylase. Step "e" may be catalyzed, for example, by branched chain alcohol dehydrogenase. Step "f" may be catalyzed, for example, by branched chain keto acid dehydrogenase. Step "g" may be catalyzed, for example, by acetylating aldehyde dehydrogenase.
Figure 2:
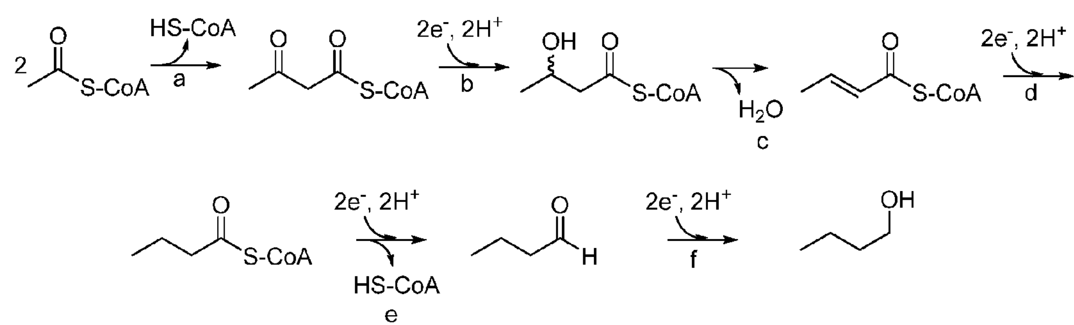
FIG. 2 depicts the 1-butanol biosynthetic pathway. The steps labeled "a", "b", "c", "d", "e", and "f" represent substrate to product conversions described below. Step "a" may be catalyzed, for example, by acetyl-CoA acetyl transferase. Step "b" may be catalyzed, for example, by 3-hydroxybutyryl-CoA dehydrogenase. Step "c" may be catalyzed, for example, by crotonase. Step "d" may be catalyzed, for example, by butyryl-CoA dehydrogenase. Step "e" may be catalyzed, for example, by butyraldehyde dehydrogenase. Step "f" may be catalyzed, for example, by butanol dehydrogenase.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

Those skilled in the art will recognize, or be able to ascertain using no more than routine experimentation, many equivalents to the specific embodiments of the invention described herein. Such equivalents are intended to be encompassed by the claims.

Provided herein are methods for fermentative production of butanol isomers using recombinant microorganisms expressing engineered butanol biosynthetic pathways and having one or more disruptions of genes involved in by-product formation during the fermentation process, wherein acetate is added to the fermentation medium.

As disclosed herein, applicants have discovered that butanologens having PDC gene deletions (and optionally ALD6 gene deletions) have an improved growth rate or butanol isomer production when they are grown in a fermentation medium with acetate as an exogeneous C2 supplement. Since acetate is less expensive than ethanol, using acetate as a C2 supplement reduces the production cost of the butanol isomers.

In embodiments, host cells with a PDC-KO phenotype may comprise a reduced or eliminated requirement for exogenous two-carbon substrate supplementation for their growth. For example, host cells with a PDC-KO phenotype may be engineered (including, but not limited to, for example, to comprise heterologous polynucleotides encoding a polypeptide with phosphoketolase activity and/or a heterologous polynucleotide encoding a polypeptide with phosphotransacetylase activity) or evolved to reduce or eliminate the requirement for C2 supplements for growth. While in such embodiments, at least in theory, acetate may not be absolutely required to satisfy a C2 auxotrophy, as demonstrated in the Examples, methods provided herein can provide improvements in butanol production employing such host cells.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

Although methods and materials similar or equivalent to those disclosed herein can be used in practice or testing of the present invention, suitable methods and materials are disclosed below. The materials, methods and examples are illustrative only and are not intended to be limiting. Other features and advantages of the invention will be apparent from the detailed description and from the claims. In order to further define this invention, the following terms and definitions are herein provided.

As used herein, the terms "comprises," "comprising," "includes," "including," "has," "having," "contains," "containing" or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or." For example, a condition A or B is satisfied by any one of the following: A is true (or present) and B is false (or not present), A is false (or not present) and B is true (or present), and both A and B are true (or present).

As used herein, the term "consists of" or variations such as "consist of" or "consisting of," as used throughout the specification and claims, indicate the inclusion of any recited integer or group of integers, but that no additional integer or group of integers may be added to the specified method, structure, or composition.

As used herein, the term "consists essentially of" or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. §2111.03.

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term “about” modifying the quantity of an ingredient or reactant of the invention or the reaction conditions described herein refers to variation in the numerical quantity that can occur, for example, through typical measuring and liquid handling procedures used for making concentrates or solutions in the real world; through inadvertent error in these procedures; through differences in the manufacture, source or purity of the ingredients employed to make the compositions or to carry out the methods; and the like. The term “about” also encompasses amounts that differ due to different equilibrium conditions for a composition resulting from a particular initial mixture. Whether or not modified by the term “about”, the claims include equivalents to the quantities. In one embodiment, the term “about” means within 10% of the reported numerical value, and sometimes within 5% of the reported numerical value.

In some instances, “biomass” as used herein refers to the cell biomass of the fermentation product-producing microorganism, typically provided in units g/L dry cell weight (dcw).

The term “fermentation product” includes any desired product of interest, including, but not limited to 1-butanol, isobutanol, etc.

The term “butanol isomer” or “butanol” refers to 1-butanol, isobutanol or mixtures thereof. Isobutanol is also known as 2-methyl-1-propanol.

The term “butanol biosynthetic pathway” as used herein refers to an enzyme pathway to produce 1-butanol or isobutanol. For example, butanol biosynthetic pathways are disclosed in U.S. Pat. No. 7,993,889, which is incorporated herein by reference.

The term “isobutanol biosynthetic pathway” refers to the enzymatic pathway to produce isobutanol. From time to time “isobutanol biosynthetic pathway” is used synonymously with “isobutanol production pathway.”

The term “1-butanol biosynthetic pathway” as used herein refers to an enzyme pathway to produce 1-butanol.

A “recombinant host cell” is defined as a host cell that has been genetically manipulated to express a biosynthetic production pathway, wherein the host cell either produces a biosynthetic product in greater quantities relative to an unmodified host cell or produces a biosynthetic product that is not ordinarily produced by an unmodified host cell.

The term “engineered” as applied to a butanol biosynthetic pathway refers to the butanol biosynthetic pathway that is manipulated, such that the carbon flux from pyruvate through the engineered butanol biosynthetic pathway is maximized, thereby producing an increased amount of butanol directly from the fermentable carbon substrate. Such engineering includes expression of heterologous polynucleotides or polypeptides, overexpression of endogenous polynucleotides or polypeptides, cytosolic localization of proteins that do not naturally localize to cytosol, increased cofactor availability, decreased activity of competitive pathways, etc.

The term “fermentable carbon substrate” refers to a carbon source capable of being metabolized by the microorganisms such as those disclosed herein. Suitable fermentable carbon substrates include, but are not limited to, sugars, including monosaccharides, such as glucose, fructose, arabinose or xylose; oligosaccharides such as lactose or sucrose; polysaccharides, such as starch, cellulose, lignocellulose or hemicellulose; one-carbon substrates, fatty acids; and a combination of these.

“Fermentation medium” as used herein means a mixture of water, fermentable carbon substrates, dissolved solids, fermentation product and all other constituents of the material held in the fermentation vessel in which the fermentation product is being made by the reaction of fermentable carbon substrates to fermentation products, water and carbon dioxide ($CO_2$) by the microorganisms present. From time to time, as used herein the term “fermentation broth” and “fermentation mixture” can be used synonymously with “fermentation medium.”

The term “aerobic conditions” as used herein means growth conditions in the presence of oxygen.

The term “microaerobic conditions” as used herein means growth conditions with low levels of dissolved oxygen. For example, the oxygen level may be less than about 1% of air-saturation.

The term “anaerobic conditions” as used herein means growth conditions in the absence of oxygen.

The term “carbon substrate” refers to a carbon source capable of being metabolized by the recombinant host cells disclosed herein. Non-limiting examples of carbon substrates are provided herein and include, but are not limited to, monosaccharides, oligosaccharides, polysaccharides, ethanol, lactate, succinate, glycerol, carbon dioxide, acetate, methanol, glucose, fructose, sucrose, xylose, arabinose, dextrose, and mixtures thereof.

The term “C2 supplement” refers to a carbon source having two carbon atoms, when added to the fermentation medium, the C2 supplement increases the growth and/or butanol production of butanologens having disruption of the activity of the proteins involved in the formation of the by-products during the fermentation process. Non-limiting examples of C2 supplements include acetate and ethanol.

The term “butanologen” as used herein refers to a microorganism capable of producing butanol isomers. Such microorganisms are typically recombinant microorganisms comprising an engineered butanol biosynthetic pathway. The term “isobutanologen” as used herein refers to a microorganism capable of producing isobutanol isomers. Such microorganisms are typically recombinant microorganisms comprising an engineered isobutanol biosynthetic pathway.

The term “PDC knock-out” as used herein refers to a host cell comprising disruptions, deletions, mutations, and/or substitutions in the polynucleotide or gene encoding a polypeptide having PDC activity, or in the endogenous polypeptides having PDC1, PDC5 or PDC6 activity or any combinations thereof, such that PDC activity is eliminated or reduced.

The term “ALD knock-out” as used herein refers to a host cell comprising disruptions, deletions, mutations, and/or substitutions in the polynucleotide or gene encoding a polypeptide having aldehyde dehydrogenase activity, or in the endogenous polypeptides having ALD2, ALD3, ALD4, ALD5 or ALD6 activity or any combinations thereof, such that ALD activity is eliminated or reduced.

As used herein, the term “improved butanol production” refers to an improvement in a butanol production parameter including, but not limited to, an increase in at least one of yield, effective rate, effective titer or specific productivity or a decrease in yield of at least one byproduct such as, for example, isobutyric acid. Increases or decreases associated with acetate are determined relative to the appropriate control method in the absence of acetate.

As used herein, the term “yield” refers to the amount of product per amount of carbon source in g/g. The yield may be exemplified for glucose as the carbon source. It is understood unless otherwise noted that yield is expressed as a percentage of the theoretical yield. In reference to a microorganism or metabolic pathway, “theoretical yield” is defined as the maximum amount of product that can be generated per total amount of substrate as dictated by the stoichiometry of the metabolic pathway used to make the product. For example, the theoretical yield for one typical conversion of glucose to isopropanol is 0.33 g/g. As such, a yield of isopropanol from glucose of 0.297 g/g would be expressed as 90% of theoretical or 90% theoretical yield. It is understood that while in the present disclosure the yield is exemplified for glucose as a carbon source, the invention can be applied to other carbon sources and the yield may vary depending on the carbon source used. One skilled in the art can calculate yields on various carbon sources.

The term "effective titer" as used herein, refers to the total amount of butanol isomer produced by fermentation per liter of fermentation medium. The total amount of butanol isomer includes: (i) the amount of butanol in the fermentation medium; (ii) the amount of butanol isomer recovered from the organic extractant; and (iii) the amount of butanol isomer recovered from the gas phase, if gas stripping is used.

The term "effective rate" as used herein, refers to the total amount of butanol isomer produced by fermentation per liter of fermentation medium per hour of fermentation.

The term "specific productivity" as used herein, refers to the g of butanol isomer produced per g of dry cell weight of cells per unit time.

The term "growth rate" as used herein, refers to the rate at which the microorganisms grow in the culture medium. The growth rate of the recombinant microorganisms can be monitored, for example, by measuring the optical density at 600 nanometers. The doubling time may be calculated from the logarithmic part of the growth curve and used as a measure of the growth rate.

Polypeptides and Polynucleotides for Use in the Invention

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain" or any other term used to refer to a chain or chains of two or more amino acids, are included within the definition of "polypeptide," and the term "polypeptide" may be used instead of, or interchangeably with any of these terms. A polypeptide may be derived from a natural biological source or produced by recombinant technology, but is not necessarily translated from a designated nucleic acid sequence. It may be generated in any manner, including by chemical synthesis. The polypeptides used in this invention comprise full-length polypeptides and fragments thereof.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purposes of the invention, as are native or recombinant polypeptides which have been separated, fractionated, or partially or substantially purified by any suitable technique.

Polypeptides and other enzymes suitable for use in the present invention and fragments thereof are encoded by polynucleotides. The term "polynucleotide" is intended to encompass a singular nucleic acid as well as plural nucleic acids, and refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. Polynucleotides according to the present invention further include such molecules produced synthetically. Polynucleotides of the invention may be native to the host cell or heterologous. In addition, a polynucleotide or a nucleic acid may be or may include a regulatory element such as a promoter, ribosome binding site, or a transcription terminator.

In certain embodiments, the polynucleotide or nucleic acid is DNA. In the case of DNA, a polynucleotide comprising a nucleic acid, which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. Other transcription control elements, besides a promoter, for example enhancers, operators, repressors, and transcription termination signals, can be operably associated with the polynucleotide. Suitable promoters and other transcription control regions are disclosed herein.

A polynucleotide sequence can be referred to as "isolated," in which it has been removed from its native environment. For example, a heterologous polynucleotide encoding a polypeptide or polypeptide fragment having enzymatic activity (e.g., the ability to convert a substrate to xylulose) contained in a vector is considered isolated for the purposes of the present invention. Further examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. An isolated polynucleotide fragment in the form of a polymer of DNA can be comprised of one or more segments of cDNA, genomic DNA, or synthetic DNA.

The term "gene" refers to a nucleic acid fragment that is capable of being expressed as a specific protein, optionally including regulatory sequences preceding (5' non-coding sequences) and following (3' non-coding sequences) the coding sequence.

As used herein, a "coding region" or "ORF" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' non-translated regions, and the like, are not part of a coding region. "Suitable regulatory sequences" refer to nucleotide sequences located upstream (5' non-coding sequences), within, or downstream (3' non-coding sequences) of a coding sequence that influence the transcription, RNA processing or stability, or translation of the associated coding sequence. Regulatory sequences can include promoters, translation leader sequences, introns, polyadenylation recognition sequences, RNA processing sites, effector binding sites and stem-loop structures.

A variety of translation control elements are known to those of ordinary skill in the art. These include, but are not limited to ribosome binding sites, translation initiation and termination codons, and elements derived from viral systems (particularly an internal ribosome entry site, or IRES). In other embodiments, a polynucleotide of the present invention is RNA, for example, in the form of messenger RNA (mRNA). RNA of the present invention may be single stranded or double stranded.

As used herein, the term "transformation" refers to the transfer of a nucleic acid fragment into the genome of a host organism, resulting in genetically stable inheritance. Host organisms containing the transformed nucleic acid fragments are referred to as "recombinant" or "transformed" organisms.

The terms "plasmid," "vector," and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

As used herein, "native" refers to the form of a polynucleotide, gene, or polypeptide as found in nature with its own regulatory sequences, if present.

The term "endogenous," when used in reference to a polynucleotide, a gene, or a polypeptide refers to a native polynucleotide or gene in its natural location in the genome of an organism, or for a native polypeptide, is transcribed and translated from this location in the genome.

The term "heterologous" when used in reference to a polynucleotide, a gene, or a polypeptide refers to a polynucleotide, gene, or polypeptide not normally found in the host organism. "Heterologous" also includes a native coding region, or portion thereof, that is reintroduced into the source organism in a form that is different from the corresponding native gene, e.g., not in its natural location in the organism's genome. The heterologous polynucleotide or gene may be introduced into the host organism by, e.g., gene transfer. A heterologous gene may include a native coding region with non-native regulatory regions that is reintroduced into the native host. A "transgene" is a gene that has been introduced into the genome by a transformation procedure.

"Regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, operators, repressors, transcription termination signals, translation leader sequences, introns, polyadenylation recognition sequences, RNA processing site, effector binding site and stem-loop structure.

The term "promoter" refers to a nucleic acid sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". "Inducible promoters," on the other hand, cause a gene to be expressed when the promoter is induced or turned on by a promoter-specific signal or molecule. It is further recognized that since in most cases the exact boundaries of regulatory sequences have not been completely defined, DNA fragments of different lengths may have identical promoter activity. For example, it will be understood that "FBA1 promoter" can be used to refer to a fragment derived from the promoter region of the FBA1 gene.

The term "terminator" as used herein refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence. It is recognized that since in most cases the exact boundaries of regulatory sequences have not been completely defined, DNA fragments of different lengths may have identical terminator activity. For example, it will be understood that "CYC1 terminator" can be used to refer to a fragment derived from the terminator region of the CYC1 gene.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

Standard recombinant DNA and molecular cloning techniques used here are well known in the art and are described by Sambrook et al. (Sambrook, Fritsch, and Maniatis, *Molecular Cloning: A Laboratory Manual*, Second Edition, Cold Spring Harbor Laboratory Press, Cold Spring Harbor, N.Y., 1989) (hereinafter "Maniatis"); and by Silhavy et al. (Silhavy et al., *Experiments with Gene Fusions*, Cold Spring Harbor Laboratory Press Cold Spring Harbor, N.Y., 1984);

and by Ausubel, F. M. et al., (Ausubel et al., *Current Protocols in Molecular Biology*, published by Greene Publishing Assoc. and Wiley-Interscience, 1987).

Butanol Biosynthetic Pathways

Carbohydrate utilizing microorganisms employ the Embden-Meyerhof-Parnas (EMP) pathway, the Entner-Doudoroff pathway and the pentose phosphate cycle as the central, metabolic routes to provide energy and cellular precursors for growth and maintenance. These pathways have in common the intermediate glyceraldehyde-3-phosphate and, ultimately, pyruvate is formed directly or in combination with the EMP pathway. Subsequently, pyruvate is transformed to acetyl-coenzyme A (acetyl-CoA) via a variety of means. Acetyl-CoA serves as a key intermediate, for example, in generating fatty acids, amino acids and secondary metabolites. The combined reactions of sugar conversion to pyruvate produce energy (e.g., adenosine-5'-triphosphate, ATP) and reducing equivalents (e.g., reduced nicotinamide adenine dinucleotide, NADH, and reduced nicotinamide adenine dinucleotide phosphate, NADPH). NADH and NADPH must be recycled to their oxidized forms ($NAD^+$ and $NADP^+$, respectively). In the presence of inorganic electron acceptors (e.g., $O_2$, $NO_3^-$ and $SO_4^{2-}$), the reducing equivalents may be used to augment the energy pool; alternatively, a reduced carbon by-product may be formed.

Engineered biosynthetic pathways for the production of butanol isomers from a fermentable carbon source that may be used in the present invention are, for example, described in U.S. Pat. Nos. 7,851,188 and 7,993,889, which are incorporated herein by reference. In one embodiment, the engineered butanol biosynthetic pathway is an isobutanol biosynthetic pathway, which comprises the following substrate to product conversions:

a) pyruvate to acetolactate, which may be catalyzed, for example, by acetolactate synthase;
b) acetolactate to 2,3-dihydroxyisovalerate, which may be catalyzed, for example, by acetohydroxy acid isomeroreductase;
c) 2,3-dihydroxyisovalerate to α-ketoisovalerate, which may be catalyzed, for example, by dihydroxyacid dehydratase;
d) α-ketoisovalerate to isobutyraldehyde, which may be catalyzed, for example, by an α-keto acid decarboxylase; and,
e) isobutyraldehyde to isobutanol, which may be catalyzed, for example, by an alcohol dehydrogenase.

In another embodiment, the isobutanol biosynthetic pathway comprises the following substrate to product conversions:

a) pyruvate to acetolactate, which may be catalyzed, for example, by acetolactate synthase;
b) acetolactate to 2,3-dihydroxyisovalerate, which may be catalyzed, for example, by acetohydroxy acid isomeroreductase;
c) 2,3-dihydroxyisovalerate to α-ketoisovalerate, which may be catalyzed, for example, by dihydroxyacid dehydratase;
d) α-ketoisovalerate to isobutyryl-CoA, which may be catalyzed, for example, by branched-chain keto acid dehydrogenase;
e) isobutyryl-CoA to isobutyraldehyde, which may be catalyzed, for example, by acetylating aldehyde dehydrogenase; and,
f) isobutyraldehyde to isobutanol, which may be catalyzed, for example, by a alcohol dehydrogenase.

Engineered biosynthetic pathways for the production of 1-butanol that may be used include those described in U.S. Appl. Pub. No. 20080182308, which is incorporated herein by reference. In one embodiment, the 1-butanol biosynthetic pathway comprises the following substrate to product conversions:

a) acetyl-CoA to acetoacetyl-CoA, which may be catalyzed, for example, by acetyl-CoA acetyl transferase;
b) acetoacetyl-CoA to 3-hydroxybutyryl-CoA, which may be catalyzed, for example, by 3-hydroxybutyryl-CoA dehydrogenase;
c) 3-hydroxybutyryl-CoA to crotonyl-CoA, which may be catalyzed, for example, by crotonase;
d) crotonyl-CoA to butyryl-CoA, which may be catalyzed, for example, by butyryl-CoA dehydrogenase;
e) butyryl-CoA to butyraldehyde, which may be catalyzed, for example, by butyraldehyde dehydrogenase; and,
f) butyraldehyde to 1-butanol, which may be catalyzed, for example, by butanol dehydrogenase.

In one embodiment, the invention produces butanol from plant derived carbon sources, avoiding the negative environmental impact associated with the standard petrochemical processes for butanol production. In one embodiment, the invention provides a method for the production of butanol using recombinant industrial host cells comprising an engineered butanol biosynthetic pathway.

In some embodiments, the butanol biosynthetic pathway comprises at least one polynucleotide, at least two polynucleotides, at least three polynucleotides, or at least four polynucleotides that is/are heterologous to the host cell. In some embodiments, each substrate to product conversion of a butanol biosynthetic pathway in a recombinant host cell is catalyzed by a heterologous polypeptide. In embodiments, the polypeptide catalyzing the substrate to product conversions of acetolactate to 2,3-dihydroxyisovalerate and/or the polypeptide catalyzing the substrate to product conversion of isobutyraldehyde to isobutanol are capable of utilizing NADH as a cofactor.

In some embodiments, the engineered butanol pathway of the butanologen comprises at least one polypeptide selected from the group of enzymes having the following Enzyme Commission Numbers: EC 2.2.1.6, EC 1.1.1.86, EC 4.2.1.9, EC 4.1.1.72, EC 1.1.1.1, EC 1.1.1.265, EC 1.1.1.2, EC 1.2.4.4, EC 1.3.99.2, EC 1.2.1.10, EC 2.3.1.9, EC 2.3.1.16, EC 1.1.1.35, EC 1.1.1.157, EC 1.1.1.36, EC 4.2.1.17, EC 4.2.1.55, EC 1.3.1.44, EC 1.3.1.38, and EC 1.2.1.57.

In some embodiments, the engineered butanol pathway of the butanologen comprises at least one polypeptide selected from the following group of enzymes: acetolactate synthase, acetohydroxy acid isomeroreductase, dihydroxyacid dehydratase, branched-chain alpha-keto acid decarboxylase, branched-chain alcohol dehydrogenase, acylating aldehyde dehydrogenase, branched-chain keto acid dehydrogenase, butyryl-CoA dehydrogenase, butyraldehyde dehydrogenase, acetyl-CoA acetyltransferase, 3-hydroxybutyryl-CoA dehydrogenase, crotonase, butyryl-CoA dehydrogenase, butanol dehydrogenase, and butyraldehyde dehydrogenase.

The terms "acetohydroxyacid synthase," "acetolactate synthase" and "acetolactate synthetase" (abbreviated "ALS") are used interchangeably herein to refer to any polypeptide having a biological function of an acetolactate synthase. Such polypeptides include a polypeptide that catalyzes the conversion of pyruvate to acetolactate and $CO_2$. Example acetolactate synthases are known by the EC number 2.2.1.6 (Enzyme Nomenclature 1992, Academic Press, San Diego). These unmodified enzymes are available from a number of sources, including, but not limited to, *Bacillus subtilis* (GenBank Nos: CAB15618 and Z99122, NCBI (National Center for Biotechnology Information) amino acid sequence, NCBI nucleotide sequence, respectively), *Klebsiella pneumoniae* (GenBank Nos: AAA25079 and M73842), and *Lactococcus lactis* (GenBank Nos: AAA25161 and L16975).

The terms "ketol-acid reductoisomerase" ("KARI"), "acetohydroxy acid isomeroreductase" and "acetohydroxy acid reductoisomerase" will be used interchangeably and refer to any polypeptide having a biological function of a ketol-acid reductoisomerase. Such polypeptides include a polypeptide capable of catalyzing the reaction of (S)-acetolactate to 2,3-dihydroxyisovalerate. Example KARI enzymes may be classified as EC number EC 1.1.1.86 (Enzyme Nomenclature 1992, Academic Press, San Diego), and are available from a vast array of microorganisms, including, but not limited to, *Escherichia coli* (SEQ ID NO: 1) (GenBank Nos: NP_418222 and NC_000913), *Saccharomyces cerevisiae* (GenBank Nos: NP_013459 and NC_001144), *Methanococcus maripaludis* (GenBank Nos: CAF30210 and BX957220), *Pseudomonas fluorescens* (SEQ ID NO: 2) and *Bacillus subtilis* (GenBank Nos: CAB14789 and Z99118). KARIs include *Anaerostipes caccae* KARI variants "K9G9" (SEQ ID NO: 132), "K9D3" (SEQ ID NO: 133), "K9JBP4P" (SEQ ID NO: 130), and "K9SB2-SH" (SEQ ID NO: 126). Ketol-acid reductoisomerase (KARI) enzymes are described in U.S. Pat. Nos. 7,910,342, and 8,129,162; U.S. Patent Appl. Pub. No. 20100197519; and International Appl. Pub. No. WO/2011/041415, which are incorporated herein by reference. Examples of KARIs disclosed therein are those from *Lactococcus lactis, Vibrio cholera, Pseudomonas aeruginosa* PAO1 and *Pseudomonas fluorescens* PF5 mutants. In some embodiments, the KARI utilizes NADH as a co-factor. In some embodiments, the KARI utilizes NADPH as a cofactor. PCT Patent Appl. Pub. No. WO2012/129555 further describes KARI mutants useful in the present invention, and is incorporated herein by reference.

The terms "acetohydroxy acid dehydratase" and "dihydroxyacid dehydratase" ("DHAD") refer to any polypeptide having a biological function of a dihydroxyacid dehydratase. Such polypeptides include a polypeptide that catalyzes the conversion of 2,3-dihydroxyisovalerate to α-ketoisovalerate. Example dihydroxyacid dehydratases are known by the EC number 4.2.1.9. Such enzymes are available from a vast array of microorganisms, including, but not limited to, *E. coli* (GenBank Nos: YP_026248 and NC_000913), *S. cerevisiae* (GenBank Nos: NP_012550 and NC_001142), *M. maripaludis* (GenBank Nos: CAF29874 and BX957219), *B. subtilis* (GenBank Nos: CAB14105 and Z99115), *Lactococcus lactis* (SEQ ID NO: 3), *Streptococcus mutans* (SEQ ID NO: 4) and *N. crassa*. US Appl. Pub. No. 20100081154 A1 and U.S. Pat. No. 7,993,889, which are incorporated herein by reference, describe dihydroxyacid dehydratases (DHADs), including a DHAD from *Streptococcus mutans* (SEQ ID NO: 131). Suitable DHADs also include variants of *Streptococcus mutans* such as "L2V4" (SEQ ID NO: 134).

The term "branched-chain α-keto acid decarboxylase" or "α-ketoacid decarboxylase" or "α-ketoisovalerate decarboxylase" or "2-ketoisovalerate decarboxylase" ("KIVD") refers to any polypeptide having a biological function of a 2-ketoisovalerate decarboxylase. Such polypeptides include a polypeptide that catalyzes the conversion of α-ketoisovalerate to isobutyraldehyde and $CO_2$. Example branched-chain α-keto acid decarboxylases are known by the EC number 4.1.1.72 and are available from a number of sources, including, but not limited to, *Lactococcus lactis* (GenBank Nos: AAS49166, AY548760, CAG34226 and AJ746364), *Salmonella typhimurium* (GenBank Nos: NP_461346 and NC_003197), *Clostridium acetobutylicum* (GenBank Nos: NP_149189 and NC_001988), *Macrococcus caseolyticus* (SEQ ID NO: 5), and *Listeria grayi* (SEQ ID NO: 6).

The terms "branched-chain alcohol dehydrogenase" or "alcohol dehydrogenase" ("ADH") refer to any polypeptide having a biological function of an alcohol dehydrogenase. Such polypeptides include a polypeptide that catalyzes the conversion of isobutyraldehyde to isobutanol. Example branched-chain alcohol dehydrogenases are known by the EC number 1.1.1.265, but may also be classified under other alcohol dehydrogenases (specifically, EC 1.1.1.1 or 1.1.1.2). Alcohol dehydrogenases may use NADPH or NADH as a co-factor. Such enzymes are available from a number of sources, including, but not limited to, *S. cerevisiae* (GenBank Nos: NP_010656, NC_001136, NP_014051 and NC_001145), *E. coli* (GenBank Nos: NP_417484 and NC_000913), *C. acetobutylicum* (GenBank Nos: NP_349892, NC_003030, NP_349891 and NC_003030), *B. indica* (SEQ ID NO: 7) and *A. xylosoxidans* (SEQ ID NO: 8). U.S. Patent Appl. Publ. No. 20090269823 A1, which is incorporated herein by reference, describes SadB, an alcohol dehydrogenase (ADH) from *Achromobacter xylosoxidans*. Alcohol dehydrogenases also include horse liver ADH and *Beijerinkia indica* ADH (as described by U.S. Appl. Publ. No. 20110269199, which is incorporated herein by reference).

The term "butanol dehydrogenase" refers to any polypeptide having a biological function of a butanol dehydrogenase. Such polypeptides include a polypeptide that catalyzes the conversion of isobutyraldehyde to isobutanol or the conversion of 2-butanone to 2-butanol. Butanol dehydrogenases are a subset of a broad family of alcohol dehydrogenases. Butanol dehydrogenase may be NADH or NADPH dependent. The NADH dependent enzymes are known as EC 1.1.1.1 and are available, for example, from *Rhodococcus ruber* (GenBank Nos: CAD36475 and AJ491307). The NADPH dependent enzymes are known as EC 1.1.1.2 and are available, for example, from *Pyrococcus furiosus* (GenBank Nos: AAC25556 and AF013169). Additionally, a butanol dehydrogenase is available from *Escherichia coli* (GenBank Nos: NP_417484 and NC_000913) and a cyclohexanol dehydrogenase is available from *Acinetobacter* sp. (GenBank Nos: AAG10026 and AF282240). The term "butanol dehydrogenase" also refers to an enzyme that catalyzes the conversion of butyraldehyde to 1-butanol, using either NADH or NADPH as cofactor. Butanol dehydrogenases are available from, for example, *C. acetobutylicum* (GenBank Nos: NP_149325 and NC_001988 (note: this enzyme possesses both aldehyde and alcohol dehydrogenase activity), NP_349891, NC_003030, NP_349892 and NC_003030) and *E. coli* (GenBank Nos: NP_417484 and NC_000913).

The term "branched-chain keto acid dehydrogenase" refers to any polypeptide having a biological function of a branched-chain keto acid dehydrogenase. Such polypeptides include a polypeptide that catalyzes the conversion of α-ketoisovalerate to isobutyryl-CoA (isobutyryl-coenzyme A), typically using $NAD^+$ (nicotinamide adenine dinucleotide) as an electron acceptor. Example branched-chain keto acid dehydrogenases are known by the EC number 1.2.4.4. Such branched-chain keto acid dehydrogenases are comprised of four subunits and sequences from all subunits are available from a vast array of microorganisms, including, but not limited to, *B. subtilis* (GenBank Nos: CAB14336, Z99116, CAB14335, Z99116, CAB14334, Z99116, CAB14337 and Z99116) and *Pseudomonas putida* (GenBank Nos: AAA65614, M57613, AAA65615, M57613, AAA65617, M57613, AAA65618 and M57613).

The term "acylating aldehyde dehydrogenase" refers to any polypeptide having a biological function of an acylating aldehyde dehydrogenase. Such polypeptides include a polypeptide that catalyzes the conversion of isobutyryl-CoA to isobutyraldehyde, typically using either NADH or NADPH as an electron donor. Example acylating aldehyde dehydrogenases are known by the EC numbers 1.2.1.10 and 1.2.1.57. Such enzymes are available from multiple sources, including, but not limited to, *Clostridium beijerinckii* (GenBank Nos: AAD31841 and AF157306), *C. acetobutylicum* (GenBank Nos: NP_149325, NC_001988, NP_149199 and NC_001988), *P. putida* (GenBank Nos: AAA89106 and U13232), and *Thermus thermophilus* (GenBank Nos: YP_145486 and NC_006461).

The term "acetyl-CoA acetyltransferase" refers to any polypeptide having a biological function of an acetyl-CoA acetyltransferase. Such polypeptides include a polypeptide that catalyzes the conversion of two molecules of acetyl-CoA to acetoacetyl-CoA and coenzyme A (CoA). Example acetyl-CoA acetyltransferases are acetyl-CoA acetyltransferases with substrate preferences (reaction in the forward direction) for a short chain acyl-CoA and acetyl-CoA and are classified as E.C. 2.3.1.9 [Enzyme Nomenclature 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728 and NC_000913), *Clostridium acetobutylicum* (GenBank Nos: NP_349476.1, NC_003030, NP_149242 and NC_001988, *Bacillus subtilis* (GenBank Nos: NP_390297 and NC_000964), and *Saccharomyces cerevisiae* (GenBank Nos: NP_015297 and NC_001148).

The term "3-hydroxybutyryl-CoA dehydrogenase" refers to any polypeptide having a biological function of a 3-hydroxybutyryl-CoA dehydrogenase. Such polypeptides include a polypeptide that catalyzes the conversion of acetoacetyl-CoA to 3-hydroxybutyryl-CoA. 3-Example hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA. Examples may be classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank Nos: NP_349314 and NC_003030), *B. subtilis* (GenBank Nos: AAB09614 and U29084), *Ralstonia eutropha* (GenBank Nos: YP_294481 and NC_007347), and *Alcaligenes eutrophus* (GenBank Nos: AAA21973 and J04987).

The term "crotonase" refers to any polypeptide having a biological function of a crotonase. Such polypeptides include a polypeptide that catalyzes the conversion of 3-hydroxybutyryl-CoA to crotonyl-CoA and $H_2O$. Example crotonases may have a substrate preference for (S)-3-hydroxybutyryl-CoA or (R)-3-hydroxybutyryl-CoA and may be classified as E.C. 4.2.1.17 and E.C. 4.2.1.55, respectively. Crotonases are available from a number of sources, for example, *E. coli* (GenBank Nos: NP_415911 and NC_000913), *C. acetobutylicum* (GenBank Nos: NP_349318 and NC_003030), *B. subtilis* (GenBank Nos: CAB13705 and Z99113), and *Aeromonas caviae* (GenBank Nos: BAA21816 and D88825).

The term "butyryl-CoA dehydrogenase" refers to any polypeptide having a biological function of a butyryl-CoA dehydrogenase. Such polypeptides include a polypeptide that catalyzes the conversion of crotonyl-CoA to butyryl-CoA. Example butyryl-CoA dehydrogenases may be NADH-dependent, NADPH-dependent, or flavin-dependent and may be classified as E.C. 1.3.1.44, E.C. 1.3.1.38, and E.C. 1.3.99.2, respectively. Butyryl-CoA dehydrogenases are available from a number of sources, for example, *C. acetobutylicum* (GenBank Nos: NP_347102 and NC_003030), *Euglena gracilis* (GenBank Nos: □5EU90 and AY741582), *Streptomyces collinus* (GenBank Nos: AAA92890 and U37135), and *Streptomyces coelicolor* (GenBank Nos: CAA22721 and AL939127).

The term "butyraldehyde dehydrogenase" refers to any polypeptide having a biological function of a butyraldehyde dehydrogenase. Such polypeptides include a polypeptide that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank Nos: AAD31841 and AF157306) and *C. acetobutylicum* (GenBank Nos: NP_149325 and NC_001988).

Host Cells

Host cells for butanol production may be selected from bacteria and yeast. In embodiments, suitable host cells include any bacterial or yeast cell useful for genetic modification and recombinant gene expression. The criteria for selection of suitable microbial hosts include the following: intrinsic tolerance to the butanol isomer being produced, high rate of glucose utilization, availability of genetic tools for gene manipulation, and the ability to generate stable chromosomal alterations.

The ability to genetically modify the host is essential for the production of any recombinant microorganism. The mode of gene transfer technology may be by electroporation, conjugation, transduction or natural transformation. A broad range of host conjugative plasmids and drug resistance markers are available. The cloning vectors are tailored to the host organisms based on the nature of antibiotic resistance markers that can function in that host.

The microbial host also has to be manipulated in order to inactivate competing pathways for carbon flow by deleting various genes. This requires the availability of either transposons to direct inactivation or chromosomal integration vectors. Additionally, the production host should be amenable to chemical mutagenesis so that mutations to improve intrinsic butanol tolerance may be obtained.

The microbial host cell used for the production butanol isomers is preferably tolerant to the butanol isomer that is being produced so that the yield of the butanol isomer is not limited by the toxicity of the butanol isomer. In one embodiment, the host used for the isobutanol production is tolerant to isobutanol. Suitable host strains with a tolerance for isobutanol may be identified by a screening method based on the intrinsic tolerance of the strain as described in U.S. Pat. No. 7,993,889 (incorporated herein by reference).

The microbial host for isobutanol production should also utilize carbohydrates, including monosaccharides, oligosaccharides and polysaccharides, at a high rate. Most microbes are capable of utilizing carbohydrates. However, certain environmental microbes cannot utilize carbohydrates to high efficiency, and therefore would not be suitable hosts.

Based on the criteria described above, suitable microbial hosts for the production of butanol include, but are not limited to, members of the genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula, Schizosaccharomyces, Issatchenkia, Kluyveromyces, Yarrowia, Pichia, Candida, Hansenula* and *Saccharomyces*. Preferred hosts include: *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis, Schizosaccharomyces pombe, Kluyveromyces lactis, Kluyveromyces thermotolerans, Kluyveromyces marxianus, Candida glabrata, Candida albicans, Pichia stipitis, Yarrowia lipolytica, E. coli, L. plantarum* and *Saccharomyces cerevisiae*. In some embodiments, the host cell is *Saccharomyces cerevisiae. S. cerevisiae* yeast are known in the art and are available from a variety of sources, including, but not limited to, American Type Culture Collection (Rockville, Md.); Centraalbureau voor Schimmelcultures (CBS) Fungal Biodiversity Centre; LeSaffre; Gert Strand AB; Ferm Solutions; North American Bioproducts; Martrex and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

Host Cells for Butanol Production

Recombinant microorganisms containing the genes necessary to encode the enzymatic pathway for conversion of a fermentable carbon substrate to butanol isomers may be constructed using techniques well known in the art. In the present invention, genes encoding the enzymes of one of the butanol biosynthetic pathways, for example, acetolactate synthase, acetohydroxy acid isomeroreductase, dihydroxyacid dehydratase, branched-chain α-keto acid decarboxylase, and branched-chain alcohol dehydrogenase, may be isolated from various sources, as described, for example, in U.S. Pat. No. 7,993,889.

Once the relevant pathway genes are identified and isolated, the relevant enzymes of the butanol biosynthetic pathway may be introduced into the host cells or manipulated, as described, for example, in U.S. Pat. No. 7,993,889, to produce butanologens. The butanologens generated comprise an engineered butanol biosynthetic pathway. In some embodiments, the butanologen is an isobutanologen, which comprises an engineered isobutanol biosynthetic pathway.

In some embodiments, the butanologen is a yeast. In some embodiments, the butanologen is a bacterium. In some embodiments, the butanologen is *Saccharomyces cerevisiae*.

In some embodiments, the engineered butanologen contains one or more polypeptides selected from a group of enzymes having the following Enzyme Commission Numbers: EC 2.2.1.6, EC 1.1.1.86, EC 4.2.1.9, EC 4.1.1.72, EC 1.1.1.1, EC 1.1.1.265, EC 1.1.1.2, EC 1.2.4.4, EC 1.3.99.2, EC 1.2.1.10, EC 2.3.1.9, EC 2.3.1.16, EC 1.1.1.35, EC 1.1.1.157, EC 1.1.1.36, EC 4.2.1.17, EC 4.2.1.55, EC 1.3.1.44, EC 1.3.1.38, and EC 1.2.1.57.

In some embodiments, the engineered isobutanologen contains one or more polypeptides selected from acetolactate synthase, acetohydroxy acid isomeroreductase, dihydroxyacid dehydratase, branched-chain alpha-keto acid decarboxylase, branched-chain alcohol dehydrogenase, acylating aldehyde dehydrogenase, branched-chain keto acid dehydrogenase, butyryl-CoA dehydrogenase, butyraldehyde dehydrogenase, acetyl-CoA acetyltransferase, 3-hydroxybutyryl-CoA dehydrogenase, crotonase, butyryl-CoA dehydrogenase, butanol dehydrogenase, and butyraldehyde dehydrogenase.

In some embodiments, enzymes of the butanol biosynthetic pathway that are usually localized to the mitochondria are not localized to the mitochondria. In some embodiments, enzymes of the engineered butanol biosynthetic pathway are localized to the cytosol. In some embodiments, an enzyme of the biosynthetic pathway is localized to the cytosol by removing the mitochondrial targeting sequence. In some embodiments, mitochondrial targeting is eliminated by generating new start codons as described in for example, U.S. Pat. No. 7,993,889, incorporated herein by reference. In some embodiments, the enzyme of the biosynthetic pathway that is localized to the cytosol is DHAD. In some embodiments, the enzyme from the biosynthetic pathway that is localized to the cytosol is KARI.

In some embodiments, the enzymes of the engineered butanol biosynthetic pathway may use NADH or NADPH as a co-factor, wherein NADH or NADPH acts as an electron donor. In some embodiments, one or more enzymes of the butanol biosynthetic pathway use NADH as an electron donor. In some embodiments, one or more enzymes of the butanol biosynthetic pathway use NADPH as an electron donor.

Additional Modifications of Butanologens

The butanologens. as provided herein. may further comprise one or more additional modifications. Such modifications, for example, may include disruption of the activity of the genes involved in the production of by-products during the fermentative production of butanol isomers via the engineered butanol biosynthetic pathway. The disruption of the activity of the genes involved in the production of by-products during the fermentative production of butanol isomers reduces yield loss from the competing pathways for carbon flow and increases butanol production. In some embodiments, such modifications include disruption of the activity of pyruvate decarboxylase, aldehyde dehydrogenase or both.

The term “pyruvate decarboxylase” refers to any polypeptide having a biological function of a pyruvate decarboxylase. Such polypeptides include a polypeptide that catalyzes the decarboxylation of pyruvic acid to acetaldehyde and carbon dioxide. Pyruvate decarboxylases are known by the EC number 4.1.1.1. Such polypeptides can be determined by methods well known in the art and disclosed in PCT Patent Appl. Pub. No. WO2012/129555. These enzymes are found in a number of yeast, including *Saccharomyces cerevisiae* (GenBank Nos: CAA97575, CAA97705 and CAA97091). Additional examples of PDC are provided in U.S. Appl. Pub. No. 2009035363, which is incorporated herein by reference.

In some embodiments, a butanologen disclosed herein can comprise a modification or disruption of an endogenous polynucleotide and/or gene encoding a polypeptide having pyruvate decarboxylase activity and/or an endogenous polypeptide having pyruvate decarboxylase activity. In some embodiments, a butanologen disclosed herein can comprise a deletion, mutation, and/or substitution in an endogenous polynucleotide or gene encoding a polypeptide having PDC activity, or in an endogenous polypeptide having PDC activity. Such modifications, disruptions, deletions, mutations, and/or substitutions can result in PDC activity that is reduced or eliminated, resulting, for example, in a PDC knock-out (PDC-KO) phenotype.

Endogenous pyruvate decarboxylase in yeast converts pyruvate to acetaldehyde, which is then converted to ethanol or to acetyl-CoA via acetate. Yeast may have one or more genes encoding pyruvate decarboxylase. For example, there is one gene encoding pyruvate decarboxylase in *Candida glabrata, Schizosaccharomyces pombe* and *Kluyveromyces lactis*, while there are three isozymes of pyruvate decarboxylase encoded by the PDC1, PCD5 and/or PDC6 genes in *Saccharomyces*. In some embodiments, in the present yeast cells at least one PDC gene is inactivated. If the yeast cell used has more than one expressed (active) PDC gene, then each of the active PDC genes may be modified or inactivated thereby producing a pdc− cell. For example, in *S. cerevisiae* the PDC1, PDC5 and PDC6 genes may be modified or inactivated. If a PDC gene is not active under the fermentation conditions to be used then such a gene would not need to be modified or inactivated. In some embodiments, the pyruvate decarboxylase that is deleted or down-regulated is selected from the group consisting of: PDC1, PDC5, PDC6 and combinations thereof. U.S. Patent Appl. Pub. No. 20090305363 and PCT Patent Appl. Pub. No. WO2012/129555 (incorporated herein by reference) further describe the modifications in the endogenous pyruvate decarboxylase, and are incorporated herein by reference. U.S. Appl. Pub. No. 20090305363 (incorporated herein by reference) discloses increased conversion of pyruvate to acetolactate by engineering yeast for expression of a cytosol-localized acetolactate synthase and substantial elimination of pyruvate decarboxylase activity. Yeast having a reduced enzymatic activity can be identified using various methods. For example, yeast having reduced pyruvate decarboxylase activity can be identified using common methods, including, for example, measuring ethanol formation via gas chromatography.

Other target genes, such as those encoding pyruvate decarboxylase proteins having at least about 70-75%, at least about 75-85%, at least about 80-85%, at least about 85%-90%, at least about 90%-95%, or at least about 96%, at least about 97%, at least about 98%, or at least about 99% sequence identity to the pyruvate decarboxylases may be identified in the literature and in bioinformatics databases well known to the skilled person. The methods for disruption of pyruvate decarboxylase activity along with the methods for identification of butanologens with modified or deleted pyruvate decarboxylase are described in detail in U.S. Patent Appl. Pub. No. 20090305363 and PCT Patent Appl. Pub. No. WO2012/129555.

In some embodiments, a butanologen comprises modifications to reduce glycerol-3-phosphate dehydrogenase activity and/or disruption of at least one gene encoding a polypeptide having PDC activity or a disruption in at least one gene encoding a regulatory element controlling PDC gene expression as described in U.S. Patent Appl. Pub. No. 20090305363 and PCT Patent Appl. Pub. No. WO2012/129555, the modifications that would provide for an increased carbon flux through Entner-Doudoroff Pathway, or reducing equivalents balance as described in U.S. Patent Appl. Pub. No. 20100120105 (incorporated herein by reference). Yeast cells with inactivated endogenous PDC gene and an engineered biosynthetic pathway having improved growth and product yield when glucose repression was reduced are described in U.S. Appl. Publication No. 20110124060, incorporated herein by reference.

The term "aldehyde dehydrogenases" refers to any polypeptide having a biological function of an aldehyde dehydrogenase. Such polypeptides include a polypeptide that catalyzes the oxidation (dehydrogenation) of aldehydes (Wang et al., *J. Bacteriol.* 180:822-30, 1998; Navarro-Avino et al., *Yeast* 15:829-42, 1999; and Saint-Prix et al., *Microbiology* 150:2209-20, 2004). Such polypeptides include a polypeptide that catalyzes the conversion of isobutyraldehyde to isobutyric acid. Such polypeptides also include a polypeptide that corresponds to EC Numbers 1.2.1.3, EC 1.2.1.4 or 1.2.1.5. Such polypeptides can be determined by methods well known in the art and are disclosed in PCT Patent Appl. Pub. No. WO2012/129555.

In some embodiments, a butanologen can comprise deletion, mutation and/or substitution in an endogenous polynucleotide or gene encoding a polypeptide having aldehyde dehydrogenase (ALD) and/or aldehyde oxidase activity or deletion, mutation and/or substitution in an endogenous polypeptide having aldehyde dehydrogenase activity and/or aldehyde oxidase activity. In some embodiments, a recombinant host cell of the invention can be *S. cerevisiae*, and a polypeptide having aldehyde dehydrogenase activity can be ALD2, ALD3, ALD4, ALD5, ALD6, or combinations thereof. In some embodiments, a recombinant host cell can be *Kluyveromyces lactis*, and a polypeptide having aldehyde dehydrogenase activity can be KLLA0F00440, KLLA0E23057, KLLA0D10021, KLLA0D09999G, or combinations thereof. In other embodiments, a recombinant host cell can be *Pichia stipitis*, and a polypeptide having aldehyde dehydrogenase activity can be ALD2, ALD3, ALD4, ALD5, ALD7, or combinations thereof. In other embodiments, a recombinant host cell can be *Lactobacillus plantarum*, and a polypeptide having aldehyde dehydrogenase activity can be AldH. In other embodiments, a recombinant host cell can be *E. coli*, and a polypeptide having aldehyde dehydrogenase activity can be aldA, aldB, aldH, or combinations thereof.

In some embodiments, the polypeptide having aldehyde dehydrogenase activity is ALD6 in *Saccharomyces cerevisiae* or a homolog thereof. Such modifications, disruptions, deletions, mutations, and/or substitutions can result in ALD activity that is reduced or eliminated, resulting, for example, in an ALD6 knock-out (ALD6-KO) phenotype. Examples of aldehyde dehydrogenase polynucleotides, genes and polypeptides that can be targeted for modification or inactivation in a recombinant host cell are provided in further detail in PCT Patent Appl. Pub. No. WO2012/129555.

The disruption of a particular aldehyde dehydrogenase could be confirmed, for example, with PCR screening using primers internal and external to the aldehyde dehydrogenase gene or by Southern blot using a probe designed to the aldehyde dehydrogenase gene sequence. Alternatively, one could utilize gas chromatography-mass spectroscopy or liquid chromatography to screen strains exposed to isobutyraldehyde for decreased formation of isobutyric acid. For example, a method of screening for strains with decreased isobutyric acid formation can comprise: a) providing a strain comprising a modification in a polynucleotide encoding a polypeptide having aldehyde dehydrogenase activity and/or a modification in a polynucleotide encoding a polypeptide having aldehyde oxidase activity; b) contacting the cell with isobutyraldehyde; and c) measuring isobutyric acid formation; wherein isobutyric acid formation is reduced as compared to a control strain without the modification. In some embodiments, the measuring is carried out using gas chromatography-mass spectroscopy. The methods for deletion, mutation and/or substitution of polynucleotide, gene or polypeptide for aldehyde dehydrogenase and methods for identifying disruption of aldehyde dehydrogenase activity are described in detail, e.g., in PCT Patent Appl. Pub. No. WO2012/129555.

Other target genes, such as those encoding aldehyde dehydrogenase proteins having at least about 70-75%, at least about 75-85%, at least about 80-85%, at least about 85%-90%, at least about 90%-95%, or at least about 96%, at least about 97%, at least about 98%, or at least about 99% sequence identity to the aldehyde dehydrogenase may be identified in the literature and in bioinformatics databases well known to the skilled person.

In some embodiments, butanologens described herein can comprise a reduced or eliminated aldehyde dehydrogenase and/or aldehyde oxidase activity, as described in PCT Patent Appl. Pub. No. WO2012/129555. In some embodiments, a butnologen with reduced or eliminated aldehyde dehydrogenase activity can produce a butanol isomer via the engineered biosynthetic pathway at a greater yield or amount than the yield or amount of the same isomer produced by a butanologen that does not comprise reduced or eliminated aldehyde dehydrogenase activity.

In some embodiments, a butanologen as described herein can comprise a deletion, mutation, and/or substitution in an endogenous polynucleotide or gene encoding a polypeptide involved in the pathways for the production of by-products during the fermentative production of butanol isomers. In some embodiments, a butanologen can comprise one or more deletions, mutations, and/or substitutions in an endogenous polypeptide that is involved in the pathways for the production of by-products during the fermentative production of butanol isomers. In some embodiments, these modifications are in genes or polynucleotides encoding FRA2 (iron repressor protein), CCC1 (putative vacuolar $Fe2+$/$Mn2+$ transporter) or GPD2 (glycerol-2-phosphate dehydrogenase) or polypeptides having FRA2, CCC1 or GPD2 activity or combinations thereof.

In other embodiments, modifications include integration of at least one polynucleotide encoding a polypeptide that catalyzes a step in a pyruvate-utilizing biosynthetic pathway. Other modifications include at least one deletion, mutation, and/or substitution in an endogenous polynucleotide encoding a polypeptide having acetolactate reductase activity. In embodiments, the polypeptide having acetolactate reductase activity is YMR226C of *Saccharomyces cerevisae* or a homolog thereof.

In embodiments, host cells can comprise heterologous polynucleotides encoding a polypeptide with phosphoketolase activity and/or a heterologous polynucleotide encoding a polypeptide with phosphotransacetylase activity such as, for example, those encoded by SEQ ID NOs: 262 and 263, and as described in PCT Appn. Pub. No. WO 2011/159853. As described therein, PDC-KO cells so modified exhibit a reduced or eliminated requirement for exogenous two-carbon substrate supplementation for their growth compared to PDC− KO cells. Accordingly, and as demonstrated in the Examples, methods provided herein provide advantages for recombinant host cells engineered to reduce or eliminate pyruvate decarboxylase (PDC) activity and comprising a reduced or eliminated requirement for exogenous two-carbon substrate supplementation for their growth.

Fermentation Medium

Fermentation medium in the present invention must contain suitable fermentable carbon substrates. Suitable fermentable carbon substrates may include, but are not limited to, monosaccharides such as glucose, fructose, xylose, or arabinose; oligosaccharides such as lactose, maltose, galactose, or sucrose; polysaccharides such as starch or cellulose; or combinations thereof. Suitable fermentable carbon substrate may include unpurified mixtures from renewable feedstocks such as cheese whey permeate, cornsteep liquor, sugar beet molasses, and barley malt. Additionally the fermentable carbon substrate may also be one-carbon substrates such as carbon dioxide, or methanol for which metabolic conversion into key biochemical intermediates has been demonstrated. In addition to one and two fermentable carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd*., [Int. Symp.], $7^{th}$ ed., 415-32. Editor(s): Murrell, J. Collin; Kelly, Don P. Publisher: Intercept, Andover, UK (1993)). Similarly, various species of *Candida* will metabolize alanine or oleic acid (Sulter et al., *Arch. Microbiol.,* 153:485-489 (1990)). Hence it is contemplated that the source of carbon utilized in the present invention may encompass a wide variety of carbon containing substrates and will only be limited by the choice of organism. Other carbon substrates may include ethanol, lactate, succinate or glycerol.

Although it is contemplated that all of the above mentioned fermentable carbon substrates and mixtures thereof are suitable in the present invention, preferred fermentable carbon substrates are glucose, fructose, and sucrose, or mixtures of these with C5 sugars such as xylose and arabinose. Sucrose may be derived from renewable sugar sources such as sugar cane, sugar beets, cassava, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described, for example, in U.S. Pat. No. 7,932,063, which is incorporated herein by reference. Biomass includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In some embodiments, the fermentable carbon substrate is glucose derived from corn. In some embodiments, the fermentable carbon substrate is glucose derived from wheat. In some embodiments, the fermentable carbon substrate is sucrose derived from sugar cane. In some embodiments, the fermentable carbon substrate is xylose.

In addition to an appropriate carbon source, fermentation medium must contain suitable minerals, salts, cofactors, buffers and other components, known to those skilled in the art, suitable for the growth of the cultures and promotion of the enzymatic pathway necessary for isobutanol production.

In some embodiments, the fermentation medium in the present invention contains acetate as an exogenous C2 source, which is added to the fermentation medium as a supplement, in an amount sufficient for the growth of the recombinant host cells. In some embodiments, acetate is added to the fermentation medium in an amount sufficient for improved butanol production. In some embodiments, acetate is added to the fermentation medium in the range of about 0.1 mM to about 50 mM. In some embodiments, the acetate added to the fermentation medium is 0.1 mM, 0.2 mM, 0.4 mM, 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 5 mM, 10 mM, 15 mM, 20 mM, 25 mM, 30 mM, 35 mM, 40 mM, 45 mM or 50 mM. In some embodiments, the sugar to C2 supplement ratio in the fermentation medium is 95:5, 90:10, 85:15, 80:20, 75:25 or 70:30. In some embodiments, the acetate is added in growth phase, production phase, or both.

In some embodiments, the fermentation medium may further contain butanol. In some embodiments, the butanol is in the range of about 0.01 mM to about 500 mM. In some embodiments, the butanol is 0.01 mM, 1.0 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 210 mM, 220 mM, 230 mM, 240 mM, 250 mM, 260 mM, 270 mM, 280 mM, 290 mM, 300 mM, 310 mM, 320 mM, 330 mM, 340 mM, 350 mM, 360 mM, 370 mM, 380 mM, 390 mM, 400 mM, 410 mM, 420 mM, 430 mM, 440 mM, 450 mM, 460 mM, 470 mM, 480 mM, 490 mM or 500 mM. In some embodiments, butanol present in the fermentation medium is from about 0.01% to about 100% of the theoretical yield of butanol. In some embodiments, butanol present in the fermentation medium is 0.01%, 0.5%, 1%, 5%, 10%, 15%, 20%, 25%, 30%, 35%, 40%, 45%, 50%, 55%, 60%, 65%, 70%, 75%, 80%, 85%, 90%, 95% or 100% of the theoretical yield of butanol.

In some embodiments, improved butanol production is manifest as increased yield, effective rate, effective titer, or specific productivity. In embodiments, at least one of yield, effective rate, effective titer, or specific productivity is increased by at least about 3%, at least about 5%, or at least about 10%.

In some embodiments, improved butanol production is manifest as decreased by-product yield. In embodiments, yield of a by-product is decreased by at least about 3%, at least about 5%, at least about 10%, at least about 20%, at least about 30%, at least about 40%, or at least about 50%, or at least about 70%. In embodiments, the by-product is isobutyric acid.

Fermentation Conditions

Typically cells are grown at a temperature in the range of about 20° C. to about 40° C. in an appropriate medium. In some embodiments, the cells are grown at a temperature of 20° C., 22° C., 25° C., 27° C., 30° C., 32° C., 35° C., 37° C. or 40° C. Suitable growth medium in the present invention include common commercially prepared media such as Luria Bertani (LB) broth, Sabouraud Dextrose (SD) broth, Yeast Medium (YM) broth, or broth that includes yeast nitrogen base, ammonium sulfate, and dextrose (as the carbon/energy source) or YPD Medium, a blend of peptone, yeast extract, and dextrose in optimal proportions for growing most *Saccharomyces cerevisiae* strains. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are from about pH 3.0 to about pH 9.0. In one embodiment, about pH 4.0 to about pH 8.0 is used for the initial condition. In another embodiment, about pH 3.5 to about pH 9.0 is used for the initial condition. In one embodiment, about pH 4.5 to about pH 6.5 is used for the initial condition. In one embodiment, about pH 5.0 to about pH 8.0 is used for the initial condition. Suitable pH ranges for the fermentation of yeast are typically from about pH 3.0 to about pH 9.0. Suitable pH ranges for the fermentation of other microorganisms are from about pH 3.0 to about pH 7.5

In some embodiments, the contacting of the fermentation medium with the recombinant microorganism is performed under anaerobic or microaerobic conditions.

In some embodiments, the butanol is produced in one or more of the following growth phases: high growth log phase, moderate through static lag phase, stationary phase, steady state growth phase, and combinations thereof.

Industrial Batch and Continuous Fermentations

In some embodiments, the butanol isomers may be produced using batch or continuous fermentation. Butanol isomers, such as isobutanol, may be produced using a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH, dissolved oxygen and the partial pressure of waste gases such as $CO_2$. Batch and fed-batch fermentations are common and well known in the art and examples may be found in Thomas D. Brock in *Biotechnology: A Textbook of Industrial Microbiology*, Second Edition Sinauer Associates, Inc., Sunderland, Mass. (1989) ("Brock"), or Deshpande, Mukund V., *Appl. Biochem. Biotechnol.,* 36:227, (1992), incorporated herein by reference.

Butanol isomers, such as isobutanol, may also be produced using continuous fermentation methods. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by medium turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock.

It is contemplated that the production of butanol, including isobutanol, may be practiced using batch, fed-batch or continuous processes and that any known mode of fermentation would be suitable. Additionally, it is contemplated that cells may be immobilized on a substrate as whole cell catalysts and subjected to fermentation conditions for isobutanol production.

Methods for Butanol Isolation from the Fermentation Medium (Recovery)

The bioproduced butanol isomers may be recovered from the fermentation medium using methods known in the art. See, e.g., Durre, *Appl. Microbiol. Biotechnol.* 49:639-648 (1998), Groot et al., *Process. Biochem.* 27:61-75 (1992), and references therein. For example, butanol may be isolated from the fermentation medium using methods such as distillation, liquid-liquid extraction, or membrane-based separation. U.S. Patent Appl. Pub. Nos. 20090305370, 20110312043 and 20110312044, which are incorporated herein by reference, describe liquid-liquid extraction, comprising the step of contacting the fermentation broth with a water-immiscible extractant to form a two-phase mixture comprising an aqueous phase and an organic phase.

In situ product removal (ISPR) can also be utilized to remove butanol from the fermentation broth. In some embodiments, ISPR includes liquid-liquid extraction. Typically, the extractant can be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, triglycerides, and mixtures thereof, which contacts a fermentation broth and to form a two-phase mixture comprising an aqueous phase and an organic phase. The extractant may also be an organic extractant selected from the group consisting of saturated, mono-unsaturated, poly-unsaturated (and mixtures thereof) $C_4$ to $C_{22}$ fatty alcohols, $C_4$ to $C_{28}$ fatty acids, esters of $C_4$ to $C_{28}$ fatty acids, $C_4$ to $C_{22}$ fatty aldehydes, $C_4$ to $C_{22}$ fatty amides, and mixtures thereof, which contacts a fermentation broth and to form a two-phase mixture comprising an aqueous phase and an organic phase. Free fatty acids from slurry can also serve as an ISPR extractant. ISPR extractant (FFA) contacts the fermentation broth and forms a two-phase mixture comprising an aqueous phase and an organic phase. The product alcohol present in the fermentation broth preferentially partitions into the organic phase to form an alcohol-containing organic phase.

Because butanol isomers form a low boiling point, azeotropic mixture with water, distillation can only be used to separate the mixture up to its azeotropic composition. Distillation may be used in combination with another separation method to obtain separation around the azeotrope. Methods that may be used in combination with distillation to isolate and purify butanol include, but are not limited to, decantation, liquid-liquid extraction, adsorption, and membrane-based techniques. Additionally, butanol isomers may be isolated using azeotropic distillation using an entrainer (see, for example, Doherty and Malone, *Conceptual Design of Distillation Systems*, McGraw Hill, New York (2001)).

When distillation is used in combination with decantation to isolate and purify the butanol, the butanol containing fermentation broth is distilled to near the azeotropic composition. Then, the azeotropic mixture is condensed, and the butanol is separated from the fermentation medium by decantation. The decanted aqueous phase may be returned to the first distillation column as reflux. The butanol-rich decanted organic phase may be further purified by distillation in a second distillation column.

When distillation is used in combination with liquid-liquid extraction, the butanol is extracted from the fermentation broth using liquid-liquid extraction with a suitable solvent. The butanol-containing organic phase is then distilled to separate the butanol from the solvent.

When distillation is used in combination with adsorbtion, the fermentation broth containing the butanol is distilled to near the azeotropic composition and then the remaining water is removed by use of an adsorbent, such as molecular sieves (Aden et al., *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

When distillation is used in combination with pervaporation, the fermentation broth containing the butanol is distilled to near the azeotropic composition, and then the remaining water is removed by pervaporation through a hydrophilic membrane (Guo et al., *J. Membr. Sci.,* 245:199-210 (2004)).

Butanol titer in any phase can be determined by methods known in the art, such as via high performance liquid chromatography (HPLC) or gas chromatography, as described, for example in U.S. Patent Appl. Pub. No. US20090305370, incorporated herein by reference.

Methods for Removing Solids

The dried solid residue (or solids) remaining in the fermentation medium after the fermentation of fermentable carbon substrates may be removed using methods known in the art. These solids comprises of proteins, fiber and oils, and could be of three types: Distiller's Dried Grains (DDG), Distiller's Dried Solubles (DDS), and Distiller's Dried Grains with Solubles (DDGS). Of these solids, only DDGS can be used in the animal feed industry. DDGS has high nutrient value, and is therefore suitable as animal feed.

Solids may be removed from the fermentation medium by centrifugation, filtration, decantation, or the like. Subsequent to the removal of the solids, butanol may be isolated from the fermentation medium using methods such as distillation, azeotropic distillation, liquid-liquid extraction, adsorption, gas stripping, membrane evaporation, or pervaporation.

EXAMPLES

The present invention is further defined in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Materials and methods suitable for the maintenance and growth of bacterial cultures are well known in the art. Techniques suitable for use in the following examples may be found as set out in *Manual of Methods for General Bacteriology* (Phillipp et al., eds., American Society for Microbiology, Washington, D.C., (1994)) or by in Brock, *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Sigma-Aldrich Chemicals (St. Louis, Mo.), BD Diagnostic Systems (Sparks, Md.), Invitrogen (Carlsbad, Calif.), HiMedia (Mumbai, India), SD Fine chemicals (India), or Takara Bio Inc. (Shiga, Japan), unless otherwise specified.

Methods for Determining Isobutanol Concentration in Culture Medium

The concentration of isobutanol in the culture medium can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01M $H_2SO_4$ as the mobile phase with a flow rate of 0.5 mL/min and a column temperature of 50° C. Isobutanol had a retention time of 46.6 min under the conditions used. Alternatively, gas chromatography (GC) methods are available. For example, a specific GC method utilized an HP-INNOWax column (30 m×0.53 mm id, 1 μm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention time of isobutanol was 4.5 min.

The meaning of abbreviations is as follows: "sec" means second(s), "min" means minute(s), "h" means hour(s), "nm" means nanometers, "uL" means microliter(s), "mL" means milliliter(s), "mg/mL" means milligram per milliliter, "L" means liter(s), "nm" means nanometers, "mM" means millimolar, "M" means molar, "mmol" means millimole(s), "μmole" means micromole(s), "kg" means kilogram, "g" means gram(s), "μg" means microgram(s) and "ng" means nanogram(s), "PCR" means polymerase chain reaction, "OD" means optical density, "OD600" means the optical density measured at a wavelength of 600 nm, "kDa" means kilodaltons, "g" can also mean the gravitation constant, "bp" means base pair(s), "kbp" means kilobase pair(s), "kb" means kilobase, "%" means percent, "% w/v" means weight/volume percent, "% v/v" means volume/volume percent, "HPLC" means high performance liquid chromatography, "g/L" means gram per liter, "μg/L" means microgram per liter, "ng/μL" means nanogram per microliter, "pmol/μL" means picomol per microliter, "RPM" means rotation per minute, "μmol/min/mg" means micromole per minute per milligram, "w/v" means weight per volume, "v/v" means volume per volume.

Microbial strains were obtained from The American Type Culture Collection (ATCC), Manassas, Va., unless otherwise noted.

Certain oligonucleotide primers used in the following Examples are provided in TABLE 1. All the oligonucleotide primers are synthesized by Sigma-Genosys (Woodlands, Tex.) or Integrated DNA Technologies (IDT) (Coralville, Iowa).

TABLE 1

Oligonucleotide Primers

| Primer Name | SEQ ID NO |
|---|---|
| BK505 | 10 |
| BK506 | 11 |
| LA468 | 12 |
| LA492 | 13 |
| AK109-1 | 14 |
| AK109-2 | 15 |
| AK109-3 | 16 |
| oBP452 | 17 |
| oBP453 | 18 |
| oBP454 | 19 |
| oBP455 | 20 |
| oBP456 | 21 |
| oBP457 | 22 |
| oBP458 | 23 |
| oBP459 | 24 |
| oBP460 | 25 |
| LA135 | 26 |
| oBP461 | 27 |
| LA92 | 28 |
| LA678 | 30 |
| LA679 | 31 |
| LA337 | 32 |
| LA692 | 33 |
| LA693 | 34 |
| LA722 | 36 |
| LA733 | 37 |
| LA453 | 38 |
| LA694 | 39 |
| LA695 | 40 |
| oBP594 | 41 |
| oBP595 | 42 |
| oBP596 | 43 |
| oBP597 | 44 |
| oBP598 | 45 |
| oBP599 | 46 |
| oBP600 | 47 |
| oBP601 | 48 |
| oBP602 | 49 |
| oBP603 | 50 |
| LA811 | 51 |
| LA817 | 52 |
| LA812 | 53 |
| LA818 | 54 |
| LA512 | 55 |
| LA513 | 56 |
| LA516 | 57 |
| LA514 | 58 |
| LA515 | 59 |
| LA829 | 61 |
| LA834 | 62 |
| N1257 | 63 |
| LA830 | 64 |
| LA850 | 66 |
| LA851 | 67 |
| N1262 | 68 |
| LA740 | 69 |
| N1263 | 70 |
| LA855 | 72 |
| LA856 | 73 |
| LA414 | 74 |
| LA749 | 75 |

TABLE 1-continued

| Oligonucleotide Primers | |
|---|---|
| Primer Name | SEQ ID NO |
| LA413 | 76 |
| LA860 | 77 |
| N1093 | 78 |
| LA681 | 79 |

Construction of Strains Used in the Examples

Construction of PNY2068

*Saccharomyces cerevisiae* strain PNY0827 is used as the host cell for further genetic manipulation. PNY0827 refers to a strain derived from *Saccharomyces cerevisiae* which has been deposited at the ATCC under the Budapest Treaty on Sep. 22, 2011 at the American Type Culture Collection, Patent Depository 10801 University Boulevard, Manassas, Va. 20110-2209 and has the patent deposit designation PTA-12105.

Deletion of URA3 and Sporulation into Haploids

In order to delete the endogenous URA3 coding region, a deletion cassette was PCR-amplified from pLA54 (SEQ ID NO: 9) which contains a $P_{TEF1}$-kanMX4-TEF1t cassette flanked by loxP sites to allow homologous recombination in vivo and subsequent removal of the KANMX4 marker. PCR was done by using Phusion High Fidelity PCR Master Mix (New England BioLabs; Ipswich, Mass.) and primers BK505 (SEQ ID NO: 10) and BK506 (SEQ ID NO: 11). The URA3 portion of each primer was derived from the 5' region 180 bp upstream of the URA3 ATG and 3' region 78 bp downstream of the coding region such that integration of the kanMX4 cassette results in replacement of the URA3 coding region. The PCR product was transformed into PNY0827 using standard genetic techniques (Methods in Yeast Genetics, 2005, Cold Spring Harbor Laboratory Press, Cold Spring Harbor, N.Y., pp. 201-202) and transformants were selected on YEP medium supplemented 2% glucose and 100 μg/ml Geneticin at 30° C. Transformants were screened by colony PCR with primers LA468 (SEQ ID NO: 12) and LA492 (SEQ ID NO: 13) to verify presence of the integration cassette. A heterozygous diploid was obtained: NYLA98, which has the genotype MATa/α URA3/ura3::loxP-kanMX4-loxP. To obtain haploids, NYLA98 was sporulated using standard methods (Codón A C, Gasent-Ramirez J M, Benitez T. Factors which affect the frequency of sporulation and tetrad formation in *Saccharomyces cerevisiae* baker's yeast. Appl Environ Microbiol. 1995 PMID: 7574601). Tetrads were dissected using a micromanipulator and grown on rich YPE medium supplemented with 2% glucose. Tetrads containing four viable spores were patched onto synthetic complete medium lacking uracil supplemented with 2% glucose, and the mating type was verified by multiplex colony PCR using primers AK109-1 (SEQ ID NO: 14), AK109-2 (SEQ ID NO: 15), and AK109-3 (SEQ ID NO: 16). The resulting indentified haploid strain called NYLA103, which has the genotype: MATα ura3Δ::loxP-kanMX4-loxP, and NYLA106, which has the genotype: MATa ura3Δ::loxP-kanMX4-loxP.

Deletion of His3

To delete the endogenous HIS3 coding region, a scarless deletion cassette was used. The four fragments for the PCR cassette for the scarless HIS3 deletion were amplified using Phusion High Fidelity PCR Master Mix (New England BioLabs; Ipswich, Mass.) and CEN.PK 113-7D genomic DNA as template, prepared with a Gentra Puregene Yeast/Bact kit (Qiagen; Valencia, Calif.). HIS3 Fragment A was amplified with primer oBP452 (SEQ ID NO: 17) and primer oBP453 (SEQ ID NO: 18), containing a 5' tail with homology to the 5' end of HIS3 Fragment B. HIS3 Fragment B was amplified with primer oBP454 (SEQ ID NO: 19), containing a 5' tail with homology to the 3' end of HIS3 Fragment A, and primer oBP455 (SEQ ID NO: 20) containing a 5' tail with homology to the 5' end of HIS3 Fragment U. HIS3 Fragment U was amplified with primer oBP456 (SEQ ID NO: 21), containing a 5' tail with homology to the 3' end of HIS3 Fragment B, and primer oBP457 (SEQ ID NO: 22), containing a 5' tail with homology to the 5' end of HIS3 Fragment C. HIS3 Fragment C was amplified with primer oBP458 (SEQ ID NO: 23), containing a 5' tail with homology to the 3' end of HIS3 Fragment U, and primer oBP459 (SEQ ID NO: 24). PCR products were purified with a PCR Purification kit (Qiagen). HIS3 Fragment AB was created by overlapping PCR by mixing HIS3 Fragment A and HIS3 Fragment B and amplifying with primers oBP452 (SEQ ID NO: 17) and oBP455 (SEQ ID NO: 20). HIS3 Fragment UC was created by overlapping PCR by mixing HIS3 Fragment U and HIS3 Fragment C and amplifying with primers oBP456 (SEQ ID NO: 21) and oBP459 (SEQ ID NO: 24). The resulting PCR products were purified on an agarose gel followed by a Gel Extraction kit (Qiagen). The HIS3 ABUC cassette was created by overlapping PCR by mixing HIS3 Fragment AB and HIS3 Fragment UC and amplifying with primers oBP452 (SEQ ID NO: 17) and oBP459 (SEQ ID NO: 24). The PCR product was purified with a PCR Purification kit (Qiagen). Competent cells of NYLA106 were transformed with the HIS3 ABUC PCR cassette and were plated on synthetic complete medium lacking uracil supplemented with 2% glucose at 30° C. Transformants were screened to verify correct integration by replica plating onto synthetic complete medium lacking histidine and supplemented with 2% glucose at 30° C. Genomic DNA preps were made to verify the integration by PCR using primers oBP460 (SEQ ID NO: 25) and LA135 (SEQ ID NO: 26) for the 5' end and primers oBP461 (SEQ ID NO: 27) and LA92 (SEQ ID NO: 28) for the 3' end. The URA3 marker was recycled by plating on synthetic complete medium supplemented with 2% glucose and 5-FOA at 30° C. following standard protocols. Marker removal was confirmed by patching colonies from the 5-FOA plates onto SD-URA medium to verify the absence of growth. The resulting identified strain, called PNY2003 has the genotype: MATa ura3Δ::loxP-kanMX4-loxP his3Δ.

Deletion of PDC1

To delete the endogenous PDC1 coding region, a deletion cassette was PCR-amplified from pLA59 (SEQ ID NO: 29), which contains a URA3 marker flanked by degenerate loxP sites to allow homologous recombination in vivo and subsequent removal of the URA3 marker. PCR was done by using Phusion High Fidelity PCR Master Mix (New England BioLabs; Ipswich, Mass.) and primers LA678 (SEQ ID NO: 30) and LA679 (SEQ ID NO: 31). The PDC1 portion of each primer was derived from the 5' region 50 bp downstream of the PDC1 start codon and 3' region 50 bp upstream of the stop codon such that integration of the URA3 cassette results in replacement of the PDC1 coding region but leaves the first 50 bp and the last 50 bp of the coding region. The PCR product was transformed into PNY2003 using standard genetic techniques and transformants were selected on synthetic complete medium lacking uracil and supplemented with 2% glucose at 30° C. Transformants were screened to verify correct integration by colony PCR using primers LA337 (SEQ ID NO: 32), external to the 5' coding region and LA135 (SEQ ID NO: 26), an internal primer to URA3. Positive transformants were then screened by colony PCR using primers LA692 (SEQ ID NO: 33) and LA693 (SEQ ID NO: 34), internal to the PDC1 coding region. The URA3 marker was recycled by transforming with pLA34 (SEQ ID NO: 35) containing the CRE recombinase under the GALL promoter and plated on synthetic complete medium lacking histidine and supplemented with 2% glucose at 30° C. Transformants were plated on rich medium supplemented with 0.5% galactose to induce the recombinase. Marker removal was confirmed by patching colonies to synthetic complete medium lacking uracil and supplemented with 2% glucose to verify absence of growth. The resulting identified strain, called PNY2008 has the genotype: MATa ura3Δ::loxP-kanMX4-loxP his3Δ pdc1Δ::loxP71/66.

Deletion of PDC5

To delete the endogenous PDC5 coding region, a deletion cassette was PCR-amplified from pLA59 (SEQ ID NO: 29), which contains a URA3 marker flanked by degenerate loxP sites to allow homologous recombination in vivo and subsequent removal of the URA3 marker. PCR was done by using Phusion High Fidelity PCR Master Mix (New England BioLabs; Ipswich, Mass.) and primers LA722 (SEQ ID NO: 36) and LA733 (SEQ ID NO: 37). The PDC5 portion of each primer was derived from the 5' region 50 bp upstream of the PDC5 start codon and 3' region 50 bp downstream of the stop codon such that integration of the URA3 cassette results in replacement of the entire PDC5 coding region. The PCR product was transformed into PNY2008 using standard genetic techniques and transformants were selected on synthetic complete medium lacking uracil and supplemented with 1% ethanol at 30° C. Transformants were screened to verify correct integration by colony PCR using primers LA453 (SEQ ID NO: 38), external to the 5' coding region and LA135 (SEQ ID NO: 26), an internal primer to URA3. Positive transformants were then screened by colony PCR using primers LA694 (SEQ ID NO: 39) and LA695 (SEQ ID NO: 40), internal to the PDC5 coding region. The URA3 marker was recycled by transforming with pLA34 (SEQ ID NO: 35) containing the CRE recombinase under the GAL1 promoter and plated on synthetic complete medium lacking histidine and supplemented with 1% ethanol at 30° C. Transformants were plated on rich YEP medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, called PNY2009 has the genotype: MATa ura3Δ::loxP-kanMX4-loxP his3 Δ pdc1Δ::loxP71/66 pdc5Δ::loxP71/66.

Deletion of FRA2

The FRA2 deletion was designed to delete 250 nucleotides from the 3' end of the coding sequence, leaving the first 113 nucleotides of the FRA2 coding sequence intact. An in-frame stop codon was present 7 nucleotides downstream of the deletion. The four fragments for the PCR cassette for the scarless FRA2 deletion were amplified using Phusion High Fidelity PCR Master Mix (New England BioLabs; Ipswich, Mass.) and CEN.PK 113-7D genomic DNA as template, prepared with a Gentra Puregene Yeast/Bact kit (Qiagen; Valencia, Calif.). FRA2 Fragment A was amplified with primer oBP594 (SEQ ID NO: 41) and primer oBP595 (SEQ ID NO: 42), containing a 5' tail with homology to the 5' end of FRA2 Fragment B. FRA2 Fragment B was amplified with primer oBP596 (SEQ ID NO: 43), containing a 5" tail with homology to the 3' end of FRA2 Fragment A, and primer oBP597 (SEQ ID NO: 44), containing a 5' tail with homology to the 5' end of FRA2 Fragment U. FRA2 Fragment U was amplified with primer oBP598 (SEQ ID NO: 45), containing a 5' tail with homology to the 3' end of FRA2 Fragment B, and primer oBP599 (SEQ ID NO: 46), containing a 5' tail with homology to the 5' end of FRA2 Fragment C. FRA2 Fragment C was amplified with primer oBP600 (SEQ ID NO: 47), containing a 5' tail with homology to the 3' end of FRA2 Fragment U, and primer oBP601 (SEQ ID NO: 48). PCR products were purified with a PCR Purification kit (Qiagen). FRA2 Fragment AB was created by overlapping PCR by mixing FRA2 Fragment A and FRA2 Fragment B and amplifying with primers oBP594 (SEQ ID NO: 41) and oBP597 (SEQ ID NO: 44). FRA2 Fragment UC was created by overlapping PCR by mixing FRA2 Fragment U and FRA2 Fragment C and amplifying with primers oBP598 (SEQ ID NO: 45) and oBP601 (SEQ ID NO: 48). The resulting PCR products were purified on an agarose gel followed by a Gel Extraction kit (Qiagen). The FRA2 ABUC cassette was created by overlapping PCR by mixing FRA2 Fragment AB and FRA2 Fragment UC and amplifying with primers oBP594 (SEQ ID NO: 41) and oBP601 (SEQ ID NO: 48). The PCR product was purified with a PCR Purification kit (Qiagen).

To delete the endogenous FRA2 coding region, the scarless deletion cassette obtained above was transformed into PNY2009 using standard techniques and plated on synthetic complete medium lacking uracil and supplemented with 1% ethanol. Genomic DNA preps were made to verify the integration by PCR using primers oBP602 (SEQ ID NO: 49) and LA135 (SEQ ID NO: 26) for the 5' end, and primers oBP602 (SEQ ID NO: 49) and oBP603 (SEQ ID NO: 50) to amplify the whole locus. The URA3 marker was recycled by plating on synthetic complete medium supplemented with 1% ethanol and 5-FOA (5-Fluoroorotic Acid) at 30° C. following standard protocols. Marker removal was confirmed by patching colonies from the 5-FOA plates onto synthetic complete medium lacking uracil and supplemented with 1% ethanol to verify the absence of growth. The resulting identified strain, PNY2037, has the genotype: MATa ura3Δ::loxP-kanMX4-loxP his3Δ pdc1Δ::loxP71/66 pdc5Δ::loxP71/66 fra2Δ.

Addition of 2 Micron Plasmid

The loxP71-URA3-loxP66 marker was PCR-amplified using Phusion DNA polymerase (New England BioLabs; Ipswich, Mass.) from pLA59 (SEQ ID NO: 29), and transformed along with the LA811x817 (SEQ ID NOs: 51, 52) and LA812x818 (SEQ ID NOs: 53, 54) 2-micron plasmid fragments into strain PNY2037 on SE-URA plates at 30° C. The resulting strain PNY2037 2μ::loxP71-URA3-loxP66 was transformed with pLA34 (pRS423::cre) (also called, pLA34) (SEQ ID NO: 35) and selected on SE-HIS-URA plates at 30° C. Transformants were patched onto YP-1% galactose plates and allowed to grow for 48 hrs at 30° C. to induce Cre recombinase expression. Individual colonies were then patched onto SE-URA, SE-HIS, and YPE plates to confirm URA3 marker removal. The resulting identified strain, PNY2050, has the genotype: MATa ura3Δ::loxP-kanMX4-loxP, his3Δ pdc1Δ::loxP71/66 pdc5Δ::loxP71/66 fra2Δ 2-micron.

Deletion of GPD2

To delete the endogenous GPD2 coding region, a deletion cassette was PCR-amplified from pLA59 (SEQ ID NO: 29), which contains a URA3 marker flanked by degenerate loxP sites to allow homologous recombination in vivo and subsequent removal of the URA3 marker. PCR was done by using Phusion High Fidelity PCR Master Mix (New England BioLabs; Ipswich, Mass.) and primers LA512 (SEQ ID NO: 55) and LA513 (SEQ ID NO: 56). The GPD2 portion of each primer was derived from the 5' region 50 bp upstream of the GPD2 start codon and 3' region 50 bp downstream of the stop codon such that integration of the URA3 cassette results in replacement of the entire GPD2 coding region. The PCR product was transformed into PNY2050 using standard genetic techniques and transformants were selected on synthetic complete medium lacking uracil and supplemented with 1% ethanol at 30° C. Transformants were screened to verify correct integration by colony PCR using primers LA516 (SEQ ID NO: 57), external to the 5' coding region and LA135 (SEQ ID NO: 26), internal to URA3. Positive transformants were then screened by colony PCR using primers LA514 (SEQ ID NO: 58) and LA515 (SEQ ID NO: 59), internal to the GPD2 coding region. The URA3 marker was recycled by transforming with pLA34 (SEQ ID NO: 35) containing the CRE recombinase under the GAL1 promoter and plated on synthetic complete medium lacking histidine and supplemented with 1% ethanol at 30° C. Transformants were plated on rich medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, PNY2056, has the genotype: MATa ura3Δ::loxP-kanMX4-loxP his3Δ pdc1Δ::loxP71/66 pdc5Δ::loxP71/66 fra2Δ 2-micron gpd2Δ.

Deletion of YMR226 and Integration of AlsS

To delete the endogenous YMR226C coding region, an integration cassette was PCR-amplified from pLA71 (SEQ ID NO: 60), which contains the gene acetolactate synthase from the species *Bacillus subtilis* with a FBA1 promoter and a CYC1 terminator, and a URA3 marker flanked by degenerate loxP sites to allow homologous recombination in vivo and subsequent removal of the URA3 marker. PCR was done by using KAPA HiFi from Kapa Biosystems, Woburn, Mass. and primers LA829 (SEQ ID NO: 61) and LA834 (SEQ ID NO: 62). The YMR226C portion of each primer was derived from the first 60 bp of the coding sequence and 65 bp that are 409 bp upstream of the stop codon. The PCR product was transformed into PNY2056 using standard genetic techniques and transformants were selected on synthetic complete medium lacking uracil and supplemented with 1% ethanol at 30° C. Transformants were screened to verify correct integration by colony PCR using primers N1257 (SEQ ID NO: 63), external to the 5' coding region and LA740 (SEQ ID NO: 69), internal to the FBA1 promoter. Positive transformants were then screened by colony PCR using primers N1257 (SEQ ID NO: 63) and LA830 (SEQ ID NO: 64), internal to the YMR226C coding region, and primers LA830 (SEQ ID NO: 64), external to the 3' coding region, and LA92 (SEQ ID NO: 28), internal to the URA3 marker. The URA3 marker was recycled by transforming with pLA34 (SEQ ID NO: 35) containing the CRE recombinase under the GAL1 promoter and plated on synthetic complete medium lacking histidine and supplemented with 1% ethanol at 30° C. Transformants were plated on rich medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, PNY2061, has the genotype: MATa ura3Δ::loxP-kanMX4-loxP his3Δ pdc1Δ::loxP71/66 pdc5Δ::loxP71/66 fra2Δ 2-micron gpd2Δymr226cΔ::$P_{FBA1}$-alsS_Bs-CYC1t-loxP71/66.

Deletion of ALD6 and Integration of KivD

To delete the endogenous ALD6 coding region, an integration cassette was PCR-amplified from pLA78 (SEQ ID NO: 65), which contains the kivD gene from the species *Listeria grayi* with a hybrid FBA1 promoter and a TDH3 terminator, and a URA3 marker flanked by degenerate loxP sites to allow homologous recombination in vivo and subsequent removal of the URA3 marker. PCR was done by using KAPA HiFi from Kapa Biosystems, Woburn, Mass. and primers LA850 (SEQ ID NO: 66) and LA851 (SEQ ID NO: 67). The ALD6 portion of each primer was derived from the first 65 bp of the coding sequence and the last 63 bp of the coding region. The PCR product was transformed into PNY2061 using standard genetic techniques and transformants were selected on synthetic complete medium lacking uracil and supplemented with 1% ethanol at 30° C. Transformants were screened to verify correct integration by colony PCR using primers N1262 (SEQ ID NO: 68), external to the 5' coding region and LA740 (SEQ ID NO: 69), internal to the FBA1 promoter. Positive transformants were then screened by colony PCR using primers N1263 (SEQ ID NO: 70), external to the 3' coding region, and LA92 (SEQ ID NO: 28), internal to the URA3 marker. The URA3 marker was recycled by transforming with pLA34 (SEQ ID NO: 35) containing the CRE recombinase under the GAL1 promoter and plated on synthetic complete medium lacking histidine and supplemented with 1% ethanol at 30° C. Transformants were plated on rich medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, PNY2065, has the genotype: MATa ura3Δ::loxP-kanMX4-loxP his3Δ pdc1Δ::loxP71/66 pdc5Δ::loxP71/66 fra2Δ 2-micron gpd2Δ ymr226cΔ::$P_{FBA1}$-alsS_Bs-CYC1t-loxP71/66 ald6Δ::(UAS)PGK1-$P_{FBA1}$-kivD_Lg-TDH3t-loxP71.

Deletion of ADH1 and Integration of ADH

ADH1 is the endogenous alcohol dehydrogenase present in *Saccharomyces cerevisiae*. As described below, the endogenous ADH1 was replaced with alcohol dehydrogenase (ADH) from *Beijerinckii indica*.

To delete the endogenous ADH1 coding region, an integration cassette was PCR-amplified from pLA65 (SEQ ID NO: 71), which contains the alcohol dehydrogenase from the species *Beijerinckii indica* with an ILV5 promoter and a ADH1 terminator, and a URA3 marker flanked by degenerate loxP sites to allow homologous recombination in vivo and subsequent removal of the URA3 marker. PCR was done by using KAPA HiFi from Kapa Biosystems, Woburn, Mass. and primers LA855 (SEQ ID NO: 72) and LA856 (SEQ ID NO: 73). The ADH1 portion of each primer was derived from the 5' region 50 bp upstream of the ADH1 start codon and the last 50 bp of the coding region. The PCR product was transformed into PNY2065 using standard genetic techniques and transformants were selected on synthetic complete medium lacking uracil and supplemented with 1% ethanol at 30° C. Transformants were screened to verify correct integration by colony PCR using primers LA414 (SEQ ID NO: 74), external to the 5' coding region and LA749 (SEQ ID NO: 75), internal to the ILV5 promoter. Positive transformants were then screened by colony PCR using primers LA413 (SEQ ID NO: 76), external to the 3' coding region, and LA92 (SEQ ID NO: 28), internal to the URA3 marker. The URA3 marker was recycled by transforming with pLA34 (SEQ ID NO: 35) containing the CRE recombinase under the GAL1 promoter and plated on synthetic complete medium lacking histidine and supplemented with 1% ethanol at 30° C. Transformants were plated on rich medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, called PNY2066 has the genotype: MATa ura3Δ::loxP-kanMX4-loxP his3Δ pdc1Δ::loxP71/66 pdc5Δ::loxP71/66 fra2Δ 2-micron gpd2Δ ymr226cΔ::$P_{FBA1}$-alsS_Bs-CYC1t-loxP71/66 ald6Δ::(UAS)PGK1-$P_{FBA1}$-kivD_Lg-TDH3t-loxP71/66 adh1Δ::$P_{ILV5}$-ADH_Bi(y)-ADH1t-loxP71/66.

Integration of ADH into pdc1Δ Locus

To integrate an additional copy of ADH at the pdc1Δ region, an integration cassette was PCR-amplified from pLA65 (SEQ ID NO: 71), which contains the alcohol dehydrogenase from the species *Beijerinckii indica* with an ADH1 terminator, and a URA3 marker flanked by degenerate loxP sites to allow homologous recombination in vivo and subsequent removal of the URA3 marker. PCR was done by using KAPA HiFi from Kapa Biosystems, Woburn, Mass. and primers LA860 (SEQ ID NO: 77) and LA679 (SEQ ID NO: 31). The PDC1 portion of each primer was derived from the 5' region 60 bp upstream of the PDC1 start codon and 50 bp that are 103 bp upstream of the stop codon. The endogenous PDC1 promoter was used. The PCR product was transformed into PNY2066 using standard genetic techniques and transformants were selected on synthetic complete medium lacking uracil and supplemented with 1% ethanol at 30° C. Transformants were screened to verify correct integration by colony PCR using primers LA337 (SEQ ID NO: 32), external to the 5' coding region and N1093 (SEQ ID NO: 78), internal to the BiADH gene. Positive transformants were then screened by colony PCR using primers LA681 (SEQ ID NO: 79), external to the 3' coding region, and LA92 (SEQ ID NO: 28), internal to the URA3 marker. The URA3 marker was recycled by transforming with pLA34 (SEQ ID NO: 35) containing the CRE recombinase under the GAL1 promoter and plated on synthetic complete medium lacking histidine and supplemented with 1% ethanol at 30° C. Transformants were plated on rich medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, called PNY2068 has the genotype: MATa ura3Δ::loxP-kanMX4-loxP his3Δ pdc1Δ::loxP71/66 pdc5Δ::loxP71/66 fra2Δ 2-micron gpd2Δ ymr226cΔ::$P_{FBA1}$-alsS_Bs-CYC1t-loxP71/66 ald6Δ::(UAS)PGK1-$P_{FBA1}$-kivD_Lg-TDH3t-loxP71/66 adh1Δ::$P_{ILV5}$-ADH_Bi(y)-ADH1t-loxP71/66 pdc1Δ::$P_{PDC1}$-ADH_Bi(y)-ADH1t-loxP71/66.

Construction of Isobutanologen Strain PNY2270

Strain PNY2270 was created from strain PNY2068 (described above) by transformation of the cells with two plasmids, pHR81-ILV5p-K9SB2 (SEQ ID NO: 80) and pYZ067DkivDDhADH (SEQ ID NO: 81). Plasmids were introduced by lithium acetate transformation method (Methods in Yeast Genetics, 2005, page 113), and transformants were selected on synthetic complete medium, minus histidine and uracil, with 1% ethanol as carbon source. Transformants were then transferred to plates containing synthetic complete medium, minus histidine and uracil, with 2% glucose as carbon source and either ethanol (0.05%) or acetate (2 mM) as a C2 supplement.

pHR81-ILV5p-K9SB2 (SEQ ID NO: 80) contains *A. caccae* K9SB2 KARI gene driven by ILV5 promoter and ILV5 terminator in pHR81 plasmid backbone. pYZ067DkivDDhADH (SEQ ID NO: 81) contains *S. mutans* ilvD gene driven by the FBA1 promoter and FBA1 terminator in pRS423 plasmid backbone.

Construction of Isobutanologen Strain PNY2092

Strain PNY2092 was constructed by plasmid transformation of the base strain PNY2061 (described above) which has genotype: MATa ura3Δ::loxP-kanMX4-loxP his3Δ pdc1Δ::loxP71/66 pdc5Δ::loxP71/66 fra2Δ 2-micron gpd2Δ ymr226cΔ::$P_{FBA1}$-alsS_Bs-CYC1t-loxP71/66 with plasmids: pHR81-ILV5p-R8B2y2 (SEQ ID NO: 82) and pLA84 (SEQ ID NO: 83).

pHR81-ILV5p-R8B2y2 (SEQ ID NO: 82) contains *P. fluorescens* R8B2 KARI (codon-optimized for yeast) driven by ILV5 promoter and ILV5 terminator in pHR81 plasmid backbone. pLA84 (SEQ ID NO: 83) contains IlvD from *S. mutans* driven by FBA1 promoter and FBA1 terminator, ADH from *B. indica* driven by GPM1 promoter and ADH1 terminator and KivD from *L. grayi* driven by TDH3 promoter and TDH3 terminator in pRS423 plasmid backbone.

Construction of Isobutanologen Strains PNY2118, PNY2120 and PNY2318

Construction of PNY2115 from PNY2050

Construction of PNY2115 [MATa ura3Δ::loxP his3Δ pdc5Δ::loxP66/71 fra2Δ 2-micron plasmid (CEN.PK2) pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66 gpd2Δ::loxP71/66] from PNY2050 was as follows.

Pdc1Δ::P[PDC1]-ALS|alsS_Bs-CYC1t-loxP71/66

To integrate alsS into the pdc1Δ::loxP66/71 locus of PNY2050 using the endogenous PDC1 promoter, An integration cassette was PCR-amplified from pLA71 (SEQ ID NO: 60), which contains the gene acetolactate synthase from the species *Bacillus subtilis* with a FBA1 promoter and a CYC1 terminator, and a URA3 marker flanked by degenerate loxP sites to allow homologous recombination in vivo and subsequent removal of the URA3 marker. PCR was done by using KAPA HiFi and primers 895 (SEQ ID NO: 84) and 679 (SEQ ID NO: 31). The PDC1 portion of each primer was derived from 60 bp of the upstream of the coding sequence and 50 bp that are 53 bp upstream of the stop codon. The PCR product was transformed into PNY2050 using standard genetic techniques and transformants were selected on synthetic complete media lacking uracil and supplemented with 1% ethanol at 30° C. Transformants were screened to verify correct integration by colony PCR using primers 681 (SEQ ID NO: 79), external to the 3' coding region and LA92 (SEQ ID NO: 28), internal to the URA3 gene. Positive transformants were then prepped for genomic DNA and screened by PCR using primers N245 (SEQ ID NO: 85) and N246 (SEQ ID NO: 86). The URA3 marker was recycled by transforming with pLA34 (SEQ ID NO: 35) containing the CRE recombinase under the GALL promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2090 has the genotype MATa ura3Δ::loxP, his3Δ, pdc1Δ::loxP71/66, pdc5Δ::loxP71/66 fra2Δ 2-micron pdc1Δ::P[PDC1]-ALS|alsS_Bs-CYC1t-loxP71/66.

Pdc6Δ::(UAS)PGK1-P[FBA1]-KIVD|Lg(y)-TDH3t-loxP71/66

To delete the endogenous PDC6 coding region, an integration cassette was PCR-amplified from pLA78 (SEQ ID NO: 65), which contains the kivD gene from the species *Listeria grayi* with a hybrid FBA1 promoter and a TDH3 terminator, and a URA3 marker flanked by degenerate loxP sites to allow homologous recombination in vivo and subsequent removal of the URA3 marker. PCR was done by using KAPA HiFi and primers 896 (SEQ ID NO: 87) and 897 (SEQ ID NO: 88). The PDC6 portion of each primer was derived from 60 bp upstream of the coding sequence and 59 bp downstream of the coding region. The PCR product was transformed into PNY2090 using standard genetic techniques and transformants were selected on synthetic complete media lacking uracil and supplemented with 1% ethanol at 30° C. Transformants were screened to verify correct integration by colony PCR using primers 365 (SEQ ID NO: 89) and 366 (SEQ ID NO: 90), internal primers to the PDC6 gene. Transformants with an absence of product were then screened by colony PCR N638 (SEQ ID NO: 91), external to the 5' end of the gene, and 740 (SEQ ID NO: 69), internal to the FBA1 promoter. Positive transformants were than the prepped for genomic DNA and screened by PCR with two external primers to the PDC6 coding sequence. Positive integrants would yield a 4720 bp product, while PDC6 wild type transformants would yield a 2130 bp product. The URA3 marker was recycled by transforming with pLA34 containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain is called PNY2093 and has the genotype MATa ura3Δ::loxP his3Δ pdc5Δ::loxP71/66 fra2Δ 2-micron pdc1Δ::P[PDC1]-ALS|alsS_Bs-CYC1t-loxP71/66 pdc6Δ:: (UAS)PGK1-P[FBA1]-KIVD|Lg(y)-TDH3t-loxP71/66.

Adh1Δ::P[ADH1]-ADH|Bi(y)-ADHt-loxP71/66

To delete the endogenous ADH1 coding region and integrate BiADH using the endogenous ADH1 promoter, an integration cassette was PCR-amplified from pLA65 (SEQ ID NO: 71), which contains the alcohol dehydrogenase from the species *Beijerinckii* with an ILV5 promoter and a ADH1 terminator, and a URA3 marker flanked by degenerate loxP sites to allow homologous recombination in vivo and subsequent removal of the URA3 marker. PCR was done by using KAPA HiFi and primers 856 (SEQ ID NO: 73) and 857 (SEQ ID NO: 110). The ADH1 portion of each primer was derived from the 5' region 50 bp upstream of the ADH1 start codon and the last 50 bp of the coding region. The PCR product was transformed into PNY2093 using standard genetic techniques and transformants were selected on synthetic complete media lacking uracil and supplemented with 1% ethanol at 30° C. Transformants were screened to verify correct integration by colony PCR using primers BK415 (SEQ ID NO: 92), external to the 5' coding region and N1092 (SEQ ID NO: 93), internal to the BiADH gene. Positive transformants were then screened by colony PCR using primers 413 (SEQ ID NO: 76), external to the 3' coding region, and 92 (SEQ ID NO: 28), internal to the URA3 marker. The URA3 marker was recycled by transforming with pLA34 (SEQ ID NO: 35) containing the CRE recombinase under the GALL promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2101 has the genotype MATa ura3Δ::loxP his3Δ pdc5Δ::loxP71/66 fra2Δ 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66.

Fra2Δ::P[ILV5]-ADH|Bi(y)-ADHt-loxP71/66

To integrate BiADH into the fra2Δ locus of PNY2101, an integration cassette was PCR-amplified from pLA65 (SEQ ID NO: 71), which contains the alcohol dehydrogenase from the species *Beijerinckii indica* with an ILV5 promoter and an ADH1 terminator, and a URA3 marker flanked by degenerate loxP sites to allow homologous recombination in vivo and subsequent removal of the URA3 marker. PCR was done by using KAPA HiFi and primers 906 (SEQ ID NO: 94) and 907 (SEQ ID NO: 95). The FRA2 portion of each primer was derived from the first 60 bp of the coding sequence starting at the ATG and 56 bp downstream of the stop codon. The PCR product was transformed into PNY2101 using standard genetic techniques and transformants were selected on synthetic complete media lacking uracil and supplemented with 1% ethanol at 30° C. Transformants were screened to verify correct integration by colony PCR using primers 667 (SEQ ID NO: 96), external to the 5' coding region and 749 (SEQ ID NO: 75), internal to the ILV5 promoter. The URA3 marker was recycled by transforming with pLA34 (SEQ ID NO: 35) containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2110 has the genotype MATa ura3Δ::loxP his3Δ pdc5Δ::loxP66/71 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66.

GPD2 Deletion

To delete the endogenous GPD2 coding region, a deletion cassette was PCR amplified from pLA59 (SEQ ID NO: 29), which contains a URA3 marker flanked by degenerate loxP sites to allow homologous recombination in vivo and subsequent removal of the URA3 marker. PCR was done by using KAPA HiFi and primers LA512 (SEQ ID NO: 55) and LA513 (SEQ ID NO: 56). The GPD2 portion of each primer was derived from the 5' region 50 bp upstream of the GPD2 start codon and 3' region 50 bp downstream of the stop codon such that integration of the URA3 cassette results in replacement of the entire GPD2 coding region. The PCR product was transformed into PNY2110 using standard genetic techniques and transformants were selected on synthetic complete medium lacking uracil and supplemented with 1% ethanol at 30° C. Transformants were screened to verify correct integration by colony PCR using primers LA516 (SEQ ID NO: 57) external to the 5' coding region and LA135 (SEQ ID NO: 26), internal to URA3. Positive transformants were then screened by colony PCR using primers LA514 (SEQ ID NO: 58) and LA515 (SEQ ID NO: 59), internal to the GPD2 coding region. The URA3 marker was recycled by transforming with pLA34 (SEQ ID NO: 35) containing the CRE recombinase under the GALL promoter and plated on synthetic complete medium lacking histidine and supplemented with 1% ethanol at 30° C. Transformants were plated on rich medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, called PNY2115, has the genotype MATa ura3Δ::loxP his3Δ pdc5Δ::loxP66/71 fra2Δ 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66 gpd2Δ::loxP71/66.

Construction of PNY2145 from PNY2115

PNY2145 was constructed from PNY2115 by the additional integration of a phosphoketolase gene cassette at the pdc5Δ locus and by replacing the native AMN1 gene with a codon optimized version of the ortholog from CEN.PK. Integration constructs are further described below.

pdc5Δ::FBA(L8)-xpk1-CYC1t-loxP71/66

The TEF(M4)-xpk1-CYC1t gene from pRS423::TEF(M4)-xpk1+ENO1-eutD (SEQ ID NO: 111) was PCR amplified using primers N1341 and N1338 (SEQ ID Nos. 112 and 113), generating a 3.1 kb product. The loxP-flanked URA3 gene cassette from pLA59 (SEQ ID NO: 29) was amplified with primers N1033c and N1342 (SEQ ID Nos. 114 and 115), generating a 1.6 kb product. The xpk1 and URA3 PCR products were fused by combining them without primers for an additional 10 cycles of PCR using Phusion DNA polymerase. The resulting reaction mix was then used as a template for a PCR reaction with KAPA Hi Fi and primers N1342 and N1364 (SEQ ID Nos. 115 and 116). A 4.2 kb PCR product was recovered by purification from an electrophoresis agarose gel (Zymo kit). FBA promoter variant L8 (SEQ ID No. 117) was amplified using primers N1366 and N1368 (SEQ ID Nos. 118 and 119). The xpk1::URA3 PCR product was combined with the FBA promoter by additional rounds of PCR. The resulting product was phosphorylated with polynucleotide kinase and ligated into pBR322 that had been digested with EcoRV and treated with calf intestinal phosphatase. The ligation reaction was transformed into *E. coli* cells (Stbl3 competent cells from Invitrogen). The integration cassette was confirmed by sequencing. To prepare DNA for integration, the plasmid was used as a template in a PCR reaction with Kapa HiFi and primers N1371 and N1372 (SEQ ID Nos. 120 and 121). The PCR product was isolated by phenol-chloroform extraction and ethanol precipitation (using standard methods; eg. Maniatas, et al.). Five micrograms of DNA were used to transform strain PNY2115. Transformants were selected on medium lacking uracil (synthetic complete medium minus uracil with 1% ethanol as the carbon source). Colonies were screened for the integration event using PCR (JumpStart) with primers BK93 and N1114 (SEQ ID Nos. 122 and 123). Two clones were selected to carry forward. The URA3 marker was recycled by transforming with pJT254 (SEQ ID NO: 97) containing the CRE recombinase under the GAL1 promoter and plating on synthetic complete medium lacking histidine and supplemented with 1% ethanol at 30° C. Transformants were grown in rich medium supplemented with 1% ethanol to derepress the recombinase. Marker removal was confirmed for single colony isolates by patching to synthetic complete medium lacking uracil and supplemented with 1% ethanol to verify absence of growth. Loss of the recombinase plasmid, pJT254, was confirmed by patching the colonies to synthetic complete medium lacking histidine and supplemented with 1% ethanol. Proper marker removal was confirmed by PCR (primers N160SeqF5 (SEQ ID NO: 124) and BK380 (SEQ ID NO: 125). One resulting clone was designated PNY2293.

amn1Δ::AMN1(y)-loxP71/66

To replace the endogenous copy of AMN1 with a codon-optimized version of the AMN1 gene from CEN.PK2, an integration cassette containing the CEN.PK AMN1 promoter, AMN1(y) gene (nucleic acid SEQ ID NO: 98; amino acid SEQ ID NO: 99 translation), and CEN.PK AMN1 terminator was assembled by SOE PCR and subcloned into the shuttle vector pLA59. The AMN1(y) gene was ordered from DNA 2.0 with codon-optimization for *S. cerevisiae*. The completed pLA67 plasmid (SEQ ID NO: 100) contained: 1) pUC19 vector backbone sequence containing an *E. coli* replication origin and ampicillin resistance gene; 2) URA3 selection marker flanked by loxP71 and loxP66 sites; and 3) $P_{AMN1(CEN.PK)}$-AMN1(y)-$term_{AMN1(CEN.PK)}$ expression cassette PCR amplification of the AMN1(y)-loxP71-URA3-loxP66 cassette was done by using KAPA HiFi from Kapa Biosystems, Woburn, Mass. and primers LA712 (SEQ ID NO: 101) and LA746 (SEQ ID NO: 102). The PCR product was transformed into PNY2293 using standard genetic techniques and transformants were selected on synthetic complete medium lacking uracil and supplemented with 1% ethanol at 30° C. Transformants were observed under magnification for the absence of a clumping phenotype with respect to the control (PNY2293). The URA3 marker was recycled using the pJT254 Cre recombinase plasmid as described above. After marker recycle, clones were again observed under magnification to confirm absence of the clumping phenotype. A resulting identified strain, PNY2145, has the genotype: MATa ura3Δ::loxP his3Δ pdc5Δ::P[FBA(L8)]-XPK|xpk1_Lp-CYCt-loxP66/71 fra2Δ 2-micron plasmid (CEN.PK2) pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66 gpd2Δ::loxP71/66 amn1Δ::AMN1(y)

PNY2118 and PNY2120 were both constructed by transforming yeast-*E. coli* shuttle vectors into strain PNY2115. Plasmid transformants were selected by plating cells on synthetic complete medium without uracil or histidine containing 1% ethanol (v/v) as the sole carbon source. PNY2118 is a clone that received plasmids pYZ067ΔkivDΔhADH (SEQ ID NO: 103), described in PCT Pub. No. WO2012/129555 and pHR81-ILV5p-K9JB4P (SEQ ID NO: 104). PNY2120 is a clone that received plasmids pHR81-ILV5p-K9SB2-SH (SEQ ID NO: 105) and pYZ067ΔkivDΔhADH. The pHR81-ILV5p-K9JB4P and pHR81-ILV5p-K9SB2-SH plasmids are based on pHR81 (available from ATCC, #87541, Manassas, Va.) and contain a gene for expression of KARI (variants K9JB4P, SEQ ID NO: 106 nt and SEQ ID NO: 107 protein; and K9SB2-SH, SEQ ID NO: 126 respectively). Plasmid pYZ067ΔkivDΔhADH was derived from pRS423 (available from ATCC, #77104) and contains a gene for expression of DHAD.

PNY2318 was constructed by transforming PNY2145 with plasmids pLH689-L2V4 (SEQ ID 108) and pRS413::BiADH-kivD (SEQ ID 109). Transformants were obtained as described above for PNY2118 and PNY2120. Plasmid pLH689-L2V4 is based on pHR81 and contains genes for the expression of KARI (K9JB4P variant, amino acid SEQ ID NO: 107; under control of the ILV5 promoter) and DHAD (L2V4 variant comprising C-terminal Lumio® tag, amino acid SEQ ID NO: 127; under control of the TEF(M7) promoter). Plasmid pRS413::BiADH-kivD is based on pRS413 (ATCC#) and contains genes for expression of BiADH (amino acid SEQ ID NO: 128; under control of the PDC1 promoter) and *L. grayi* kivD (amino acid SEQ ID NO: 129, under control of the PGK(UAS)-FBA1 hybrid promoter).

Example 1

Isobutanol Production by PNY2270

The purpose of this example is to demonstrate growth and isobutanol production by strain PNY2270 in a growth medium containing either ethanol or acetate as a C2 supplement.

PNY2270 was cultured aerobically (10 ml medium in a vented 125 ml flask) in synthetic complete medium with 0.3% glucose and either 2 mM acetate or 0.3% (vol/vol) ethanol at 30° C. in a platform shaker (220 rpm). The logarithmic growth rate in the acetate-supplemented medium was 40% higher than with ethanol. Cultures in either medium were grown to an optical density of approximately 2 (as measured using an Eppendorf BioPhotometer, Eppendorf AG, Hamburg, Germany). Culture medium was then used to inoculate synthetic complete medium with 2% glucose, BME vitamins and either 2 mM acetate or 0.05% (vol/vol) ethanol in serum vials (10 ml medium in 15 ml vials) to a starting OD of 0.2. The vials were stoppered, crimped and incubated at 30° C. in a platform shaker (220 rpm). After 48 h, crimps and stoppers were removed, optical densities were measured, and culture filtrates were analyzed by HPLC for isobutanol production.

The strains grown in the culture medium containing acetate were found to produce isobutanol in higher concentration than the strains grown in the culture medium without acetate (results shown in TABLE 2, below).

TABLE 2

Isobutanol Production by PNY2270

| Preculture medium supplement | Serum vial medium supplement | 48 h Isobutanol concentration (mM) |
|---|---|---|
| 0.3% ethanol | 0.05% ethanol | 42.1 +/− 0.8 |
| 2 mM acetate | 0.05% ethanol | 19 +/− 1 |
| 0.3% ethanol | 2 mM acetate | 60.1 +/− 0.6 |
| 2 mM acetate | 2 mM acetate | 66.5 +/− 0.1 |

Example 2

Isobutanol Production by PNY2092

The purpose of this example is to demonstrate growth and isobutanol production by strain PNY2092 in a growth medium containing either ethanol or acetate as a C2 supplement.

PNY2092 was cultured aerobically (10 ml medium in a vented 125 ml flask) in synthetic complete medium with 0.3% glucose and either 2 mM acetate or 0.3% (vol/vol) ethanol at 30° C. in a platform shaker (220 rpm). The logarithmic growth rate in the acetate-supplemented medium was higher than with ethanol. Cultures in either medium were grown to an optical density of approximately 2 (as measured using an Eppendorf BioPhotometer, Eppendorf AG, Hamburg, Germany). Culture medium was then used to inoculate synthetic complete medium with 2% glucose, BME vitamins and either 2 mM acetate or 0.05% (vol/vol) ethanol in serum vials (10 ml medium in 15 ml vials) to a starting OD of 0.2. The vials were stoppered, crimped and incubated at 30° C. in a platform shaker (220 rpm). After 48 h, crimps and stoppers were removed, optical densities were measured, and culture filtrates were analyzed by HPLC.

The strains grown in the culture medium containing acetate were found to produce isobutanol in higher concentration than the strains grown in the culture medium without acetate (results shown in TABLE 3, below).

TABLE 3

Isobutanol Production by PNY2092

| Pre-culture medium supplement | Serum vial medium supplement | 48 h Isobutanol concentration (mM) |
|---|---|---|
| 0.3% ethanol | 0.05% ethanol | 41.5 +/− 0.4 |
| 2 mM acetate | 2 mM acetate | 45.90 +/− 0.02 |

Example 3

Isobutanol Production by Strains PNY2118 and PNY2120

The purpose of this example is to demonstrate isobutanol production by strains PNY2118 and PNY2120 in a medium containing either ethanol or acetate as a C2 supplement.

Strains were cultured and then evaluated for isobutanol production in serum vials as described above in Example 2 except that samples were collected for analyses at 47.3 hours.

| Strain | Pre-culture medium supplement | Serum vial medium supplement | 48 h Isobutanol concentration (mM) |
|---|---|---|---|
| PNY2118 | 0.3% ethanol | 0.05% ethanol | 53.7 ± 0.5 |
| PNY2118 | 2 mM acetate | 2 mM acetate | 62.6 ± 0.6 |
| PNY2120 | 0.3% ethanol | 0.05% ethanol | 40.8 ± 0.7 |
| PNY2120 | 2 mM acetate | 2 mM acetate | 63.7 ± 0.2 |

Example 4

Isobutanol Production by PNY2318

The purpose of this example is to demonstrate isobutanol production by strain PNY2318 in a medium containing either ethanol or acetate as a C2 supplement.

Strains were cultured and then evaluated for isobutanol production in serum vials similar the experiments described above (Examples 2 and 3). In this case, PNY2318 does not require C2-supplementation for growth. Thus strains were cultured with or without C2 and then inoculated into serum vials, again with or without C2. Samples were collected for analyses at 36 hours.

| Pre-culture medium supplement | Serum vial medium supplement | 36 h Isobutanol concentration (mM) | Isobutyric acid yield (mole/mole) |
|---|---|---|---|
| none | none | 59.6 ± 0.6 | 0.021 ± 0.000 |
| none | 2 mM acetate | 57.3 ± 1.7 | 0.009 ± 0.001 |
| none | 0.05% ethanol | 60.2 ± 0.4 | 0.015 ± 0.001 |

-continued

| Pre-culture medium supplement | Serum vial medium supplement | 36 h Isobutanol concentration (mM) | Isobutyric acid yield (mole/mole) |
|---|---|---|---|
| 2 mM acetate | 2 mM acetate | 60.1 ± 5.3 | 0.009 ± 0.003 |
| 2 mM acetate | none | 63.4 ± 1.2 | 0.019 ± 0.000 |
| 0.3% ethanol | 0.05% ethanol | 58.2 ± 0.7 | 0.014 ± 0.001 |
| 0.3% ethanol | none | 59.6 ± 1.0 | 0.017 ± 0.02 |

What is claimed is:

1. A method for producing isobutanol comprising:

a) providing a recombinant host cell comprising an engineered isobutanol biosynthetic pathway, wherein said engineered isobutanol biosynthetic pathway comprises heterologous polynucleotides encoding polypeptides for the following substrate to product conversions:

i) pyruvate to acetolactate performed by an acetolactate synthase enzyme;

ii) acetolactate to 2,3-dihydroxyisovalerate performed by an acetohydroxy acid isomeroreductase enzyme;

iii) 2,3-dihydroxyisovalerate to α-ketoisovalerate performed by a dihydroxyacid dehydratase enzyme, wherein said dihydroxyacid dehydratase enzyme comprises the amino acid sequence of SEQ ID NO: 127;

iv) α-ketoisovalerate to isobutyraldehyde performed by an α-ketoacid decarboxylase enzyme; and v) isobutyraldehyde to isobutanol performed by an alcohol dehydrogenase enzyme; and b) contacting said recombinant host cell of step a) with a fermentation medium comprising:

i) a fermentable carbon substrate; and ii) acetate in an amount sufficient for improved isobutanol production, wherein said acetate is added to the fermentation medium, thereby producing isobutanol directly from said fermentable carbon substrate via said engineered isobutanol biosynthetic pathway, and wherein isobutanol production is improved as compared to isobutanol production in a fermentation medium without the addition of acetate;

wherein said recombinant host cell has been engineered to eliminate pyruvate decarboxylase (PDC) activity and FRA2 activity, wherein said PDC activity is eliminated by a deletion of an endogenous gene encoding a pyruvate decarboxylase enzyme and said FRA2 activity is eliminated by a deletion of an endogenous gene encoding FRA2; and wherein said recombinant host cell has been engineered to comprise a heterologous polynucleotide encoding a polypeptide with phosphoketolase activity.

2. The method of claim 1, wherein said endogenous gene is PDC1, PDC5, PDC6 or a combination thereof.

3. The method of claim 1, wherein said recombinant host cell has been engineered to eliminate aldehyde dehydrogenase activity, wherein said aldehyde dehydrogenase activity is eliminated by a deletion of an endogenous gene encoding an aldehyde dehydrogenase.

4. The method of claim 3, wherein said endogenous gene is ALD2, ALD3, ALD4, ALD5, ALD6 or a combination thereof.

5. The method of claim 1, wherein isobutyric acid production is decreased as compared to isobutyric production in fermentation medium without the addition of acetate.

6. The method of claim 1, wherein isobutanol yield or effective titer is increased as compared to isobutanol yield or effective titer in a fermentation medium without the addition of acetate.

7. A composition comprising:

a) a recombinant host cell comprising an engineered isobutanol biosynthetic pathway, wherein said engineered isobutanol biosynthetic pathway comprises heterologous polynucleotides encoding polypeptides for the following substrate to product conversions:

i) pyruvate to acetolactate performed by an acetolactate synthase enzyme;

ii) acetolactate to 2,3-dihydroxyisovalerate performed by an acetohydroxy acid isomeroreductase enzyme;

iii) 2,3-dihydroxyisovalerate to α-ketoisovalerate performed by a dihydroxyacid dehydratase enzyme, wherein said dihydroxyacid dehydratase enzyme comprises the amino acid sequence of SEQ ID NO: 127;

iv) α-ketoisovalerate to isobutyraldehyde performed by an α-ketoacid decarboxylase enzyme; and v) isobutyraldehyde to isobutanol performed by an alcohol dehydrogenase enzyme; and b) a fermentation medium comprising:

i) a fermentable carbon substrate; and ii) acetate in an amount sufficient for improved isobutanol production, wherein said acetate is added to the fermentation medium, wherein isobutanol production is improved as compared to isobutanol production in a fermentation medium without the addition of acetate;

wherein said recombinant host cell has been engineered to eliminate pyruvate decarboxylase (PDC) activity and FRA2 activity, wherein said PDC activity is eliminated by a deletion of an endogenous gene encoding a pyruvate decarboxylase enzyme and said FRA2 activity is eliminated by a deletion of an endogenous gene encoding FRA2;

wherein said recombinant host cell has been engineered to comprise a heterologous polynucleotide encoding a polypeptide with phosphoketolase activity.

8. The composition of claim 7, wherein said fermentation medium further comprises isobutanol.

* * * * *

SEQUENCE LISTING

```
<160> NUMBER OF SEQ ID NOS: 134

<210> SEQ ID NO 1
<211> LENGTH: 491
<212> TYPE: PRT
<213> ORGANISM: Artificial
<220> FEATURE:
<223> OTHER INFORMATION: Escherichia coli ketol-acid reductoisomerase

<400> SEQUENCE: 1

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
```

```
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490


<210> SEQ ID NO 2
<211> LENGTH: 338
<212> TYPE: PRT
<213> ORGANISM: Artificial
<220> FEATURE:
<223> OTHER INFORMATION: Pseudomonas fluorescens ketol-acid
      reductoisomerase

<400> SEQUENCE: 2

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Arg Lys
        35                  40                  45

Gly Ser Ala Thr Val Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140
```

```
Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 3
<211> LENGTH: 570
<212> TYPE: PRT
<213> ORGANISM: Artificial
<220> FEATURE:
<223> OTHER INFORMATION: Lactococcus lactis dihydroxyacid dehydratase

<400> SEQUENCE: 3

Met Glu Phe Lys Tyr Asn Gly Lys Val Glu Ser Ile Glu Leu Asn Lys
1               5                   10                  15

Tyr Ser Lys Thr Leu Thr Gln Asp Pro Thr Gln Pro Ala Thr Gln Ala
            20                  25                  30

Met His Tyr Gly Ile Gly Phe Lys Asp Glu Asp Phe Lys Lys Ala Gln
        35                  40                  45

Val Gly Ile Val Ser Met Asp Trp Asp Gly Asn Pro Cys Asn Met His
    50                  55                  60

Leu Gly Thr Leu Gly Ser Lys Ile Lys Asn Ser Val Asn Gln Thr Asp
65                  70                  75                  80

Gly Leu Ile Gly Leu Gln Phe His Thr Ile Gly Val Ser Asp Gly Ile
                85                  90                  95

Ala Asn Gly Lys Leu Gly Met Arg Tyr Ser Leu Val Ser Arg Glu Val
            100                 105                 110

Ile Ala Asp Ser Ile Glu Thr Asn Ala Gly Ala Glu Tyr Tyr Asp Ala
        115                 120                 125

Ile Val Ala Val Pro Gly Cys Asp Lys Asn Met Pro Gly Ser Ile Ile
    130                 135                 140

Gly Met Ala Arg Leu Asn Arg Pro Ser Ile Met Val Tyr Gly Gly Thr
145                 150                 155                 160

Ile Glu His Gly Glu Tyr Lys Gly Glu Lys Leu Asn Ile Val Ser Ala
```

```
                165                 170                 175

Phe Glu Ala Leu Gly Gln Lys Ile Thr Gly Asn Ile Ser Glu Glu Asp
            180                 185                 190

Tyr His Gly Val Ile Cys Asn Ala Ile Pro Gly Gln Gly Ala Cys Gly
        195                 200                 205

Gly Met Tyr Thr Ala Asn Thr Leu Ala Ser Ala Ile Glu Thr Leu Gly
    210                 215                 220

Met Ser Leu Pro Tyr Ser Ala Ser Asn Pro Ala Val Ser Gln Glu Lys
225                 230                 235                 240

Glu Asp Glu Cys Asp Glu Ile Gly Leu Ala Ile Lys Asn Leu Leu Glu
                245                 250                 255

Lys Asp Ile Lys Pro Ser Asp Ile Met Thr Lys Glu Ala Phe Glu Asn
            260                 265                 270

Ala Ile Thr Ile Val Met Val Leu Gly Gly Ser Thr Asn Ala Val Leu
        275                 280                 285

His Ile Ile Ala Met Ala Asn Ala Ile Gly Val Glu Ile Thr Gln Asp
    290                 295                 300

Asp Phe Gln Arg Ile Ser Asp Val Thr Pro Val Leu Gly Asp Phe Lys
305                 310                 315                 320

Pro Ser Gly Lys Tyr Met Met Glu Asp Leu His Lys Ile Gly Gly Val
                325                 330                 335

Pro Ala Val Leu Lys Tyr Leu Leu Lys Glu Gly Lys Leu His Gly Asp
            340                 345                 350

Cys Leu Thr Val Thr Gly Lys Thr Leu Ala Glu Asn Val Glu Thr Ala
        355                 360                 365

Leu Asp Leu Asp Phe Asp Ser Gln Asp Ile Ile Arg Pro Leu Glu Asn
    370                 375                 380

Pro Ile Lys Ala Thr Gly His Leu Gln Ile Leu Tyr Gly Asn Leu Ala
385                 390                 395                 400

Glu Gly Gly Ser Val Ala Lys Ile Ser Gly Lys Glu Gly Glu Phe Phe
                405                 410                 415

Lys Gly Thr Ala Arg Val Phe Asp Gly Glu Gln His Phe Ile Asp Gly
            420                 425                 430

Ile Glu Ser Gly Arg Leu His Ala Gly Asp Val Ala Val Ile Arg Asn
        435                 440                 445

Ile Gly Pro Val Gly Gly Pro Gly Met Pro Glu Met Leu Lys Pro Thr
    450                 455                 460

Ser Ala Leu Ile Gly Ala Gly Leu Gly Lys Ser Cys Ala Leu Ile Thr
465                 470                 475                 480

Asp Gly Arg Phe Ser Gly Gly Thr His Gly Phe Val Val Gly His Ile
                485                 490                 495

Val Pro Glu Ala Val Glu Gly Gly Leu Ile Gly Leu Val Glu Asp Asp
            500                 505                 510

Asp Ile Ile Glu Ile Asp Ala Val Asn Asn Ser Ile Ser Leu Lys Val
        515                 520                 525

Ala Asp Asp Glu Ile Ala Arg Arg Arg Ala Asn Tyr Gln Lys Pro Ala
    530                 535                 540

Pro Lys Ala Thr Arg Gly Val Leu Ala Lys Phe Ala Lys Leu Thr Arg
545                 550                 555                 560

Pro Ala Ser Glu Gly Cys Val Thr Asp Leu
                565                 570
```

<210> SEQ ID NO 4

```
<211> LENGTH: 571
<212> TYPE: PRT
<213> ORGANISM: Artificial
<220> FEATURE:
<223> OTHER INFORMATION: Streptococcus mutans dihydroxyacid dehydratase

<400> SEQUENCE: 4

Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365

Gln Lys Val Ile Met Pro Leu Glu Asn Pro Lys Arg Glu Asp Gly Pro
    370                 375                 380
```

```
Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
            420                 425                 430

Asp Gly Asp Val Val Val Val Arg Phe Val Gly Pro Lys Gly Gly Pro
        435                 440                 445

Gly Met Pro Glu Met Leu Ser Leu Ser Ser Met Ile Val Gly Lys Gly
    450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570


<210> SEQ ID NO 5
<211> LENGTH: 1641
<212> TYPE: DNA
<213> ORGANISM: Artificial
<220> FEATURE:
<223> OTHER INFORMATION: Macrococcus caseolyticus 2-ketoisovalerate
      decarboxylase

<400> SEQUENCE: 5

atgaaacaac gtatcgggca atacttgatc gatgccctac acgttaatgg tgtcgataag      60

atctttggag tcccaggtga tttcacttta gcctttttgg acgatatcat aagacatgac     120

aacgtggaat gggtgggaaa tactaatgag ttgaacgccg cttacgccgc tgatggttac     180

gctagagtta atggattagc cgctgtatct accacttttg ggttggcga gttatctgct     240

gtgaatggta ttgctggaag ttacgcagag cgtgttcctg taatcaaaat ctcaggcggt     300

ccttcatcag ttgctcaaca agagggtaga tatgtccacc attcattggg tgaaggaatc     360

tttgattcat attcaaagat gtacgctcac ataaccgcaa caactacaat cttatccgtt     420

gacaacgcag tcgacgaaat tgatagagtt attcattgtg ctttgaagga aaagaggcca     480

gtgcatattc atttgcctat tgacgtagcc ttaactgaga ttgaaatccc tcatgcacca     540

aaagtttaca cacacgaatc ccagaacgtc gatgcttaca ttcaagctgt tgagaaaaag     600

ttaatgtctg caaaacaacc agtaatcata gcaggtcatg aaatcaattc attcaagttg     660

cacgaacaac tggaacagtt tgtcaatcag acaaacatcc ctgttgcaca actttccttg     720

ggtaagtctg ctttcaatga agagaatgaa cattaccttg gtatctacga tggcaaaatc     780

gcaaaggaaa atgtgagaga gtacgtcgac aatgctgatg tcatattgaa cataggtgcc     840

aaactgactg attctgctac agctggattt tcctacaagt tcgatacaaa caacataatc     900

tacattaacc ataatgactt caaagctgaa gatgtgattt ctgataatgt ttcactgatt     960
```

```
gatcttgtga atggcctgaa ttctattgac tatagaaatg aaacacacta cccatcttat   1020

caaagatctg atatgaaata cgaattgaat gacgcaccac ttacacaatc taactatttc   1080

aaaatgatga acgcttttct agaaaaagat gacatcctac tagctgaaca aggtacatcc   1140

tttttcggcg catatgactt atccctatac aagggaaatc agtttatcgg tcagccttta   1200

tgggggtcaa tagggtatac ttttccatct ttactaggaa gtcaactagc agacatgcat   1260

aggagaaaca ttttgcttat aggcgatggt agtttacaac ttactgttca agccctaagt   1320

acaatgatta gaaaggatat caaaccaatc attttcgtta tcaataacga cggttacacc   1380

gtcgaaagac ttatccacgg catggaagag ccatacaatg atatccaaat gtggaactac   1440

aagcaattgc cagaagtatt tggtggaaaa gatactgtaa aagttcatga tgctaaaacc   1500

tccaacgaac tgaaaactgt aatggattct gttaaagcag acaaagatca catgcatttc   1560

attgaagtgc atatggcagt agaggacgcc ccaaagaagt tgattgatat agctaaagcc   1620

tttagtgatg ctaacaagta a                                             1641
```

```
<210> SEQ ID NO 6
<211> LENGTH: 1647
<212> TYPE: DNA
<213> ORGANISM: Artificial
<220> FEATURE:
<223> OTHER INFORMATION: Listeria grayi, 2-ketoisovalerate decarboxylase

<400> SEQUENCE: 6

atgtacaccg tcggccaata cttagtagac cgcttagaag agatcggcat cgataaggtt     60

tttggtgtcc cgggtgacta caacctgacc tttttggact acatccagaa ccacgaaggt    120

ctgagctggc aaggtaatac gaatgaactg aatgccgcgt acgcagctga tggctatgct    180

cgtgaacgcg gtgttagcgc tttggtcacg accttcggcg ttggtgagct gtccgcaatc    240

aatggcaccg caggtagctt cgcggagcaa gttccggtga ttcatatcgt gggcagcccg    300

accatgaatg ttcagagcaa caagaaactg gttcatcaca gcctgggtat gggcaacttt    360

cacaacttca gcgagatggc gaaagaagtc accgccgcaa ccacgatgct gacggaagag    420

aatgcggcgt cggagattga tcgtgttctg gaaaccgccc tgctggagaa acgcccagtg    480

tacatcaatc tgccgatcga cattgctcac aaggcgatcg tcaagccggc gaaagccctg    540

caaaccgaga agagctctgg cgagcgtgag gcacaactgg cggagatcat tctgagccat    600

ctggagaagg ctgcacagcc gattgtgatt gcgggtcacg agatcgcgcg cttccagatc    660

cgtgagcgtt tcgagaattg gattaatcaa acgaaactgc cggtgaccaa tctggcctac    720

ggcaagggta gcttcaacga agaaaacgag catttcattg gtacctatta tcctgcattt    780

agcgataaga acgtgctgga ctacgtggat aactccgact ttgtcctgca ctttggtggt    840

aaaatcattg ataacagcac ctccagcttc tcccaaggct tcaaaaccga gaacaccctg    900

actgcggcga acgatatcat tatgctgccg gacggtagca cgtattctgg tattagcctg    960

aatggcctgc tggccgagct ggaaaaactg aatttcacgt ttgccgacac cgcagcaaag   1020

caggcggagt tggcggtgtt tgagccgcag gctgaaaccc cgttgaaaca ggaccgtttt   1080

caccaggcgg tgatgaattt tctgcaagct gacgatgtcc tggttacgga acagggcacc   1140

tcttcttttg gcttgatgct ggcgcctctg aaaaagggta tgaacttgat ctcgcaaacg   1200

ctgtggggta gcattggtta cacgttgccg gcgatgattg gtagccaaat tgcggcaccg   1260

gagcgtcgtc atatcctgag cattggtgat ggtagctttc agctgactgc gcaggaaatg   1320
```

agcaccattt tccgtgagaa actgacccca gtcatcttca tcattaacaa tgatggctat 1380
accgttgagc gtgcgatcca tggcgaagat gaaagctata acgacattcc gacgtggaac 1440
ttgcaactgg tggcggaaac cttcggtggt gacgccgaaa ccgtcgacac tcacaatgtg 1500
ttcacggaga ctgatttcgc caacaccctg gcggcaattg acgcgacgcc gcagaaagca 1560
cacgttgtgg aagttcacat ggaacaaatg gatatgccgg agagcctgcg ccagatcggt 1620
ctggcactgt ccaagcagaa tagctaa 1647

<210> SEQ ID NO 7
<211> LENGTH: 347
<212> TYPE: PRT
<213> ORGANISM: Artificial
<220> FEATURE:
<223> OTHER INFORMATION: B. indica alcohol dehydrogenase

<400> SEQUENCE: 7

Met Lys Ala Leu Val Tyr Arg Gly Pro Gly Gln Lys Leu Val Glu Glu
1 5 10 15

Arg Gln Lys Pro Glu Leu Lys Glu Pro Gly Asp Ala Ile Val Lys Val
20 25 30

Thr Lys Thr Thr Ile Cys Gly Thr Asp Leu His Ile Leu Lys Gly Asp
35 40 45

Val Ala Thr Cys Lys Pro Gly Arg Val Leu Gly His Glu Gly Val Gly
50 55 60

Val Ile Glu Ser Val Gly Ser Gly Val Thr Ala Phe Gln Pro Gly Asp
65 70 75 80

Arg Val Leu Ile Ser Cys Ile Ser Ser Cys Gly Lys Cys Ser Phe Cys
85 90 95

Arg Arg Gly Met Phe Ser His Cys Thr Thr Gly Gly Trp Ile Leu Gly
100 105 110

Asn Glu Ile Asp Gly Thr Gln Ala Glu Tyr Val Arg Val Pro His Ala
115 120 125

Asp Thr Ser Leu Tyr Arg Ile Pro Ala Gly Ala Asp Glu Glu Ala Leu
130 135 140

Val Met Leu Ser Asp Ile Leu Pro Thr Gly Phe Glu Cys Gly Val Leu
145 150 155 160

Asn Gly Lys Val Ala Pro Gly Ser Ser Val Ala Ile Val Gly Ala Gly
165 170 175

Pro Val Gly Leu Ala Ala Leu Leu Thr Ala Gln Phe Tyr Ser Pro Ala
180 185 190

Glu Ile Ile Met Ile Asp Leu Asp Asp Asn Arg Leu Gly Leu Ala Lys
195 200 205

Gln Phe Gly Ala Thr Arg Thr Val Asn Ser Thr Gly Gly Asn Ala Ala
210 215 220

Ala Glu Val Lys Ala Leu Thr Glu Gly Leu Gly Val Asp Thr Ala Ile
225 230 235 240

Glu Ala Val Gly Ile Pro Ala Thr Phe Glu Leu Cys Gln Asn Ile Val
245 250 255

Ala Pro Gly Gly Thr Ile Ala Asn Val Gly Val His Gly Ser Lys Val
260 265 270

Asp Leu His Leu Glu Ser Leu Trp Ser His Asn Val Thr Ile Thr Thr
275 280 285

Arg Leu Val Asp Thr Ala Thr Thr Pro Met Leu Leu Lys Thr Val Gln
290 295 300

```
Ser His Lys Leu Asp Pro Ser Arg Leu Ile Thr His Arg Phe Ser Leu
305                 310                 315                 320

Asp Gln Ile Leu Asp Ala Tyr Glu Thr Phe Gly Gln Ala Ala Ser Thr
                325                 330                 335

Gln Ala Leu Lys Val Ile Ile Ser Met Glu Ala
            340                 345


<210> SEQ ID NO 8
<211> LENGTH: 348
<212> TYPE: PRT
<213> ORGANISM: Artificial
<220> FEATURE:
<223> OTHER INFORMATION: Achromobacter xylosoxidans alcohol
      dehydrogenase

<400> SEQUENCE: 8

Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
    290                 295                 300

Asp Lys Leu Pro Leu Lys Lys Met Ile Thr His Arg Phe Glu Leu Ala
305                 310                 315                 320
```

```
Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345


<210> SEQ ID NO 9
<211> LENGTH: 4519
<212> TYPE: DNA
<213> ORGANISM: Artificial
<220> FEATURE:
<223> OTHER INFORMATION: pLA54

<400> SEQUENCE: 9

caccttggct aactcgttgt atcatcactg gataacttcg tataatgtat gctatacgaa     60

gttatcgaac agagaaacta aatccacatt aattgagagt tctatctatt agaaaatgca    120

aactccaact aaatgggaaa acagataacc tcttttattt ttttttaatg tttgatattc    180

gagtcttttt cttttgttag gtttatattc atcatttcaa tgaataaaag aagcttctta    240

ttttggttgc aaagaatgaa aaaaaaggat tttttcatac ttctaaagct tcaattataa    300

ccaaaaattt tataaatgaa gagaaaaaat ctagtagtat caagttaaac ttagaaaaac    360

tcatcgagca tcaaatgaaa ctgcaattta ttcatatcag gattatcaat accatatttt    420

tgaaaaagcc gtttctgtaa tgaaggagaa aactcaccga ggcagttcca taggatggca    480

agatcctggt atcggtctgc gattccgact cgtccaacat caatacaacc tattaatttc    540

ccctcgtcaa aaataaggtt atcaagtgag aaatcaccat gagtgacgac tgaatccggt    600

gagaatggca aaagcttatg catttctttc cagacttgtt caacaggcca gccattacgc    660

tcgtcatcaa aatcactcgc atcaaccaaa ccgttattca ttcgtgattg cgcctgagcg    720

agacgaaata cgcgatcgct gttaaaagga caattacaaa caggaatcga atgcaaccgg    780

cgcaggaaca ctgccagcgc atcaacaata ttttcacctg aatcaggata ttcttctaat    840

acctggaatg ctgttttgcc ggggatcgca gtggtgagta accatgcatc atcaggagta    900

cggataaaat gcttgatggt cggaagaggc ataaattccg tcagccagtt tagtctgacc    960

atctcatctg taacatcatt ggcaacgcta cctttgccat gtttcagaaa caactctggc   1020

gcatcgggct tcccatacaa tcgatagatt gtcgcacctg attgcccgac attatcgcga   1080

gcccatttat acccatataa atcagcatcc atgttggaat ttaatcgcgg cctcgaaacg   1140

tgagtctttt ccttacccat ctcgagtttt aatgttactt ctcttgcagt tagggaacta   1200

taatgtaact caaaataaga ttaaacaaac taaaataaaa agaagttata cagaaaaacc   1260

catataaacc agtactaatc cataataata atacacaaaa aaactatcaa ataaaaccag   1320

aaaacagatt gaatagaaaa attttttcga tctcctttta tattcaaaat tcgatatatg   1380

aaaaagggaa ctctcagaaa atcaccaaat caatttaatt agatttttct tttccttcta   1440

gcgttggaaa gaaaaatttt tctttttttt tttagaaatg aaaaattttt gccgtaggaa   1500

tcaccgtata aaccctgtat aaacgctact ctgttcacct gtgtaggcta tgattgaccc   1560

agtgttcatt gttattgcga gagagcggga gaaaagaacc gatacaagag atccatgctg   1620

gtatagttgt ctgtccaaca ctttgatgaa cttgtaggac gatgatgtgt atttagacga   1680

gtacgtgtgt gactattaag tagttatgat agagaggttt gtacggtgtg ttctgtgtaa   1740

ttcgattgag aaaatggtta tgaatcccta gataacttcg tataatgtat gctatacgaa   1800

gttatctgaa cattagaata cgtaatccgc aatgcgggga tcctctagag tcgacctgca   1860
```

```
ggcatgcaag cttggcgtaa tcatggtcat agctgtttcc tgtgtgaaat tgttatccgc   1920
tcacaattcc acacaacata cgagccggaa gcataaagtg taaagcctgg ggtgcctaat   1980
gagtgagcta actcacatta attgcgttgc gctcactgcc cgctttccag tcgggaaacc   2040
tgtcgtgcca gctgcattaa tgaatcggcc aacgcgcggg gagaggcggt ttgcgtattg   2100
ggcgctcttc cgcttcctcg ctcactgact cgctgcgctc ggtcgttcgg ctgcggcgag   2160
cggtatcagc tcactcaaag gcggtaatac ggttatccac agaatcaggg gataacgcag   2220
gaaagaacat gtgagcaaaa ggccagcaaa aggccaggaa ccgtaaaaag gccgcgttgc   2280
tggcgttttt ccataggctc cgcccccctg acgagcatca caaaaatcga cgctcaagtc   2340
agaggtggcg aaacccgaca ggactataaa gataccaggc gtttccccct ggaagctccc   2400
tcgtgcgctc tcctgttccg accctgccgc ttaccggata cctgtccgcc tttctccctt   2460
cgggaagcgt ggcgctttct catagctcac gctgtaggta tctcagttcg gtgtaggtcg   2520
ttcgctccaa gctgggctgt gtgcacgaac cccccgttca gcccgaccgc tgcgccttat   2580
ccggtaacta tcgtcttgag tccaacccgg taagacacga cttatcgcca ctggcagcag   2640
ccactggtaa caggattagc agagcgaggt atgtaggcgg tgctacagag ttcttgaagt   2700
ggtggcctaa ctacggctac actagaagga cagtatttgg tatctgcgct ctgctgaagc   2760
cagttacctt cggaaaaaga gttggtagct cttgatccgg caaacaaacc accgctggta   2820
gcggtggttt ttttgtttgc aagcagcaga ttacgcgcag aaaaaaagga tctcaagaag   2880
atcctttgat cttttctacg gggtctgacg ctcagtggaa cgaaaactca cgttaaggga   2940
ttttggtcat gagattatca aaaaggatct tcacctagat ccttttaaat taaaaatgaa   3000
gttttaaatc aatctaaagt atatatgagt aaacttggtc tgacagttac caatgcttaa   3060
tcagtgaggc acctatctca gcgatctgtc tatttcgttc atccatagtt gcctgactcc   3120
ccgtcgtgta gataactacg atacgggagg gcttaccatc tggccccagt gctgcaatga   3180
taccgcgaga cccacgctca ccggctccag atttatcagc aataaaccag ccagccggaa   3240
gggccgagcg cagaagtggt cctgcaactt tatccgcctc catccagtct attaattgtt   3300
gccgggaagc tagagtaagt agttcgccag ttaatagttt gcgcaacgtt gttgccattg   3360
ctacaggcat cgtggtgtca cgctcgtcgt ttggtatggc ttcattcagc tccggttccc   3420
aacgatcaag gcgagttaca tgatccccca tgttgtgcaa aaaagcggtt agctccttcg   3480
gtcctccgat cgttgtcaga agtaagttgg ccgcagtgtt atcactcatg gttatggcag   3540
cactgcataa ttctcttact gtcatgccat ccgtaagatg cttttctgtg actggtgagt   3600
actcaaccaa gtcattctga gaatagtgta tgcggcgacc gagttgctct tgcccggcgt   3660
caatacggga taataccgcg ccacatagca gaactttaaa agtgctcatc attggaaaac   3720
gttcttcggg gcgaaaactc tcaaggatct taccgctgtt gagatccagt tcgatgtaac   3780
ccactcgtgc acccaactga tcttcagcat cttttacttt caccagcgtt tctgggtgag   3840
caaaaacagg aaggcaaaat gccgcaaaaa agggaataag ggcgacacgg aaatgttgaa   3900
tactcatact cttccttttt caatattatt gaagcattta tcagggttat tgtctcatga   3960
gcggatacat atttgaatgt atttagaaaa ataaacaaat aggggttccg cgcacatttc   4020
cccgaaaagt gccacctgac gtctaagaaa ccattattat catgacatta acctataaaa   4080
ataggcgtat cacgaggccc tttcgtctcg cgcgtttcgg tgatgacggt gaaaacctct   4140
gacacatgca gctcccggag acggtcacag cttgtctgta agcggatgcc gggagcagac   4200
aagcccgtca gggcgcgtca gcgggtgttg gcgggtgtcg gggctggctt aactatgcgg   4260
```

```
catcagagca gattgtactg agagtgcacc atatgcggtg tgaaataccg cacagatgcg   4320

taaggagaaa ataccgcatc aggcgccatt cgccattcag gctgcgcaac tgttgggaag   4380

ggcgatcggt gcgggcctct tcgctattac gccagctggc gaaaggggga tgtgctgcaa   4440

ggcgattaag ttgggtaacg ccagggtttt cccagtcacg acgttgtaaa acgacggcca   4500

gtgaattcga gctcggtac                                                4519


<210> SEQ ID NO 10
<211> LENGTH: 80
<212> TYPE: DNA
<213> ORGANISM: Artificial
<220> FEATURE:
<223> OTHER INFORMATION: BK505

<400> SEQUENCE: 10

ttccggtttc tttgaaattt ttttgattcg gtaatctccg agcagaagga gcattgcgga     60

ttacgtattc taatgttcag                                                 80


<210> SEQ ID NO 11
<211> LENGTH: 81
<212> TYPE: DNA
<213> ORGANISM: Artificial
<220> FEATURE:
<223> OTHER INFORMATION: BK506

<400> SEQUENCE: 11

gggtaataac tgatataatt aaattgaagc tctaatttgt gagtttagta caccttggct     60

aactcgttgt atcatcactg g                                               81


<210> SEQ ID NO 12
<211> LENGTH: 38
<212> TYPE: DNA
<213> ORGANISM: Artificial
<220> FEATURE:
<223> OTHER INFORMATION: LA468

<400> SEQUENCE: 12

gcctcgagtt ttaatgttac ttctcttgca gttaggga                             38


<210> SEQ ID NO 13
<211> LENGTH: 31
<212> TYPE: DNA
<213> ORGANISM: Artificial
<220> FEATURE:
<223> OTHER INFORMATION: LA492

<400> SEQUENCE: 13

gctaaattcg agtgaaacac aggaagacca g                                    31


<210> SEQ ID NO 14
<211> LENGTH: 23
<212> TYPE: DNA
<213> ORGANISM: Artificial
<220> FEATURE:
<223> OTHER INFORMATION: AK109-1

<400> SEQUENCE: 14

agtcacatca agatcgttta tgg                                             23


<210> SEQ ID NO 15
<211> LENGTH: 23
<212> TYPE: DNA
```

<213> ORGANISM: Artificial
<220> FEATURE:
<223> OTHER INFORMATION: AK109-2

<400> SEQUENCE: 15
gcacggaata tgggactact tcg 23

<210> SEQ ID NO 16
<211> LENGTH: 23
<212> TYPE: DNA
<213> ORGANISM: Artificial
<220> FEATURE:
<223> OTHER INFORMATION: AK109-3

<400> SEQUENCE: 16
actccacttc aagtaagagt ttg 23

<210> SEQ ID NO 17
<211> LENGTH: 24
<212> TYPE: DNA
<213> ORGANISM: Artificial
<220> FEATURE:
<223> OTHER INFORMATION: oBP452

<400> SEQUENCE: 17
ttctcgacgt gggccttttt cttg 24

<210> SEQ ID NO 18
<211> LENGTH: 49
<212> TYPE: DNA
<213> ORGANISM: Artificial
<220> FEATURE:
<223> OTHER INFORMATION: oBP453

<400> SEQUENCE: 18
tgcagcttta aataatcggt gtcactactt tgccttcgtt tatcttgcc 49

<210> SEQ ID NO 19
<211> LENGTH: 49
<212> TYPE: DNA
<213> ORGANISM: Artificial
<220> FEATURE:
<223> OTHER INFORMATION: oBP454

<400> SEQUENCE: 19
gagcaggcaa gataaacgaa ggcaaagtag tgacaccgat tatttaaag 49

<210> SEQ ID NO 20
<211> LENGTH: 49
<212> TYPE: DNA
<213> ORGANISM: Artificial
<220> FEATURE:
<223> OTHER INFORMATION: oBP455

<400> SEQUENCE: 20
tatggaccct gaaaccacag ccacattgta accaccacga cggttgttg 49

<210> SEQ ID NO 21
<211> LENGTH: 49
<212> TYPE: DNA
<213> ORGANISM: Artificial
<220> FEATURE:
<223> OTHER INFORMATION: oBP456

<400> SEQUENCE: 21
tttagcaaca accgtcgtgg tggttacaat gtggctgtgg tttcagggt 49

<210> SEQ ID NO 22
<211> LENGTH: 49
<212> TYPE: DNA
<213> ORGANISM: Artificial
<220> FEATURE:
<223> OTHER INFORMATION: oBP457

<400> SEQUENCE: 22
ccagaaaccc tatacctgtg tggacgtaag gccatgaagc tttttcttt 49

<210> SEQ ID NO 23
<211> LENGTH: 49
<212> TYPE: DNA
<213> ORGANISM: Artificial
<220> FEATURE:
<223> OTHER INFORMATION: oBP458

<400> SEQUENCE: 23
attggaaaga aaaagcttca tggccttacg tccacacagg tatagggtt 49

<210> SEQ ID NO 24
<211> LENGTH: 22
<212> TYPE: DNA
<213> ORGANISM: Artificial
<220> FEATURE:
<223> OTHER INFORMATION: oBP459

<400> SEQUENCE: 24
cataagaaca cctttggtgg ag 22

<210> SEQ ID NO 25
<211> LENGTH: 22
<212> TYPE: DNA
<213> ORGANISM: Artificial
<220> FEATURE:
<223> OTHER INFORMATION: BP460

<400> SEQUENCE: 25
aggattatca ttcataagtt tc 22

<210> SEQ ID NO 26
<211> LENGTH: 20
<212> TYPE: DNA
<213> ORGANISM: Artificial
<220> FEATURE:
<223> OTHER INFORMATION: LA135

<400> SEQUENCE: 26
cttggcagca acaggactag 20

<210> SEQ ID NO 27
<211> LENGTH: 23
<212> TYPE: DNA
<213> ORGANISM: Artificial
<220> FEATURE:
<223> OTHER INFORMATION: BP461

<400> SEQUENCE: 27
ttcttggagc tgggacatgt ttg 23

<210> SEQ ID NO 28
<211> LENGTH: 22
<212> TYPE: DNA
<213> ORGANISM: Artificial
<220> FEATURE:

<223> OTHER INFORMATION: LA92

<400> SEQUENCE: 28
gagaagatgc ggccagcaaa ac 22

<210> SEQ ID NO 29
<211> LENGTH: 4242
<212> TYPE: DNA
<213> ORGANISM: Artificial
<220> FEATURE:
<223> OTHER INFORMATION: pLA59

<400> SEQUENCE: 29
aaacgccagc aacgcggcct ttttacggtt cctggccttt tgctggcctt ttgctcacat 60
gttctttcct gcgttatccc ctgattctgt ggataaccgt attaccgcct ttgagtgagc 120
tgataccgct cgccgcagcc gaacgaccga gcgcagcgag tcagtgagcg aggaagcgga 180
agagcgccca atacgcaaac cgcctctccc cgcgcgttgg ccgattcatt aatgcagctg 240
gcacgacagg tttcccgact ggaaagcggg cagtgagcgc aacgcaatta atgtgagtta 300
gctcactcat taggcacccc aggctttaca ctttatgctt ccggctcgta tgttgtgtgg 360
aattgtgagc ggataacaat ttcacacagg aaacagctat gaccatgatt acgccaagct 420
tgcatgcctg caggtcgact ctagaggatc cgcaatgcgg atccgcattg cggattacgt 480
attctaatgt tcagtaccgt tcgtataatg tatgctatac gaagttatgc agattgtact 540
gagagtgcac cataccacct tttcaattca tcattttttt tttattcttt tttttgattt 600
cggtttcctt gaaatttttt tgattcggta atctccgaac agaaggaaga acgaaggaag 660
gagcacagac ttagattggt atatatacgc atatgtagtg ttgaagaaac atgaaattgc 720
ccagtattct taacccaact gcacagaaca aaaacctgca ggaaacgaag ataaatcatg 780
tcgaaagcta catataagga acgtgctgct actcatccta gtcctgttgc tgccaagcta 840
tttaatatca tgcacgaaaa gcaaacaaac ttgtgtgctt cattggatgt tcgtaccacc 900
aaggaattac tggagttagt tgaagcatta ggtcccaaaa tttgtttact aaaaacacat 960
gtggatatct tgactgattt ttccatggag ggcacagtta agccgctaaa ggcattatcc 1020
gccaagtaca atttttact cttcgaagac agaaaatttg ctgacattgg taatacagtc 1080
aaattgcagt actctgcggg tgtatacaga atagcagaat gggcagacat tacgaatgca 1140
cacggtgtgg tgggcccagg tattgttagc ggtttgaagc aggcggcaga agaagtaaca 1200
aaggaaccta gaggcctttt gatgttagca gaattgtcat gcaagggctc cctatctact 1260
ggagaatata ctaagggtac tgttgacatt gcgaagagcg acaaagattt tgttatcggc 1320
tttattgctc aaagagacat gggtggaaga gatgaaggtt acgattggtt gattatgaca 1380
cccggtgtgg gtttagatga caagggagac gcattgggtc aacagtatag aaccgtggat 1440
gatgtggtct ctacaggatc tgacattatt attgttggaa gaggactatt tgcaaaggga 1500
agggatgcta aggtagaggg tgaacgttac agaaaagcag gctgggaagc atatttgaga 1560
agatgcggcc agcaaaacta aaaaactgta ttataagtaa atgcatgtat actaaactca 1620
caaattagag cttcaattta attatatcag ttattaccct atgcggtgtg aaataccgca 1680
cagatgcgta aggagaaaat accgcatcag gaaattgtaa acgttaatat tttgttaaaa 1740
ttcgcgttaa atttttgtta aatcagctca ttttttaacc aataggccga aatcggcaaa 1800
atcccttata aatcaaaaga atagaccgag atagggttga gtgttgttcc agtttggaac 1860
aagagtccac tattaaagaa cgtggactcc aacgtcaaag ggcgaaaaac cgtctatcag 1920

```
ggcgatggcc cactacgtga accatcaccc taatcaagat aacttcgtat aatgtatgct   1980
atacgaacgg taccagtgat gatacaacga gttagccaag gtgaattcac tggccgtcgt   2040
tttacaacgt cgtgactggg aaaaccctgg cgttacccaa cttaatcgcc ttgcagcaca   2100
tccccctttc gccagctggc gtaatagcga agaggcccgc accgatcgcc cttcccaaca   2160
gttgcgcagc ctgaatggcg aatggcgcct gatgcggtat tttctcctta cgcatctgtg   2220
cggtatttca caccgcatat ggtgcactct cagtacaatc tgctctgatg ccgcatagtt   2280
aagccagccc cgacacccgc caacacccgc tgacgcgccc tgacgggctt gtctgctccc   2340
ggcatccgct tacagacaag ctgtgaccgt ctccgggagc tgcatgtgtc agaggttttc   2400
accgtcatca ccgaaacgcg cgagacgaaa gggcctcgtg atacgcctat ttttataggt   2460
taatgtcatg ataataatgg tttcttagac gtcaggtggc acttttcggg gaaatgtgcg   2520
cggaacccct atttgtttat ttttctaaat acattcaaat atgtatccgc tcatgagaca   2580
ataaccctga taaatgcttc aataatattg aaaaaggaag agtatgagta ttcaacattt   2640
ccgtgtcgcc cttattccct tttttgcggc attttgcctt cctgtttttg ctcacccaga   2700
aacgctggtg aaagtaaaag atgctgaaga tcagttgggt gcacgagtgg gttacatcga   2760
actggatctc aacagcggta agatccttga gagttttcgc cccgaagaac gttttccaat   2820
gatgagcact tttaaagttc tgctatgtgg cgcggtatta tcccgtattg acgccgggca   2880
agagcaactc ggtcgccgca tacactattc tcagaatgac ttggttgagt actcaccagt   2940
cacagaaaag catcttacgg atggcatgac agtaagagaa ttatgcagtg ctgccataac   3000
catgagtgat aacactgcgg ccaacttact tctgacaacg atcggaggac cgaaggagct   3060
aaccgctttt ttgcacaaca tgggggatca tgtaactcgc cttgatcgtt gggaaccgga   3120
gctgaatgaa gccataccaa acgacgagcg tgacaccacg atgcctgtag caatggcaac   3180
aacgttgcgc aaactattaa ctggcgaact acttactcta gcttcccggc aacaattaat   3240
agactggatg gaggcggata aagttgcagg accacttctg cgctcggccc ttccggctgg   3300
ctggtttatt gctgataaat ctggagccgg tgagcgtggg tctcgcggta tcattgcagc   3360
actggggcca gatggtaagc cctcccgtat cgtagttatc tacacgacgg ggagtcaggc   3420
aactatggat gaacgaaata gacagatcgc tgagataggt gcctcactga ttaagcattg   3480
gtaactgtca gaccaagttt actcatatat actttagatt gatttaaaac ttcattttta   3540
atttaaaagg atctaggtga agatcctttt tgataatctc atgaccaaaa tcccttaacg   3600
tgagttttcg ttccactgag cgtcagaccc cgtagaaaag atcaaaggat cttcttgaga   3660
tccttttttt ctgcgcgtaa tctgctgctt gcaaacaaaa aaaccaccgc taccagcggt   3720
ggtttgtttg ccggatcaag agctaccaac tctttttccg aaggtaactg gcttcagcag   3780
agcgcagata ccaaatactg tccttctagt gtagccgtag ttaggccacc acttcaagaa   3840
ctctgtagca ccgcctacat acctcgctct gctaatcctg ttaccagtgg ctgctgccag   3900
tggcgataag tcgtgtctta ccgggttgga ctcaagacga tagttaccgg ataaggcgca   3960
gcggtcgggc tgaacggggg gttcgtgcac acagcccagc ttggagcgaa cgacctacac   4020
cgaactgaga tacctacagc gtgagctatg agaaagcgcc acgcttcccg aagggagaaa   4080
ggcggacagg tatccggtaa gcggcagggt cggaacagga gagcgcacga gggagcttcc   4140
agggggaaac gcctggtatc tttatagtcc tgtcgggttt cgccacctct gacttgagcg   4200
tcgatttttg tgatgctcgt caggggggcg gagcctatgg aa                      4242
```

<210> SEQ ID NO 30
<211> LENGTH: 80
<212> TYPE: DNA
<213> ORGANISM: Artificial
<220> FEATURE:
<223> OTHER INFORMATION: LA678

<400> SEQUENCE: 30
caacgttaac accgttttcg gtttgccagg tgacttcaac ttgtccttgt gcattgcgga 60
ttacgtattc taatgttcag 80

<210> SEQ ID NO 31
<211> LENGTH: 81
<212> TYPE: DNA
<213> ORGANISM: Artificial
<220> FEATURE:
<223> OTHER INFORMATION: LA679

<400> SEQUENCE: 31
gtggagcatc gaagactggc aacatgattt caatcattct gatcttagag caccttggct 60
aactcgttgt atcatcactg g 81

<210> SEQ ID NO 32
<211> LENGTH: 23
<212> TYPE: DNA
<213> ORGANISM: Artificial
<220> FEATURE:
<223> OTHER INFORMATION: LA337

<400> SEQUENCE: 32
ctcatttgaa tcagcttatg gtg 23

<210> SEQ ID NO 33
<211> LENGTH: 24
<212> TYPE: DNA
<213> ORGANISM: Artificial
<220> FEATURE:
<223> OTHER INFORMATION: LA692

<400> SEQUENCE: 33
ggaagtcatt gacaccatct tggc 24

<210> SEQ ID NO 34
<211> LENGTH: 24
<212> TYPE: DNA
<213> ORGANISM: Artificial
<220> FEATURE:
<223> OTHER INFORMATION: LA693

<400> SEQUENCE: 34
agaagctggg acagcagcgt tagc 24

<210> SEQ ID NO 35
<211> LENGTH: 7523
<212> TYPE: DNA
<213> ORGANISM: Artificial
<220> FEATURE:
<223> OTHER INFORMATION: pLA34

<400> SEQUENCE: 35
ccagcttttg ttccctttag tgagggttaa ttgcgcgctt ggcgtaatca tggtcatagc 60
tgtttcctgt gtgaaattgt tatccgctca caattccaca caacatagga gccggaagca 120
taaagtgtaa agcctggggt gcctaatgag tgaggtaact cacattaatt gcgttgcgct 180

```
cactgcccgc tttccagtcg ggaaacctgt cgtgccagct gcattaatga atcggccaac    240
gcgcggggag aggcggtttg cgtattgggc gctcttccgc ttcctcgctc actgactcgc    300
tgcgctcggt cgttcggctg cggcgagcgg tatcagctca ctcaaaggcg gtaatacggt    360
tatccacaga atcaggggat aacgcaggaa agaacatgtg agcaaaaggc cagcaaaagg    420
ccaggaaccg taaaaaggcc gcgttgctgg cgtttttcca taggctccgc ccccctgacg    480
agcatcacaa aaatcgacgc tcaagtcaga ggtggcgaaa cccgacagga ctataaagat    540
accaggcgtt tccccctgga agctccctcg tgcgctctcc tgttccgacc ctgccgctta    600
ccggatacct gtccgccttt ctcccttcgg gaagcgtggc gctttctcat agctcacgct    660
gtaggtatct cagttcggtg taggtcgttc gctccaagct gggctgtgtg cacgaacccc    720
ccgttcagcc cgaccgctgc gccttatccg gtaactatcg tcttgagtcc aacccggtaa    780
gacacgactt atcgccactg gcagcagcca ctggtaacag gattagcaga gcgaggtatg    840
taggcggtgc tacagagttc ttgaagtggt ggcctaacta cggctacact agaaggacag    900
tatttggtat ctgcgctctg ctgaagccag ttaccttcgg aaaaagagtt ggtagctctt    960
gatccggcaa acaaaccacc gctggtagcg gtggtttttt tgtttgcaag cagcagatta   1020
cgcgcagaaa aaaaggatct caagaagatc ctttgatctt ttctacgggg tctgacgctc   1080
agtggaacga aaactcacgt taagggattt tggtcatgag attatcaaaa aggatcttca   1140
cctagatcct tttaaattaa aaatgaagtt ttaaatcaat ctaaagtata tatgagtaaa   1200
cttggtctga cagttaccaa tgcttaatca gtgaggcacc tatctcagcg atctgtctat   1260
ttcgttcatc catagttgcc tgactccccg tcgtgtagat aactacgata cgggagggct   1320
taccatctgg ccccagtgct gcaatgatac cgcgagaccc acgctcaccg gctccagatt   1380
tatcagcaat aaaccagcca gccggaaggg ccgagcgcag aagtggtcct gcaactttat   1440
ccgcctccat ccagtctatt aattgttgcc gggaagctag agtaagtagt tcgccagtta   1500
atagtttgcg caacgttgtt gccattgcta caggcatcgt ggtgtcacgc tcgtcgtttg   1560
gtatggcttc attcagctcc ggttcccaac gatcaaggcg agttacatga tcccccatgt   1620
tgtgcaaaaa agcggttagc tccttcggtc ctccgatcgt tgtcagaagt aagttggccg   1680
cagtgttatc actcatggtt atggcagcac tgcataattc tcttactgtc atgccatccg   1740
taagatgctt ttctgtgact ggtgagtact caaccaagtc attctgagaa tagtgtatgc   1800
ggcgaccgag ttgctcttgc ccggcgtcaa tacgggataa taccgcgcca catagcagaa   1860
ctttaaaagt gctcatcatt ggaaaacgtt cttcggggcg aaaactctca aggatcttac   1920
cgctgttgag atccagttcg atgtaaccca ctcgtgcacc caactgatct tcagcatctt   1980
ttactttcac cagcgtttct gggtgagcaa aaacaggaag gcaaaatgcc gcaaaaaagg   2040
gaataagggc gacacggaaa tgttgaatac tcatactctt cctttttcaa tattattgaa   2100
gcatttatca gggttattgt ctcatgagcg gatacatatt tgaatgtatt tagaaaaata   2160
aacaaatagg ggttccgcgc acatttcccc gaaaagtgcc acctgaacga agcatctgtg   2220
cttcattttg tagaacaaaa atgcaacgcg agagcgctaa tttttcaaac aaagaatctg   2280
agctgcattt ttacagaaca gaaatgcaac gcgaaagcgc tattttacca acgaagaatc   2340
tgtgcttcat ttttgtaaaa caaaaatgca acgcgagagc gctaattttt caaacaaaga   2400
atctgagctg catttttaca gaacagaaat gcaacgcgag agcgctattt taccaacaaa   2460
gaatctatac ttcttttttg ttctacaaaa atgcatcccg agagcgctat ttttctaaca   2520
```

-continued

```
aagcatctta gattactttt tttctccttt gtgcgctcta taatgcagtc tcttgataac   2580
tttttgcact gtaggtccgt taaggttaga agaaggctac tttggtgtct attttctctt   2640
ccataaaaaa agcctgactc cacttcccgc gtttactgat tactagcgaa gctgcgggtg   2700
catttttttca agataaaggc atccccgatt atattctata ccgatgtgga ttgcgcatac   2760
tttgtgaaca gaaagtgata gcgttgatga ttcttcattg gtcagaaaat tatgaacggt   2820
ttcttctatt ttgtctctat atactacgta taggaaatgt ttacattttc gtattgtttt   2880
cgattcactc tatgaatagt tcttactaca atttttttgt ctaaagagta atactagaga   2940
taaacataaa aaatgtagag gtcgagttta gatgcaagtt caaggagcga aaggtggatg   3000
ggtaggttat atagggatat agcacagaga tatatagcaa agagatactt ttgagcaatg   3060
tttgtggaag cggtattcgc aatattttag tagctcgtta cagtccggtg cgtttttggt   3120
tttttgaaag tgcgtcttca gagcgctttt ggttttcaaa agcgctctga agttcctata   3180
ctttctagag aataggaact tcggaatagg aacttcaaag cgtttccgaa aacgagcgct   3240
tccgaaaatg caacgcgagc tgcgcacata cagctcactg ttcacgtcgc acctatatct   3300
gcgtgttgcc tgtatatata tatacatgag aagaacggca tagtgcgtgt ttatgcttaa   3360
atgcgtactt atatgcgtct atttatgtag gatgaaaggt agtctagtac ctcctgtgat   3420
attatcccat tccatgcggg gtatcgtatg cttccttcag cactaccctt tagctgttct   3480
atatgctgcc actcctcaat tggattagtc tcatccttca atgctatcat ttcctttgat   3540
attggatcat ctaagaaacc attattatca tgacattaac ctataaaaat aggcgtatca   3600
cgaggccctt tcgtctcgcg cgtttcggtg atgacggtga aaacctctga cacatgcagc   3660
tcccggagac ggtcacagct tgtctgtaag cggatgccgg gagcagacaa gcccgtcagg   3720
gcgcgtcagc gggtgttggc gggtgtcggg gctggcttaa ctatgcggca tcagagcaga   3780
ttgtactgag agtgcaccat aaattcccgt tttaagagct tggtgagcgc taggagtcac   3840
tgccaggtat cgtttgaaca cggcattagt cagggaagtc ataacacagt cctttcccgc   3900
aattttcttt ttctattact cttggcctcc tctagtacac tctatatttt tttatgcctc   3960
ggtaatgatt ttcatttttt tttttcccct agcggatgac tcttttttttt tcttagcgat   4020
tggcattatc acataatgaa ttatacatta tataaagtaa tgtgatttct tcgaagaata   4080
tactaaaaaa tgagcaggca agataaacga aggcaaagat gacagagcag aaagccctag   4140
taaagcgtat tacaaatgaa accaagattc agattgcgat ctctttaaag ggtggtcccc   4200
tagcgataga gcactcgatc ttcccagaaa aagaggcaga agcagtagca gaacaggcca   4260
cacaatcgca agtgattaac gtccacacag gtatagggtt tctggaccat atgatacatg   4320
ctctggccaa gcattccggc tggtcgctaa tcgttgagtg cattggtgac ttacacatag   4380
acgaccatca caccactgaa gactgcggga ttgctctcgg tcaagctttt aaagaggccc   4440
tactggcgcg tggagtaaaa aggtttggat caggatttgc gcctttggat gaggcacttt   4500
ccagagcggt ggtagatctt tcgaacaggc cgtacgcagt tgtcgaactt ggtttgcaaa   4560
gggagaaagt aggagatctc tcttgcgaga tgatcccgca ttttcttgaa agctttgcag   4620
aggctagcag aattaccctc cacgttgatt gtctgcgagg caagaatgat catcaccgta   4680
gtgagagtgc gttcaaggct cttgcggttg ccataagaga agccacctcg cccaatggta   4740
ccaacgatgt tccctccacc aaaggtgttc ttatgtagtg acaccgatta tttaaagctg   4800
cagcatacga tatatataca tgtgtatata tgtataccta tgaatgtcag taagtatgta   4860
tacgaacagt atgatactga agatgacaag gtaatgcatc attctatacg tgtcattctg   4920
```

```
aacgaggcgc gctttccttt tttctttttg ctttttcttt ttttttctct tgaactcgac   4980
ggatctatgc ggtgtgaaat accgcacaga tgcgtaagga gaaaataccg catcaggaaa   5040
ttgtaaacgt taatattttg ttaaaattcg cgttaaattt ttgttaaatc agctcatttt   5100
ttaaccaata ggccgaaatc ggcaaaatcc cttataaatc aaaagaatag accgagatag   5160
ggttgagtgt tgttccagtt tggaacaaga gtccactatt aaagaacgtg gactccaacg   5220
tcaaagggcg aaaaaccgtc tatcagggcg atggcccact acgtgaacca tcaccctaat   5280
caagtttttt ggggtcgagg tgccgtaaag cactaaatcg gaaccctaaa gggagccccc   5340
gatttagagc ttgacgggga aagccggcga acgtggcgag aaaggaaggg aagaaagcga   5400
aaggagcggg cgctagggcg ctggcaagtg tagcggtcac gctgcgcgta accaccacac   5460
ccgccgcgct taatgcgccg ctacagggcg cgtcgcgcca ttcgccattc aggctgcgca   5520
actgttggga agggcgatcg gtgcgggcct cttcgctatt acgccagctg gcgaaagggg   5580
gatgtgctgc aaggcgatta agttgggtaa cgccagggtt ttcccagtca cgacgttgta   5640
aaacgacggc cagtgagcgc gcgtaatacg actcactata gggcgaattg ggtaccgggc   5700
ccccctcga ggtattagaa gccgccgagc gggcgacagc cctccgacgg aagactctcc   5760
tccgtgcgtc ctcgtcttca ccggtcgcgt tcctgaaacg cagatgtgcc tcgcgccgca   5820
ctgctccgaa caataaagat tctacaatac tagcttttat ggttatgaag aggaaaaatt   5880
ggcagtaacc tggccccaca aaccttcaaa ttaacgaatc aaattaacaa ccataggatg   5940
ataatgcgat tagtttttta gccttatttc tggggtaatt aatcagcgaa gcgatgattt   6000
ttgatctatt aacagatata taaatggaaa agctgcataa ccactttaac taatactttc   6060
aacattttca gtttgtatta cttcttattc aaatgtcata aaagtatcaa caaaaaattg   6120
ttaatatacc tctatacttt aacgtcaagg agaaaaatgt ccaatttact gcccgtacac   6180
caaaatttgc ctgcattacc ggtcgatgca acgagtgatg aggttcgcaa gaacctgatg   6240
gacatgttca gggatcgcca ggcgttttct gagcatacct ggaaaatgct tctgtccgtt   6300
tgccggtcgt gggcggcatg gtgcaagttg aataaccgga aatggtttcc cgcagaacct   6360
gaagatgttc gcgattatct tctatatctt caggcgcgcg gtctggcagt aaaaactatc   6420
cagcaacatt tgggccagct aaacatgctt catcgtcggt ccgggctgcc acgaccaagt   6480
gacagcaatg ctgtttcact ggttatgcgg cggatccgaa aagaaaacgt tgatgccggt   6540
gaacgtgcaa aacaggctct agcgttcgaa cgcactgatt tcgaccaggt tcgttcactc   6600
atggaaaata gcgatcgctg ccaggatata cgtaatctgg catttctggg gattgcttat   6660
aacaccctgt tacgtatagc cgaaattgcc aggatcaggg ttaaagatat ctcacgtact   6720
gacggtggga gaatgttaat ccatattggc agaacgaaaa cgctggttag caccgcaggt   6780
gtagagaagg cacttagcct gggggtaact aaactggtcg agcgatggat ttccgtctct   6840
ggtgtagctg atgatccgaa taactacctg ttttgccggg tcagaaaaaa tggtgttgcc   6900
gcgccatctg ccaccagcca gctatcaact cgcgccctgg aagggatttt tgaagcaact   6960
catcgattga tttacggcgc taaggatgac tctggtcaga gatacctggc ctggtctgga   7020
cacagtgccc gtgtcggagc cgcgcgagat atggcccgcg ctggagtttc aataccggag   7080
atcatgcaag ctggtggctg gaccaatgta aatattgtca tgaactatat ccgtaacctg   7140
gatagtgaaa caggggcaat ggtgcgcctg ctggaagatg gcgattagga gtaagcgaat   7200
ttcttatgat ttatgatttt tattattaaa taagttataa aaaaaataag tgtatacaaa   7260
```

```
ttttaaagtg actcttaggt tttaaaacga aaattcttat tcttgagtaa ctctttcctg   7320

taggtcaggt tgctttctca ggtatagcat gaggtcgctc ttattgacca cacctctacc   7380

ggcatgccga gcaaatgcct gcaaatcgct ccccatttca cccaattgta gatatgctaa   7440

ctccagcaat gagttgatga atctcggtgt gtattttatg tcctcagagg acaacacctg   7500

tggtccgcca ccgcggtgga gct                                           7523


<210> SEQ ID NO 36
<211> LENGTH: 96
<212> TYPE: DNA
<213> ORGANISM: Artificial
<220> FEATURE:
<223> OTHER INFORMATION: LA722

<400> SEQUENCE: 36

tgccaattat ttacctaaac atctataacc ttcaaaagta aaaaaataca caaacgttga     60

atcatcacct tggctaactc gttgtatcat cactgg                               96


<210> SEQ ID NO 37
<211> LENGTH: 80
<212> TYPE: DNA
<213> ORGANISM: Artificial
<220> FEATURE:
<223> OTHER INFORMATION: LA733

<400> SEQUENCE: 37

cataatcaat ctcaaagaga acaacacaat acaataacaa gaagaacaaa gcattgcgga     60

ttacgtattc taatgttcag                                                 80


<210> SEQ ID NO 38
<211> LENGTH: 30
<212> TYPE: DNA
<213> ORGANISM: Artificial
<220> FEATURE:
<223> OTHER INFORMATION: LA453

<400> SEQUENCE: 38

caccgaagaa gaatgcaaaa atttcagctc                                      30


<210> SEQ ID NO 39
<211> LENGTH: 25
<212> TYPE: DNA
<213> ORGANISM: Artificial
<220> FEATURE:
<223> OTHER INFORMATION: LA694

<400> SEQUENCE: 39

gctgaagttg ttagaactgt tgttg                                           25


<210> SEQ ID NO 40
<211> LENGTH: 21
<212> TYPE: DNA
<213> ORGANISM: Artificial
<220> FEATURE:
<223> OTHER INFORMATION: LA695

<400> SEQUENCE: 40

tgttagctgg agtagacttg g                                               21


<210> SEQ ID NO 41
<211> LENGTH: 22
<212> TYPE: DNA
<213> ORGANISM: Artificial
```

<220> FEATURE:
<223> OTHER INFORMATION: oBP594

<400> SEQUENCE: 41
agctgtctcg tgttgtgggt tt 22

<210> SEQ ID NO 42
<211> LENGTH: 49
<212> TYPE: DNA
<213> ORGANISM: Artificial
<220> FEATURE:
<223> OTHER INFORMATION: oBP595

<400> SEQUENCE: 42
cttaataata gaacaatatc atcctttacg ggcatcttat agtgtcgtt 49

<210> SEQ ID NO 43
<211> LENGTH: 49
<212> TYPE: DNA
<213> ORGANISM: Artificial
<220> FEATURE:
<223> OTHER INFORMATION: oBP596

<400> SEQUENCE: 43
gcgccaacga cactataaga tgcccgtaaa ggatgatatt gttctatta 49

<210> SEQ ID NO 44
<211> LENGTH: 49
<212> TYPE: DNA
<213> ORGANISM: Artificial
<220> FEATURE:
<223> OTHER INFORMATION: oBP597

<400> SEQUENCE: 44
tatggaccct gaaaccacag ccacattgca acgacgacaa tgccaaacc 49

<210> SEQ ID NO 45
<211> LENGTH: 49
<212> TYPE: DNA
<213> ORGANISM: Artificial
<220> FEATURE:
<223> OTHER INFORMATION: oBP598

<400> SEQUENCE: 45
tccttggttt ggcattgtcg tcgttgcaat gtggctgtgg tttcagggt 49

<210> SEQ ID NO 46
<211> LENGTH: 49
<212> TYPE: DNA
<213> ORGANISM: Artificial
<220> FEATURE:
<223> OTHER INFORMATION: oBP599

<400> SEQUENCE: 46
atcctctcgc ggagtccctg ttcagtaaag gccatgaagc tttttcttt 49

<210> SEQ ID NO 47
<211> LENGTH: 49
<212> TYPE: DNA
<213> ORGANISM: Artificial
<220> FEATURE:
<223> OTHER INFORMATION: oBP600

<400> SEQUENCE: 47
attggaaaga aaaagcttca tggcctttac tgaacaggga ctccgcgag 49

<210> SEQ ID NO 48
<211> LENGTH: 22
<212> TYPE: DNA
<213> ORGANISM: Artificial
<220> FEATURE:
<223> OTHER INFORMATION: oBP601

<400> SEQUENCE: 48
tcataccaca atcttagacc at 22

<210> SEQ ID NO 49
<211> LENGTH: 21
<212> TYPE: DNA
<213> ORGANISM: Artificial
<220> FEATURE:
<223> OTHER INFORMATION: oBP602

<400> SEQUENCE: 49
tgttcaaacc cctaaccaac c 21

<210> SEQ ID NO 50
<211> LENGTH: 22
<212> TYPE: DNA
<213> ORGANISM: Artificial
<220> FEATURE:
<223> OTHER INFORMATION: oBP603

<400> SEQUENCE: 50
tgttcccaca atctattacc ta 22

<210> SEQ ID NO 51
<211> LENGTH: 31
<212> TYPE: DNA
<213> ORGANISM: Artificial
<220> FEATURE:
<223> OTHER INFORMATION: LA811

<400> SEQUENCE: 51
aacgaagcat ctgtgcttca ttttgtagaa c 31

<210> SEQ ID NO 52
<211> LENGTH: 59
<212> TYPE: DNA
<213> ORGANISM: Artificial
<220> FEATURE:
<223> OTHER INFORMATION: LA817

<400> SEQUENCE: 52
cgatccactt gtatatttgg atgaattttt gaggaattct gaaccagtcc taaaacgag 59

<210> SEQ ID NO 53
<211> LENGTH: 31
<212> TYPE: DNA
<213> ORGANISM: Artificial
<220> FEATURE:
<223> OTHER INFORMATION: LA812

<400> SEQUENCE: 53
aacaaagata tgctattgaa gtgcaagatg g 31

<210> SEQ ID NO 54
<211> LENGTH: 33
<212> TYPE: DNA
<213> ORGANISM: Artificial
<220> FEATURE:
<223> OTHER INFORMATION: LA818

<400> SEQUENCE: 54
ctcaaaaatt catccaaata tacaagtgga tcg 33

<210> SEQ ID NO 55
<211> LENGTH: 90
<212> TYPE: DNA
<213> ORGANISM: Artificial
<220> FEATURE:
<223> OTHER INFORMATION: LA512

<400> SEQUENCE: 55
gtattttggt agattcaatt ctctttccct ttccttttcc ttcgctcccc ttccttatca 60
gcattgcgga ttacgtattc taatgttcag 90

<210> SEQ ID NO 56
<211> LENGTH: 90
<212> TYPE: DNA
<213> ORGANISM: Artificial
<220> FEATURE:
<223> OTHER INFORMATION: LA513

<400> SEQUENCE: 56
ttggttgggg gaaaaagagg caacaggaaa gatcagaggg ggaggggggg ggagagtgtc 60
accttggcta actcgttgta tcatcactgg 90

<210> SEQ ID NO 57
<211> LENGTH: 29
<212> TYPE: DNA
<213> ORGANISM: Artificial
<220> FEATURE:
<223> OTHER INFORMATION: LA516

<400> SEQUENCE: 57
ctcgaaacaa taagacgacg atggctctg 29

<210> SEQ ID NO 58
<211> LENGTH: 30
<212> TYPE: DNA
<213> ORGANISM: Artificial
<220> FEATURE:
<223> OTHER INFORMATION: LA514

<400> SEQUENCE: 58
cactatctgg tgcaaacttg gcaccggaag 30

<210> SEQ ID NO 59
<211> LENGTH: 29
<212> TYPE: DNA
<213> ORGANISM: Artificial
<220> FEATURE:
<223> OTHER INFORMATION: LA515

<400> SEQUENCE: 59
tgtttgtagc cactcgtgaa cttctctgc 29

<210> SEQ ID NO 60
<211> LENGTH: 6903
<212> TYPE: DNA
<213> ORGANISM: Artificial
<220> FEATURE:
<223> OTHER INFORMATION: pLA71

<400> SEQUENCE: 60

```
aaacgccagc aacgcggcct ttttacggtt cctggccttt tgctggcctt ttgctcacat     60
gttctttcct gcgttatccc ctgattctgt ggataaccgt attaccgcct ttgagtgagc    120
tgataccgct cgccgcagcc gaacgaccga gcgcagcgag tcagtgagcg aggaagcgga    180
agagcgccca atacgcaaac cgcctctccc cgcgcgttgg ccgattcatt aatgcagctg    240
gcacgacagg tttcccgact ggaaagcggg cagtgagcgc aacgcaatta atgtgagtta    300
gctcactcat taggcacccc aggctttaca ctttatgctt ccggctcgta tgttgtgtgg    360
aattgtgagc ggataacaat ttcacacagg aaacagctat gaccatgatt acgccaagct    420
tgcatgcgat ctgaaatgaa taacaatact gacagtagat ctgaaatgaa taacaatact    480
gacagtacta aataattgcc tacttggctt cacatacgtt gcatacgtcg atatagataa    540
taatgataat gacagcagga ttatcgtaat acgtaatagt tgaaaatctc aaaaatgtgt    600
gggtcattac gtaaataatg ataggaatgg gattcttcta tttttccttt ttccattcta    660
gcagccgtcg ggaaaacgtg gcatcctctc tttcgggctc aattggagtc acgctgccgt    720
gagcatcctc tctttccata tctaacaact gagcacgtaa ccaatggaaa agcatgagct    780
tagcgttgct ccaaaaaagt attggatggt taataccatt tgtctgttct cttctgactt    840
tgactcctca aaaaaaaaaa atctacaatc aacagatcgc ttcaattacg ccctcacaaa    900
aactttttc cttcttcttc gcccacgtta aattttatcc ctcatgttgt ctaacggatt    960
tctgcacttg atttattata aaaagacaaa gacataatac ttctctatca atttcagtta   1020
ttgttcttcc ttgcgttatt cttctgttct tctttttctt ttgtcatata taaccataac   1080
caagtaatac atattcaaat ctagagctga ggatgttgac aaaagcaaca aaagaacaaa   1140
aatcccttgt gaaaaacaga ggggcggagc ttgttgttga ttgcttagtg gagcaaggtg   1200
tcacacatgt atttggcatt ccaggtgcaa aaattgatgc ggtatttgac gctttacaag   1260
ataaaggacc tgaaattatc gttgcccggc acgaacaaaa cgcagcattc atggcccaag   1320
cagtcggccg tttaactgga aaaccgggag tcgtgttagt cacatcagga ccgggtgcct   1380
ctaacttggc aacaggcctg ctgacagcga acactgaagg agaccctgtc gttgcgcttg   1440
ctggaaacgt gatccgtgca gatcgtttaa aacggacaca tcaatctttg gataatgcgg   1500
cgctattcca gccgattaca aaatacagtg tagaagttca agatgtaaaa aatataccgg   1560
aagctgttac aaatgcattt aggatagcgt cagcagggca ggctggggcc gcttttgtga   1620
gctttccgca agatgttgtg aatgaagtca caaatacgaa aaacgtgcgt gctgttgcag   1680
cgccaaaact cggtcctgca gcagatgatg caatcagtgc ggccatagca aaaatccaaa   1740
cagcaaaact tcctgtcgtt ttggtcggca tgaaaggcgg aagaccggaa gcaattaaag   1800
cggttcgcaa gcttttgaaa aaggttcagc ttccatttgt tgaaacatat caagctgccg   1860
gtaccctttc tagagattta gaggatcaat attttggccg tatcggtttg ttccgcaacc   1920
agcctggcga tttactgcta gagcaggcag atgttgttct gacgatcggc tatgacccga   1980
ttgaatatga tccgaaattc tggaatatca atggagaccg gacaattatc catttagacg   2040
agattatcgc tgacattgat catgcttacc agcctgatct tgaattgatc ggtgacattc   2100
cgtccacgat caatcatatc gaacacgatg ctgtgaaagt ggaatttgca gagcgtgagc   2160
agaaaatcct ttctgattta aaacaatata tgcatgaagg tgagcaggtg cctgcagatt   2220
ggaaatcaga cagagcgcac cctcttgaaa tcgttaaaga gttgcgtaat gcagtcgatg   2280
atcatgttac agtaacttgc gatatcggtt cgcacgccat ttggatgtca cgttatttcc   2340
gcagctacga gccgttaaca ttaatgatca gtaacggtat gcaaacactc ggcgttgcgc   2400
```

```
ttccttgggc aatcggcgct tcattggtga aaccgggaga aaaagtggtt tctgtctctg   2460

gtgacggcgg tttcttattc tcagcaatgg aattagagac agcagttcga ctaaaagcac   2520

caattgtaca cattgtatgg aacgacagca catatgacat ggttgcattc cagcaattga   2580

aaaaatataa ccgtacatct gcggtcgatt tcggaaatat cgatatcgtg aaatatgcgg   2640

aaagcttcgg agcaactggc ttgcgcgtag aatcaccaga ccagctggca gatgttctgc   2700

gtcaaggcat gaacgctgaa ggtcctgtca tcatcgatgt cccggttgac tacagtgata   2760

acattaattt agcaagtgac aagcttccga aagaattcgg ggaactcatg aaaacgaaag   2820

ctctctagtt aattaatcat gtaattagtt atgtcacgct tacattcacg ccctcccccc   2880

acatccgctc taaccgaaaa ggaaggagtt agacaacctg aagtctaggt ccctatttat   2940

tttttatag ttatgttagt attaagaacg ttatttatat ttcaaatttt tctttttttt   3000

ctgtacagac gcgtgtacgc atgtaacatt atactgaaaa ccttgcttga gaaggttttg   3060

ggacgctcga aggctttaat ttaggttttg ggacgctcga aggctttaat ttggatccgc   3120

attgcggatt acgtattcta atgttcagta ccgttcgtat aatgtatgct atacgaagtt   3180

atgcagattg tactgagagt gcaccatacc acagcttttc aattcaattc atcatttttt   3240

ttttattctt ttttttgatt tcggtttctt tgaaattttt ttgattcggt aatctccgaa   3300

cagaaggaag aacgaaggaa ggagcacaga cttagattgg tatatatacg catatgtagt   3360

gttgaagaaa catgaaattg cccagtattc ttaacccaac tgcacagaac aaaaacctgc   3420

aggaaacgaa gataaatcat gtcgaaagct acatataagg aacgtgctgc tactcatcct   3480

agtcctgttg ctgccaagct atttaatatc atgcacgaaa agcaaacaaa cttgtgtgct   3540

tcattggatg ttcgtaccac caaggaatta ctggagttag ttgaagcatt aggtcccaaa   3600

atttgtttac taaaaacaca tgtggatatc ttgactgatt tttccatgga gggcacagtt   3660

aagccgctaa aggcattatc cgccaagtac aatttttac tcttcgaaga cagaaaattt   3720

gctgacattg gtaatacagt caaattgcag tactctgcgg gtgtatacag aatagcagaa   3780

tgggcagaca ttacgaatgc acacggtgtg gtgggcccag gtattgttag cggtttgaag   3840

caggcggcag aagaagtaac aaaggaacct agaggccttt tgatgttagc agaattgtca   3900

tgcaagggct ccctatctac tggagaatat actaagggta ctgttgacat tgcgaagagc   3960

gacaaagatt ttgttatcgg ctttattgct caaagagaca tgggtggaag agatgaaggt   4020

tacgattggt tgattatgac acccggtgtg ggtttagatg acaagggaga cgcattgggt   4080

caacagtata gaaccgtgga tgatgtggtc tctacaggat ctgacattat tattgttgga   4140

agaggactat ttgcaaaggg aagggatgct aaggtagagg gtgaacgtta cagaaaagca   4200

ggctgggaag catatttgag aagatgcggc cagcaaaact aaaaaactgt attataagta   4260

aatgcatgta tactaaactc acaaattaga gcttcaattt aattatatca gttattaccc   4320

tatgcggtgt gaaataccgc acagatgcgt aaggagaaaa taccgcatca ggaaattgta   4380

aacgttaata ttttgttaaa attcgcgtta aatttttgtt aaatcagctc atttttaac   4440

caataggccg aaatcggcaa aatcccttat aaatcaaaag aatagaccga gatagggttg   4500

agtgttgttc cagtttggaa caagagtcca ctattaaaga acgtggactc caacgtcaaa   4560

gggcgaaaaa ccgtctatca gggcgatggc ccactacgtg aaccatcacc ctaatcaaga   4620

taacttcgta taatgtatgc tatacgaacg gtaccagtga tgatacaacg agttagccaa   4680

ggtgaattca ctggccgtcg ttttacaacg tcgtgactgg gaaaaccctg gcgttaccca   4740
```

```
acttaatcgc cttgcagcac atccccccttt cgccagctgg cgtaatagcg aagaggcccg    4800
caccgatcgc ccttcccaac agttgcgcag cctgaatggc gaatggcgcc tgatgcggta    4860
ttttctcctt acgcatctgt gcggtatttc acaccgcata tggtgcactc tcagtacaat    4920
ctgctctgat gccgcatagt taagccagcc ccgacacccg ccaacacccg ctgacgcgcc    4980
ctgacgggct tgtctgctcc cggcatccgc ttacagacaa gctgtgaccg tctccgggag    5040
ctgcatgtgt cagaggtttt caccgtcatc accgaaacgc gcgagacgaa agggcctcgt    5100
gatacgccta tttttatagg ttaatgtcat gataataatg gtttcttaga cgtcaggtgg    5160
cacttttcgg ggaaatgtgc gcggaacccc tatttgttta tttttctaaa tacattcaaa    5220
tatgtatccg ctcatgagac aataaccctg ataaatgctt caataatatt gaaaaaggaa    5280
gagtatgagt attcaacatt tccgtgtcgc ccttattccc ttttttgcgg cattttgcct    5340
tcctgttttt gctcacccag aaacgctggt gaaagtaaaa gatgctgaag atcagttggg    5400
tgcacgagtg ggttacatcg aactggatct caacagcggt aagatccttg agagttttcg    5460
ccccgaagaa cgttttccaa tgatgagcac ttttaaagtt ctgctatgtg gcgcggtatt    5520
atcccgtatt gacgccgggc aagagcaact cggtcgccgc atacactatt ctcagaatga    5580
cttggttgag tactcaccag tcacagaaaa gcatcttacg gatggcatga cagtaagaga    5640
attatgcagt gctgccataa ccatgagtga taacactgcg gccaacttac ttctgacaac    5700
gatcggagga ccgaaggagc taaccgcttt tttgcacaac atgggggatc atgtaactcg    5760
ccttgatcgt tgggaaccgg agctgaatga agccatacca aacgacgagc gtgacaccac    5820
gatgcctgta gcaatggcaa caacgttgcg caaactatta actggcgaac tacttactct    5880
agcttcccgg caacaattaa tagactggat ggaggcggat aaagttgcag gaccacttct    5940
gcgctcggcc cttccggctg gctggtttat tgctgataaa tctggagccg gtgagcgtgg    6000
gtctcgcggt atcattgcag cactggggcc agatggtaag ccctcccgta tcgtagttat    6060
ctacacgacg gggagtcagg caactatgga tgaacgaaat agacagatcg ctgagatagg    6120
tgcctcactg attaagcatt ggtaactgtc agaccaagtt tactcatata tactttagat    6180
tgatttaaaa cttcattttt aatttaaaag gatctaggtg aagatccttt ttgataatct    6240
catgaccaaa atcccttaac gtgagttttc gttccactga gcgtcagacc ccgtagaaaa    6300
gatcaaagga tcttcttgag atcctttttt tctgcgcgta atctgctgct tgcaaacaaa    6360
aaaaccaccg ctaccagcgg tggtttgttt gccggatcaa gagctaccaa ctctttttcc    6420
gaaggtaact ggcttcagca gagcgcagat accaaatact gtccttctag tgtagccgta    6480
gttaggccac cacttcaaga actctgtagc accgcctaca tacctcgctc tgctaatcct    6540
gttaccagtg gctgctgcca gtggcgataa gtcgtgtctt accgggttgg actcaagacg    6600
atagttaccg gataaggcgc agcggtcggg ctgaacgggg ggttcgtgca cacagcccag    6660
cttggagcga acgacctaca ccgaactgag atacctacag cgtgagctat gagaaagcgc    6720
cacgcttccc gaagggagaa aggcggacag gtatccggta agcggcaggg tcggaacagg    6780
agagcgcacg agggagcttc cagggggaaa cgcctggtat ctttatagtc ctgtcgggtt    6840
tcgccacctc tgacttgagc gtcgattttt gtgatgctcg tcaggggggc ggagcctatg    6900
gaa                                                                   6903
```

<210> SEQ ID NO 61
<211> LENGTH: 96
<212> TYPE: DNA
<213> ORGANISM: Artificial

```
<220> FEATURE:
<223> OTHER INFORMATION: LA829

<400> SEQUENCE: 61

ccaaatttac aatatctcct gaattcttgg cttggaatat gggcagtaca gcttgtgtga     60

tattgcacct tggctaactc gttgtatcat cactgg                               96


<210> SEQ ID NO 62
<211> LENGTH: 90
<212> TYPE: DNA
<213> ORGANISM: Artificial
<220> FEATURE:
<223> OTHER INFORMATION: LA834

<400> SEQUENCE: 62

atgtcccaag gtagaaaagc tgcagaaaga ttggctaaga agactgtcct cattacaggt     60

gatctgaaat gaataacaat actgacagta                                      90


<210> SEQ ID NO 63
<211> LENGTH: 29
<212> TYPE: DNA
<213> ORGANISM: Artificial
<220> FEATURE:
<223> OTHER INFORMATION: N1257

<400> SEQUENCE: 63

gatgatgcta tttggtgcag agggtgatg                                       29


<210> SEQ ID NO 64
<211> LENGTH: 29
<212> TYPE: DNA
<213> ORGANISM: Artificial
<220> FEATURE:
<223> OTHER INFORMATION: LA830

<400> SEQUENCE: 64

cacggcaaac ttagaggcac aatagatag                                       29


<210> SEQ ID NO 65
<211> LENGTH: 6924
<212> TYPE: DNA
<213> ORGANISM: Artificial
<220> FEATURE:
<223> OTHER INFORMATION: pLA78

<400> SEQUENCE: 65

gatccgcatt gcggattacg tattctaatg ttcagtaccg ttcgtataat gtatgctata     60

cgaagttatg cagattgtac tgagagtgca ccataccacc ttttcaattc atcatttttt    120

ttttattctt ttttttgatt tcggtttcct tgaaattttt ttgattcggt aatctccgaa    180

cagaaggaag aacgaaggaa ggagcacaga cttagattgg tatatatacg catatgtagt    240

gttgaagaaa catgaaattg cccagtattc ttaacccaac tgcacagaac aaaaacctgc    300

aggaaacgaa gataaatcat gtcgaaagct acatataagg aacgtgctgc tactcatcct    360

agtcctgttg ctgccaagct atttaatatc atgcacgaaa agcaaacaaa cttgtgtgct    420

tcattggatg ttcgtaccac caaggaatta ctggagttag ttgaagcatt aggtcccaaa    480

atttgtttac taaaaacaca tgtggatatc ttgactgatt tttccatgga gggcacagtt    540

aagccgctaa aggcattatc cgccaagtac aattttttac tcttcgaaga cagaaaattt    600

gctgacattg gtaatacagt caaattgcag tactctgcgg gtgtatacag aatagcagaa    660
```

-continued

```
tgggcagaca ttacgaatgc acacggtgtg gtgggcccag gtattgttag cggtttgaag    720
caggcggcag aagaagtaac aaaggaacct agaggccttt tgatgttagc agaattgtca    780
tgcaagggct ccctatctac tggagaatat actaagggta ctgttgacat tgcgaagagc    840
gacaaagatt ttgttatcgg ctttattgct caaagagaca tgggtggaag agatgaaggt    900
tacgattggt tgattatgac acccggtgtg ggtttagatg acaagggaga cgcattgggt    960
caacagtata gaaccgtgga tgatgtggtc tctacaggat ctgacattat tattgttgga   1020
agaggactat ttgcaaaggg aagggatgct aaggtagagg gtgaacgtta cagaaaagca   1080
ggctgggaag catatttgag aagatgcggc cagcaaaact aaaaaactgt attataagta   1140
aatgcatgta tactaaactc acaaattaga gcttcaattt aattatatca gttattaccc   1200
tatgcggtgt gaaataccgc acagatgcgt aaggagaaaa taccgcatca ggaaattgta   1260
aacgttaata ttttgttaaa attcgcgtta aatttttgtt aaatcagctc atttttaac    1320
caataggccg aaatcggcaa aatcccttat aaatcaaaag aatagaccga gatagggttg   1380
agtgttgttc cagtttggaa caagagtcca ctattaaaga acgtggactc caacgtcaaa   1440
gggcgaaaaa ccgtctatca gggcgatggc ccactacgtg aaccatcacc ctaatcaaga   1500
taacttcgta taatgtatgc tatacgaacg gtaccagtga tgatacaacg agttagccaa   1560
ggtgaattca ctggccgtcg ttttacaacg tcgtgactgg gaaaaccctg gcgttaccca   1620
acttaatcgc cttgcagcac atcccccttt cgccagctgg cgtaatagcg aagaggcccg   1680
caccgatcgc ccttcccaac agttgcgcag cctgaatggc gaatggcgcc tgatgcggta   1740
ttttctcctt acgcatctgt gcggtatttc acaccgcata tggtgcactc tcagtacaat   1800
ctgctctgat gccgcatagt taagccagcc ccgacacccg ccaacacccg ctgacgcgcc   1860
ctgacgggct tgtctgctcc cggcatccgc ttacagacaa gctgtgaccg tctccgggag   1920
ctgcatgtgt cagaggtttt caccgtcatc accgaaacgc gcgagacgaa agggcctcgt   1980
gatacgccta tttttatagg ttaatgtcat gataataatg gtttcttaga cgtcaggtgg   2040
cacttttcgg ggaaatgtgc gcggaacccc tatttgttta tttttctaaa tacattcaaa   2100
tatgtatccg ctcatgagac aataaccctg ataaatgctt caataatatt gaaaaaggaa   2160
gagtatgagt attcaacatt tccgtgtcgc ccttattccc ttttttgcgg cattttgcct   2220
tcctgttttt gctcacccag aaacgctggt gaaagtaaaa gatgctgaag atcagttggg   2280
tgcacgagtg ggttacatcg aactggatct caacagcggt aagatccttg agagttttcg   2340
ccccgaagaa cgttttccaa tgatgagcac ttttaaagtt ctgctatgtg gcgcggtatt   2400
atcccgtatt gacgccgggc aagagcaact cggtcgccgc atacactatt ctcagaatga   2460
cttggttgag tactcaccag tcacagaaaa gcatcttacg gatggcatga cagtaagaga   2520
attatgcagt gctgccataa ccatgagtga taacactgcg gccaacttac ttctgacaac   2580
gatcggagga ccgaaggagc taaccgcttt tttgcacaac atgggggatc atgtaactcg   2640
ccttgatcgt tgggaaccgg agctgaatga agccatacca aacgacgagc gtgacaccac   2700
gatgcctgta gcaatggcaa caacgttgcg caaactatta actggcgaac tacttactct   2760
agcttcccgg caacaattaa tagactggat ggaggcggat aaagttgcag gaccacttct   2820
gcgctcggcc cttccggctg gctggtttat tgctgataaa tctggagccg gtgagcgtgg   2880
gtctcgcggt atcattgcag cactggggcc agatggtaag ccctcccgta tcgtagttat   2940
ctacacgacg gggagtcagg caactatgga tgaacgaaat agacagatcg ctgagatagg   3000
tgcctcactg attaagcatt ggtaactgtc agaccaagtt tactcatata tactttagat   3060
```

```
tgatttaaaa cttcattttt aatttaaaag gatctaggtg aagatccttt ttgataatct   3120
catgaccaaa atcccttaac gtgagttttc gttccactga gcgtcagacc ccgtagaaaa   3180
gatcaaagga tcttcttgag atcctttttt tctgcgcgta atctgctgct tgcaaacaaa   3240
aaaaccaccg ctaccagcgg tggtttgttt gccggatcaa gagctaccaa ctctttttcc   3300
gaaggtaact ggcttcagca gagcgcagat accaaatact gtccttctag tgtagccgta   3360
gttaggccac cacttcaaga actctgtagc accgcctaca tacctcgctc tgctaatcct   3420
gttaccagtg gctgctgcca gtggcgataa gtcgtgtctt accgggttgg actcaagacg   3480
atagttaccg gataaggcgc agcggtcggg ctgaacgggg ggttcgtgca cacagcccag   3540
cttggagcga acgacctaca ccgaactgag atacctacag cgtgagctat gagaaagcgc   3600
cacgcttccc gaagggagaa aggcggacag gtatccggta agcggcaggg tcggaacagg   3660
agagcgcacg agggagcttc caggggggaaa cgcctggtat ctttatagtc ctgtcgggtt   3720
tcgccacctc tgacttgagc gtcgattttt gtgatgctcg tcaggggggc ggagcctatg   3780
gaaaaacgcc agcaacgcgg cctttttacg gttcctggcc ttttgctggc cttttgctca   3840
catgttcttt cctgcgttat cccctgattc tgtggataac cgtattaccg cctttgagtg   3900
agctgatacc gctcgccgca gccgaacgac cgagcgcagc gagtcagtga gcgaggaagc   3960
ggaagagcgc ccaatacgca aaccgcctct ccccgcgcgt tggccgattc attaatgcag   4020
ctggcacgac aggtttcccg actggaaagc gggcagtgag cgcaacgcaa ttaatgtgag   4080
ttagctcact cattaggcac cccaggcttt acactttatg cttccggctc gtatgttgtg   4140
tggaattgtg agcggataac aatttcacac aggaaacagc tatgaccatg attacgccaa   4200
gcttccaatt accgtcgctc gtgatttgtt tgcaaaaaga acaaaactga aaaaacccag   4260
acacgctcga cttcctgtct tcctattgat tgcagcttcc aatttcgtca cacaacaagg   4320
tcctgtcgac gcctacttgg cttcacatac gttgcatacg tcgatataga taataatgat   4380
aatgacagca ggattatcgt aatacgtaat agttgaaaat ctcaaaaatg tgtgggtcat   4440
tacgtaaata atgataggaa tgggattctt ctatttttcc tttttccatt ctagcagccg   4500
tcgggaaaac gtggcatcct ctctttcggg ctcaattgga gtcacgctgc cgtgagcatc   4560
ctctctttcc atatctaaca actgagcacg taaccaatgg aaaagcatga gcttagcgtt   4620
gctccaaaaa agtattggat ggttaatacc atttgtctgt tctcttctga ctttgactcc   4680
tcaaaaaaaa aaaatctaca atcaacagat cgcttcaatt acgccctcac aaaaactttt   4740
ttccttcttc ttcgcccacg ttaaatttta tccctcatgt tgtctaacgg atttctgcac   4800
ttgatttatt ataaaaagac aaagacataa tacttctcta tcaatttcag ttattgttct   4860
tccttgcgtt attcttctgt tcttcttttt cttttgtcat atataaccat aaccaagtaa   4920
tacatattca agtttaaaca tgtataccgt aggacagtac ttggtagata gactagaaga   4980
gattggtatc gataaggttt tcggtgtgcc aggggattac aatttgactt ttctagatta   5040
cattcaaaat cacgaaggac tttcctggca agggaatact aatgaactaa acgcagcata   5100
tgcagcagat ggctacgccc gtgaaagagg cgtatcagct cttgttacta cattcggagt   5160
gggtgaactg tcagccatta acggaacagc tggtagtttt gcagaacaag tccctgtcat   5220
ccacatcgtg ggttctccaa ctatgaatgt gcaatccaac aaaaagctgg ttcatcattc   5280
cttaggaatg ggtaactttc ataactttag tgaaatggct aaggaagtca ctgccgctac   5340
aaccatgctt actgaagaga atgcagcttc agagatcgac agagtattag aaacagcctt   5400
```

gttggaaaag aggccagtat acatcaatct tccaattgat atagctcata aagcaatagt 5460
taaacctgca aaagcactac aaacagagaa atcatctggt gagagagagg cacaacttgc 5520
agaaatcata ctatcacact tagaaaaggc cgctcaacct atcgtaatcg ccggtcatga 5580
gatcgcccgt ttccagataa gagaaagatt tgaaaactgg ataaaccaaa caaagttgcc 5640
agtaaccaat ttggcatatg gcaaaggctc tttcaatgaa gagaacgaac atttcattgg 5700
tacctattac ccagcttttt ctgacaaaaa cgttctggat tacgttgaca atagtgactt 5760
cgttttacat tttggtggga aaatcattga caattctacc tcctcatttt ctcaaggctt 5820
taagactgaa aacactttaa ccgctgcaaa tgacatcatt atgctgccag atgggtctac 5880
ttactctggg atttctctta acggtctttt ggcagagctg gaaaaactaa actttacttt 5940
tgctgatact gctgctaaac aagctgaatt agctgttttc gaaccacagg ccgaaacacc 6000
actaaagcaa gacagatttc accaagctgt tatgaacttt ttgcaagctg atgatgtgtt 6060
ggtcactgag caggggacat catctttcgg tttgatgttg gcacctctga aaaagggtat 6120
gaatttgatc agtcaaacat tatggggctc cataggatac acattacctg ctatgattgg 6180
ttcacaaatt gctgccccag aaaggagaca cattctatcc atcggtgatg gatcttttca 6240
actgacagca caggaaatgt ccaccatctt cagagagaaa ttgacaccag tgatattcat 6300
tatcaataac gatggctata cagtcgaaag agccatccat ggagaggatg agagttacaa 6360
tgatatacca acttggaact tgcaattagt tgctgaaaca tttggtggtg atgccgaaac 6420
tgtcgacact cacaacgttt tcacagaaac agacttcgct aatactttag ctgctatcga 6480
tgctactcct caaaaagcac atgtcgttga agttcatatg gaacaaatgg atatgccaga 6540
atcattgaga cagattggct tagccttatc taagcaaaac tcttaagttt aaactaagcg 6600
aatttcttat gatttatgat ttttattatt aaataagtta taaaaaaaat aagtgtatac 6660
aaattttaaa gtgactctta ggttttaaaa cgaaaattct tattcttgag taactctttc 6720
ctgtaggtca ggttgctttc tcaggtatag catgaggtcg ctcttattga ccacacctct 6780
accggcatgc cgagcaaatg cctgcaaatc gctccccatt tcacccaatt gtagatatgc 6840
taactccagc aatgagttga tgaatctcgg tgtgtatttt atgtcctcag aggacaacac 6900
ctgttgtaat cgttcttcca cacg 6924

<210> SEQ ID NO 66
<211> LENGTH: 92
<212> TYPE: DNA
<213> ORGANISM: Artificial
<220> FEATURE:
<223> OTHER INFORMATION: LA850

<400> SEQUENCE: 66
atgactaagc tacactttga cactgctgaa ccagtcaaga tcacacttcc aaatggtttg 60
acataaatta ccgtcgctcg tgatttgttt gc 92

<210> SEQ ID NO 67
<211> LENGTH: 94
<212> TYPE: DNA
<213> ORGANISM: Artificial
<220> FEATURE:
<223> OTHER INFORMATION: LA851

<400> SEQUENCE: 67
ttacaactta attctgacag cttttacttc agtgtatgca tggtagactt cttcacccat 60
ttccaccttg gctaactcgt tgtatcatca ctgg 94

<210> SEQ ID NO 68
<211> LENGTH: 24
<212> TYPE: DNA
<213> ORGANISM: Artificial
<220> FEATURE:
<223> OTHER INFORMATION: N1262

<400> SEQUENCE: 68
cacgtaaggg catgatagaa ttgg 24

<210> SEQ ID NO 69
<211> LENGTH: 22
<212> TYPE: DNA
<213> ORGANISM: Artificial
<220> FEATURE:
<223> OTHER INFORMATION: LA740

<400> SEQUENCE: 69
cgataatcct gctgtcatta tc 22

<210> SEQ ID NO 70
<211> LENGTH: 26
<212> TYPE: DNA
<213> ORGANISM: Artificial
<220> FEATURE:
<223> OTHER INFORMATION: N1263

<400> SEQUENCE: 70
ggatatagca gttgttgtac actagc 26

<210> SEQ ID NO 71
<211> LENGTH: 6761
<212> TYPE: DNA
<213> ORGANISM: Artificial
<220> FEATURE:
<223> OTHER INFORMATION: pLA65

<400> SEQUENCE: 71
gatccgcatt gcggattacg tattctaatg ttcagtaccg ttcgtataat gtatgctata 60
cgaagttatg cagattgtac tgagagtgca ccataccacc ttttcaattc atcatttttt 120
ttttattctt ttttttgatt tcggtttcct tgaaattttt ttgattcggt aatctccgaa 180
cagaaggaag aacgaaggaa ggagcacaga cttagattgg tatatatacg catatgtagt 240
gttgaagaaa catgaaattg cccagtattc ttaacccaac tgcacagaac aaaaacctgc 300
aggaaacgaa gataaatcat gtcgaaagct acatataagg aacgtgctgc tactcatcct 360
agtcctgttg ctgccaagct atttaatatc atgcacgaaa agcaaacaaa cttgtgtgct 420
tcattggatg ttcgtaccac caaggaatta ctggagttag ttgaagcatt aggtcccaaa 480
atttgtttac taaaaacaca tgtggatatc ttgactgatt tttccatgga gggcacagtt 540
aagccgctaa aggcattatc cgccaagtac aatttttac tcttcgaaga cagaaaattt 600
gctgacattg gtaatacagt caaattgcag tactctgcgg gtgtatacag aatagcagaa 660
tgggcagaca ttacgaatgc acacggtgtg gtgggcccag gtattgttag cggtttgaag 720
caggcggcag aagaagtaac aaaggaacct agaggccttt tgatgttagc agaattgtca 780
tgcaagggct ccctatctac tggagaatat actaagggta ctgttgacat tgcgaagagc 840
gacaaagatt ttgttatcgg ctttattgct caaagagaca tgggtggaag agatgaaggt 900
tacgattggt tgattatgac acccggtgtg ggtttagatg acaagggaga cgcattgggt 960

```
caacagtata gaaccgtgga tgatgtggtc tctacaggat ctgacattat tattgttgga   1020

agaggactat ttgcaaaggg aagggatgct aaggtagagg gtgaacgtta cagaaaagca   1080

ggctgggaag catatttgag aagatgcggc cagcaaaact aaaaaactgt attataagta   1140

aatgcatgta tactaaactc acaaattaga gcttcaattt aattatatca gttattaccc   1200

tatgcggtgt gaaataccgc acagatgcgt aaggagaaaa taccgcatca ggaaattgta   1260

aacgttaata ttttgttaaa attcgcgtta aatttttgtt aaatcagctc attttttaac   1320

caataggccg aaatcggcaa aatcccttat aaatcaaaag aatagaccga gatagggttg   1380

agtgttgttc cagtttggaa caagagtcca ctattaaaga acgtggactc caacgtcaaa   1440

gggcgaaaaa ccgtctatca gggcgatggc ccactacgtg aaccatcacc ctaatcaaga   1500

taacttcgta taatgtatgc tatacgaacg gtaccagtga tgatacaacg agttagccaa   1560

ggtgaattca ctggccgtcg ttttacaacg tcgtgactgg gaaaaccctg gcgttaccca   1620

acttaatcgc cttgcagcac atccccctttc cgccagctgg cgtaatagcg aagaggcccg   1680

caccgatcgc ccttcccaac agttgcgcag cctgaatggc gaatggcgcc tgatgcggta   1740

ttttctcctt acgcatctgt gcggtatttc acaccgcata tggtgcactc tcagtacaat   1800

ctgctctgat gccgcatagt taagccagcc ccgacacccg ccaacacccg ctgacgcgcc   1860

ctgacgggct tgtctgctcc cggcatccgc ttacagacaa gctgtgaccg tctccgggag   1920

ctgcatgtgt cagaggtttt caccgtcatc accgaaacgc gcgagacgaa agggcctcgt   1980

gatacgccta tttttatagg ttaatgtcat gataataatg gtttcttaga cgtcaggtgg   2040

cacttttcgg ggaaatgtgc gcggaacccc tatttgttta tttttctaaa tacattcaaa   2100

tatgtatccg ctcatgagac aataaccctg ataaatgctt caataatatt gaaaaaggaa   2160

gagtatgagt attcaacatt tccgtgtcgc ccttattccc ttttttgcgg cattttgcct   2220

tcctgttttt gctcacccag aaacgctggt gaaagtaaaa gatgctgaag atcagttggg   2280

tgcacgagtg ggttacatcg aactggatct caacagcggt aagatccttg agagttttcg   2340

ccccgaagaa cgttttccaa tgatgagcac ttttaaagtt ctgctatgtg gcgcggtatt   2400

atcccgtatt gacgccgggc aagagcaact cggtcgccgc atacactatt ctcagaatga   2460

cttggttgag tactcaccag tcacagaaaa gcatcttacg gatggcatga cagtaagaga   2520

attatgcagt gctgccataa ccatgagtga taacactgcg gccaacttac ttctgacaac   2580

gatcggagga ccgaaggagc taaccgcttt tttgcacaac atgggggatc atgtaactcg   2640

ccttgatcgt tgggaaccgg agctgaatga agccatacca aacgacgagc gtgacaccac   2700

gatgcctgta gcaatggcaa caacgttgcg caaactatta actggcgaac tacttactct   2760

agcttcccgg caacaattaa tagactggat ggaggcggat aaagttgcag gaccacttct   2820

gcgctcggcc cttccggctg gctggtttat tgctgataaa tctggagccg gtgagcgtgg   2880

gtctcgcggt atcattgcag cactggggcc agatggtaag ccctcccgta tcgtagttat   2940

ctacacgacg gggagtcagg caactatgga tgaacgaaat agacagatcg ctgagatagg   3000

tgcctcactg attaagcatt ggtaactgtc agaccaagtt tactcatata tactttagat   3060

tgatttaaaa cttcattttt aatttaaaag gatctaggtg aagatccttt ttgataatct   3120

catgaccaaa atcccttaac gtgagttttc gttccactga gcgtcagacc ccgtagaaaa   3180

gatcaaagga tcttcttgag atcctttttt tctgcgcgta atctgctgct tgcaaacaaa   3240

aaaaccaccg ctaccagcgg tggtttgttt gccggatcaa gagctaccaa ctctttttcc   3300

gaaggtaact ggcttcagca gagcgcagat accaaatact gtccttctag tgtagccgta   3360
```

-continued

```
gttaggccac cacttcaaga actctgtagc accgcctaca tacctcgctc tgctaatcct   3420
gttaccagtg gctgctgcca gtggcgataa gtcgtgtctt accgggttgg actcaagacg   3480
atagttaccg gataaggcgc agcggtcggg ctgaacgggg ggttcgtgca cacagcccag   3540
cttggagcga acgacctaca ccgaactgag atacctacag cgtgagctat gagaaagcgc   3600
cacgcttccc gaagggagaa aggcggacag gtatccggta agcggcaggg tcggaacagg   3660
agagcgcacg agggagcttc cagggggaaa cgcctggtat ctttatagtc ctgtcgggtt   3720
tcgccacctc tgacttgagc gtcgattttt gtgatgctcg tcaggggggc ggagcctatg   3780
gaaaaacgcc agcaacgcgg cctttttacg gttcctggcc ttttgctggc cttttgctca   3840
catgttcttt cctgcgttat cccctgattc tgtggataac cgtattaccg cctttgagtg   3900
agctgatacc gctcgccgca gccgaacgac cgagcgcagc gagtcagtga gcgaggaagc   3960
ggaagagcgc ccaatacgca aaccgcctct ccccgcgcgt tggccgattc attaatgcag   4020
ctggcacgac aggtttcccg actggaaagc gggcagtgag cgcaacgcaa ttaatgtgag   4080
ttagctcact cattaggcac cccaggcttt acactttatg cttccggctc gtatgttgtg   4140
tggaattgtg agcggataac aatttcacac aggaaacagc tatgaccatg attacgccaa   4200
gcttacctgg taaaacctct agtggagtag tagatgtaat caatgaagcg gaagccaaaa   4260
gaccagagta gaggcctata gaagaaactg cgataccttt tgtgatggct aaacaaacag   4320
acatcttttt atatgttttt acttctgtat atcgtgaagt agtaagtgat aagcgaattt   4380
ggctaagaac gttgtaagtg aacaagggac ctcttttgcc tttcaaaaaa ggattaaatg   4440
gagttaatca ttgagattta gttttcgtta gattctgtat ccctaaataa ctcccttacc   4500
cgacgggaag gcacaaaaga cttgaataat agcaaacggc cagtagccaa gaccaaataa   4560
tactagagtt aactgatggt cttaaacagg cattacgtgg tgaactccaa gaccaatata   4620
caaaatatcg ataagttatt cttgcccacc aatttaagga gcctacatca ggacagtagt   4680
accattcctc agagaagagg tatacataac aagaaaatcg cgtgaacacc ttatataact   4740
tagcccgtta ttgagctaaa aaaccttgca aaatttccta tgaataagaa tacttcagac   4800
gtgataaaaa tttactttct aactcttctc acgctgcccc tatctgttct tccgctctac   4860
cgtgagaaat aaagcatcga gtacggcagt tcgctgtcac tgaactaaaa caataaggct   4920
agttcgaatg atgaacttgc ttgctgtcaa acttctgagt tgccgctgat gtgacactgt   4980
gacaataaat tcaaaccggt tatagcggtc tcctccggta ccggttctgc cacctccaat   5040
agagctcagt aggagtcaga acctctgcgg tggctgtcag tgactcatcc gcgtttcgta   5100
agttgtgcgc gtgcacattt cgcccgttcc cgctcatctt gcagcaggcg gaaattttca   5160
tcacgctgta ggacgcaaaa aaaaaataat taatcgtaca agaatcttgg aaaaaaaatt   5220
gaaaaatttt gtataaaagg gatgacctaa cttgactcaa tggcttttac acccagtatt   5280
ttccctttcc ttgtttgtta caattataga agcaagacaa aaacatatag acaacctatt   5340
cctaggagtt atattttttt accctaccag caatataagt aaaaaactgt ttatgaaagc   5400
attagtgtat aggggcccag gccagaagtt ggtggaagag agacagaagc cagagcttaa   5460
ggaacctggt gacgctatag tgaaggtaac aaagactaca atttgcggaa ccgatctaca   5520
cattcttaaa ggtgacgttg cgacttgtaa acccggtcgt gtattagggc atgaaggagt   5580
gggggttatt gaatcagtcg gatctggggt tactgctttc caaccaggcg atagagtttt   5640
gatatcatgt atatcgagtt gcggaaagtg ctcattttgt agaagaggaa tgttcagtca   5700
```

```
ctgtacgacc gggggttgga ttctgggcaa cgaaattgat ggtacccaag cagagtacgt   5760

aagagtacca catgctgaca catcccttta tcgtattccg gcaggtgcgg atgaagaggc   5820

cttagtcatg ttatcagata ttctaccaac gggttttgag tgcggagtcc taaacggcaa   5880

agtcgcacct ggttcttcgg tggctatagt aggtgctggt cccgttggtt tggccgcctt   5940

actgacagca caattctact ccccagctga aatcataatg atcgatcttg atgataacag   6000

gctgggatta gccaaacaat ttggtgccac cagaacagta aactccacgg gtggtaacgc   6060

cgcagccgaa gtgaaagctc ttactgaagg cttaggtgtt gatactgcga ttgaagcagt   6120

tgggatacct gctacatttg aattgtgtca gaatatcgta gctcccggtg gaactatcgc   6180

taatgtcggc gttcacggta gcaaagttga tttgcatctt gaaagtttat ggtcccataa   6240

tgtcacgatt actacaaggt tggttgacac ggctaccacc ccgatgttac tgaaaactgt   6300

tcaaagtcac aagctagatc catctagatt gataacacat agattcagcc tggaccagat   6360

cttggacgca tatgaaactt ttggccaagc tgcgtctact caagcactaa aagtcatcat   6420

ttcgatggag gcttgattaa ttaagagtaa gcgaatttct tatgatttat gatttttatt   6480

attaaataag ttataaaaaa aataagtgta tacaaatttt aaagtgactc ttaggtttta   6540

aaacgaaaat tcttattctt gagtaactct ttcctgtagg tcaggttgct ttctcaggta   6600

tagcatgagg tcgctcttat tgaccacacc tctaccggca tgccgagcaa atgcctgcaa   6660

atcgctcccc atttcaccca attgtagata tgctaactcc agcaatgagt tgatgaatct   6720

cggtgtgtat tttatgtcct cagaggacaa cacctgtggt g                       6761
```

<210> SEQ ID NO 72
<211> LENGTH: 80
<212> TYPE: DNA
<213> ORGANISM: Artificial
<220> FEATURE:
<223> OTHER INFORMATION: LA855

<400> SEQUENCE: 72

```
gcacaatatt tcaagctata ccaagcatac aatcaactat ctcatataca acctggtaaa     60

acctctagtg gagtagtaga                                                 80
```

<210> SEQ ID NO 73
<211> LENGTH: 83
<212> TYPE: DNA
<213> ORGANISM: Artificial
<220> FEATURE:
<223> OTHER INFORMATION: LA856

<400> SEQUENCE: 73

```
gcttatttag aagtgtcaac aacgtatcta ccaacgattt gaccctttc cacaccttgg      60

ctaactcgtt gtatcatcac tgg                                             83
```

<210> SEQ ID NO 74
<211> LENGTH: 25
<212> TYPE: DNA
<213> ORGANISM: Artificial
<220> FEATURE:
<223> OTHER INFORMATION: LA414

<400> SEQUENCE: 74

```
ccagagctga tgaggggtat ctcga                                           25
```

<210> SEQ ID NO 75
<211> LENGTH: 25

<212> TYPE: DNA
<213> ORGANISM: Artificial
<220> FEATURE:
<223> OTHER INFORMATION: LA749

<400> SEQUENCE: 75
caagtctttt gtgccttccc gtcgg 25

<210> SEQ ID NO 76
<211> LENGTH: 25
<212> TYPE: DNA
<213> ORGANISM: Artificial
<220> FEATURE:
<223> OTHER INFORMATION: LA413

<400> SEQUENCE: 76
ggacataaaa tacacaccga gattc 25

<210> SEQ ID NO 77
<211> LENGTH: 90
<212> TYPE: DNA
<213> ORGANISM: Artificial
<220> FEATURE:
<223> OTHER INFORMATION: LA860

<400> SEQUENCE: 77
tctcaattat tattttctac tcataacctc acgcaaaata acacagtcaa atcaatcaaa 60
atgaaagcat tagtgtatag gggcccaggc 90

<210> SEQ ID NO 78
<211> LENGTH: 26
<212> TYPE: DNA
<213> ORGANISM: Artificial
<220> FEATURE:
<223> OTHER INFORMATION: N1093

<400> SEQUENCE: 78
tttcaagatg caaatcaact ttgcta 26

<210> SEQ ID NO 79
<211> LENGTH: 20
<212> TYPE: DNA
<213> ORGANISM: Artificial
<220> FEATURE:
<223> OTHER INFORMATION: LA681

<400> SEQUENCE: 79
ttattgctta gcgttggtag 20

<210> SEQ ID NO 80
<211> LENGTH: 9613
<212> TYPE: DNA
<213> ORGANISM: Artificial
<220> FEATURE:
<223> OTHER INFORMATION: pHR81-ILV5p-K9SB2

<400> SEQUENCE: 80
aaacagtatg gaagaatgta agatggctaa gatttactac caagaagact gtaacttgtc 60
cttgttggat ggtaagacta tcgccgttat cggttacggt tctcaaggtc acgctcatgc 120
cctgaatgct aaggaatccg gttgtaacgt tatcattggt ttattcgaag gtgcggagga 180
gtggaaaaga gctgaagaac aaggtttcga agtctacacc gctgctgaag ctgctaagaa 240
ggctgacatc attatgatct tgatcccaga tgaaaagcag gctaccatgt acaaaaacga 300

```
catcgaacca aacttggaag ccggtaacat gttgatgttc gctcacggtt tcaacatcca    360
tttcggttgt attgttccac caaaggacgt tgatgtcact atgatcgctc caaagggtcc    420
aggtcacacc gttagatccg aatacgaaga aggtaaaggt gtcccatgct tggttgctgt    480
cgaacaagac gctactggca aggctttgga tatggctttg gcctacgctt tagccatcgg    540
tggtgctaga gccggtgtct tggaaactac cttcagaacc gaaactgaaa ccgacttgtt    600
cggtgaacaa gctgttttat gtggtggtgt ctgcgctttg atgcaggccg gttttgaaac    660
cttggttgaa gccggttacg acccaagaaa cgcttacttc gaatgtatcc acgaaatgaa    720
gttgatcgtt gacttgatct accaatctgg tttctccggt atgcgttact ctatctccaa    780
cactgctgaa tacggtgact acattaccgg tccaaagatc attactgaag ataccaagaa    840
ggctatgaag aagattttgt ctgacattca agatggtacc tttgccaagg acttcttggt    900
tgacatgtct gatgctggtt cccaggtcca cttcaaggct atgagaaagt tggcctccga    960
acacccagct gaagttgtcg gtgaagaaat tagatccttg tactcctggt ccgacgaaga   1020
caagttgatt aacaactgag gccctgcagg ccagaggaaa ataatatcaa gtgctggaaa   1080
ctttttctct tggaattttt gcaacatcaa gtcatagtca attgaattga cccaatttca   1140
catttaagat tttttttttt tcatccgaca tacatctgta cactaggaag ccctgttttt   1200
ctgaagcagc ttcaaatata tatatttttt acatatttat tatgattcaa tgaacaatct   1260
aattaaatcg aaaacaagaa ccgaaacgcg aataaataat ttatttagat ggtgacaagt   1320
gtataagtcc tcatcgggac agctacgatt tctctttcgg ttttggctga gctactggtt   1380
gctgtgacgc agcggcatta gcgcggcgtt atgagctacc ctcgtggcct gaaagatggc   1440
gggaataaag cggaactaaa aattactgac tgagccatat tgaggtcaat ttgtcaactc   1500
gtcaagtcac gtttggtgga cggccccttt ccaacgaatc gtatatacta acatgcgcgc   1560
gcttcctata tacacatata catatatata tatatatata tgtgtgcgtg tatgtgtaca   1620
cctgtattta atttccttac tcgcgggttt ttcttttttc tcaattcttg gcttcctctt   1680
tctcgagcgg accggatcct ccgcggtgcc ggcagatcta tttaaatggc gcgccgacgt   1740
caggtggcac ttttcgggga aatgtgcgcg gaacccctat ttgtttattt ttctaaatac   1800
attcaaatat gtatccgctc atgagacaat aaccctgata aatgcttcaa taatattgaa   1860
aaaggaagag tatgagtatt caacatttcc gtgtcgccct tattcccttt tttgcggcat   1920
tttgccttcc tgtttttgct cacccagaaa cgctggtgaa agtaaaagat gctgaagatc   1980
agttgggtgc acgagtgggt tacatcgaac tggatctcaa cagcggtaag atccttgaga   2040
gttttcgccc cgaagaacgt tttccaatga tgagcacttt taaagttctg ctatgtggcg   2100
cggtattatc ccgtattgac gccgggcaag agcaactcgg tcgccgcata cactattctc   2160
agaatgactt ggttgagtac tcaccagtca cagaaaagca tcttacggat ggcatgacag   2220
taagagaatt atgcagtgct gccataacca tgagtgataa cactgcggcc aacttacttc   2280
tgacaacgat cggaggaccg aaggagctaa ccgctttttt gcacaacatg ggggatcatg   2340
taactcgcct tgatcgttgg gaaccggagc tgaatgaagc cataccaaac gacgagcgtg   2400
acaccacgat gcctgtagca atggcaacaa cgttgcgcaa actattaact ggcgaactac   2460
ttactctagc ttcccggcaa caattaatag actggatgga ggcggataaa gttgcaggac   2520
cacttctgcg ctcggccctt ccggctggct ggtttattgc tgataaatct ggagccggtg   2580
agcgtgggtc tcgcggtatc attgcagcac tggggccaga tggtaagccc tcccgtatcg   2640
tagttatcta cacgacgggg agtcaggcaa ctatggatga acgaaataga cagatcgctg   2700
```

```
agataggtgc ctcactgatt aagcattggt aactgtcaga ccaagtttac tcatatatac   2760
tttagattga tttaaaactt catttttaat ttaaaaggat ctaggtgaag atcctttttg   2820
ataatctcat gaccaaaatc ccttaacgtg agttttcgtt ccactgagcg tcagaccccg   2880
tagaaaagat caaaggatct tcttgagatc cttttttct gcgcgtaatc tgctgcttgc    2940
aaacaaaaaa accaccgcta ccagcggtgg tttgtttgcc ggatcaagag ctaccaactc   3000
tttttccgaa ggtaactggc ttcagcagag cgcagatacc aaatactgtt cttctagtgt   3060
agccgtagtt aggccaccac ttcaagaact ctgtagcacc gcctacatac ctcgctctgc   3120
taatcctgtt accagtggct gctgccagtg gcgataagtc gtgtcttacc gggttggact   3180
caagacgata gttaccggat aaggcgcagc ggtcgggctg aacggggggt tcgtgcacac   3240
agcccagctt ggagcgaacg acctacaccg aactgagata cctacagcgt gagctatgag   3300
aaagcgccac gcttcccgaa gggagaaagg cggacaggta tccggtaagc ggcagggtcg   3360
gaacaggaga gcgcacgagg gagcttccag ggggaaacgc ctggtatctt tatagtcctg   3420
tcgggtttcg ccacctctga cttgagcgtc gatttttgtg atgctcgtca ggggggcgga   3480
gcctatggaa aaacgccagc aacgcggcct ttttacggtt cctggccttt tgctggcctt   3540
ttgctcacat gttctttcct gcgttatccc ctgattctgt ggataaccgt attaccgcct   3600
ttgagtgagc tgataccgct cgccgcagcc gaacgaccga gcgcagcgag tcagtgagcg   3660
aggaagcgga agagcgccca atacgcaaac cgcctctccc cgcgcgttgg ccgattcatt   3720
aatgcagctg gcacgacagg tttcccgact ggaaagcggg cagtgagcgc aacgcaatta   3780
atgtgagtta gctcactcat taggcacccc aggctttaca ctttatgctt ccggctcgta   3840
tgttgtgtgg aattgtgagc ggataacaat ttcacacagg aaacagctat gaccatgatt   3900
acgccaagct tttctttcc aattttttt ttttcgtcat tataaaaatc attacgaccg     3960
agattcccgg gtaataactg atataattaa attgaagctc taatttgtga gtttagtata   4020
catgcattta cttataatac agttttttag ttttgctggc cgcatcttct caaatatgct   4080
tcccagcctg cttttctgta acgttcaccc tctaccttag catcccttcc ctttgcaaat   4140
agtcctcttc caacaataat aatgtcagat cctgtagaga ccacatcatc cacggttcta   4200
tactgttgac ccaatgcgtc tcccttgtca tctaaaccca caccgggtgt cataatcaac   4260
caatcgtaac cttcatctct tccacccatg tctctttgag caataaagcc gataacaaaa   4320
tctttgtcgc tcttcgcaat gtcaacagta cccttagtat attctccagt agatagggag   4380
cccttgcatg acaattctgc taacatcaaa aggcctctag gttcctttgt tacttcttct   4440
gccgcctgct tcaaaccgct aacaatacct gggcccacca caccgtgtgc attcgtaatg   4500
tctgcccatt ctgctattct gtatacaccc gcagagtact gcaatttgac tgtattacca   4560
atgtcagcaa attttctgtc ttcgaagagt aaaaaattgt acttggcgga taatgccttt   4620
agcggcttaa ctgtgccctc catggaaaaa tcagtcaaga tatccacatg tgtttttagt   4680
aaacaaattt tgggacctaa tgcttcaact aactccagta attccttggt ggtacgaaca   4740
tccaatgaag cacacaagtt tgtttgcttt tcgtgcatga tattaaatag cttggcagca   4800
acaggactag gatgagtagc agcacgttcc ttatatgtag ctttcgacat gatttatctt   4860
cgtttcctgc aggtttttgt tctgtgcagt tgggttaaga atactgggca atttcatgtt   4920
tcttcaacac tacatatgcg tatatatacc aatctaagtc tgtgctcctt ccttcgttct   4980
tccttctgtt cggagattac cgaatcaaaa aaatttcaag gaaaccgaaa tcaaaaaaa    5040
```

```
gaataaaaaa aaaatgatga attgaaaagc ttgcatgcct gcaggtcgac tctagtatac   5100
tccgtctact gtacgataca cttccgctca ggtccttgtc ctttaacgag gccttaccac   5160
tcttttgtta ctctattgat ccagctcagc aaaggcagtg tgatctaaga ttctatcttc   5220
gcgatgtagt aaaactagct agaccgagaa agagactaga aatgcaaaag gcacttctac   5280
aatggctgcc atcattatta tccgatgtga cgctgcattt tttttttttt tttttttttt   5340
tttttttttt tttttttttt tttttttttg tacaaatatc ataaaaaaag agaatctttt   5400
taagcaagga ttttcttaac ttcttcggcg acagcatcac cgacttcggt ggtactgttg   5460
gaaccaccta aatcaccagt tctgatacct gcatccaaaa ccttttttaac tgcatcttca   5520
atggctttac cttcttcagg caagttcaat gacaatttca acatcattgc agcagacaag   5580
atagtggcga tagggttgac cttattcttt ggcaaatctg gagcggaacc atggcatggt   5640
tcgtacaaac caaatgcggt gttcttgtct ggcaaagagg ccaaggacgc agatggcaac   5700
aaacccaagg agcctgggat aacggaggct tcatcggaga tgatatcacc aaacatgttg   5760
ctggtgatta taataccatt taggtgggtt gggttcttaa ctaggatcat ggcggcagaa   5820
tcaatcaatt gatgttgaac tttcaatgta gggaattcgt tcttgatggt ttcctccaca   5880
gtttttctcc ataatcttga agaggccaaa acattagctt tatccaagga ccaaataggc   5940
aatggtggct catgttgtag ggccatgaaa gcggccattc ttgtgattct ttgcacttct   6000
ggaacggtgt attgttcact atcccaagcg acaccatcac catcgtcttc ctttctctta   6060
ccaaagtaaa tacctcccac taattctcta acaacaacga agtcagtacc tttagcaaat   6120
tgtggcttga ttggagataa gtctaaaaga gagtcggatg caaagttaca tggtcttaag   6180
ttggcgtaca attgaagttc tttacggatt tttagtaaac cttgttcagg tctaacacta   6240
ccggtacccc atttaggacc acccacagca cctaacaaaa cggcatcagc cttcttggag   6300
gcttccagcg cctcatctgg aagtggaaca cctgtagcat cgatagcagc accaccaatt   6360
aaatgatttt cgaaatcgaa cttgacattg gaacgaacat cagaaatagc tttaagaacc   6420
ttaatggctt cggctgtgat ttcttgacca acgtggtcac ctggcaaaac gacgatcttc   6480
ttaggggcag acattacaat ggtatatcct tgaaatatat ataaaaaaaa aaaaaaaaaa   6540
aaaaaaaaaa aatgcagctt ctcaatgata ttcgaatacg ctttgaggag atacagccta   6600
atatccgaca aactgtttta cagatttacg atcgtacttg ttacccatca ttgaattttg   6660
aacatccgaa cctgggagtt ttccctgaaa cagatagtat atttgaacct gtataataat   6720
atatagtcta gcgctttacg gaagacaatg tatgtatttc ggttcctgga gaaactattg   6780
catctattgc ataggtaatc ttgcacgtcg catccccggt tcattttctg cgtttccatc   6840
ttgcacttca atagcatatc tttgttaacg aagcatctgt gcttcatttt gtagaacaaa   6900
aatgcaacgc gagagcgcta atttttcaaa caaagaatct gagctgcatt tttacagaac   6960
agaaatgcaa cgcgaaagcg ctattttacc aacgaagaat ctgtgcttca tttttgtaaa   7020
acaaaaatgc aacgcgagag cgctaatttt tcaaacaaag aatctgagct gcatttttac   7080
agaacagaaa tgcaacgcga gagcgctatt ttaccaacaa agaatctata cttctttttt   7140
gttctacaaa aatgcatccc gagagcgcta tttttctaac aaagcatctt agattacttt   7200
ttttctcctt tgtgcgctct ataatgcagt ctcttgataa ctttttgcac tgtaggtccg   7260
ttaaggttag aagaaggcta ctttggtgtc tattttctct tccataaaaa aagcctgact   7320
ccacttcccg cgtttactga ttactagcga agctgcgggt gcattttttc aagataaagg   7380
catccccgat tatattctat accgatgtgg attgcgcata ctttgtgaac agaaagtgat   7440
```

```
agcgttgatg attcttcatt ggtcagaaaa ttatgaacgg tttcttctat tttgtctcta   7500
tatactacgt ataggaaatg tttacatttt cgtattgttt tcgattcact ctatgaatag   7560
ttcttactac aatttttttg tctaaagagt aatactagag ataaacataa aaaatgtaga   7620
ggtcgagttt agatgcaagt tcaaggagcg aaaggtggat gggtaggtta tatagggata   7680
tagcacagag atatatagca aagagatact tttgagcaat gtttgtggaa gcggtattcg   7740
caatatttta gtagctcgtt acagtccggt gcgtttttgg ttttttgaaa gtgcgtcttc   7800
agagcgcttt tggttttcaa aagcgctctg aagttcctat actttctaga gaataggaac   7860
ttcggaatag gaacttcaaa gcgtttccga aaacgagcgc ttccgaaaat gcaacgcgag   7920
ctgcgcacat acagctcact gttcacgtcg cacctatatc tgcgtgttgc ctgtatatat   7980
atatacatga gaagaacggc atagtgcgtg tttatgctta aatgcgtact tatatgcgtc   8040
tatttatgta ggatgaaagg tagtctagta cctcctgtga tattatccca ttccatgcgg   8100
ggtatcgtat gcttccttca gcactaccct ttagctgttc tatatgctgc cactcctcaa   8160
ttggattagt ctcatccttc aatgctatca tttcctttga tattggatca tatgcatagt   8220
accgagaaac tagaggatct cccattaccg acatttgggc gctatacgtg catatgttca   8280
tgtatgtatc tgtatttaaa acacttttgt attatttttc ctcatatatg tgtataggtt   8340
tatacggatg atttaattat tacttcacca ccctttattt caggctgata tcttagcctt   8400
gttactagtc accggtggcg gccgcacctg gtaaaacctc tagtggagta gtagatgtaa   8460
tcaatgaagc ggaagccaaa agaccagagt agaggcctat agaagaaact gcgatacctt   8520
ttgtgatggc taaacaaaca gacatctttt tatatgtttt tacttctgta tatcgtgaag   8580
tagtaagtga taagcgaatt tggctaagaa cgttgtaagt gaacaaggga cctcttttgc   8640
ctttcaaaaa aggattaaat ggagttaatc attgagattt agttttcgtt agattctgta   8700
tccctaaata actcccttac ccgacgggaa ggcacaaaag acttgaataa tagcaaacgg   8760
ccagtagcca agaccaaata atactagagt taactgatgg tcttaaacag gcattacgtg   8820
gtgaactcca agaccaatat acaaaatatc gataagttat tcttgcccac caatttaagg   8880
agcctacatc aggacagtag taccattcct cagagaagag gtatacataa caagaaaatc   8940
gcgtgaacac cttatataac ttagcccgtt attgagctaa aaaaccttgc aaaatttcct   9000
atgaataaga atacttcaga cgtgataaaa atttactttc taactcttct cacgctgccc   9060
ctatctgttc ttccgctcta ccgtgagaaa taaagcatcg agtacggcag ttcgctgtca   9120
ctgaactaaa acaataaggc tagttcgaat gatgaacttg cttgctgtca aacttctgag   9180
ttgccgctga tgtgacactg tgacaataaa ttcaaaccgg ttatagcggt ctcctccggt   9240
accggttctg ccacctccaa tagagctcag taggagtcag aacctctgcg gtggctgtca   9300
gtgactcatc cgcgtttcgt aagttgtgcg cgtgcacatt tcgcccgttc ccgctcatct   9360
tgcagcaggc ggaaattttc atcacgctgt aggacgcaaa aaaaaaataa ttaatcgtac   9420
aagaatcttg gaaaaaaaat tgaaaaattt tgtataaaag ggatgaccta acttgactca   9480
atggctttta cacccagtat ttccctttc cttgtttgtt acaattatag aagcaagaca    9540
aaaacatata gacaacctat tcctaggagt tatatttttt taccctacca gcaatataag   9600
taaaaaactg ttt                                                      9613
```

<210> SEQ ID NO 81
<211> LENGTH: 7938
<212> TYPE: DNA

```
<213> ORGANISM: Artificial
<220> FEATURE:
<223> OTHER INFORMATION: pYZ067DkivDDhADH

<400> SEQUENCE: 81

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctctag tacactctat atttttttat gcctcggtaa tgattttcat    360

tttttttttt ccacctagcg gatgactctt ttttttttctt agcgattggc attatcacat    420

aatgaattat acattatata aagtaatgtg atttcttcga agaatatact aaaaaatgag    480

caggcaagat aaacgaaggc aaagatgaca gagcagaaag ccctagtaaa gcgtattaca    540

aatgaaacca agattcagat tgcgatctct ttaaagggtg gtcccctagc gatagagcac    600

tcgatcttcc cagaaaaaga ggcagaagca gtagcagaac aggccacaca atcgcaagtg    660

attaacgtcc acacaggtat agggtttctg gaccatatga tacatgctct ggccaagcat    720

tccggctggt cgctaatcgt tgagtgcatt ggtgacttac acatagacga ccatcacacc    780

actgaagact gcgggattgc tctcggtcaa gcttttaaag aggccctagg ggccgtgcgt    840

ggagtaaaaa ggtttggatc aggatttgcg cctttggatg aggcactttc cagagcggtg    900

gtagatcttt cgaacaggcc gtacgcagtt gtcgaacttg gtttgcaaag ggagaaagta    960

ggagatctct cttgcgagat gatcccgcat ttcttgaaa gctttgcaga ggctagcaga    1020

attaccctcc acgttgattg tctgcgaggc aagaatgatc atcaccgtag tgagagtgcg   1080

ttcaaggctc ttgcggttgc cataagagaa gccacctcgc ccaatggtac caacgatgtt   1140

ccctccacca aaggtgttct tatgtagtga caccgattat ttaaagctgc agcatacgat   1200

atatatacat gtgtatatat gtatacctat gaatgtcagt aagtatgtat acgaacagta   1260

tgatactgaa gatgacaagg taatgcatca ttctatacgt gtcattctga acgaggcgcg   1320

ctttcctttt ttctttttgc tttttctttt tttttctctt gaactcgacg gatctatgcg   1380

gtgtgaaata ccgcacagat gcgtaaggag aaaataccgc atcaggaaat tgtaagcgtt   1440

aatattttgt taaaattcgc gttaaatttt tgttaaatca gctcattttt taaccaatag   1500

gccgaaatcg gcaaaatccc ttataaatca aaagaataga ccgagatagg gttgagtgtt   1560

gttccagttt ggaacaagag tccactatta aagaacgtgg actccaacgt caaagggcga   1620

aaaaccgtct atcagggcga tggcccacta cgtggccggc ttcacatacg ttgcatacgt   1680

cgatatagat aataatgata atgacagcag gattatcgta atacgtaata gctgaaaatc   1740

tcaaaaatgt gtgggtcatt acgtaaataa tgataggaat gggattcttc tatttttcct   1800

ttttccattc tagcagccgt cgggaaaacg tggcatcctc tctttcgggc tcaattggag   1860

tcacgctgcc gtgagcatcc tctctttcca tatctaacaa ctgagcacgt aaccaatgga   1920

aaagcatgag cttagcgttg ctccaaaaaa gtattggatg gttaatacca tttgtctgtt   1980

ctcttctgac tttgactcct caaaaaaaaa aatctacaat caacagatcg cttcaattac   2040

gccctcacaa aaactttttt ccttcttctt cgcccacgtt aaatttttatc cctcatgttg   2100

tctaacggat ttctgcactt gatttattat aaaaagacaa agacataata cttctctatc   2160

aatttcagtt attgttcttc cttgcgttat tcttctgttc ttctttttct tttgtcatat   2220
```

```
ataaccataa ccaagtaata catattcaaa cacgtgagta tgactgacaa aaaaactctt   2280
aaagacttaa gaaatcgtag ttctgtttac gattcaatgg ttaaatcacc taatcgtgct   2340
atgttgcgtg caactggtat gcaagatgaa gactttgaaa aacctatcgt cggtgtcatt   2400
tcaacttggg ctgaaaacac accttgtaat atccacttac atgactttgg taaactagcc   2460
aaagtcggtg ttaaggaagc tggtgcttgg ccagttcagt tcggaacaat cacggtttct   2520
gatggaatcg ccatgggaac ccaaggaatg cgtttctcct tgacatctcg tgatattatt   2580
gcagattcta ttgaagcagc catgggaggt cataatgcgg atgcttttgt agccattggc   2640
ggttgtgata aaaacatgcc cggttctgtt atcgctatgg ctaacatgga tatcccagcc   2700
atttttgctt acggcggaac aattgcacct ggtaatttag acggcaaaga tatcgattta   2760
gtctctgtct ttgaaggtgt cggccattgg aaccacggcg atatgaccaa agaagaagtt   2820
aaagctttgg aatgtaatgc ttgtcccggt cctggaggct gcggtggtat gtatactgct   2880
aacacaatgg cgacagctat tgaagttttg ggacttagcc ttccgggttc atcttctcac   2940
ccggctgaat ccgcagaaaa gaaagcagat attgaagaag ctggtcgcgc tgttgtcaaa   3000
atgctcgaaa tgggcttaaa accttctgac attttaacgc gtgaagcttt tgaagatgct   3060
attactgtaa ctatggctct gggaggttca accaactcaa cccttcacct cttagctatt   3120
gcccatgctg ctaatgtgga attgacactt gatgatttca atactttcca agaaaaagtt   3180
cctcatttgg ctgatttgaa accttctggt caatatgtat tccaagacct ttacaaggtc   3240
ggaggggtac cagcagttat gaaatatctc cttaaaaatg gcttccttca tggtgaccgt   3300
atcacttgta ctggcaaaac agtcgctgaa aatttgaagg cttttgatga tttaacacct   3360
ggtcaaaagg ttattatgcc gcttgaaaat cctaaacgtg aagatggtcc gctcattatt   3420
ctccatggta acttggctcc agacggtgcc gttgccaaag tttctggtgt aaaagtgcgt   3480
cgtcatgtcg gtcctgctaa ggtctttaat tctgaagaag aagccattga agctgtcttg   3540
aatgatgata ttgttgatgg tgatgttgtt gtcgtacgtt ttgtaggacc aaagggcggt   3600
cctggtatgc ctgaaatgct ttccctttca tcaatgattg ttggtaaagg gcaaggtgaa   3660
aaagttgccc ttctgacaga tggccgcttc tcaggtggta cttatggtct tgtcgtgggt   3720
catatcgctc ctgaagcaca agatggcggt ccaatcgcct acctgcaaac aggagacata   3780
gtcactattg accaagacac taaggaatta cactttgata tctccgatga agagttaaaa   3840
catcgtcaag agaccattga attgccaccg ctctattcac gcggtatcct tggtaaatat   3900
gctcacatcg tttcgtctgc ttctagggga gccgtaacag acttttggaa gcctgaagaa   3960
actggcaaaa aatgttgtcc tggttgctgt ggttaagcgg ccgcgttaat tcaaattaat   4020
tgatatagtt ttttaatgag tattgaatct gtttagaaat aatggaatat tatttttatt   4080
tatttattta tattattggt cggctctttt cttctgaagg tcaatgacaa aatgatatga   4140
aggaaataat gatttctaaa attttacaac gtaagatatt tttacaaaag cctagctcat   4200
cttttgtcat gcactatttt actcacgctt gaaattaacg gccagtccac tgcggagtca   4260
tttcaaagtc atcctaatcg atctatcgtt tttgatagct cattttggag ttcgcgagga   4320
tcccagcttt tgttcccttt agtgagggtt aattgcgcgc ttggcgtaat catggtcata   4380
gctgtttcct gtgtgaaatt gttatccgct cacaattcca cacaacatac gagccggaag   4440
cataaagtgt aaagcctggg gtgcctaatg agtgagctaa ctcacattaa ttgcgttgcg   4500
ctcactgccc gctttccagt cgggaaacct gtcgtgccag ctgcattaat gaatcggcca   4560
```

```
acgcgcgggg agaggcggtt tgcgtattgg gcgctcttcc gcttcctcgc tcactgactc   4620
gctgcgctcg gtcgttcggc tgcggcgagc ggtatcagct cactcaaagg cggtaatacg   4680
gttatccaca gaatcagggg ataacgcagg aaagaacatg tgagcaaaag gccagcaaaa   4740
ggccaggaac cgtaaaaagg ccgcgttgct ggcgtttttc cataggctcc gcccccctga   4800
cgagcatcac aaaaatcgac gctcaagtca gaggtggcga aacccgacag gactataaag   4860
ataccaggcg tttccccctg gaagctccct cgtgcgctct cctgttccga ccctgccgct   4920
taccggatac ctgtccgcct ttctcccttc gggaagcgtg gcgctttctc atagctcacg   4980
ctgtaggtat ctcagttcgg tgtaggtcgt tcgctccaag ctgggctgtg tgcacgaacc   5040
ccccgttcag cccgaccgct gcgccttatc cggtaactat cgtcttgagt ccaacccggt   5100
aagacacgac ttatcgccac tggcagcagc cactggtaac aggattagca gagcgaggta   5160
tgtaggcggt gctacagagt tcttgaagtg gtggcctaac tacggctaca ctagaagaac   5220
agtatttggt atctgcgctc tgctgaagcc agttaccttc ggaaaaagag ttggtagctc   5280
ttgatccggc aaacaaacca ccgctggtag cggtggtttt tttgtttgca agcagcagat   5340
tacgcgcaga aaaaaaggat ctcaagaaga tcctttgatc ttttctacgg ggtctgacgc   5400
tcagtggaac gaaaactcac gttaagggat tttggtcatg agattatcaa aaaggatctt   5460
cacctagatc cttttaaatt aaaaatgaag ttttaaatca atctaaagta tatatgagta   5520
aacttggtct gacagttacc aatgcttaat cagtgaggca cctatctcag cgatctgtct   5580
atttcgttca tccatagttg cctgactccc cgtcgtgtag ataactacga tacgggaggg   5640
cttaccatct ggccccagtg ctgcaatgat accgcgagac ccacgctcac cggctccaga   5700
tttatcagca ataaaccagc cagccggaag ggccgagcgc agaagtggtc ctgcaacttt   5760
atccgcctcc atccagtcta ttaattgttg ccgggaagct agagtaagta gttcgccagt   5820
taatagtttg cgcaacgttg ttgccattgc tacaggcatc gtggtgtcac gctcgtcgtt   5880
tggtatggct tcattcagct ccggttccca acgatcaagg cgagttacat gatcccccat   5940
gttgtgcaaa aaagcggtta gctccttcgg tcctccgatc gttgtcagaa gtaagttggc   6000
cgcagtgtta tcactcatgg ttatggcagc actgcataat tctcttactg tcatgccatc   6060
cgtaagatgc ttttctgtga ctggtgagta ctcaaccaag tcattctgag aatagtgtat   6120
gcggcgaccg agttgctctt gcccggcgtc aatacgggat aataccgcgc cacatagcag   6180
aactttaaaa gtgctcatca ttggaaaacg ttcttcgggg cgaaaactct caaggatctt   6240
accgctgttg agatccagtt cgatgtaacc cactcgtgca cccaactgat cttcagcatc   6300
ttttactttc accagcgttt ctgggtgagc aaaaacagga aggcaaaatg ccgcaaaaaa   6360
gggaataagg gcgacacgga aatgttgaat actcatactc ttcctttttc aatattattg   6420
aagcatttat cagggttatt gtctcatgag cggatacata tttgaatgta tttagaaaaa   6480
taaacaaata ggggttccgc gcacatttcc ccgaaaagtg ccacctgaac gaagcatctg   6540
tgcttcattt tgtagaacaa aaatgcaacg cgagagcgct aatttttcaa acaaagaatc   6600
tgagctgcat ttttacagaa cagaaatgca acgcgaaagc gctattttac caacgaagaa   6660
tctgtgcttc atttttgtaa aacaaaaatg caacgcgaga gcgctaattt ttcaaacaaa   6720
gaatctgagc tgcattttta cagaacagaa atgcaacgcg agagcgctat tttaccaaca   6780
aagaatctat acttcttttt tgttctacaa aaatgcatcc cgagagcgct atttttctaa   6840
caaagcatct tagattactt tttttctcct ttgtgcgctc tataatgcag tctcttgata   6900
actttttgca ctgtaggtcc gttaaggtta gaagaaggct actttggtgt ctattttctc   6960
```

```
ttccataaaa aaagcctgac tccacttccc gcgtttactg attactagcg aagctgcggg   7020

tgcatttttt caagataaag gcatccccga ttatattcta taccgatgtg gattgcgcat   7080

actttgtgaa cagaaagtga tagcgttgat gattcttcat tggtcagaaa attatgaacg   7140

gtttcttcta ttttgtctct atatactacg tataggaaat gtttacattt tcgtattgtt   7200

ttcgattcac tctatgaata gttcttacta caattttttt gtctaaagag taatactaga   7260

gataaacata aaaaatgtag aggtcgagtt tagatgcaag ttcaaggagc gaaaggtgga   7320

tgggtaggtt atatagggat atagcacaga gatatatagc aaagagatac ttttgagcaa   7380

tgtttgtgga agcggtattc gcaatatttt agtagctcgt tacagtccgg tgcgtttttg   7440

gtttttgaa agtgcgtctt cagagcgctt ttggttttca aaagcgctct gaagttccta   7500

tactttctag agaataggaa cttcggaata ggaacttcaa agcgtttccg aaaacgagcg   7560

cttccgaaaa tgcaacgcga gctgcgcaca tacagctcac tgttcacgtc gcacctatat   7620

ctgcgtgttg cctgtatata tatatacatg agaagaacgg catagtgcgt gtttatgctt   7680

aaatgcgtac ttatatgcgt ctatttatgt aggatgaaag gtagtctagt acctcctgtg   7740

atattatccc attccatgcg gggtatcgta tgcttccttc agcactaccc tttagctgtt   7800

ctatatgctg ccactcctca attggattag tctcatcctt caatgctatc atttcctttg   7860

atattggatc atactaagaa accattatta tcatgacatt aacctataaa aataggcgta   7920

tcacgaggcc ctttcgtc                                                 7938
```

<210> SEQ ID NO 82
<211> LENGTH: 9585
<212> TYPE: DNA
<213> ORGANISM: Artificial
<220> FEATURE:
<223> OTHER INFORMATION: pHR81-ILV5p-R8B2y2

<400> SEQUENCE: 82

```
ggccgcacct ggtaaaacct ctagtggagt agtagatgta atcaatgaag cggaagccaa     60

aagaccagag tagaggccta tagaagaaac tgcgatacct tttgtgatgg ctaaacaaac    120

agacatcttt ttatatgttt ttacttctgt atatcgtgaa gtagtaagtg ataagcgaat    180

ttggctaaga acgttgtaag tgaacaaggg acctcttttg cctttcaaaa aaggattaaa    240

tggagttaat cattgagatt tagttttcgt tagattctgt atccctaaat aactccctta    300

cccgacggga aggcacaaaa gacttgaata atagcaaacg gccagtagcc aagaccaaat    360

aatactagag ttaactgatg gtcttaaaca ggcattacgt ggtgaactcc aagaccaata    420

tacaaaatat cgataagtta ttcttgccca ccaatttaag gagcctacat caggacagta    480

gtaccattcc tcagagaaga ggtatacata acaagaaaat cgcgtgaaca ccttatataa    540

cttagcccgt tattgagcta aaaaaccttg caaaatttcc tatgaataag aatacttcag    600

acgtgataaa aatttacttt ctaactcttc tcacgctgcc cctatctgtt cttccgctct    660

accgtgagaa ataaagcatc gagtacggca gttcgctgtc actgaactaa aacaataagg    720

ctagttcgaa tgatgaactt gcttgctgtc aaacttctga gttgccgctg atgtgacact    780

gtgacaataa attcaaaccg gttatagcgg tctcctccgg taccggttct gccacctcca    840

atagagctca gtaggagtca gaacctctgc ggtggctgtc agtgactcat ccgcgtttcg    900

taagttgtgc gcgtgcacat ttcgcccgtt cccgctcatc ttgcagcagg cgaaattttc    960

atcacgctgt aggacgcaaa aaaaaaataa ttaatcgtac aagaatcttg gaaaaaaaat   1020
```

```
tgaaaaattt tgtataaaag ggatgaccta acttgactca atggctttta cacccagtat   1080
tttccctttc cttgtttgtt acaattatag aagcaagaca aaaacatata gacaacctat   1140
tcctaggagt tatatttttt taccctacca gcaatataag taaaaaactg tttaaacagt   1200
atgaaggttt tctacgacaa ggattgtgac ttgtctatca ttcaaggtaa aaaggtcgcc   1260
atcatcggtt ttggttccca aggtcacgct caagccttga acttaaagga ctctggtgtc   1320
gatgttaccg tcggtctacc aaagggtttc gctgacgttg ccaaggccga agctcacggt   1380
ttcaaggtta ctgacgtcgc cgctgccgtt gctggtgctg atttggtcat gatcctaatt   1440
ccagacgaat tccaatccca attgtacaaa aacgaaatcg aaccaaacat caaaaagggt   1500
gccactttgg ctttctccca cggtttcgct atccactaca accaagttgt tccaagagct   1560
gacttggacg ttatcatgat tgctcctaag gctccaggtc ataccgttag atctgaattc   1620
gtcaagggtg gtggtatccc agacttgatt gctgtttacc aagacgtttc tggtaatgcc   1680
aaaaacgtcg ctttgtccta cgctgccggt gttggtggtg gtcgtactgg tatcatcgaa   1740
actaccttca aggacgaaac cgaaaccgac ttattcggtg aacaagctgt tttgtgtggt   1800
ggtaccgtcg aattggtcaa ggctggtttt gaaactttgg tcgaagctgg ttacgctcca   1860
gaaatggctt acttcgaatg tttacacgaa ttgaagttga ttgttgattt gatgtacgaa   1920
ggtggtattg ctaacatgaa ctactctatc tctaacaacg ctgaatacgg tgaatacgtt   1980
actggtccag aagtcattaa cgccgaatct agacaagcta tgagaaatgc tttgaagaga   2040
attcaagatg gtgaattcgc taagatgttc atctctgaag gtgctaccgg ttacccttct   2100
atgactgcta agcgtagaaa caacgctgct cacggtatcg aaatcatcgg tgaacaacta   2160
agagctatga tgccatggat tggtgctaac aagatcgtcg ataagagaaa aaactgaagg   2220
ccctgcaggc cagaggaaaa taatatcaag tgctggaaac tttttctctt ggaatttttg   2280
caacatcaag tcatagtcaa ttgaattgac ccaatttcac atttaagatt tttttttttt   2340
catccgacat acatctgtac actaggaagc cctgtttttc tgaagcagct tcaaatatat   2400
atattttta catatttatt atgattcaat gaacaatcta attaaatcga aaacaagaac   2460
cgaaacgcga ataaataatt tatttagatg gtgacaagtg tataagtcct catcgggaca   2520
gctacgattt ctctttcggt tttggctgag ctactggttg ctgtgacgca gcggcattag   2580
cgcggcgtta tgagctaccc tcgtggcctg aaagatggcg ggaataaagc ggaactaaaa   2640
attactgact gagccatatt gaggtcaatt tgtcaactcg tcaagtcacg tttggtggac   2700
ggcccctttc caacgaatcg tatatactaa catgcgcgcg cttcctatat acacatatac   2760
atatatatat atatatatgt gtgcgtgtat gtgtacacct gtatttaatt tccttactcg   2820
cgggtttttc ttttttctca attcttggct tcctctttct cgagcggacc ggatcctccg   2880
cggtgccggc agatctattt aaatggcgcg ccgacgtcag gtggcacttt tcggggaaat   2940
gtgcgcggaa cccctatttg tttatttttc taaatacatt caaatatgta tccgctcatg   3000
agacaataac cctgataaat gcttcaataa tattgaaaaa ggaagagtat gagtattcaa   3060
catttccgtg tcgcccttat tccctttttt gcggcatttt gccttcctgt ttttgctcac   3120
ccagaaacgc tggtgaaagt aaaagatgct gaagatcagt tgggtgcacg agtgggttac   3180
atcgaactgg atctcaacag cggtaagatc cttgagagtt ttcgccccga agaacgtttt   3240
ccaatgatga gcacttttaa agttctgcta tgtggcgcgg tattatcccg tattgacgcc   3300
gggcaagagc aactcggtcg ccgcatacac tattctcaga atgacttggt tgagtactca   3360
ccagtcacag aaaagcatct tacggatggc atgacagtaa gagaattatg cagtgctgcc   3420
```

```
ataaccatga gtgataacac tgcggccaac ttacttctga caacgatcgg aggaccgaag   3480
gagctaaccg ctttttgca caacatgggg gatcatgtaa ctcgccttga tcgttgggaa   3540
ccggagctga atgaagccat accaaacgac gagcgtgaca ccacgatgcc tgtagcaatg   3600
gcaacaacgt tgcgcaaact attaactggc gaactactta ctctagcttc ccggcaacaa   3660
ttaatagact ggatggaggc ggataaagtt gcaggaccac ttctgcgctc ggcccttccg   3720
gctggctggt ttattgctga taaatctgga gccggtgagc gtggttctcg cggtatcatt   3780
gcagcactgg ggccagatgg taagccctcc cgtatcgtag ttatctacac gacggggagt   3840
caggcaacta tggatgaacg aaatagacag atcgctgaga taggtgcctc actgattaag   3900
cattggtaac tgtcagacca agtttactca tatatacttt agattgattt aaaacttcat   3960
ttttaattta aaaggatcta ggtgaagatc ctttttgata atctcatgac caaaatccct   4020
taacgtgagt tttcgttcca ctgagcgtca gaccccgtag aaaagatcaa aggatcttct   4080
tgagatcctt tttttctgcg cgtaatctgc tgcttgcaaa caaaaaaacc accgctacca   4140
gcggtggttt gtttgccgga tcaagagcta ccaactcttt ttccgaaggt aactggcttc   4200
agcagagcgc agataccaaa tactgttctt ctagtgtagc cgtagttagg ccaccacttc   4260
aagaactctg tagcaccgcc tacatacctc gctctgctaa tcctgttacc agtggctgct   4320
gccagtggcg ataagtcgtg tcttaccggg ttggactcaa gacgatagtt accggataag   4380
gcgcagcggt cgggctgaac ggggggttcg tgcacacagc ccagcttgga gcgaacgacc   4440
tacaccgaac tgagatacct acagcgtgag ctatgagaaa gcgccacgct tcccgaaggg   4500
agaaaggcgg acaggtatcc ggtaagcggc agggtcggaa caggagagcg cacgagggag   4560
cttccagggg gaaacgcctg gtatctttat agtcctgtcg ggtttcgcca cctctgactt   4620
gagcgtcgat ttttgtgatg ctcgtcaggg gggcggagcc tatggaaaaa cgccagcaac   4680
gcggcctttt tacggttcct ggccttttgc tggccttttg ctcacatgtt ctttcctgcg   4740
ttatcccctg attctgtgga taaccgtatt accgcctttg agtgagctga taccgctcgc   4800
cgcagccgaa cgaccgagcg cagcgagtca gtgagcgagg aagcggaaga gcgcccaata   4860
cgcaaaccgc ctctccccgc gcgttggccg attcattaat gcagctggca cgacaggttt   4920
cccgactgga aagcgggcag tgagcgcaac gcaattaatg tgagttagct cactcattag   4980
gcaccccagg ctttacactt tatgcttccg gctcgtatgt tgtgtggaat tgtgagcgga   5040
taacaatttc acacaggaaa cagctatgac catgattacg ccaagctttt tctttccaat   5100
ttttttttt tcgtcattat aaaaatcatt acgaccgaga ttcccgggta ataactgata   5160
taattaaatt gaagctctaa tttgtgagtt tagtatacat gcatttactt ataatacagt   5220
tttttagttt tgctggccgc atcttctcaa atatgcttcc cagcctgctt ttctgtaacg   5280
ttcaccctct accttagcat cccttccctt tgcaaatagt cctcttccaa caataataat   5340
gtcagatcct gtagagacaa catcatccac ggttctatac tgttgaccca atgcatctcc   5400
cttgtcatct aaacccacac cgggtgtcat aatcaaccaa tcgtaacctt catctcttcc   5460
acccatgtct ctttgagcaa taaagccgat aacaaaatct ttgtcgctct tcgcaatgtc   5520
aacagtaccc ttagtatatt ctccagtaga tagggagccc ttgcatgaca attctgctaa   5580
catcaaaagg cctctaggtt cctttgttac ttcttctgcc gcctgcttca aaccgctaac   5640
aatacctggg cccaccacac cgtgtgcatt cgtaatgtct gcccattctg ctattctgta   5700
tacacccgca gagtactgca atttgactgt attaccaatg tcagcaaatt ttctgtcttc   5760
```

-continued

```
gaagagtaaa aaattgtact tggcggataa tgcctttagc ggcttaactg tgccctccat   5820
ggaaaaatca gtcaagatat ccacatgtgt ttttagtaaa caaattttgg gacctaatgc   5880
ttcaactaac tccagtaatt ccttggtggt acgaacatcc aatgaagcac acaagtttgt   5940
ttgcttttcg tgcatgatat taaatagctt ggcagcaaca ggactaggat gagtagcagc   6000
acgttcctta tatgtagctt tcgacatgat ttatcttcgt ttcctgcagg tttttgttct   6060
gtgcagttgg gttaagaata ctgggcaatt tcatgtttct tcaacactac atatgcgtat   6120
atataccaat ctaagtctgt gctccttcct tcgttcttcc ttctgttcgg agattaccga   6180
atcaaaaaaa tttcaaggaa accgaaatca aaaaaaagaa taaaaaaaaa atgatgaatt   6240
gaaaagcttg catgcctgca ggtcgactct agtatactcc gtctactgta cgatacactt   6300
ccgctcaggt ccttgtcctt taacgaggcc ttaccactct tttgttactc tattgatcca   6360
gctcagcaaa ggcagtgtga tctaagattc tatcttcgcg atgtagtaaa actagctaga   6420
ccgagaaaga gactagaaat gcaaaaggca cttctacaat ggctgccatc attattatcc   6480
gatgtgacgc tgcatttttt tttttttttt tttttttttt tttttttttt tttttttttt   6540
tttttgtac aaatatcata aaaaaagaga atctttttaa gcaaggattt tcttaacttc   6600
ttcggcgaca gcatcaccga cttcggtggt actgttggaa ccacctaaat caccagttct   6660
gatacctgca tccaaaacct ttttaactgc atcttcaatg gctttacctt cttcaggcaa   6720
gttcaatgac aatttcaaca tcattgcagc agacaagata gtggcgatag ggttgacctt   6780
attctttggc aaatctggag cggaaccatg gcatggttcg tacaaaccaa atgcggtgtt   6840
cttgtctggc aaagaggcca aggacgcaga tggcaacaaa cccaaggagc ctgggataac   6900
ggaggcttca tcggagatga tatcaccaaa catgttgctg gtgattataa taccatttag   6960
gtgggttggg ttcttaacta ggatcatggc ggcagaatca atcaattgat gttgaacttt   7020
caatgtaggg aattcgttct tgatggtttc ctccacagtt tttctccata atcttgaaga   7080
ggccaaaaca ttagctttat ccaaggacca aataggcaat ggtggctcat gttgtagggc   7140
catgaaagcg gccattcttg tgattctttg cacttctgga acggtgtatt gttcactatc   7200
ccaagcgaca ccatcaccat cgtcttcctt tctcttacca aagtaaatac ctcccactaa   7260
ttctctaaca acaacgaagt cagtaccttt agcaaattgt ggcttgattg gagataagtc   7320
taaaagagag tcggatgcaa agttacatgg tcttaagttg gcgtacaatt gaagttcttt   7380
acggattttt agtaaacctt gttcaggtct aacactaccg gtaccccatt taggaccacc   7440
cacagcacct aacaaaacgg catcagcctt cttggaggct tccagcgcct catctggaag   7500
tggaacacct gtagcatcga tagcagcacc accaattaaa tgattttcga aatcgaactt   7560
gacattggaa cgaacatcag aaatagcttt aagaacctta atggcttcgg ctgtgatttc   7620
ttgaccaacg tggtcacctg gcaaaacgac gatcttctta ggggcagaca ttacaatggt   7680
atatccttga aatatatata aaaaaaaaaa aaaaaaaaaa aaaaaaaaat gcagcttctc   7740
aatgatattc gaatacgctt tgaggagata cagcctaata tccgacaaac tgttttacag   7800
atttacgatc gtacttgtta cccatcattg aattttgaac atccgaacct gggagttttc   7860
cctgaaacag atagtatatt tgaacctgta taataatata tagtctagcg ctttacggaa   7920
gacaatgtat gtatttcggt tcctggagaa actattgcat ctattgcata ggtaatcttg   7980
cacgtcgcat ccccggttca ttttctgcgt ttccatcttg cacttcaata gcatatcttt   8040
gttaacgaag catctgtgct tcattttgta gaacaaaaat gcaacgcgag agcgctaatt   8100
tttcaaacaa agaatctgag ctgcattttt acagaacaga aatgcaacgc gaaagcgcta   8160
```

ttttaccaac gaagaatctg tgcttcattt ttgtaaaaca aaaatgcaac gcgagagcgc 8220
taatttttca aacaaagaat ctgagctgca tttttacaga acagaaatgc aacgcgagag 8280
cgctatttta ccaacaaaga atctatactt cttttttgtt ctacaaaaat gcatcccgag 8340
agcgctattt ttctaacaaa gcatcttaga ttactttttt tctcctttgt gcgctctata 8400
atgcagtctc ttgataactt tttgcactgt aggtccgtta aggttagaag aaggctactt 8460
tggtgtctat tttctcttcc ataaaaaaag cctgactcca cttcccgcgt ttactgatta 8520
ctagcgaagc tgcgggtgca tttttcaag ataaaggcat ccccgattat attctatacc 8580
gatgtggatt gcgcatactt tgtgaacaga aagtgatagc gttgatgatt cttcattggt 8640
cagaaaatta tgaacggttt cttctatttt gtctctatat actacgtata ggaaatgttt 8700
acattttcgt attgttttcg attcactcta tgaatagttc ttactacaat ttttttgtct 8760
aaagagtaat actagagata aacataaaaa atgtagaggt cgagtttaga tgcaagttca 8820
aggagcgaaa ggtggatggg taggttatat agggatatag cacagagata tatagcaaag 8880
agatactttt gagcaatgtt tgtggaagcg gtattcgcaa tattttagta gctcgttaca 8940
gtccggtgcg tttttggttt tttgaaagtg cgtcttcaga gcgcttttgg ttttcaaaag 9000
cgctctgaag ttcctatact ttctagagaa taggaacttc ggaataggaa cttcaaagcg 9060
tttccgaaaa cgagcgcttc cgaaaatgca acgcgagctg cgcacataca gctcactgtt 9120
cacgtcgcac ctatatctgc gtgttgcctg tatatatata tacatgagaa gaacggcata 9180
gtgcgtgttt atgcttaaat gcgtacttat atgcgtctat ttatgtagga tgaaaggtag 9240
tctagtacct cctgtgatat tatcccattc catgcggggt atcgtatgct tccttcagca 9300 ctaccettta gctgttctat atgctgccac tcctcaattg gattagtctc atccttcaat 9360
gctatcattt cctttgatat tggatcatat gcatagtacc gagaaactag aggatctccc 9420
attaccgaca tttgggcgct atacgtgcat atgttcatgt atgtatctgt atttaaaaca 9480
cttttgtatt atttttcctc atatatgtgt ataggtttat acggatgatt taattattac 9540
ttcaccaccc tttatttcag gctgatatct tagccttgtt actag 9585

<210> SEQ ID NO 83
<211> LENGTH: 13022
<212> TYPE: DNA
<213> ORGANISM: Artificial
<220> FEATURE:
<223> OTHER INFORMATION: pLA84

<400> SEQUENCE: 83
ccagcttttg ttccctttag tgagggttaa ttgcgcgctt ggcgtaatca tggtcatagc 60
tgtttcctgt gtgaaattgt tatccgctca caattccaca caacatacga gccggaagca 120
taaagtgtaa agcctggggt gcctaatgag tgagctaact cacattaatt gcgttgcgct 180
cactgcccgc tttccagtcg ggaaacctgt cgtgccagct gcattaatga atcggccaac 240
gcgcggggag aggcggtttg cgtattgggc gctcttccgc ttcctcgctc actgactcgc 300
tgcgctcggt cgttcggctg cggcgagcgg tatcagctca ctcaaaggcg gtaatacggt 360
tatccacaga atcaggggat aacgcaggaa agaacatgtg agcaaaaggc cagcaaaagg 420
ccaggaaccg taaaaaggcc gcgttgctgg cgtttttcca taggctccgc ccccctgacg 480
agcatcacaa aaatcgacgc tcaagtcaga ggtggcgaaa cccgacagga ctataaagat 540
accaggcgtt tccccctgga agctccctcg tgcgctctcc tgttccgacc ctgccgctta 600

-continued

```
ccggatacct gtccgccttt ctcccttcgg gaagcgtggc gctttctcat agctcacgct    660
gtaggtatct cagttcggtg taggtcgttc gctccaagct gggctgtgtg cacgaacccc    720
ccgttcagcc cgaccgctgc gccttatccg gtaactatcg tcttgagtcc aacccggtaa    780
gacacgactt atcgccactg gcagcagcca ctggtaacag gattagcaga gcgaggtatg    840
taggcggtgc tacagagttc ttgaagtggt ggcctaacta cggctacact agaagaacag    900
tatttggtat ctgcgctctg ctgaagccag ttaccttcgg aaaaagagtt ggtagctctt    960
gatccggcaa acaaaccacc gctggtagcg gtggtttttt tgtttgcaag cagcagatta   1020
cgcgcagaaa aaaaggatct caagaagatc ctttgatctt ttctacgggg tctgacgctc   1080
agtggaacga aaactcacgt taagggattt tggtcatgag attatcaaaa aggatcttca   1140
cctagatcct tttaaattaa aaatgaagtt ttaaatcaat ctaaagtata tatgagtaaa   1200
cttggtctga cagttaccaa tgcttaatca gtgaggcacc tatctcagcg atctgtctat   1260
ttcgttcatc catagttgcc tgactccccg tcgtgtagat aactacgata cgggagggct   1320
taccatctgg ccccagtgct gcaatgatac cgcgagaccc acgctcaccg gctccagatt   1380
tatcagcaat aaaccagcca gccggaaggg ccgagcgcag aagtggtcct gcaactttat   1440
ccgcctccat ccagtctatt aattgttgcc gggaagctag agtaagtagt tcgccagtta   1500
atagtttgcg caacgttgtt gccattgcta caggcatcgt ggtgtcacgc tcgtcgtttg   1560
gtatggcttc attcagctcc ggttcccaac gatcaaggcg agttacatga tcccccatgt   1620
tgtgcaaaaa agcggttagc tccttcggtc ctccgatcgt tgtcagaagt aagttggccg   1680
cagtgttatc actcatggtt atggcagcac tgcataattc tcttactgtc atgccatccg   1740
taagatgctt ttctgtgact ggtgagtact caaccaagtc attctgagaa tagtgtatgc   1800
ggcgaccgag ttgctcttgc ccggcgtcaa tacgggataa taccgcgcca catagcagaa   1860
ctttaaaagt gctcatcatt ggaaaacgtt cttcggggcg aaaactctca aggatcttac   1920
cgctgttgag atccagttcg atgtaaccca ctcgtgcacc caactgatct tcagcatctt   1980
ttactttcac cagcgtttct gggtgagcaa aaacaggaag gcaaaatgcc gcaaaaaagg   2040
gaataagggc gacacggaaa tgttgaatac tcatactctt cctttttcaa tattattgaa   2100
gcatttatca gggttattgt ctcatgagcg gatacatatt tgaatgtatt tagaaaaata   2160
aacaaatagg ggttccgcgc acatttcccc gaaaagtgcc acctgaacga agcatctgtg   2220
cttcattttg tagaacaaaa atgcaacgcg agagcgctaa tttttcaaac aaagaatctg   2280
agctgcattt ttacagaaca gaaatgcaac gcgaaagcgc tattttacca acgaagaatc   2340
tgtgcttcat ttttgtaaaa caaaaatgca acgcgagagc gctaattttt caaacaaaga   2400
atctgagctg catttttaca gaacagaaat gcaacgcgag agcgctattt taccaacaaa   2460
gaatctatac ttcttttttg ttctacaaaa atgcatcccg agagcgctat ttttctaaca   2520
aagcatctta gattactttt tttctccttt gtgcgctcta taatgcagtc tcttgataac   2580
tttttgcact gtaggtccgt taaggttaga agaaggctac tttggtgtct attttctctt   2640
ccataaaaaa agcctgactc cacttcccgc gtttactgat tactagcgaa gctgcgggtg   2700
catttttca agataaaggc atccccgatt atattctata ccgatgtgga ttgcgcatac   2760
tttgtgaaca gaaagtgata gcgttgatga ttcttcattg gtcagaaaat tatgaacggt   2820
ttcttctatt ttgtctctat atactacgta taggaaatgt ttacattttc gtattgtttt   2880
cgattcactc tatgaatagt tcttactaca attttttgt ctaaagagta atactagaga   2940
taaacataaa aaatgtagag gtcgagttta gatgcaagtt caaggagcga aaggtggatg   3000
```

```
ggtaggttat atagggatat agcacagaga tatatagcaa agagatactt ttgagcaatg   3060

tttgtggaag cggtattcgc aatattttag tagctcgtta cagtccggtg cgtttttggt   3120

tttttgaaag tgcgtcttca gagcgctttt ggttttcaaa agcgctctga agttcctata   3180

ctttctagag aataggaact tcggaatagg aacttcaaag cgtttccgaa aacgagcgct   3240

tccgaaaatg caacgcgagc tgcgcacata cagctcactg ttcacgtcgc acctatatct   3300

gcgtgttgcc tgtatatata tatacatgag aagaacggca tagtgcgtgt ttatgcttaa   3360

atgcgtactt atatgcgtct atttatgtag gatgaaaggt agtctagtac ctcctgtgat   3420

attatcccat tccatgcggg gtatcgtatg cttccttcag cactaccctt tagctgttct   3480

atatgctgcc actcctcaat tggattagtc tcatccttca atgctatcat ttcctttgat   3540

attggatcat actaagaaac cattattatc atgacattaa cctataaaaa taggcgtatc   3600

acgaggccct ttcgtctcgc gcgtttcggt gatgacggtg aaaacctctg acacatgcag   3660

ctcccggaga cggtcacagc ttgtctgtaa gcggatgccg ggagcagaca agcccgtcag   3720

ggcgcgtcag cgggtgttgg cgggtgtcgg ggctggctta actatgcggc atcagagcag   3780

attgtactga gagtgcacca taaattcccg ttttaagagc ttggtgagcg ctaggagtca   3840

ctgccaggta tcgtttgaac acggcattag tcagggaagt cataacacag tcctttcccg   3900

caattttctt tttctattac tcttggcctc ctctagtaca ctctatattt ttttatgcct   3960

cggtaatgat tttcattttt ttttttccac ctagcggatg actctttttt tttcttagcg   4020

attggcatta tcacataatg aattatacat tatataaagt aatgtgattt cttcgaagaa   4080

tatactaaaa aatgagcagg caagataaac gaaggcaaag atgacagagc agaaagccct   4140

agtaaagcgt attacaaatg aaaccaagat tcagattgcg atctctttaa agggtggtcc   4200

cctagcgata gagcactcga tcttcccaga aaaagaggca gaagcagtag cagaacaggc   4260

cacacaatcg caagtgatta acgtccacac aggtataggg tttctggacc atatgataca   4320

tgctctggcc aagcattccg gctggtcgct aatcgttgag tgcattggtg acttacacat   4380

agacgaccat cacaccactg aagactgcgg gattgctctc ggtcaagctt ttaaagaggc   4440

cctaggggcc gtgcgtggag taaaaaggtt tggatcagga tttgcgcctt tggatgaggc   4500

actttccaga gcggtggtag atctttcgaa caggccgtac gcagttgtcg aacttggttt   4560

gcaaagggag aaagtaggag atctctcttg cgagatgatc ccgcattttc ttgaaagctt   4620

tgcagaggct agcagaatta ccctccacgt tgattgtctg cgaggcaaga atgatcatca   4680

ccgtagtgag agtgcgttca aggctcttgc ggttgccata agagaagcca cctcgcccaa   4740

tggtaccaac gatgttccct ccaccaaagg tgttcttatg tagtgacacc gattatttaa   4800

agctgcagca tacgatatat atacatgtgt atatatgtat acctatgaat gtcagtaagt   4860

atgtatacga acagtatgat actgaagatg acaaggtaat gcatcattct atacgtgtca   4920

ttctgaacga ggcgcgcttt ccttttttct ttttgctttt tctttttttt tctcttgaac   4980

tcgacggatc tatgcggtgt gaaataccgc acagatgcgt aaggagaaaa taccgcatca   5040

ggaaattgta agcgttaata ttttgttaaa attcgcgtta aatttttgtt aaatcagctc   5100

atttttaac caataggccg aaatcggcaa aatcccttat aaatcaaaag aatagaccga   5160

gatagggttg agtgttgttc cagtttggaa caagagtcca ctattaaaga acgtggactc   5220

caacgtcaaa gggcgaaaaa ccgtctatca gggcgatggc ccactacgtg gccggcttca   5280

catacgttgc atacgtcgat atagataata atgataatga cagcaggatt atcgtaatac   5340
```

```
gtaatagctg aaaatctcaa aaatgtgtgg gtcattacgt aaataatgat aggaatggga   5400
ttcttctatt tttcctttt ccattctagc agccgtcggg aaaacgtggc atcctctctt   5460
tcgggctcaa ttggagtcac gctgccgtga gcatcctctc tttccatatc taacaactga   5520
gcacgtaacc aatggaaaag catgagctta gcgttgctcc aaaaaagtat tggatggtta   5580
ataccatttg tctgttctct tctgactttg actcctcaaa aaaaaaaatc tacaatcaac   5640
agatcgcttc aattacgccc tcacaaaaac ttttttcctt cttcttcgcc cacgttaaat   5700
tttatccctc atgttgtcta acggatttct gcacttgatt tattataaaa agacaaagac   5760
ataatacttc tctatcaatt tcagttattg ttcttccttg cgttattctt ctgttcttct   5820
ttttcttttg tcatatataa ccataaccaa gtaatacata ttcaaacacg tgagtatgac   5880
tgacaaaaaa actcttaaag acttaagaaa tcgtagttct gtttacgatt caatggttaa   5940
atcacctaat cgtgctatgt tgcgtgcaac tggtatgcaa gatgaagact ttgaaaaacc   6000
tatcgtcggt gtcatttcaa cttgggctga aaacacacct tgtaatatcc acttacatga   6060
ctttggtaaa ctagccaaag tcggtgttaa ggaagctggt gcttggccag ttcagttcgg   6120
aacaatcacg gtttctgatg gaatcgccat gggaacccaa ggaatgcgtt tctccttgac   6180
atctcgtgat attattgcag attctattga agcagccatg ggaggtcata atgcggatgc   6240
ttttgtagcc attggcggtt gtgataaaaa catgcccggt tctgttatcg ctatggctaa   6300
catggatatc ccagccattt ttgcttacgg cggaacaatt gcacctggta atttagacgg   6360
caaagatatc gatttagtct ctgtctttga aggtgtcggc cattggaacc acggcgatat   6420
gaccaaagaa gaagttaaag ctttggaatg taatgcttgt cccggtcctg gaggctgcgg   6480
tggtatgtat actgctaaca caatggcgac agctattgaa gttttgggac ttagccttcc   6540
gggttcatct tctcacccgg ctgaatccgc agaaaagaaa gcagatattg aagaagctgg   6600
tcgcgctgtt gtcaaaatgc tcgaaatggg cttaaaacct tctgacattt taacgcgtga   6660
agcttttgaa gatgctatta ctgtaactat ggctctggga ggttcaacca actcaaccct   6720
tcacctctta gctattgccc atgctgctaa tgtggaattg acacttgatg atttcaatac   6780
tttccaagaa aaagttcctc atttggctga tttgaaacct tctggtcaat atgtattcca   6840
agacctttac aaggtcggag ggtaccagc agttatgaaa tatctcctta aaaatggctt   6900
ccttcatggt gaccgtatca cttgtactgg caaaacagtc gctgaaaatt tgaaggcttt   6960
tgatgattta acacctggtc aaaaggttat tatgccgctt gaaaatccta aacgtgaaga   7020
tggtccgctc attattctcc atggtaactt ggctccagac ggtgccgttg ccaaagtttc   7080
tggtgtaaaa gtgcgtcgtc atgtcggtcc tgctaaggtc tttaattctg aagaagaagc   7140
cattgaagct gtcttgaatg atgatattgt tgatggtgat gttgttgtcg tacgttttgt   7200
aggaccaaag ggcggtcctg gtatgcctga aatgctttcc ctttcatcaa tgattgttgg   7260
taaagggcaa ggtgaaaaag ttgcccttct gacagatggc cgcttctcag gtggtactta   7320
tggtcttgtc gtgggtcata tcgctcctga agcacaagat ggcggtccaa tcgcctacct   7380
gcaaacagga gacatagtca ctattgacca agacactaag gaattacact ttgatatctc   7440
cgatgaagag ttaaaacatc gtcaagagac cattgaattg ccaccgctct attcacgcgg   7500
tatccttggt aaatatgctc acatcgtttc gtctgcttct aggggagccg taacagactt   7560
ttggaagcct gaagaaactg gcaaaaaatg ttgtcctggt tgctgtggtt aagcggccgc   7620
gttaattcaa attaattgat atagtttttt aatgagtatt gaatctgttt agaaataatg   7680
gaatattatt tttatttatt tatttatatt attggtcggc tcttttcttc tgaaggtcaa   7740
```

```
tgacaaaatg atatgaagga aataatgatt tctaaaattt tacaacgtaa gatattttta   7800
caaaagccta gctcatcttt tgtcatgcac tattttactc acgcttgaaa ttaacggcca   7860
gtccactgcg gagtcatttc aaagtcatcc taatcgatct atcgtttttg atagctcatt   7920
ttggagttcg cgaggatcca ctagttctag agcggccgct ctagaactag taccacaggt   7980
gttgtcctct gaggacataa aatacacacc gagattcatc aactcattgc tggagttagc   8040
atatctacaa ttgggtgaaa tggggagcga tttgcaggca tttgctcggc atgccggtag   8100
aggtgtggtc aataagagcg acctcatgct atacctgaga aagcaacctg acctacagga   8160
aagagttact caagaataag aattttcgtt ttaaaaccta agagtcactt taaaatttgt   8220
atacacttat ttttttata acttatttaa taataaaaat cataaatcat aagaaattcg   8280
cttactctta attaatcaag cctccatcga aatgatgact tttagtgctt gagtagacgc   8340
agcttggcca aaagtttcat atgcgtccaa gatctggtcc aggctgaatc tatgtgttat   8400
caatctagat ggatctagct tgtgactttg aacagttttc agtaacatcg ggtggtagc   8460
cgtgtcaacc aaccttgtag taatcgtgac attatgggac cataaacttt caagatgcaa   8520
atcaactttg ctaccgtgaa cgccgacatt agcgatagtt ccaccgggag ctacgatatt   8580
ctgacacaat tcaaatgtag caggtatccc aactgcttca atcgcagtat caacacctaa   8640
gccttcagta agagctttca cttcggctgc ggcgttacca cccgtggagt ttactgttct   8700
ggtggcacca aattgtttgg ctaatcccag cctgttatca tcaagatcga tcattatgat   8760
ttcagctggg gagtagaatt gtgctgtcag taaggcggcc aaaccaacgg gaccagcacc   8820
tactatagcc accgaagaac caggtgcgac tttgccgttt aggactccgc actcaaaacc   8880
cgttggtaga atatctgata acatgactaa ggcctcttca tccgcacctg ccggaatacg   8940
ataaagggat gtgtcagcat gtggtactct tacgtactct gcttgggtac catcaatttc   9000
gttgcccaga atccaacccc cggtcgtaca gtgactgaac attcctcttc tacaaaatga   9060
gcactttccg caactcgata tacatgatat caaaactcta tcgcctggtt ggaaagcagt   9120
aaccccagat ccgactgatt caataacccc cactccttca tgccctaata cacgaccggg   9180
tttacaagtc gcaacgtcac ctttaagaat gtgtagatcg gttccgcaaa ttgtagtctt   9240
tgttaccttc actatagcgt caccaggttc cttaagctct ggcttctgtc tctcttccac   9300
caacttctgg cctgggcccc tatacactaa tgctttcatc ctcagctagc tattgtaata   9360
tgtgtgtttg tttggattat taagaagaat aattacaaaa aaaattacaa aggaaggtaa   9420
ttacaacaga attaagaaag gacaagaagg aggaagagaa tcagttcatt atttcttctt   9480
tgttatataa caaacccaag tagcgatttg gccatacatt aaaagttgag aaccaccctc   9540
cctggcaaca gccacaactc gttaccattg ttcatcacga tcatgaaact cgctgtcagc   9600
tgaaatttca cctcagtgga tctctctttt tattcttcat cgttccacta acctttttcc   9660
atcagctggc agggaacgga aagtggaatc ccatttagcg agcttcctct tttcttcaag   9720
aaaagacgaa gcttgtgtgt gggtgcgcgc gctagtatct ttccacatta agaaatatac   9780
cataaaggtt acttagacat cactatggct atatatatat atatatatat atgtaactta   9840
gcaccatcgc gcgtgcatca ctgcatgtgt taaccgaaaa gtttggcgaa cacttcaccg   9900
acacggtcat ttagatctgt cgtctgcatt gcacgtccct tagccttaaa tcctaggcgg   9960
gagcattctc gtgtaattgt gcagcctgcg tagcaactca acatagcgta gtctacccag  10020
tttttcaagg gtttatcgtt agaagattct cccttttctt cctgctcaca aatcttaaag  10080
```

```
tcatacattg cacgactaaa tgcaagcgac gtcagggaaa gatatgagct atacagcgga  10140
atttccatat cactcagatt ttgttatcta attttttcct tcccacgtcc gcgggaatct  10200
gtgtatatta ctgcatctag atatatgtta tcttatcttg gcgcgtacat ttaattttca  10260
acgtattcta taagaaattg cgggagtttt tttcatgtag atgatactga ctgcacgcaa  10320
atataggcat gatttatagg catgatttga tggctgtacc gataggaacg ctaagagtaa  10380
cttcagaatc gttatcctgg cggaaaaaat tcatttgtaa actttaaaaa aaaaagccaa  10440
tatccccaaa attattaaga gcgcctccat tattaactaa aatttcactc agcatccaca  10500
atgtatcagg tatctactac agatattaca tgtggcgaaa aagacaagaa caatgcaata  10560
gcgcatcaag aaaaaacaca aagctttcaa tcaatgaatc gaaaatgtca ttaaaatagt  10620
atataaattg aaactaagtc ataaagctat aaaaagaaaa tttatttaaa tgcaagattt  10680
aaagtaaatt cacggccctg caggccttaa gagttttgct tagataaggc taagccaatc  10740
tgtctcaatg attctggcat atccatttgt tccatatgaa cttcaacgac atgtgctttt  10800
tgaggagtag catcgatagc agctaaagta ttagcgaagt ctgtttctgt gaaaacgttg  10860
tgagtgtcga cagtttcggc atcaccacca aatgtttcag caactaattg caagttccaa  10920
gttggtatat cattgtaact ctcatcctct ccatggatgg ctctttcgac tgtatagcca  10980
tcgttattga taatgaatat cactggtgtc aatttctctc tgaagatggt ggacatttcc  11040
tgtgctgtca gttgaaaaga tccatcaccg atggatagaa tgtgtctcct ttctggggca  11100
gcaatttgtg aaccaatcat agcaggtaat gtgtatccta tggagcccca taatgtttga  11160
ctgatcaaat tcataccctt tttcagaggt gccaacatca aaccgaaaga tgatgtcccc  11220
tgctcagtga ccaacacatc atcagcttgc aaaaagttca taacagcttg gtgaaatctg  11280
tcttgcttta gtggtgtttc ggcctgtggt tcgaaaacag ctaattcagc ttgtttagca  11340
gcagtatcag caaaagtaaa gtttagtttt tccagctctg ccaaaagacc gttaagagaa  11400
atcccagagt aagtagaccc atctggcagc ataatgatgt catttgcagc ggttaaagtg  11460
ttttcagtct taaagccttg agaaaatgag gaggtagaat tgtcaatgat tttcccacca  11520
aaatgtaaaa cgaagtcact attgtcaacg taatccagaa cgtttttgtc agaaaaagct  11580
gggtaatagg taccaatgaa atgttcgttc tcttcattga aagagccttt gccatatgcc  11640
aaattggtta ctggcaactt tgtttggttt atccagtttt caaatctttc tcttatctgg  11700
aaacgggcga tctcatgacc ggcgattacg ataggttgag cggccttttc taagtgtgat  11760
agtatgattt ctgcaagttg tgcctctctc tcaccagatg atttctctgt ttgtagtgct  11820
tttgcaggtt taactattgc tttatgagct atatcaattg gaagattgat gtatactggc  11880
ctcttttcca acaaggctgt ttctaatact ctgtcgatct ctgaagctgc attctcttca  11940
gtaagcatgg ttgtagcggc agtgacttcc ttagccattt cactaaagtt atgaaagtta  12000
cccattccta aggaatgatg aaccagcttt ttgttggatt gcacattcat agttggagaa  12060
cccacgatgt ggatgacagg gacttgttct gcaaaactac cagctgttcc gttaatggct  12120
gacagttcac ccactccgaa tgtagtaaca agagctgata cgcctctttc acgggcgtag  12180
ccatctgctg catatgctgc gtttagttca ttagtattcc cttgccagga aagtccttcg  12240
tgattttgaa tgtaatctag aaaagtcaaa ttgtaatccc ctggcacacc gaaaacctta  12300
tcgataccaa tctcttctag tctatctacc aagtactgtc ctacggtata cattttgttt  12360
actagtttat gtgtgtttat tcgaaactaa gttcttggtg ttttaaaact aaaaaaaaga  12420
ctaactataa aagtagaatt taagaagttt aagaaataga tttacagaat tacaatcaat  12480
```

acctaccgtc tttatatact tattagtcaa gtaggggaat aatttcaggg aactggtttc 12540 aaccttttttt ttcagctttt tccaaatcag agagagcaga aggtaataga aggtgtaaga 12600
aaatgagata gatacatgcg tgggtcaatt gccttgtgtc atcatttact ccaggcaggt 12660
tgcatcactc cattgaggtt gtgcccgttt tttgcctgtt tgtgcccctg ttctctgtag 12720
ttgcgctaag agaatggacc tatgaactga tggttggtga agaaaacaat attttggtgc 12780
tgggattctt ttttttctg gatgccagct taaaaagcgg gctccattat atttagtgga 12840
tgccaggaat aaactgttca cccagacacc tacgatgtta tatattctgt gtaacccgcc 12900
ccctattttg ggcatgtacg ggttacagca gaattaaaag gctaattttt tgactaaata 12960
aagttaggaa aatcactact attaattatt tacgtattct ttgaaatggc agtattggag 13020
ct 13022

<210> SEQ ID NO 84
<211> LENGTH: 90
<212> TYPE: DNA
<213> ORGANISM: Artificial Sequence
<220> FEATURE:
<223> OTHER INFORMATION: Primer 895

<400> SEQUENCE: 84
tctcaattat tattttctac tcataacctc acgcaaaata acacagtcaa atcaatcaaa 60
atgttgacaa aagcaacaaa agaacaaaaa 90

<210> SEQ ID NO 85
<211> LENGTH: 25
<212> TYPE: DNA
<213> ORGANISM: Artificial Sequence
<220> FEATURE:
<223> OTHER INFORMATION: N245

<400> SEQUENCE: 85
agggtagcct ccccataaca taaac 25

<210> SEQ ID NO 86
<211> LENGTH: 25
<212> TYPE: DNA
<213> ORGANISM: Artificial Sequence
<220> FEATURE:
<223> OTHER INFORMATION: N246

<400> SEQUENCE: 86
tctccaaata tatacctctt gtgtg 25

<210> SEQ ID NO 87
<211> LENGTH: 90
<212> TYPE: DNA
<213> ORGANISM: Artificial Sequence
<220> FEATURE:
<223> OTHER INFORMATION: Primer 896

<400> SEQUENCE: 87
ttttatatac agtataaata aaaaacccac gtaatatagc aaaaacatat tgccaacaaa 60
aattaccgtc gctcgtgatt tgtttgcaaa 90

<210> SEQ ID NO 88
<211> LENGTH: 90
<212> TYPE: DNA
<213> ORGANISM: Artificial Sequence
<220> FEATURE:

<223> OTHER INFORMATION: Primer 897

<400> SEQUENCE: 88
caaactgtgt aagtttattt atttgcaaca ataattcgtt tgagtacact actaatggcc 60
accttggcta actcgttgta tcatcactgg 90

<210> SEQ ID NO 89
<211> LENGTH: 28
<212> TYPE: DNA
<213> ORGANISM: Artificial Sequence
<220> FEATURE:
<223> OTHER INFORMATION: primer 365

<400> SEQUENCE: 89
ctctatctcc gctcaggcta agcaattg 28

<210> SEQ ID NO 90
<211> LENGTH: 26
<212> TYPE: DNA
<213> ORGANISM: Artificial Sequence
<220> FEATURE:
<223> OTHER INFORMATION: Primer 366

<400> SEQUENCE: 90
cagccgactc aacggcctgt ttcacg 26

<210> SEQ ID NO 91
<211> LENGTH: 28
<212> TYPE: DNA
<213> ORGANISM: Artificial Sequence
<220> FEATURE:
<223> OTHER INFORMATION: N638

<400> SEQUENCE: 91
aaaagatagt gtagtagtga taaactgg 28

<210> SEQ ID NO 92
<211> LENGTH: 25
<212> TYPE: DNA
<213> ORGANISM: Artificial Sequence
<220> FEATURE:
<223> OTHER INFORMATION: BK415

<400> SEQUENCE: 92
gcctcattga tggtggtaca taacg 25

<210> SEQ ID NO 93
<211> LENGTH: 26
<212> TYPE: DNA
<213> ORGANISM: Artificial Sequence
<220> FEATURE:
<223> OTHER INFORMATION: N1092

<400> SEQUENCE: 93
agagttttga tatcatgtat atcgag 26

<210> SEQ ID NO 94
<211> LENGTH: 92
<212> TYPE: DNA
<213> ORGANISM: Artificial Sequence
<220> FEATURE:
<223> OTHER INFORMATION: Primer 906

<400> SEQUENCE: 94
atgacaggtg aaagaattga aaaggtgaaa ataaatgacg aatttgcaaa atcacatttc 60
acctggtaaa acctctagtg gagtagtaga tg 92

<210> SEQ ID NO 95
<211> LENGTH: 87
<212> TYPE: DNA
<213> ORGANISM: Artificial Sequence
<220> FEATURE:
<223> OTHER INFORMATION: Primer 907

<400> SEQUENCE: 95
aaaaagattc aatgccgtct cctttcgaaa cttaataata gaacaatatc atccttcacc 60
ttggctaact cgttgtatca tcactgg 87

<210> SEQ ID NO 96
<211> LENGTH: 70
<212> TYPE: DNA
<213> ORGANISM: Artificial Sequence
<220> FEATURE:
<223> OTHER INFORMATION: Primer 667

<400> SEQUENCE: 96
tctcctttcg aaacttaata atagaacaat atcatccttt tgtaaaacga cggccagtga 60
attcaccttg 70

<210> SEQ ID NO 97
<211> LENGTH: 6728
<212> TYPE: DNA
<213> ORGANISM: Artificial Sequence
<220> FEATURE:
<223> OTHER INFORMATION: pJT254

<400> SEQUENCE: 97
tcgcgcgttt cggtgatgac ggtgaaaacc tctgacacat gcagctcccg gagacggtca 60
cagcttgtct gtaagcggat gccgggagca gacaagcccg tcagggcgcg tcagcgcgtg 120
ttggcgggtg tcggggctgg cttaactatg cggcatcaga gcagattgta ctgagagtgc 180
accataaatt cccgttttaa gagcttggtg agcgctagga gtcactgcca ggtatcgttt 240
gaacacggca ttagtcaggg aagtcataac acagtccttt cccgcaattt tctttttcta 300
ttactcttgg cctcctctag tacactctat atttttttat gcctcggtaa tgattttcat 360
tttttttttt cccctagcgg atgactcttt ttttttctta gcgattggca ttatcacata 420
atgaattata cattatataa agtaatgtga tttcttcgaa gaatatacta aaaaatgagc 480
aggcaagata aacgaaggca aagatgacag agcagaaagc cctagtaaag cgtattacaa 540
atgaaaccaa gattcagatt gcgatctctt taaagggtgg tcccctagcg atagagcact 600
cgatcttccc agaaaaagag gcagaagcag tagcagaaca ggccacacaa tcgcaagtga 660
ttaacgtcca cacaggtata gggtttctgg accatatgat acatgctctg gccaagcatt 720
ccggctggtc gctaatcgtt gagtgcattg gtgacttaca catagacgac catcacacca 780
ctgaagactg cgggattgct ctcggtcaag cttttaaaga ggccctactg gcgcgtggag 840
taaaaaggtt tggatcagga tttgcgcctt tggatgaggc actttccaga gcggtggtag 900
atctttcgaa caggccgtac gcagttgtcg aacttggttt gcaaagggag aaagtaggag 960
atctctcttg cgagatgatc ccgcattttc ttgaaagctt tgcagaggct agcagaatta 1020
ccctccacgt tgattgtctg cgaggcaaga atgatcatca ccgtagtgag agtgcgttca 1080
aggctcttgc ggttgccata agagaagcca cctcgcccaa tggtaccaac gatgttccct 1140

```
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
cctttttttct ttttgctttt tctttttttt tctcttgaac tcgacggatc tatgcggtgt   1380
gaaataccgc acagatgcgt aaggagaaaa taccgcatca ggaaattgta aacgttaata   1440
ttttgttaaa attcgcgtta aatttttgtt aaatcagctc attttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta aatcggaacc ctaaagggag cccccgattt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa aggggggatgt gctgcaaggc   1980
gattaagttg ggtaacgcca gggttttccc agtcacgacg ttgtaaaacg acggccagtg   2040
agcgcgcgta atacgactca ctatagggcg aattgggtac cgggcccccc ctcgaggtcg   2100
acggtatcga taagcttgat tagaagccgc cgagcgggcg acagccctcc gacggaagac   2160
tctcctccgt gcgtcctcgt cttcaccggt cgcgttcctg aaacgcagat gtgcctcgcg   2220
ccgcactgct ccgaacaata aagattctac aatactagct tttatggtta tgaagaggaa   2280
aaattggcag taacctggcc ccacaaacct tcaaattaac gaatcaaatt aacaaccata   2340
ggatgataat gcgattagtt ttttagcctt atttctgggg taattaatca gcgaagcgat   2400
gatttttgat ctattaacag atatataaat ggaaaagctg cataaccact ttaactaata   2460
ctttcaacat tttcagtttg tattacttct tattcaaatg tcataaaagt atcaacaaaa   2520
aattgttaat atacctctat actttaacgt caaggagaaa aatgtccaat ttactgcccg   2580
tacaccaaaa tttgcctgca ttaccggtcg atgcaacgag tgatgaggtt cgcaagaacc   2640
tgatggacat gttcagggat cgccaggcgt tttctgagca tacctggaaa atgcttctgt   2700
ccgtttgccg gtcgtgggcg gcatggtgca agttgaataa ccggaaatgg tttcccgcag   2760
aacctgaaga tgttcgcgat tatcttctat atcttcaggc gcgcggtctg gcagtaaaaa   2820
ctatccagca acatttgggc cagctaaaca tgcttcatcg tcggtccggg ctgccacgac   2880
caagtgacag caatgctgtt tcactggtta tgcggcggat ccgaaaagaa aacgttgatg   2940
ccggtgaacg tgcaaaacag gctctagcgt tcgaacgcac tgatttcgac caggttcgtt   3000
cactcatgga aaatagcgat cgctgccagg atatacgtaa tctggcattt ctggggattg   3060
cttataacac cctgttacgt atagccgaaa ttgccaggat cagggttaaa gatatctcac   3120
gtactgacgg tgggagaatg ttaatccata ttggcagaac gaaaacgctg gttagcaccg   3180
caggtgtaga gaaggcactt agcctggggg taactaaact ggtcgagcga tggatttccg   3240
tctctggtgt agctgatgat ccgaataact acctgttttg ccgggtcaga aaaaatggtg   3300
ttgccgcgcc atctgccacc agccagctat caactcgcgc cctggaaggg atttttgaag   3360
caactcatcg attgatttac ggcgctaagg atgactctgg tcagagatac ctggcctggt   3420
ctggacacag tgcccgtgtc ggagccgcgc gagatatggc ccgcgctgga gtttcaatac   3480
cggagatcat gcaagctggt ggctggacca atgtaaatat tgtcatgaac tatatccgta   3540
```

```
acctggatag tgaaacaggg gcaatggtgc gcctgctgga agatggcgat taggagtaag   3600
cgaatttctt atgatttatg atttttatta ttaaataagt tataaaaaaa ataagtgtat   3660
acaaatttta aagtgactct taggttttaa aacgaaaatt cttattcttg agtaactctt   3720
tcctgtaggt caggttgctt tctcaggtat agcatgaggt cgctcttatt gaccacacct   3780
ctaccggcat gccgagcaaa tgcctgcaaa tcgctcccca tttcacccaa ttgtagatat   3840
gctaactcca gcaatgagtt gatgaatctc ggtgtgtatt ttatgtcctc agaggacaac   3900
acctgtggtg ttctagagcg gccgccaccg cggtggagct ccagcttttg ttccctttag   3960
tgagggttaa ttgcgcgctt ggcgtaatca tggtcatagc tgtttcctgt gtgaaattgt   4020
tatccgctca caattccaca caacatagga gccggaagca taaagtgtaa agcctggggt   4080
gcctaatgag tgaggtaact cacattaatt gcgttgcgct cactgcccgc tttccagtcg   4140
ggaaacctgt cgtgccagct gcattaatga atcggccaac gcgcggggag aggcggtttg   4200
cgtattgggc gctcttccgc ttcctcgctc actgactcgc tgcgctcggt cgttcggctg   4260
cggcgagcgg tatcagctca ctcaaaggcg gtaatacggt tatccacaga atcaggggat   4320
aacgcaggaa agaacatgtg agcaaaaggc cagcaaaagg ccaggaaccg taaaaaggcc   4380
gcgttgctgg cgtttttcca taggctccgc ccccctgacg agcatcacaa aaatcgacgc   4440
tcaagtcaga ggtggcgaaa cccgacagga ctataaagat accaggcgtt tccccctgga   4500
agctccctcg tgcgctctcc tgttccgacc ctgccgctta ccggatacct gtccgccttt   4560
ctcccttcgg gaagcgtggc gctttctcat agctcacgct gtaggtatct cagttcggtg   4620
taggtcgttc gctccaagct gggctgtgtg cacgaacccc ccgttcagcc cgaccgctgc   4680
gccttatccg gtaactatcg tcttgagtcc aacccggtaa gacacgactt atcgccactg   4740
gcagcagcca ctggtaacag gattagcaga gcgaggtatg taggcggtgc tacagagttc   4800
ttgaagtggt ggcctaacta cggctacact agaaggacag tatttggtat ctgcgctctg   4860
ctgaagccag ttaccttcgg aaaaagagtt ggtagctctt gatccggcaa acaaaccacc   4920
gctggtagcg gtggtttttt tgtttgcaag cagcagatta cgcgcagaaa aaaaggatct   4980
caagaagatc ctttgatctt ttctacgggg tctgacgctc agtggaacga aaactcacgt   5040
taagggattt tggtcatgag attatcaaaa aggatcttca cctagatcct tttaaattaa   5100
aaatgaagtt ttaaatcaat ctaaagtata tatgagtaaa cttggtctga cagttaccaa   5160
tgcttaatca gtgaggcacc tatctcagcg atctgtctat ttcgttcatc catagttgcc   5220
tgactccccg tcgtgtagat aactacgata cgggagggct taccatctgg ccccagtgct   5280
gcaatgatac cgcgagaccc acgctcaccg gctccagatt tatcagcaat aaaccagcca   5340
gccggaaggg ccgagcgcag aagtggtcct gcaactttat ccgcctccat ccagtctatt   5400
aattgttgcc gggaagctag agtaagtagt tcgccagtta atagtttgcg caacgttgtt   5460
gccattgcta caggcatcgt ggtgtcacgc tcgtcgtttg gtatggcttc attcagctcc   5520
ggttcccaac gatcaaggcg agttacatga tcccccatgt tgtgcaaaaa agcggttagc   5580
tccttcggtc ctccgatcgt tgtcagaagt aagttggccg cagtgttatc actcatggtt   5640
atggcagcac tgcataattc tcttactgtc atgccatccg taagatgctt ttctgtgact   5700
ggtgagtact caaccaagtc attctgagaa tagtgtatgc ggcgaccgag ttgctcttgc   5760
ccggcgtcaa tacgggataa taccgcgcca catagcagaa ctttaaaagt gctcatcatt   5820
ggaaaacgtt cttcggggcg aaaactctca aggatcttac cgctgttgag atccagttcg   5880
```

```
atgtaaccca ctcgtgcacc caactgatct tcagcatctt ttactttcac cagcgtttct   5940

gggtgagcaa aaacaggaag gcaaaatgcc gcaaaaaagg gaataagggc gacacggaaa   6000

tgttgaatac tcatactctt cctttttcaa tattattgaa gcatttatca gggttattgt   6060

ctcatgagcg gatacatatt tgaatgtatt tagaaaaata aacaaatagg ggttccgcgc   6120

acatttcccc gaaaagtgcc acctgggtcc ttttcatcac gtgctataaa aataattata   6180

atttaaattt tttaatataa atatataaat taaaaataga aagtaaaaaa agaaattaaa   6240

gaaaaaatag tttttgtttt ccgaagatgt aaaagactct agggggatcg ccaacaaata   6300

ctacctttta tcttgctctt cctgctctca ggtattaatg ccgaattgtt tcatcttgtc   6360

tgtgtagaag accacacacg aaaatcctgt gattttacat tttacttatc gttaatcgaa   6420

tgtatatcta tttaatctgc ttttcttgtc taataaatat atatgtaaag tacgcttttt   6480

gttgaaattt tttaaacctt tgtttatttt tttttcttca ttccgtaact cttctacctt   6540

ctttatttac tttctaaaat ccaaatacaa aacataaaaa taaataaaca cagagtaaat   6600

tcccaaatta ttccatcatt aaaagatacg aggcgcgtgt aagttacagg caagcgatcc   6660

gtcctaagaa accattatta tcatgacatt aacctataaa aataggcgta tcacgaggcc   6720

ctttcgtc                                                            6728
```

<210> SEQ ID NO 98
<211> LENGTH: 1650
<212> TYPE: DNA
<213> ORGANISM: Artificial Sequence
<220> FEATURE:
<223> OTHER INFORMATION: AMN1

<400> SEQUENCE: 98

```
atgaagctgg agcgcgtgag ttctaacggg agctttaagc gtggccgtga catccaaagt     60

ttggagagtc cgtgtacccg cccattaaag aaaatgtcgc catcaccttc atttacgagc    120

ctgaagatgg aaaaaccgtt taaggacatt gttcgaaaat acgggggtca cctgcaccag    180

tcctcgtata acccaggttc ttcaaaagtt gaactcgtgc gtccggacct gagcttgaaa    240

acggaccaat catttttgca gagcagcgtg cagacaaccc cgaacaaaaa gagttgtaac    300

gagtatctgt ccacacccga agccactccc cttaagaaca cggccaccga gaatgcgtgg    360

gctacgtcaa gggtggtgag cgcatcaagc ctgtcaatcg tcacgccgac cgaaatcaaa    420

aatatactgg ttgacgagtt tagtgaacta aaacttggtc agcccttaac agcccagcac    480

caacggagcc atgcagtttt cgagatacct gagatcgtag agaacataat caagatgatc    540

gtttccctcg agagcgccaa tattccgaaa gaacgtccgt gcctgcgtcg caacccgcag    600

agttatgagc attcccttct gatgtataaa gacgaggaac gcgcgaagaa agcatggtcc    660

gcggctcaac aactgcgcga tccgccgctg gtgggtcata aggaaaaaaa acagggcgct    720

ctgtttagct gcatgatggt caaccgcctg tggttgaatg tcacgcgtcc gttcttattt    780

aagtctctgc atttcaaatc agtgcacaac ttcaaagaat ttctgcgcac aagtcaggaa    840

accacgcaag tgatgaggcc atcgcacttt atcctgcata aattgcacca ggtaacgcag    900

ccggatattg agagactgtc tagaatggaa tgccagaacc tcaagtggtt ggaattttat    960

gtatgtcccc gtattacacc tccactgtct tggttcgaca atttgcataa gttagaaaaa   1020

ttaatcatcc ccggaaacaa gaatatcgac gataatttcc tcttacggct gtctcagagt   1080

attcctaacc tgaaacacct cgtgcttcgt gcttgcgaca atgtttccga tagtggtgta   1140

gtttgtatcg ccctgaactg ccctaagctg aagacgttca acatcggacg tcatcgccgc   1200
```

```
ggcaatctga ttacatcagt tagcttggtt gccctgggta agtatacgca agttgagacc   1260

gttggttttg caggctgcga tgtggacgac gcaggcatat gggagttcgc gcgtttaaac   1320

gggaaaaacg tcgagcgcct gtcactcaac agttgccggc ttttaaccga ctatagcttg   1380

ccaatcctgt ttgcccttaa tagtttcccg aaccttgcgg tgttggaaat tcgaaacctc   1440

gataaaatta cagatgtccg ccattttgtg aaatataatc tgtggaagaa atcactggat   1500

gctcctatcc tgattgaggc gtgcgaacgc ataacaaagc tgattgatca ggaagagaac   1560

cgggtcaaac gcataaatag cctggtcgct ttaaaggata tgaccgcgtg ggtgaacgct   1620

gacgatgaaa ttgaaaacaa cgtcgattga                                    1650
```

```
<210> SEQ ID NO 99
<211> LENGTH: 549
<212> TYPE: PRT
<213> ORGANISM: Artificial Sequence
<220> FEATURE:
<223> OTHER INFORMATION: AMN1

<400> SEQUENCE: 99

Met Lys Leu Glu Arg Val Ser Ser Asn Gly Ser Phe Lys Arg Gly Arg
1               5                   10                  15

Asp Ile Gln Ser Leu Glu Ser Pro Cys Thr Arg Pro Leu Lys Lys Met
            20                  25                  30

Ser Pro Ser Pro Ser Phe Thr Ser Leu Lys Met Glu Lys Pro Phe Lys
        35                  40                  45

Asp Ile Val Arg Lys Tyr Gly Gly His Leu His Gln Ser Ser Tyr Asn
    50                  55                  60

Pro Gly Ser Ser Lys Val Glu Leu Val Arg Pro Asp Leu Ser Leu Lys
65                  70                  75                  80

Thr Asp Gln Ser Phe Leu Gln Ser Ser Val Gln Thr Thr Pro Asn Lys
                85                  90                  95

Lys Ser Cys Asn Glu Tyr Leu Ser Thr Pro Glu Ala Thr Pro Leu Lys
            100                 105                 110

Asn Thr Ala Thr Glu Asn Ala Trp Ala Thr Ser Arg Val Val Ser Ala
        115                 120                 125

Ser Ser Leu Ser Ile Val Thr Pro Thr Glu Ile Lys Asn Ile Leu Val
    130                 135                 140

Asp Glu Phe Ser Glu Leu Lys Leu Gly Gln Pro Leu Thr Ala Gln His
145                 150                 155                 160

Gln Arg Ser His Ala Val Phe Glu Ile Pro Glu Ile Val Glu Asn Ile
                165                 170                 175

Ile Lys Met Ile Val Ser Leu Glu Ser Ala Asn Ile Pro Lys Glu Arg
            180                 185                 190

Pro Cys Leu Arg Arg Asn Pro Gln Ser Tyr Glu His Ser Leu Leu Met
        195                 200                 205

Tyr Lys Asp Glu Glu Arg Ala Lys Lys Ala Trp Ser Ala Ala Gln Gln
    210                 215                 220

Leu Arg Asp Pro Pro Leu Val Gly His Lys Glu Lys Lys Gln Gly Ala
225                 230                 235                 240

Leu Phe Ser Cys Met Met Val Asn Arg Leu Trp Leu Asn Val Thr Arg
                245                 250                 255

Pro Phe Leu Phe Lys Ser Leu His Phe Lys Ser Val His Asn Phe Lys
            260                 265                 270

Glu Phe Leu Arg Thr Ser Gln Glu Thr Thr Gln Val Met Arg Pro Ser
```

```
        275                 280                 285

His Phe Ile Leu His Lys Leu His Gln Val Thr Gln Pro Asp Ile Glu
    290                 295                 300

Arg Leu Ser Arg Met Glu Cys Gln Asn Leu Lys Trp Leu Glu Phe Tyr
305                 310                 315                 320

Val Cys Pro Arg Ile Thr Pro Pro Leu Ser Trp Phe Asp Asn Leu His
                325                 330                 335

Lys Leu Glu Lys Leu Ile Ile Pro Gly Asn Lys Asn Ile Asp Asp Asn
            340                 345                 350

Phe Leu Leu Arg Leu Ser Gln Ser Ile Pro Asn Leu Lys His Leu Val
        355                 360                 365

Leu Arg Ala Cys Asp Asn Val Ser Asp Ser Gly Val Val Cys Ile Ala
    370                 375                 380

Leu Asn Cys Pro Lys Leu Lys Thr Phe Asn Ile Gly Arg His Arg Arg
385                 390                 395                 400

Gly Asn Leu Ile Thr Ser Val Ser Leu Val Ala Leu Gly Lys Tyr Thr
                405                 410                 415

Gln Val Glu Thr Val Gly Phe Ala Gly Cys Asp Val Asp Asp Ala Gly
            420                 425                 430

Ile Trp Glu Phe Ala Arg Leu Asn Gly Lys Asn Val Glu Arg Leu Ser
        435                 440                 445

Leu Asn Ser Cys Arg Leu Leu Thr Asp Tyr Ser Leu Pro Ile Leu Phe
    450                 455                 460

Ala Leu Asn Ser Phe Pro Asn Leu Ala Val Leu Glu Ile Arg Asn Leu
465                 470                 475                 480

Asp Lys Ile Thr Asp Val Arg His Phe Val Lys Tyr Asn Leu Trp Lys
                485                 490                 495

Lys Ser Leu Asp Ala Pro Ile Leu Ile Glu Ala Cys Glu Arg Ile Thr
            500                 505                 510

Lys Leu Ile Asp Gln Glu Glu Asn Arg Val Lys Arg Ile Asn Ser Leu
        515                 520                 525

Val Ala Leu Lys Asp Met Thr Ala Trp Val Asn Ala Asp Asp Glu Ile
    530                 535                 540

Glu Asn Asn Val Asp
545
```

<210> SEQ ID NO 100
<211> LENGTH: 6638
<212> TYPE: DNA
<213> ORGANISM: Artificial Sequence
<220> FEATURE:
<223> OTHER INFORMATION: pLA67

<400> SEQUENCE: 100

```
aaacgccagc aacgcggcct ttttacggtt cctggccttt tgctggcctt ttgctcacat      60

gttctttcct gcgttatccc ctgattctgt ggataaccgt attaccgcct ttgagtgagc     120

tgataccgct cgccgcagcc gaacgaccga gcgcagcgag tcagtgagcg aggaagcgga     180

agagcgccca atacgcaaac cgcctctccc cgcgcgttgg ccgattcatt aatgcagctg     240

gcacgacagg tttcccgact ggaaagcggg cagtgagcgc aacgcaatta atgtgagtta     300

gctcactcat taggcacccc aggctttaca ctttatgctt ccggctcgta tgttgtgtgg     360

aattgtgagc ggataacaat ttcacacagg aaacagctat gaccatgatt acgccaagct     420

tgcatgcctg caggtcgact ctagaggatc cgcattgcgg attacgtatt ctaatgttca     480
```

-continued

```
gtaccgttcg tataatgtat gctatacgaa gttatgcaga ttgtactgag agtgcaccat    540
accacagctt ttcaattcaa ttcatcattt ttttttattt cttttttttg atttcggttt    600
ctttgaaatt tttttgattc ggtaatctcc gaacagaagg aagaacgaag gaaggagcac    660
agacttagat tggtatatat acgcatatgt agtgttgaag aaacatgaaa ttgcccagta    720
ttcttaaccc aactgcacag aacaaaaacc tgcaggaaac gaagataaat catgtcgaaa    780
gctacatata aggaacgtgc tgctactcat cctagtcctg ttgctgccaa gctatttaat    840
atcatgcacg aaaagcaaac aaacttgtgt gcttcattgg atgttcgtac caccaaggaa    900
ttactggagt tagttgaagc attaggtccc aaaatttgtt tactaaaaac acatgtggat    960
atcttgactg atttttccat ggagggcaca gttaagccgc taaaggcatt atccgccaag   1020
tacaattttt tactcttcga agacagaaaa tttgctgaca ttggtaatac agtcaaattg   1080
cagtactctg cgggtgtata cagaatagca gaatgggcag acattacgaa tgcacacggt   1140
gtggtgggcc caggtattgt tagcggtttg aagcaggcgg cagaagaagt aacaaaggaa   1200
cctagaggcc ttttgatgtt agcagaattg tcatgcaagg gctccctatc tactggagaa   1260
tatactaagg gtactgttga cattgcgaag agcgacaaag attttgttat cggctttatt   1320
gctcaaagag acatgggtgg aagagatgaa ggttacgatt ggttgattat gacacccggt   1380
gtgggtttag atgacaaggg agacgcattg ggtcaacagt atagaaccgt ggatgatgtg   1440
gtctctacag gatctgacat tattattgtt ggaagaggac tatttgcaaa gggaagggat   1500
gctaaggtag agggtgaacg ttacagaaaa gcaggctggg aagcatattt gagaagatgc   1560
ggccagcaaa actaaaaaac tgtattataa gtaaatgcat gtatactaaa ctcacaaatt   1620
agagcttcaa tttaattata tcagttatta ccctatgcgg tgtgaaatac cgcacagatg   1680
cgtaaggaga aaataccgca tcaggaaatt gtaaacgtta atattttgtt aaaattcgcg   1740
ttaaattttt gttaaatcag ctcatttttt aaccaatagg ccgaaatcgg caaaatccct   1800
tataaatcaa aagaatagac cgagataggg ttgagtgttg ttccagtttg gaacaagagt   1860
ccactattaa agaacgtgga ctccaacgtc aaagggcgaa aaaccgtcta tcagggcgat   1920
ggcccactac gtgaaccatc accctaatca agataacttc gtataatgta tgctatacga   1980
acggtaccag tgatgataca acgagttagc caaggtgaat tcgacttagg atgtctcatc   2040
aatcatctta ttcctgctgg tgtttttgt atcgccttgc cttggagtgt ttatgcttgt   2100
cctttgttca gtaaccattc ttcaagtttg tttcaagtag taggatacct tcagatatac   2160
gaaagaaagg gagtatagtt gtggatatat atatatatag caacccttct ttataagggt   2220
cctatagact atactcttca cactttaaag tacggaatta aggcccaagg gaactaacaa   2280
aaacgttcaa aaagttttaa aactatatgt gttaactgta caaaaataac ttatttatca   2340
tatcattttt ttctctgttt atttcttcta gaacttatac ctgtcttttc cttttattct   2400
ttgaatttgk tttaatatcc ctttttgktt taatatccat ccattccttt cacttagaac   2460
taataattcc cttcgtttga taatttatca ttttcctttt ctgttagtaa agtacccatt   2520
aaatgaagct ggagcgcgtg agttctaacg ggagctttaa gcgtggccgt gacatccaaa   2580
gtttggagag tccgtgtacc cgcccattaa agaaaatgtc gccatcacct tcatttacga   2640
gcctgaagat ggaaaaaccg tttaaggaca ttgttcgaaa atacgggggt cacctgcacc   2700
agtcctcgta taacccaggt tcttcaaaag ttgaactcgt gcgtccggac ctgagcttga   2760
aaacggacca atcatttttg cagagcagcg tgcagacaac cccgaacaaa aagagttgta   2820
acgagtatct gtccacaccc gaagccactc cccttaagaa cacggccacc gagaatgcgt   2880
```

```
gggctacgtc aagggtggtg agcgcatcaa gcctgtcaat cgtcacgccg accgaaatca   2940
aaaatatact ggttgacgag tttagtgaac taaaacttgg tcagccctta acagcccagc   3000
accaacggag ccatgcagtt ttcgagatac ctgagatcgt agagaacata atcaagatga   3060
tcgtttccct cgagagcgcc aatattccga aagaacgtcc gtgcctgcgt cgcaacccgc   3120
agagttatga gcattccctt ctgatgtata aagacgagga acgcgcgaag aaagcatggt   3180
ccgcggctca acaactgcgc gatccgccgc tggtgggtca taaggaaaaa aaacagggcg   3240
ctctgtttag ctgcatgatg gtcaaccgcc tgtggttgaa tgtcacgcgt ccgttcttat   3300
ttaagtctct gcatttcaaa tcagtgcaca acttcaaaga atttctgcgc acaagtcagg   3360
aaaccacgca agtgatgagg ccatcgcact ttatcctgca taaattgcac caggtaacgc   3420
agccggatat tgagagactg tctagaatgg aatgccagaa cctcaagtgg ttggaatttt   3480
atgtatgtcc ccgtattaca cctccactgt cttggttcga caatttgcat aagttagaaa   3540
aattaatcat ccccggaaac aagaatatcg acgataattt cctcttacgg ctgtctcaga   3600
gtattcctaa cctgaaacac ctcgtgcttc gtgcttgcga caatgtttcc gatagtggtg   3660
tagtttgtat cgccctgaac tgccctaagc tgaagacgtt caacatcgga cgtcatcgcc   3720
gcggcaatct gattacatca gttagcttgg ttgccctggg taagtatacg caagttgaga   3780
ccgttggttt tgcaggctgc gatgtggacg acgcaggcat atgggagttc gcgcgtttaa   3840
acgggaaaaa cgtcgagcgc ctgtcactca acagttgccg gcttttaacc gactatagct   3900
tgccaatcct gtttgccctt aatagtttcc cgaaccttgc ggtgttggaa attcgaaacc   3960
tcgataaaat tacagatgtc cgccattttg tgaaatataa tctgtggaag aaatcactgg   4020
atgctcctat cctgattgag gcgtgcgaac gcataacaaa gctgattgat caggaagaga   4080
accgggtcaa acgcataaat agcctggtcg ctttaaagga tatgaccgcg tgggtgaacg   4140
ctgacgatga aattgaaaac aacgtcgatt gagacgatga aattgaaaac aacgtcgatt   4200
gaggtaccat ggtttttgtg actttaccta taaatagtac acaacagacc accagtaatt   4260
ctacacactt cttaactgat aatattatta taattgtaac tttttagcag cactaaattt   4320
aatgaataca tagattttta actagcattt tactattctg tactttttac ttgaaattcc   4380
agaagggccg aagaaaccag aattccttca cagaaaacga attcactggc cgtcgtttta   4440
caacgtcgtg actgggaaaa ccctggcgtt acccaactta atcgccttgc agcacatccc   4500
cctttcgcca gctggcgtaa tagcgaagag gcccgcaccg atcgcccttc ccaacagttg   4560
cgcagcctga atggcgaatg gcgcctgatg cggtattttc tccttacgca tctgtgcggt   4620
atttcacacc gcatatggtg cactctcagt acaatctgct ctgatgccgc atagttaagc   4680
cagccccgac acccgccaac acccgctgac gcgccctgac gggcttgtct gctcccggca   4740
tccgcttaca gacaagctgt gaccgtctcc gggagctgca tgtgtcagag gttttcaccg   4800
tcatcaccga aacgcgcgag acgaaagggc ctcgtgatac gcctattttt ataggttaat   4860
gtcatgataa taatggtttc ttagacgtca ggtggcactt ttcggggaaa tgtgcgcgga   4920
acccctattt gtttattttt ctaaatacat tcaaatatgt atccgctcat gagacaataa   4980
ccctgataaa tgcttcaata atattgaaaa aggaagagta tgagtattca acatttccgt   5040
gtcgccctta ttcccttttt tgcggcattt tgccttcctg tttttgctca cccagaaacg   5100
ctggtgaaag taaaagatgc tgaagatcag ttgggtgcac gagtgggtta catcgaactg   5160
gatctcaaca gcggtaagat ccttgagagt tttcgccccg aagaacgttt tccaatgatg   5220
```

agcactttta aagttctgct atgtggcgcg gtattatccc gtattgacgc cgggcaagag 5280
caactcggtc gccgcataca ctattctcag aatgacttgg ttgagtactc accagtcaca 5340
gaaaagcatc ttacggatgg catgacagta agagaattat gcagtgctgc cataaccatg 5400
agtgataaca ctgcggccaa cttacttctg acaacgatcg gaggaccgaa ggagctaacc 5460
gcttttttgc acaacatggg ggatcatgta actcgccttg atcgttggga accggagctg 5520
aatgaagcca taccaaacga cgagcgtgac accacgatgc ctgtagcaat ggcaacaacg 5580
ttgcgcaaac tattaactgg cgaactactt actctagctt cccggcaaca attaatagac 5640
tggatggagg cggataaagt tgcaggacca cttctgcgct cggcccttcc ggctggctgg 5700
tttattgctg ataaatctgg agccggtgag cgtgggtctc gcggtatcat tgcagcactg 5760
gggccagatg gtaagccctc ccgtatcgta gttatctaca cgacggggag tcaggcaact 5820
atggatgaac gaaatagaca gatcgctgag ataggtgcct cactgattaa gcattggtaa 5880
ctgtcagacc aagtttactc atatatactt tagattgatt taaaacttca tttttaattt 5940
aaaaggatct aggtgaagat cctttttgat aatctcatga ccaaaatccc ttaacgtgag 6000
ttttcgttcc actgagcgtc agaccccgta gaaaagatca aaggatcttc ttgagatcct 6060 tttttctgc gcgtaatctg ctgcttgcaa acaaaaaaac caccgctacc agcggtggtt 6120
tgtttgccgg atcaagagct accaactctt tttccgaagg taactggctt cagcagagcg 6180
cagataccaa atactgtcct tctagtgtag ccgtagttag gccaccactt caagaactct 6240
gtagcaccgc ctacatacct cgctctgcta atcctgttac cagtggctgc tgccagtggc 6300
gataagtcgt gtcttaccgg gttggactca agacgatagt taccggataa ggcgcagcgg 6360
tcgggctgaa cggggggttc gtgcacacag cccagcttgg agcgaacgac ctacaccgaa 6420
ctgagatacc tacagcgtga gctatgagaa agcgccacgc ttcccgaagg gagaaaggcg 6480
gacaggtatc cggtaagcgg cagggtcgga acaggagagc gcacgaggga gcttccaggg 6540
ggaaacgcct ggtatcttta tagtcctgtc gggtttcgcc acctctgact tgagcgtcga 6600
tttttgtgat gctcgtcagg ggggcggagc ctatggaa 6638

<210> SEQ ID NO 101
<211> LENGTH: 100
<212> TYPE: DNA
<213> ORGANISM: Artificial Sequence
<220> FEATURE:
<223> OTHER INFORMATION: LA712

<400> SEQUENCE: 101
cttaattgaa agaaagaatt tccttcaact tcggtttcct ggttccgcta tttctcgctt 60
gtttcttcta gcattgcgga ttacgtattc taatgttcag 100

<210> SEQ ID NO 102
<211> LENGTH: 30
<212> TYPE: DNA
<213> ORGANISM: Artificial Sequence
<220> FEATURE:
<223> OTHER INFORMATION: LA746

<400> SEQUENCE: 102
gttttctgtg aaggaattct ggtttcttcg 30

<210> SEQ ID NO 103
<211> LENGTH: 7938
<212> TYPE: DNA
<213> ORGANISM: Artificial Sequence
<220> FEATURE:
<223> OTHER INFORMATION: pYZ067deltakivDdeltahADH

<400> SEQUENCE: 103

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctctag tacactctat atttttttat gcctcggtaa tgattttcat    360
tttttttttt ccacctagcg gatgactctt tttttttctt agcgattggc attatcacat    420
aatgaattat acattatata aagtaatgtg atttcttcga agaatatact aaaaaatgag    480
caggcaagat aaacgaaggc aaagatgaca gagcagaaag ccctagtaaa gcgtattaca    540
aatgaaacca agattcagat tgcgatctct ttaaagggtg gtcccctagc gatagagcac    600
tcgatcttcc cagaaaaaga ggcagaagca gtagcagaac aggccacaca atcgcaagtg    660
attaacgtcc acacaggtat agggtttctg gaccatatga tacatgctct ggccaagcat    720
tccggctggt cgctaatcgt tgagtgcatt ggtgacttac acatagacga ccatcacacc    780
actgaagact gcgggattgc tctcggtcaa gcttttaaag aggccctagg ggccgtgcgt    840
ggagtaaaaa ggtttggatc aggatttgcg cctttggatg aggcactttc cagagcggtg    900
gtagatcttt cgaacaggcc gtacgcagtt gtcgaacttg gtttgcaaag ggagaaagta    960
ggagatctct cttgcgagat gatcccgcat ttcttgaaa gctttgcaga ggctagcaga   1020
attaccctcc acgttgattg tctgcgaggc aagaatgatc atcaccgtag tgagagtgcg   1080
ttcaaggctc ttgcggttgc cataagagaa gccacctcgc ccaatggtac caacgatgtt   1140
ccctccacca aaggtgttct tatgtagtga caccgattat ttaaagctgc agcatacgat   1200
atatatacat gtgtatatat gtatacctat gaatgtcagt aagtatgtat acgaacagta   1260
tgatactgaa gatgacaagg taatgcatca ttctatacgt gtcattctga acgaggcgcg   1320
ctttcctttt ttcttttttgc tttttctttt tttttctctt gaactcgacg gatctatgcg   1380
gtgtgaaata ccgcacagat gcgtaaggag aaaataccgc atcaggaaat tgtaagcgtt   1440
aatattttgt taaaattcgc gttaaatttt tgttaaatca gctcattttt taaccaatag   1500
gccgaaatcg gcaaaatccc ttataaatca aaagaataga ccgagatagg gttgagtgtt   1560
gttccagttt ggaacaagag tccactatta aagaacgtgg actccaacgt caaagggcga   1620
aaaaccgtct atcagggcga tggcccacta cgtggccggc ttcacatacg ttgcatacgt   1680
cgatatagat aataatgata atgacagcag gattatcgta atacgtaata gctgaaaatc   1740
tcaaaaatgt gtgggtcatt acgtaaataa tgataggaat gggattcttc tatttttcct   1800
ttttccattc tagcagccgt cgggaaaacg tggcatcctc tctttcgggc tcaattggag   1860
tcacgctgcc gtgagcatcc tctctttcca tatctaacaa ctgagcacgt aaccaatgga   1920
aaagcatgag cttagcgttg ctccaaaaaa gtattggatg gttaatacca tttgtctgtt   1980
ctcttctgac tttgactcct caaaaaaaaa aatctacaat caacagatcg cttcaattac   2040
gccctcacaa aaactttttt ccttcttctt cgcccacgtt aaattttatc cctcatgttg   2100
tctaacggat ttctgcactt gatttattat aaaaagacaa agacataata cttctctatc   2160
aatttcagtt attgttcttc cttgcgttat tcttctgttc ttcttttttct tttgtcatat   2220
```

```
ataaccataa ccaagtaata catattcaaa cacgtgagta tgactgacaa aaaaactctt   2280
aaagacttaa gaaatcgtag ttctgtttac gattcaatgg ttaaatcacc taatcgtgct   2340
atgttgcgtg caactggtat gcaagatgaa gactttgaaa aacctatcgt cggtgtcatt   2400
tcaacttggg ctgaaaacac accttgtaat atccacttac atgactttgg taaactagcc   2460
aaagtcggtg ttaaggaagc tggtgcttgg ccagttcagt tcggaacaat cacggtttct   2520
gatggaatcg ccatgggaac ccaaggaatg cgtttctcct tgacatctcg tgatattatt   2580
gcagattcta ttgaagcagc catgggaggt cataatgcgg atgcttttgt agccattggc   2640
ggttgtgata aaaacatgcc cggttctgtt atcgctatgg ctaacatgga tatcccagcc   2700
atttttgctt acggcggaac aattgcacct ggtaatttag acggcaaaga tatcgattta   2760
gtctctgtct ttgaaggtgt cggccattgg aaccacggcg atatgaccaa agaagaagtt   2820
aaagctttgg aatgtaatgc ttgtcccggt cctggaggct gcggtggtat gtatactgct   2880
aacacaatgg cgacagctat tgaagttttg ggacttagcc ttccgggttc atcttctcac   2940
ccggctgaat ccgcagaaaa gaaagcagat attgaagaag ctggtcgcgc tgttgtcaaa   3000
atgctcgaaa tgggcttaaa accttctgac attttaacgc gtgaagcttt tgaagatgct   3060
attactgtaa ctatggctct gggaggttca accaactcaa cccttcacct cttagctatt   3120
gcccatgctg ctaatgtgga attgacactt gatgatttca atactttcca agaaaaagtt   3180
cctcatttgg ctgatttgaa accttctggt caatatgtat tccaagacct ttacaaggtc   3240
ggaggggtac cagcagttat gaaatatctc cttaaaaatg gcttccttca tggtgaccgt   3300
atcacttgta ctggcaaaac agtcgctgaa aatttgaagg cttttgatga tttaacacct   3360
ggtcaaaagg ttattatgcc gcttgaaaat cctaaacgtg aagatggtcc gctcattatt   3420
ctccatggta acttggctcc agacggtgcc gttgccaaag tttctggtgt aaaagtgcgt   3480
cgtcatgtcg gtcctgctaa ggtctttaat tctgaagaag aagccattga agctgtcttg   3540
aatgatgata ttgttgatgg tgatgttgtt gtcgtacgtt ttgtaggacc aaagggcggt   3600
cctggtatgc ctgaaatgct ttccctttca tcaatgattg ttggtaaagg gcaaggtgaa   3660
aaagttgccc ttctgacaga tggccgcttc tcaggtggta cttatggtct tgtcgtgggt   3720
catatcgctc ctgaagcaca agatggcggt ccaatcgcct acctgcaaac aggagacata   3780
gtcactattg accaagacac taaggaatta cactttgata tctccgatga agagttaaaa   3840
catcgtcaag agaccattga attgccaccg ctctattcac gcggtatcct tggtaaatat   3900
gctcacatcg tttcgtctgc ttctagggga gccgtaacag acttttggaa gcctgaagaa   3960
actggcaaaa aatgttgtcc tggttgctgt ggttaagcgg ccgcgttaat tcaaattaat   4020
tgatatagtt ttttaatgag tattgaatct gtttagaaat aatggaatat tatttttatt   4080
tatttattta tattattggt cggctctttt cttctgaagg tcaatgacaa aatgatatga   4140
aggaaataat gatttctaaa attttacaac gtaagatatt tttacaaaag cctagctcat   4200
cttttgtcat gcactatttt actcacgctt gaaattaacg gccagtccac tgcggagtca   4260
tttcaaagtc atcctaatcg atctatcgtt tttgatagct cattttggag ttcgcgagga   4320
tcccagcttt tgttcccttt agtgagggtt aattgcgcgc ttggcgtaat catggtcata   4380
gctgtttcct gtgtgaaatt gttatccgct cacaattcca cacaacatac gagccggaag   4440
cataaagtgt aaagcctggg gtgcctaatg agtgagctaa ctcacattaa ttgcgttgcg   4500
ctcactgccc gctttccagt cgggaaacct gtcgtgccag ctgcattaat gaatcggcca   4560
acgcgcgggg agaggcggtt tgcgtattgg gcgctcttcc gcttcctcgc tcactgactc   4620
```

```
gctgcgctcg gtcgttcggc tgcggcgagc ggtatcagct cactcaaagg cggtaatacg   4680
gttatccaca gaatcagggg ataacgcagg aaagaacatg tgagcaaaag gccagcaaaa   4740
ggccaggaac cgtaaaaagg ccgcgttgct ggcgtttttc cataggctcc gcccccctga   4800
cgagcatcac aaaaatcgac gctcaagtca gaggtggcga aacccgacag gactataaag   4860
ataccaggcg tttccccctg gaagctccct cgtgcgctct cctgttccga ccctgccgct   4920
taccggatac ctgtccgcct ttctcccttc gggaagcgtg gcgctttctc atagctcacg   4980
ctgtaggtat ctcagttcgg tgtaggtcgt tcgctccaag ctgggctgtg tgcacgaacc   5040
ccccgttcag cccgaccgct gcgccttatc cggtaactat cgtcttgagt ccaacccggt   5100
aagacacgac ttatcgccac tggcagcagc cactggtaac aggattagca gagcgaggta   5160
tgtaggcggt gctacagagt tcttgaagtg gtggcctaac tacggctaca ctagaagaac   5220
agtatttggt atctgcgctc tgctgaagcc agttaccttc ggaaaaagag ttggtagctc   5280
ttgatccggc aaacaaacca ccgctggtag cggtggtttt tttgtttgca agcagcagat   5340
tacgcgcaga aaaaaaggat ctcaagaaga tcctttgatc ttttctacgg ggtctgacgc   5400
tcagtggaac gaaaactcac gttaagggat tttggtcatg agattatcaa aaaggatctt   5460
cacctagatc cttttaaatt aaaaatgaag ttttaaatca atctaaagta tatatgagta   5520
aacttggtct gacagttacc aatgcttaat cagtgaggca cctatctcag cgatctgtct   5580
atttcgttca tccatagttg cctgactccc cgtcgtgtag ataactacga tacgggaggg   5640
cttaccatct ggccccagtg ctgcaatgat accgcgagac ccacgctcac cggctccaga   5700
tttatcagca ataaaccagc cagccggaag ggccgagcgc agaagtggtc ctgcaacttt   5760
atccgcctcc atccagtcta ttaattgttg ccgggaagct agagtaagta gttcgccagt   5820
taatagtttg cgcaacgttg ttgccattgc tacaggcatc gtggtgtcac gctcgtcgtt   5880
tggtatggct tcattcagct ccggttccca acgatcaagg cgagttacat gatcccccat   5940
gttgtgcaaa aaagcggtta gctccttcgg tcctccgatc gttgtcagaa gtaagttggc   6000
cgcagtgtta tcactcatgg ttatggcagc actgcataat tctcttactg tcatgccatc   6060
cgtaagatgc ttttctgtga ctggtgagta ctcaaccaag tcattctgag aatagtgtat   6120
gcggcgaccg agttgctctt gcccggcgtc aatacgggat aataccgcgc cacatagcag   6180
aactttaaaa gtgctcatca ttggaaaacg ttcttcgggg cgaaaactct caaggatctt   6240
accgctgttg agatccagtt cgatgtaacc cactcgtgca cccaactgat cttcagcatc   6300
ttttactttc accagcgttt ctgggtgagc aaaaacagga aggcaaaatg ccgcaaaaaa   6360
gggaataagg gcgacacgga aatgttgaat actcatactc ttcctttttc aatattattg   6420
aagcatttat cagggttatt gtctcatgag cggatacata tttgaatgta tttagaaaaa   6480
taaacaaata ggggttccgc gcacatttcc ccgaaaagtg ccacctgaac gaagcatctg   6540
tgcttcattt tgtagaacaa aaatgcaacg cgagagcgct aatttttcaa acaaagaatc   6600
tgagctgcat ttttacagaa cagaaatgca acgcgaaagc gctattttac caacgaagaa   6660
tctgtgcttc atttttgtaa aacaaaaatg caacgcgaga gcgctaattt ttcaaacaaa   6720
gaatctgagc tgcattttta cagaacagaa atgcaacgcg agagcgctat tttaccaaca   6780
aagaatctat acttcttttt tgttctacaa aaatgcatcc cgagagcgct atttttctaa   6840
caaagcatct tagattactt tttttctcct ttgtgcgctc tataatgcag tctcttgata   6900
actttttgca ctgtaggtcc gttaaggtta gaagaaggct actttggtgt ctattttctc   6960
```

```
ttccataaaa aaagcctgac tccacttccc gcgtttactg attactagcg aagctgcggg   7020

tgcatttttt caagataaag gcatccccga ttatattcta taccgatgtg gattgcgcat   7080

actttgtgaa cagaaagtga tagcgttgat gattcttcat tggtcagaaa attatgaacg   7140

gtttcttcta ttttgtctct atatactacg tataggaaat gtttacattt tcgtattgtt   7200

ttcgattcac tctatgaata gttcttacta caattttttt gtctaaagag taatactaga   7260

gataaacata aaaaatgtag aggtcgagtt tagatgcaag ttcaaggagc gaaaggtgga   7320

tgggtaggtt atatagggat atagcacaga gatatatagc aaagagatac ttttgagcaa   7380

tgtttgtgga agcggtattc gcaatatttt agtagctcgt tacagtccgg tgcgtttttg   7440

gtttttttgaa agtgcgtctt cagagcgctt ttggttttca aaagcgctct gaagttccta   7500

tactttctag agaataggaa cttcggaata ggaacttcaa agcgtttccg aaaacgagcg   7560

cttccgaaaa tgcaacgcga gctgcgcaca tacagctcac tgttcacgtc gcacctatat   7620

ctgcgtgttg cctgtatata tatatacatg agaagaacgg catagtgcgt gtttatgctt   7680

aaatgcgtac ttatatgcgt ctatttatgt aggatgaaag gtagtctagt acctcctgtg   7740

atattatccc attccatgcg gggtatcgta tgcttccttc agcactaccc tttagctgtt   7800

ctatatgctg ccactcctca attggattag tctcatcctt caatgctatc atttcctttg   7860

atattggatc atactaagaa accattatta tcatgacatt aacctataaa aataggcgta   7920

tcacgaggcc ctttcgtc                                                 7938
```

```
<210> SEQ ID NO 104
<211> LENGTH: 9613
<212> TYPE: DNA
<213> ORGANISM: Artificial Sequence
<220> FEATURE:
<223> OTHER INFORMATION: pHR81-ILV5p-K9JB4P

<400> SEQUENCE: 104

aaacagtatg gaagaatgta agatggctaa gatttactac caagaagact gtaacttgtc     60

cttgttggat ggtaagacta tcgccgttat cggttacggt tctcaaggtc acgctcatgc    120

cctgaatgct aaggaatccg gttgtaacgt tatcattggt ttatacgaag gtgcggagga    180

gtggaaaaga gctgaagaac aaggtttcga agtctacacc gctgctgaag ctgctaagaa    240

ggctgacatc attatgatct tgatcccaga tgaaaagcag gctaccatgt acaaaaacga    300

catcgaacca aacttggaag ccggtaacat gttgatgttc gctcacggtt tcaacatcca    360

tttcggttgt attgttccac caaaggacgt tgatgtcact atgatcgctc caaagggtcc    420

aggtcacacc gttagatccg aatacgaaga aggtaaaggt gtcccatgct tggttgctgt    480

cgaacaagac gctactggca aggctttgga tatggctttg gcctacgctt tagccatcgg    540

tggtgctaga gccggtgtct tggaaactac cttcagaacc gaaactgaaa ccgacttgtt    600

cggtgaacaa gctgttttat gtggtggtgt ctgcgctttg atgcaggccg gttttgaaac    660

cttggttgaa gccggttacg acccaagaaa cgcttacttc gaatgtatcc acgaaatgaa    720

gttgatcgtt gacttgatct accaatctgg tttctccggt atgcgttact ctatctccaa    780

cactgctgaa tacggtgact acattaccgg tccaaagatc attactgaag ataccaagaa    840

ggctatgaag aagattttgt ctgacattca agatggtacc tttgccaagg acttcttggt    900

tgacatgtct gatgctggtt cccaggtcca cttcaaggct atgagaaagt tggcctccga    960

acacccagct gaagttgtcg gtgaagaaat tagatccttg tactcctggt ccgacgaaga   1020

caagttgatt aacaactgag gccctgcagg ccagaggaaa ataatatcaa gtgctggaaa   1080
```

```
cttttctct tggaatttttt gcaacatcaa gtcatagtca attgaattga cccaatttca   1140
catttaagat tttttttttt tcatccgaca tacatctgta cactaggaag ccctgttttt   1200
ctgaagcagc ttcaaatata tatatttttt acatatttat tatgattcaa tgaacaatct   1260
aattaaatcg aaaacaagaa ccgaaacgcg aataaataat ttatttagat ggtgacaagt   1320
gtataagtcc tcatcgggac agctacgatt tctctttcgg ttttggctga gctactggtt   1380
gctgtgacgc agcggcatta gcgcggcgtt atgagctacc ctcgtggcct gaaagatggc   1440
gggaataaag cggaactaaa aattactgac tgagccatat tgaggtcaat ttgtcaactc   1500
gtcaagtcac gtttggtgga cggccccttt ccaacgaatc gtatatacta acatgcgcgc   1560
gcttcctata tacacatata catatatata tatatatata tgtgtgcgtg tatgtgtaca   1620
cctgtattta atttccttac tcgcgggttt ttcttttttc tcaattcttg gcttcctctt   1680
tctcgagcgg accggatcct ccgcggtgcc ggcagatcta tttaaatggc gcgccgacgt   1740
caggtggcac ttttcgggga aatgtgcgcg gaacccctat ttgtttattt ttctaaatac   1800
attcaaatat gtatccgctc atgagacaat aaccctgata aatgcttcaa taatattgaa   1860
aaaggaagag tatgagtatt caacatttcc gtgtcgccct tattcccttt tttgcggcat   1920
tttgccttcc tgtttttgct cacccagaaa cgctggtgaa agtaaaagat gctgaagatc   1980
agttgggtgc acgagtgggt tacatcgaac tggatctcaa cagcggtaag atccttgaga   2040
gttttcgccc cgaagaacgt tttccaatga tgagcacttt taaagttctg ctatgtggcg   2100
cggtattatc ccgtattgac gccgggcaag agcaactcgg tcgccgcata cactattctc   2160
agaatgactt ggttgagtac tcaccagtca cagaaaagca tcttacggat ggcatgacag   2220
taagagaatt atgcagtgct gccataacca tgagtgataa cactgcggcc aacttacttc   2280
tgacaacgat cggaggaccg aaggagctaa ccgctttttt gcacaacatg ggggatcatg   2340
taactcgcct tgatcgttgg gaaccggagc tgaatgaagc cataccaaac gacgagcgtg   2400
acaccacgat gcctgtagca atggcaacaa cgttgcgcaa actattaact ggcgaactac   2460
ttactctagc ttcccggcaa caattaatag actggatgga ggcggataaa gttgcaggac   2520
cacttctgcg ctcggccctt ccggctggct ggtttattgc tgataaatct ggagccggtg   2580
agcgtgggtc tcgcggtatc attgcagcac tggggccaga tggtaagccc tcccgtatcg   2640
tagttatcta cacgacgggg agtcaggcaa ctatggatga acgaaataga cagatcgctg   2700
agataggtgc ctcactgatt aagcattggt aactgtcaga ccaagtttac tcatatatac   2760
tttagattga tttaaaactt catttttaat ttaaaaggat ctaggtgaag atcctttttg   2820
ataatctcat gaccaaaatc ccttaacgtg agttttcgtt ccactgagcg tcagaccccg   2880
tagaaaagat caaaggatct tcttgagatc ctttttttct gcgcgtaatc tgctgcttgc   2940
aaacaaaaaa accaccgcta ccagcggtgg tttgtttgcc ggatcaagag ctaccaactc   3000
tttttccgaa ggtaactggc ttcagcagag cgcagatacc aaatactgtt cttctagtgt   3060
agccgtagtt aggccaccac ttcaagaact ctgtagcacc gcctacatac ctcgctctgc   3120
taatcctgtt accagtggct gctgccagtg gcgataagtc gtgtcttacc gggttggact   3180
caagacgata gttaccggat aaggcgcagc ggtcgggctg aacggggggt tcgtgcacac   3240
agcccagctt ggagcgaacg acctacaccg aactgagata cctacagcgt gagctatgag   3300
aaagcgccac gcttcccgaa gggagaaagg cggacaggta tccggtaagc ggcagggtcg   3360
gaacaggaga gcgcacgagg gagcttccag ggggaaacgc ctggtatctt tatagtcctg   3420
```

```
tcgggtttcg ccacctctga cttgagcgtc gatttttgtg atgctcgtca ggggggcgga   3480
gcctatggaa aaacgccagc aacgcggcct ttttacggtt cctggccttt tgctggcctt   3540
ttgctcacat gttctttcct gcgttatccc ctgattctgt ggataaccgt attaccgcct   3600
ttgagtgagc tgataccgct cgccgcagcc gaacgaccga gcgcagcgag tcagtgagcg   3660
aggaagcgga agagcgccca atacgcaaac cgcctctccc cgcgcgttgg ccgattcatt   3720
aatgcagctg gcacgacagg tttcccgact ggaaagcggg cagtgagcgc aacgcaatta   3780
atgtgagtta gctcactcat taggcacccc aggctttaca ctttatgctt ccggctcgta   3840
tgttgtgtgg aattgtgagc ggataacaat ttcacacagg aaacagctat gaccatgatt   3900
acgccaagct tttctttcc aattttttt ttttcgtcat tataaaaatc attacgaccg   3960
agattcccgg gtaataactg atataattaa attgaagctc taatttgtga gtttagtata   4020
catgcattta cttataatac agttttttag ttttgctggc cgcatcttct caaatatgct   4080
tcccagcctg cttttctgta acgttcaccc tctaccttag catcccttcc ctttgcaaat   4140
agtcctcttc caacaataat aatgtcagat cctgtagaga ccacatcatc cacggttcta   4200
tactgttgac ccaatgcgtc tcccttgtca tctaaaccca caccgggtgt cataatcaac   4260
caatcgtaac cttcatctct tccacccatg tctctttgag caataaagcc gataacaaaa   4320
tctttgtcgc tcttcgcaat gtcaacagta cccttagtat attctccagt agatagggag   4380
cccttgcatg acaattctgc taacatcaaa aggcctctag gttcctttgt tacttcttct   4440
gccgcctgct tcaaaccgct aacaatacct gggcccacca caccgtgtgc attcgtaatg   4500
tctgcccatt ctgctattct gtatacaccc gcagagtact gcaatttgac tgtattacca   4560
atgtcagcaa attttctgtc ttcgaagagt aaaaaattgt acttggcgga taatgccttt   4620
agcggcttaa ctgtgccctc catggaaaaa tcagtcaaga tatccacatg tgtttttagt   4680
aaacaaattt tgggacctaa tgcttcaact aactccagta attccttggt ggtacgaaca   4740
tccaatgaag cacacaagtt tgtttgcttt tcgtgcatga tattaaatag cttggcagca   4800
acaggactag gatgagtagc agcacgttcc ttatatgtag ctttcgacat gatttatctt   4860
cgtttcctgc aggtttttgt tctgtgcagt tgggttaaga atactgggca atttcatgtt   4920
tcttcaacac tacatatgcg tatatatacc aatctaagtc tgtgctcctt ccttcgttct   4980
tccttctgtt cggagattac cgaatcaaaa aaatttcaag gaaaccgaaa tcaaaaaaaa   5040
gaataaaaaa aaaatgatga attgaaaagc ttgcatgcct gcaggtcgac tctagtatac   5100
tccgtctact gtacgataca cttccgctca ggtccttgtc ctttaacgag gccttaccac   5160
tcttttgtta ctctattgat ccagctcagc aaaggcagtg tgatctaaga ttctatcttc   5220
gcgatgtagt aaaactagct agaccgagaa agagactaga aatgcaaaag gcacttctac   5280
aatggctgcc atcattatta tccgatgtga cgctgcattt ttttttttt ttttttttt   5340
ttttttttt ttttttttt tttttttttg tacaaatatc ataaaaaaag agaatctttt   5400
taagcaagga ttttcttaac ttcttcggcg acagcatcac cgacttcggt ggtactgttg   5460
gaaccaccta aatcaccagt tctgatacct gcatccaaaa cctttttaac tgcatcttca   5520
atggctttac cttcttcagg caagttcaat gacaatttca acatcattgc agcagacaag   5580
atagtggcga tagggttgac cttattcttt ggcaaatctg gagcggaacc atggcatggt   5640
tcgtacaaac caaatgcggt gttcttgtct ggcaaagagg ccaaggacgc agatggcaac   5700
aaacccaagg agcctgggat aacggaggct tcatcggaga tgatatcacc aaacatgttg   5760
ctggtgatta taataccatt taggtgggtt gggttcttaa ctaggatcat ggcggcagaa   5820
```

```
tcaatcaatt gatgttgaac tttcaatgta gggaattcgt tcttgatggt ttcctccaca   5880
gtttttctcc ataatcttga agaggccaaa acattagctt tatccaagga ccaaataggc   5940
aatggtggct catgttgtag ggccatgaaa gcggccattc ttgtgattct ttgcacttct   6000
ggaacggtgt attgttcact atcccaagcg acaccatcac catcgtcttc ctttctctta   6060
ccaaagtaaa tacctcccac taattctcta acaacaacga agtcagtacc tttagcaaat   6120
tgtggcttga ttggagataa gtctaaaaga gagtcggatg caaagttaca tggtcttaag   6180
ttggcgtaca attgaagttc tttacggatt tttagtaaac cttgttcagg tctaacacta   6240
ccggtacccc atttaggacc acccacagca cctaacaaaa cggcatcagc cttcttggag   6300
gcttccagcg cctcatctgg aagtggaaca cctgtagcat cgatagcagc accaccaatt   6360
aaatgatttt cgaaatcgaa cttgacattg gaacgaacat cagaaatagc tttaagaacc   6420
ttaatggctt cggctgtgat ttcttgacca acgtggtcac ctggcaaaac gacgatcttc   6480
ttaggggcag acattacaat ggtatatcct tgaaatatat ataaaaaaaa aaaaaaaaaa   6540
aaaaaaaaaa aatgcagctt ctcaatgata ttcgaatacg ctttgaggag atacagccta   6600
atatccgaca aactgtttta cagatttacg atcgtacttg ttacccatca ttgaattttg   6660
aacatccgaa cctgggagtt ttccctgaaa cagatagtat atttgaacct gtataataat   6720
atatagtcta gcgctttacg gaagacaatg tatgtatttc ggttcctgga gaaactattg   6780
catctattgc ataggtaatc ttgcacgtcg catccccggt tcattttctg cgtttccatc   6840
ttgcacttca atagcatatc tttgttaacg aagcatctgt gcttcatttt gtagaacaaa   6900
aatgcaacgc gagagcgcta atttttcaaa caaagaatct gagctgcatt tttacagaac   6960
agaaatgcaa cgcgaaagcg ctattttacc aacgaagaat ctgtgcttca tttttgtaaa   7020
acaaaaatgc aacgcgagag cgctaatttt tcaaacaaag aatctgagct gcatttttac   7080
agaacagaaa tgcaacgcga gagcgctatt ttaccaacaa agaatctata cttctttttt   7140
gttctacaaa aatgcatccc gagagcgcta tttttctaac aaagcatctt agattacttt   7200
ttttctcctt tgtgcgctct ataatgcagt ctcttgataa ctttttgcac tgtaggtccg   7260
ttaaggttag aagaaggcta ctttggtgtc tattttctct tccataaaaa aagcctgact   7320
ccacttcccg cgtttactga ttactagcga agctgcgggt gcattttttc aagataaagg   7380
catccccgat tatattctat accgatgtgg attgcgcata ctttgtgaac agaaagtgat   7440
agcgttgatg attcttcatt ggtcagaaaa ttatgaacgg tttcttctat tttgtctcta   7500
tatactacgt ataggaaatg tttacatttt cgtattgttt tcgattcact ctatgaatag   7560
ttcttactac aatttttttg tctaaagagt aatactagag ataaacataa aaaatgtaga   7620
ggtcgagttt agatgcaagt tcaaggagcg aaaggtggat gggtaggtta tatagggata   7680
tagcacagag atatatagca aagagatact tttgagcaat gtttgtggaa gcggtattcg   7740
caatatttta gtagctcgtt acagtccggt gcgtttttgg tttttgaaa gtgcgtcttc   7800
agagcgcttt tggttttcaa aagcgctctg aagttcctat actttctaga gaataggaac   7860
ttcggaatag gaacttcaaa gcgtttccga aaacgagcgc ttccgaaaat gcaacgcgag   7920
ctgcgcacat acagctcact gttcacgtcg cacctatatc tgcgtgttgc ctgtatatat   7980
atatacatga gaagaacggc atagtgcgtg tttatgctta aatgcgtact tatatgcgtc   8040
tatttatgta ggatgaaagg tagtctagta cctcctgtga tattatccca ttccatgcgg   8100
ggtatcgtat gcttccttca gcactaccct ttagctgttc tatatgctgc cactcctcaa   8160
```

```
ttggattagt ctcatccttc aatgctatca tttcctttga tattggatca tatgcatagt   8220

accgagaaac tagaggatct cccattaccg acatttgggc gctatacgtg catatgttca   8280

tgtatgtatc tgtatttaaa acacttttgt attatttttc ctcatatatg tgtataggtt   8340

tatacggatg atttaattat tacttcacca ccctttattt caggctgata tcttagcctt   8400

gttactagtc accggtggcg gccgcacctg gtaaaacctc tagtggagta gtagatgtaa   8460

tcaatgaagc ggaagccaaa agaccagagt agaggcctat agaagaaact gcgatacctt   8520

ttgtgatggc taaacaaaca gacatctttt tatatgtttt tacttctgta tatcgtgaag   8580

tagtaagtga taagcgaatt tggctaagaa cgttgtaagt gaacaaggga cctcttttgc   8640

ctttcaaaaa aggattaaat ggagttaatc attgagattt agttttcgtt agattctgta   8700

tccctaaata actcccttac ccgacgggaa ggcacaaaag acttgaataa tagcaaacgg   8760

ccagtagcca agaccaaata atactagagt taactgatgg tcttaaacag gcattacgtg   8820

gtgaactcca agaccaatat acaaaatatc gataagttat tcttgcccac caatttaagg   8880

agcctacatc aggacagtag taccattcct cagagaagag gtatacataa caagaaaatc   8940

gcgtgaacac cttatataac ttagcccgtt attgagctaa aaaaccttgc aaaatttcct   9000

atgaataaga atacttcaga cgtgataaaa atttactttc taactcttct cacgctgccc   9060

ctatctgttc ttccgctcta ccgtgagaaa taaagcatcg agtacggcag ttcgctgtca   9120

ctgaactaaa acaataaggc tagttcgaat gatgaacttg cttgctgtca aacttctgag   9180

ttgccgctga tgtgacactg tgacaataaa ttcaaaccgg ttatagcggt ctcctccggt   9240

accggttctg ccacctccaa tagagctcag taggagtcag aacctctgcg gtggctgtca   9300

gtgactcatc cgcgtttcgt aagttgtgcg cgtgcacatt tcgcccgttc ccgctcatct   9360

tgcagcaggc ggaaattttc atcacgctgt aggacgcaaa aaaaaaataa ttaatcgtac   9420

aagaatcttg gaaaaaaaat tgaaaaattt tgtataaaag ggatgaccta acttgactca   9480

atggctttta cacccagtat tttccctttc cttgtttgtt acaattatag aagcaagaca   9540

aaaacatata gacaacctat tcctaggagt tatatttttt taccctacca gcaatataag   9600

taaaaaactg ttt                                                      9613
```

<210> SEQ ID NO 105
<211> LENGTH: 9598
<212> TYPE: DNA
<213> ORGANISM: Artificial Sequence
<220> FEATURE:
<223> OTHER INFORMATION: pHR81-ILV5p-K9SB2-SH

<400> SEQUENCE: 105

```
aaacagtatg gctaagattt actaccaaga agactgtaac ttgtccttgt tggatggtaa     60

gactatcgcc gttatcggtt acggttctca aggtcacgct catgccctga atgctaagga    120

atccggttgt aacgttatca ttggtttatt cgaaggtgcg gaggagtgga aaagagctga    180

agaacaaggt ttcgaagtct acaccgctgc tgaagctgct aagaaggctg acatcattat    240

gatcttgatc ccagatgaaa agcaggctac catgtacaaa aacgacatcg aaccaaactt    300

ggaagccggt aacatgttga tgttcgctca cggtttcaac atccatttcg gttgtattgt    360

tccaccaaag gacgttgatg tcactatgat cgctccaaag ggtccaggtc acaccgttag    420

atccgaatac gaagaaggta aaggtgtccc atgcttggtt gctgtcgaac aagacgctac    480

tggcaaggct ttggatatgg ctttggccta cgctttagcc atcggtggtg ctagagccgg    540

tgtcttggaa actaccttca gaaccgaaac tgaaaccgac ttgttcggtg aacaagctgt    600
```

```
tttatgtggt ggtgtctgcg ctttgatgca ggccggtttt gaaaccttgg ttgaagccgg    660
ttacgaccca agaaacgctt acttcgaatg tatccacgaa atgaagttga tcgttgactt    720
gatctaccaa tctggtttct ccggtatgcg ttactctatc tccaacactg ctgaatacgg    780
tgactacatt accggtccaa agatcattac tgaagatacc aagaaggcta tgaagaagat    840
tttgtctgac attcaagatg gtacctttgc caaggacttc ttggttgaca tgtctgatgc    900
tggttcccag gtccacttca aggctatgag aaagttggcc tccgaacacc cagctgaagt    960
tgtcggtgaa gaaattagat ccttgtactc ctggtccgac gaagacaagt tgattaacaa   1020
ctgaggccct gcaggccaga ggaaaataat atcaagtgct ggaaactttt tctcttggaa   1080
tttttgcaac atcaagtcat agtcaattga attgacccaa tttcacattt aagatttttt   1140
ttttttcatc cgacatacat ctgtacacta ggaagccctg tttttctgaa gcagcttcaa   1200
atatatatat tttttacata tttattatga ttcaatgaac aatctaatta aatcgaaaac   1260
aagaaccgaa acgcgaataa ataatttatt tagatggtga caagtgtata agtcctcatc   1320
gggacagcta cgatttctct ttcggttttg gctgagctac tggttgctgt gacgcagcgg   1380
cattagcgcg gcgttatgag ctaccctcgt ggcctgaaag atggcgggaa taaagcggaa   1440
ctaaaaatta ctgactgagc catattgagg tcaatttgtc aactcgtcaa gtcacgtttg   1500
gtggacggcc cctttccaac gaatcgtata tactaacatg cgcgcgcttc ctatatacac   1560
atatacatat atatatatat atatatgtgt gcgtgtatgt gtacacctgt atttaatttc   1620
cttactcgcg ggtttttctt ttttctcaat tcttggcttc ctctttctcg agcggaccgg   1680
atcctccgcg gtgccggcag atctatttaa atggcgcgcc gacgtcaggt ggcacttttc   1740
ggggaaatgt gcgcggaacc cctatttgtt tatttttcta aatacattca aatatgtatc   1800
cgctcatgag acaataaccc tgataaatgc ttcaataata ttgaaaaagg aagagtatga   1860
gtattcaaca tttccgtgtc gcccttattc ccttttttgc ggcattttgc cttcctgttt   1920
ttgctcaccc agaaacgctg gtgaaagtaa aagatgctga agatcagttg ggtgcacgag   1980
tgggttacat cgaactggat ctcaacagcg gtaagatcct tgagagtttt cgccccgaag   2040
aacgttttcc aatgatgagc acttttaaag ttctgctatg tggcgcggta ttatcccgta   2100
ttgacgccgg gcaagagcaa ctcggtcgcc gcatacacta ttctcagaat gacttggttg   2160
agtactcacc agtcacagaa aagcatctta cggatggcat gacagtaaga gaattatgca   2220
gtgctgccat aaccatgagt gataacactg cggccaactt acttctgaca acgatcggag   2280
gaccgaagga gctaaccgct tttttgcaca acatggggga tcatgtaact cgccttgatc   2340
gttgggaacc ggagctgaat gaagccatac caaacgacga gcgtgacacc acgatgcctg   2400
tagcaatggc aacaacgttg cgcaaactat taactggcga actacttact ctagcttccc   2460
ggcaacaatt aatagactgg atggaggcgg ataaagttgc aggaccactt ctgcgctcgg   2520
cccttccggc tggctggttt attgctgata aatctggagc cggtgagcgt gggtctcgcg   2580
gtatcattgc agcactgggg ccagatggta agccctcccg tatcgtagtt atctacacga   2640
cggggagtca ggcaactatg gatgaacgaa atagacagat cgctgagata ggtgcctcac   2700
tgattaagca ttggtaactg tcagaccaag tttactcata tatactttag attgatttaa   2760
aacttcattt ttaatttaaa aggatctagg tgaagatcct ttttgataat ctcatgacca   2820
aaatccctta acgtgagttt tcgttccact gagcgtcaga ccccgtagaa aagatcaaag   2880
gatcttcttg agatcctttt tttctgcgcg taatctgctg cttgcaaaca aaaaaaccac   2940
```

```
cgctaccagc ggtggtttgt ttgccggatc aagagctacc aactcttttt ccgaaggtaa   3000
ctggcttcag cagagcgcag ataccaaata ctgttcttct agtgtagccg tagttaggcc   3060
accacttcaa gaactctgta gcaccgccta catacctcgc tctgctaatc ctgttaccag   3120
tggctgctgc cagtggcgat aagtcgtgtc ttaccgggtt ggactcaaga cgatagttac   3180
cggataaggc gcagcggtcg ggctgaacgg ggggttcgtg cacacagccc agcttggagc   3240
gaacgaccta caccgaactg agatacctac agcgtgagct atgagaaagc gccacgcttc   3300
ccgaagggag aaaggcggac aggtatccgg taagcggcag ggtcggaaca ggagagcgca   3360
cgagggagct tccaggggga aacgcctggt atctttatag tcctgtcggg tttcgccacc   3420
tctgacttga gcgtcgattt ttgtgatgct cgtcaggggg gcggagccta tggaaaaacg   3480
ccagcaacgc ggccttttta cggttcctgg ccttttgctg gccttttgct cacatgttct   3540
ttcctgcgtt atcccctgat tctgtggata accgtattac cgcctttgag tgagctgata   3600
ccgctcgccg cagccgaacg accgagcgca gcgagtcagt gagcgaggaa gcggaagagc   3660
gcccaatacg caaaccgcct ctccccgcgc gttggccgat tcattaatgc agctggcacg   3720
acaggtttcc cgactggaaa gcgggcagtg agcgcaacgc aattaatgtg agttagctca   3780
ctcattaggc accccaggct ttacacttta tgcttccggc tcgtatgttg tgtggaattg   3840
tgagcggata acaatttcac acaggaaaca gctatgacca tgattacgcc aagctttttc   3900
tttccaattt tttttttttc gtcattataa aaatcattac gaccgagatt cccgggtaat   3960
aactgatata attaaattga agctctaatt tgtgagttta gtatacatgc atttacttat   4020
aatacagttt tttagttttg ctggccgcat cttctcaaat atgcttccca gcctgctttt   4080
ctgtaacgtt caccctctac cttagcatcc cttccctttg caaatagtcc tcttccaaca   4140
ataataatgt cagatcctgt agagaccaca tcatccacgg ttctatactg ttgacccaat   4200
gcgtctccct tgtcatctaa acccacaccg ggtgtcataa tcaaccaatc gtaaccttca   4260
tctcttccac ccatgtctct ttgagcaata aagccgataa caaaatcttt gtcgctcttc   4320
gcaatgtcaa cagtaccctt agtatattct ccagtagata gggagccctt gcatgacaat   4380
tctgctaaca tcaaaaggcc tctaggttcc tttgttactt cttctgccgc ctgcttcaaa   4440
ccgctaacaa tacctgggcc caccacaccg tgtgcattcg taatgtctgc ccattctgct   4500
attctgtata cacccgcaga gtactgcaat ttgactgtat taccaatgtc agcaaatttt   4560
ctgtcttcga agagtaaaaa attgtacttg gcggataatg cctttagcgg cttaactgtg   4620
ccctccatgg aaaaatcagt caagatatcc acatgtgttt ttagtaaaca aattttggga   4680
cctaatgctt caactaactc cagtaattcc ttggtggtac gaacatccaa tgaagcacac   4740
aagtttgttt gcttttcgtg catgatatta aatagcttgg cagcaacagg actaggatga   4800
gtagcagcac gttccttata tgtagctttc gacatgattt atcttcgttt cctgcaggtt   4860
tttgttctgt gcagttgggt taagaatact gggcaatttc atgtttcttc aacactacat   4920
atgcgtatat ataccaatct aagtctgtgc tccttccttc gttcttcctt ctgttcggag   4980
attaccgaat caaaaaaatt tcaaggaaac cgaaatcaaa aaaaagaata aaaaaaaaat   5040
gatgaattga aaagcttgca tgcctgcagg tcgactctag tatactccgt ctactgtacg   5100
atacacttcc gctcaggtcc ttgtccttta acgaggcctt accactcttt tgttactcta   5160
ttgatccagc tcagcaaagg cagtgtgatc taagattcta tcttcgcgat gtagtaaaac   5220
tagctagacc gagaaagaga ctagaaatgc aaaaggcact tctacaatgg ctgccatcat   5280
tattatccga tgtgacgctg catttttttt tttttttttt tttttttttt tttttttttt   5340
```

```
ttttttttt ttttgtacaa atatcataaa aaaagagaat ctttttaagc aaggattttc   5400
ttaacttctt cggcgacagc atcaccgact tcggtggtac tgttggaacc acctaaatca   5460
ccagttctga tacctgcatc caaaaccttt ttaactgcat cttcaatggc tttaccttct   5520
tcaggcaagt tcaatgacaa tttcaacatc attgcagcag acaagatagt ggcgataggg   5580
ttgaccttat tctttggcaa atctggagcg gaaccatggc atggttcgta caaaccaaat   5640
gcggtgttct tgtctggcaa agaggccaag gacgcagatg gcaacaaacc caaggagcct   5700
gggataacgg aggcttcatc ggagatgata tcaccaaaca tgttgctggt gattataata   5760
ccatttaggt gggttgggtt cttaactagg atcatggcgg cagaatcaat caattgatgt   5820
tgaactttca atgtagggaa ttcgttcttg atggtttcct ccacagtttt tctccataat   5880
cttgaagagg ccaaaacatt agctttatcc aaggaccaaa taggcaatgg tggctcatgt   5940
tgtagggcca tgaaagcggc cattcttgtg attctttgca cttctggaac ggtgtattgt   6000
tcactatccc aagcgacacc atcaccatcg tcttcctttc tcttaccaaa gtaaatacct   6060
cccactaatt ctctaacaac aacgaagtca gtacctttag caaattgtgg cttgattgga   6120
gataagtcta aaagagagtc ggatgcaaag ttacatggtc ttaagttggc gtacaattga   6180
agttctttac ggatttttag taaaccttgt tcaggtctaa cactaccggt accccattta   6240
ggaccaccca cagcacctaa caaaacggca tcagccttct tggaggcttc cagcgcctca   6300
tctggaagtg gaacacctgt agcatcgata gcagcaccac caattaaatg attttcgaaa   6360
tcgaacttga cattggaacg aacatcagaa atagctttaa gaaccttaat ggcttcggct   6420
gtgatttctt gaccaacgtg gtcacctggc aaaacgacga tcttcttagg ggcagacatt   6480
acaatggtat atccttgaaa tatatataaa aaaaaaaaaa aaaaaaaaaa aaaaaaatgc   6540
agcttctcaa tgatattcga atacgctttg aggagataca gcctaatatc cgacaaactg   6600
ttttacagat ttacgatcgt acttgttacc catcattgaa ttttgaacat ccgaacctgg   6660
gagttttccc tgaaacagat agtatatttg aacctgtata ataatatata gtctagcgct   6720
ttacggaaga caatgtatgt atttcggttc ctggagaaac tattgcatct attgcatagg   6780
taatcttgca cgtcgcatcc ccggttcatt ttctgcgttt ccatcttgca cttcaatagc   6840
atatctttgt taacgaagca tctgtgcttc attttgtaga acaaaaatgc aacgcgagag   6900
cgctaatttt tcaaacaaag aatctgagct gcatttttac agaacagaaa tgcaacgcga   6960
aagcgctatt ttaccaacga agaatctgtg cttcattttt gtaaaacaaa aatgcaacgc   7020
gagagcgcta atttttcaaa caaagaatct gagctgcatt tttacagaac agaaatgcaa   7080
cgcgagagcg ctattttacc aacaaagaat ctatacttct tttttgttct acaaaaatgc   7140
atcccgagag cgctattttt ctaacaaagc atcttagatt actttttttc tcctttgtgc   7200
gctctataat gcagtctctt gataactttt tgcactgtag gtccgttaag gttagaagaa   7260
ggctactttg gtgtctattt tctcttccat aaaaaaagcc tgactccact tcccgcgttt   7320
actgattact agcgaagctg cgggtgcatt ttttcaagat aaaggcatcc ccgattatat   7380
tctataccga tgtggattgc gcatactttg tgaacagaaa gtgatagcgt tgatgattct   7440
tcattggtca gaaaattatg aacggtttct tctattttgt ctctatatac tacgtatagg   7500
aaatgtttac attttcgtat tgttttcgat tcactctatg aatagttctt actacaattt   7560
ttttgtctaa agagtaatac tagagataaa cataaaaaat gtagaggtcg agtttagatg   7620
caagttcaag gagcgaaagg tggatgggta ggttatatag ggatatagca cagagatata   7680
```

```
tagcaaagag atacttttga gcaatgtttg tggaagcggt attcgcaata ttttagtagc   7740
tcgttacagt ccggtgcgtt tttggttttt tgaaagtgcg tcttcagagc gcttttggtt   7800
ttcaaaagcg ctctgaagtt cctatacttt ctagagaata ggaacttcgg aataggaact   7860
tcaaagcgtt tccgaaaacg agcgcttccg aaaatgcaac gcgagctgcg cacatacagc   7920
tcactgttca cgtcgcacct atatctgcgt gttgcctgta tatatatata catgagaaga   7980
acggcatagt gcgtgtttat gcttaaatgc gtacttatat gcgtctattt atgtaggatg   8040
aaaggtagtc tagtacctcc tgtgatatta tcccattcca tgcggggtat cgtatgcttc   8100
cttcagcact accctttagc tgttctatat gctgccactc ctcaattgga ttagtctcat   8160
ccttcaatgc tatcatttcc tttgatattg gatcatatgc atagtaccga gaaactagag   8220
gatctcccat taccgacatt tggcgctat acgtgcatat gttcatgtat gtatctgtat   8280
ttaaaacact tttgtattat ttttcctcat atatgtgtat aggtttatac ggatgattta   8340
attattactt caccaccctt tatttcaggc tgatatctta gccttgttac tagtcaccgg   8400
tggcggccgc acctggtaaa acctctagtg gagtagtaga tgtaatcaat gaagcggaag   8460
ccaaaagacc agagtagagg cctatagaag aaactgcgat accttttgtg atggctaaac   8520
aaacagacat ctttttatat gtttttactt ctgtatatcg tgaagtagta agtgataagc   8580
gaatttggct aagaacgttg taagtgaaca agggacctct tttgcctttc aaaaaaggat   8640
taaatggagt taatcattga gatttagttt tcgttagatt ctgtatccct aaataactcc   8700
cttacccgac gggaaggcac aaaagacttg aataatagca aacggccagt agccaagacc   8760
aaataatact agagttaact gatggtctta aacaggcatt acgtggtgaa ctccaagacc   8820
aatatacaaa atatcgataa gttattcttg cccaccaatt taaggagcct acatcaggac   8880
agtagtacca ttcctcagag aagaggtata cataacaaga aaatcgcgtg aacaccttat   8940
ataacttagc ccgttattga gctaaaaaac cttgcaaaat ttcctatgaa taagaatact   9000
tcagacgtga taaaaattta ctttctaact cttctcacgc tgcccctatc tgttcttccg   9060
ctctaccgtg agaaataaag catcgagtac ggcagttcgc tgtcactgaa ctaaaacaat   9120
aaggctagtt cgaatgatga acttgcttgc tgtcaaactt ctgagttgcc gctgatgtga   9180
cactgtgaca ataaattcaa accggttata gcggtctcct ccggtaccgg ttctgccacc   9240
tccaatagag ctcagtagga gtcagaacct ctgcggtggc tgtcagtgac tcatccgcgt   9300
ttcgtaagtt gtgcgcgtgc acatttcgcc cgttcccgct catcttgcag caggcggaaa   9360
ttttcatcac gctgtaggac gcaaaaaaaa aataattaat cgtacaagaa tcttggaaaa   9420
aaaattgaaa aattttgtat aaaagggatg acctaacttg actcaatggc ttttacaccc   9480
agtattttcc ctttccttgt ttgttacaat tatagaagca agacaaaaac atatagacaa   9540
cctattccta ggagttatat ttttttaccc taccagcaat ataagtaaaa aactgttt     9598
```

<210> SEQ ID NO 106
<211> LENGTH: 1032
<212> TYPE: DNA
<213> ORGANISM: Artificial Sequence
<220> FEATURE:
<223> OTHER INFORMATION: K9JB4P KARI

<400> SEQUENCE: 106

```
atggaagaat gtaagatggc taagatttac taccaagaag actgtaactt gtccttgttg     60
gatggtaaga ctatcgccgt tatcggttac ggttctcaag gtcacgctca tgccctgaat    120
gctaaggaat ccggttgtaa cgttatcatt ggtttatacg aaggtgcgga ggagtggaaa    180
```

```
agagctgaag aacaaggttt cgaagtctac accgctgctg aagctgctaa gaaggctgac    240

atcattatga tcttgatccc agatgaaaag caggctacca tgtacaaaaa cgacatcgaa    300

ccaaacttgg aagccggtaa catgttgatg ttcgctcacg gtttcaacat ccatttcggt    360

tgtattgttc caccaaagga cgttgatgtc actatgatcg ctccaaaggg tccaggtcac    420

accgttagat ccgaatacga agaaggtaaa ggtgtcccat gcttggttgc tgtcgaacaa    480

gacgctactg gcaaggcttt ggatatggct ttggcctacg ctttagccat cggtggtgct    540

agagccggtg tcttggaaac taccttcaga accgaaactg aaaccgactt gttcggtgaa    600

caagctgttt tatgtggtgg tgtctgcgct ttgatgcagg ccggttttga aaccttggtt    660

gaagccggtt acgacccaag aaacgcttac ttcgaatgta tccacgaaat gaagttgatc    720

gttgacttga tctaccaatc tggtttctcc ggtatgcgtt actctatctc caacactgct    780

gaatacggtg actacattac cggtccaaag atcattactg aagataccaa gaaggctatg    840

aagaagattt tgtctgacat tcaagatggt acctttgcca aggacttctt ggttgacatg    900

tctgatgctg gttcccaggt ccacttcaag gctatgagaa agttggcctc cgaacaccca    960

gctgaagttg tcggtgaaga aattagatcc ttgtactcct ggtccgacga agacaagttg   1020

attaacaact ga                                                       1032
```

<210> SEQ ID NO 107
<211> LENGTH: 343
<212> TYPE: PRT
<213> ORGANISM: Artificial Sequence
<220> FEATURE:
<223> OTHER INFORMATION: K9JB4P KARI

<400> SEQUENCE: 107

```
Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30

Gln Gly His Ala His Ala Leu Asn Ala Lys Glu Ser Gly Cys Asn Val
        35                  40                  45

Ile Ile Gly Leu Tyr Glu Gly Ala Glu Glu Trp Lys Arg Ala Glu Glu
    50                  55                  60

Gln Gly Phe Glu Val Tyr Thr Ala Ala Glu Ala Ala Lys Lys Ala Asp
65                  70                  75                  80

Ile Ile Met Ile Leu Ile Pro Asp Glu Lys Gln Ala Thr Met Tyr Lys
                85                  90                  95

Asn Asp Ile Glu Pro Asn Leu Glu Ala Gly Asn Met Leu Met Phe Ala
            100                 105                 110

His Gly Phe Asn Ile His Phe Gly Cys Ile Val Pro Pro Lys Asp Val
        115                 120                 125

Asp Val Thr Met Ile Ala Pro Lys Gly Pro Gly His Thr Val Arg Ser
    130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Gly Val
        195                 200                 205
```

```
Cys Ala Leu Met Gln Ala Gly Phe Glu Thr Leu Val Glu Ala Gly Tyr
    210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
            260                 265                 270

Thr Glu Asp Thr Lys Lys Ala Met Lys Lys Ile Leu Ser Asp Ile Gln
        275                 280                 285

Asp Gly Thr Phe Ala Lys Asp Phe Leu Val Asp Met Ser Asp Ala Gly
    290                 295                 300

Ser Gln Val His Phe Lys Ala Met Arg Lys Leu Ala Ser Glu His Pro
305                 310                 315                 320

Ala Glu Val Val Gly Glu Glu Ile Arg Ser Leu Tyr Ser Trp Ser Asp
                325                 330                 335

Glu Asp Lys Leu Ile Asn Asn
            340
```

<210> SEQ ID NO 108
<211> LENGTH: 12319
<212> TYPE: DNA
<213> ORGANISM: Artificial Sequence
<220> FEATURE:
<223> OTHER INFORMATION: pLH689-L2V4

<400> SEQUENCE: 108

```
tcccattacc gacatttggg cgctatacgt gcatatgttc atgtatgtat ctgtatttaa     60

aacacttttg tattattttt cctcatatat gtgtataggt ttatacggat gatttaatta    120

ttacttcacc accctttatt tcaggctgat atcttagcct tgttactaga ttaatcatgt    180

aattagttat gtcacgctta cattcacgcc ctccccccac atccgctcta accgaaaagg    240

aaggagttag acaacctgaa gtctaggtcc ctatttattt ttttatagtt atgttagtat    300

taagaacgtt atttatattt caaatttttc ttttttttct gtacagacgc gtgtacgcat    360

gtaacattat actgaaaacc ttgcttgaga aggttttggg acgctcgaag gctttaattt    420

gcgggcggcc gcacctggta aaacctctag tggagtagta gatgtaatca atgaagcgga    480

agccaaaaga ccagagtaga ggcctataga agaaactgcg ataccttttg tgatggctaa    540

acaaacagac atctttttat atgtttttac ttctgtatat cgtgaagtag taagtgataa    600

gcgaatttgg ctaagaacgt tgtaagtgaa caagggacct cttttgcctt tcaaaaaagg    660

attaaatgga gttaatcatt gagatttagt tttcgttaga ttctgtatcc ctaaataact    720

cccttacccg acgggaaggc acaaaagact tgaataatag caaacggcca gtagccaaga    780

ccaaataata ctagagttaa ctgatggtct taaacaggca ttacgtggtg aactccaaga    840

ccaatataca aaatatcgat aagttattct tgcccaccaa tttaaggagc ctacatcagg    900

acagtagtac cattcctcag agaagaggta tacataacaa gaaaatcgcg tgaacacctt    960

atataactta gcccgttatt gagctaaaaa accttgcaaa atttcctatg aataagaata   1020

cttcagacgt gataaaaatt tactttctaa ctcttctcac gctgccccta tctgttcttc   1080

cgctctaccg tgagaaataa agcatcgagt acggcagttc gctgtcactg aactaaaaca   1140

ataaggctag ttcgaatgat gaacttgctt gctgtcaaac ttctgagttg ccgctgatgt   1200

gacactgtga caataaattc aaaccggtta tagcggtctc ctccggtacc ggttctgcca   1260
```

```
cctccaatag agctcagtag gagtcagaac ctctgcggtg gctgtcagtg actcatccgc   1320
gtttcgtaag ttgtgcgcgt gcacatttcg cccgttcccg ctcatcttgc agcaggcgga   1380
aattttcatc acgctgtagg acgcaaaaaa aaaataatta atcgtacaag aatcttggaa   1440
aaaaaattga aaaattttgt ataaaaggga tgacctaact tgactcaatg gcttttacac   1500
ccagtatttt ccctttcctt gtttgttaca attatagaag caagacaaaa acatatagac   1560
aacctattcc taggagttat attttttac cctaccagca atataagtaa aaaactgttt   1620
aaacagtatg gaagaatgta agatggctaa gatttactac caagaagact gtaacttgtc   1680
cttgttggat ggtaagacta tcgccgttat cggttacggt tctcaaggtc acgctcatgc   1740
cctgaatgct aaggaatccg gttgtaacgt tatcattggt ttatacgaag gtgcggagga   1800
gtggaaaaga gctgaagaac aaggtttcga agtctacacc gctgctgaag ctgctaagaa   1860
ggctgacatc attatgatct tgatcccaga tgaaaagcag gctaccatgt acaaaaacga   1920
catcgaacca aacttggaag ccggtaacat gttgatgttc gctcacggtt tcaacatcca   1980
tttcggttgt attgttccac caaaggacgt tgatgtcact atgatcgctc caaagggtcc   2040
aggtcacacc gttagatccg aatacgaaga aggtaaaggt gtcccatgct tggttgctgt   2100
cgaacaagac gctactggca aggctttgga tatggctttg gcctacgctt tagccatcgg   2160
tggtgctaga gccggtgtct tggaaactac cttcagaacc gaaactgaaa ccgacttgtt   2220
cggtgaacaa gctgttttat gtggtggtgt ctgcgctttg atgcaggccg gttttgaaac   2280
cttggttgaa gccggttacg acccaagaaa cgcttacttc gaatgtatcc acgaaatgaa   2340
gttgatcgtt gacttgatct accaatctgg tttctccggt atgcgttact ctatctccaa   2400
cactgctgaa tacggtgact acattaccgg tccaaagatc attactgaag ataccaagaa   2460
ggctatgaag aagattttgt ctgacattca agatggtacc tttgccaagg acttcttggt   2520
tgacatgtct gatgctggtt cccaggtcca cttcaaggct atgagaaagt tggcctccga   2580
acacccagct gaagttgtcg gtgaagaaat tagatccttg tactcctggt ccgacgaaga   2640
caagttgatt aacaactgag gccctgcagg ccagaggaaa ataatatcaa gtgctggaaa   2700
ctttttctct tggaattttt gcaacatcaa gtcatagtca attgaattga cccaatttca   2760
catttaagat ttttttttt tcatccgaca tacatctgta cactaggaag ccctgtttt   2820
ctgaagcagc ttcaaatata tatattttt acatatttat tatgattcaa tgaacaatct   2880
aattaaatcg aaaacaagaa ccgaaacgcg aataaataat ttatttagat ggtgacaagt   2940
gtataagtcc tcatcgggac agctacgatt tctctttcgg ttttggctga gctactggtt   3000
gctgtgacgc agcggcatta gcgcggcgtt atgagctacc ctcgtggcct gaaagatggc   3060
gggaataaag cggaactaaa aattactgac tgagccatat tgaggtcaat ttgtcaactc   3120
gtcaagtcac gtttggtgga cggccccttt ccaacgaatc gtatatacta acatgcgcgc   3180
gcttcctata tacacatata catatatata tatatatata tgtgtgcgtg tatgtgtaca   3240
cctgtattta atttccttac tcgcgggttt ttcttttttc tcaattcttg gcttcctctt   3300
tctcgagcgg accggatcct cgcgaactcc aaaatgagct atcaaaaacg atagatcgat   3360
taggatgact ttgaaatgac tccgcagtgg actggccgtt aatttcaagc gtgagtaaaa   3420
tagtgcatga caaaagatga gctaggcttt tgtaaaaata tcttacgttg taaaatttta   3480
gaaatcatta tttccttcat atcattttgt cattgacctt cagaagaaaa gagccgacca   3540
ataatataaa taaataaata aaaataatat tccattattt ctaaacagat tcaatactca   3600
```

-continued

```
ttaaaaaact atatcaatta atttgaatta acgcggccgc ttaaccacag caaccaggac   3660
aacatttttt gccagtttct tcaggcttcc aaaagtctgt tacggctccc ctagaagcag   3720
acgaaacgat gtgagcatat ttaccaagga taccgcgtga atagagcggt ggcaattcaa   3780
tggtctcttg acgatgtttt aactcttcat cggagatatc aaagtgtaat tccttagtgt   3840
cttggtcaat agtgactatg tctcctgttt gcaggtaggc gattggaccg ccatcttgtg   3900
cttcaggagc gatatgaccc acgacaagac cataagtacc acctgagaag cggccatctg   3960
tcagaagggc aactttttca ccttgccctt taccaacaat cattgatgaa agggaaagca   4020
tttcaggcat accaggaccg ccctttggtc ctacaaaacg tacgacaaca acatcaccat   4080
caacaatatc atcattcaag acagcttcaa tggcttcttc ttcagaatta aagaccttag   4140
caggaccgac atgacgacgc acttttacac cagaaacttt ggcaacggca ccgtctggag   4200
ccaagttacc atggagaata atgaccggac catcttcacg tttaggattt tcaagcggca   4260
taataacctt ttgaccaggt gttaaatcat caaaagcctt caaattttca gcgactgttt   4320
tgccagtaca agtgatacgg tcaccatgaa ggaagccatt tttaaggaga tatttcataa   4380
ctgctggtac ccctccgacc ttgtaaaggt cttggaatac atattgacca gaaggtttca   4440
aatcagccaa atgaggaact ttttcttgga aagtattgaa atcatcaagt gtcaattcca   4500
cattagcagc atgggcaata gctaagaggt gaagggttga gttggttgaa cctcccagag   4560
ccatagttac agtaatagca tcttcaaaag cttcacgcgt taaaatgtca gaaggtttta   4620
agcccatttc gagcattttg acaacagcgc gaccagcttc ttcaatatct gctttctttt   4680
ctgcggattc agccgggtga gaagatgaac ccggaaggct aagtcccaaa acttcaatag   4740
ctgtcgccat tgtgttagca gtatacatac caccgcagcc tccaggaccg ggacaagcat   4800
tacattccaa agctttaact tcttctttgg tcatatcgcc gtggttccaa tggccgacac   4860
cttcaaagac agagactaaa tcgatatctt tgccgtctaa attaccaggt gcaattgttc   4920
cgccgtaagc aaaaatggct gggatatcca tgttagccat agcgataaca gaaccgggca   4980
tgtttttatc acaaccgcca atggctacaa aagcatccgc attatgacct cccatggctg   5040
cttcaataga atctgcaata atatcacgag atgtcaagga gaaacgcatt ccttgggttc   5100
ccatggcgat tccatcagaa accgtgattg ttccgaactg aactggccaa gcaccagctt   5160
ccttaacacc gactttggct agtttaccaa agtcatgtaa gtggatatta caaggtgtgt   5220
tttcagccca agttgaaatg acaccgacga taggtttttc aaagtcttca tcttgcatac   5280
cagttgcacg caacatagca cgattaggtg atttaaccat tgaatcgtaa acagaactac   5340
gatttcttaa gtctttaaga gtttttttgt cagtcatact cacgtgaaac ttagattaga   5400
ttgctatgct ttctttccaa tgagcaagaa gtaaaaaaag ttgtaataga acaggaaaaa   5460
tgaagctgaa acttgagaaa ttgaagaccg tttgttaact caaatatcaa tgggaggtcg   5520
tcgaaagaga acaaaatcga aaaaaaagtt ttcaagagaa agaaacgtga taaaaatttt   5580
tattgccttc tccgacgaag aaaaagggac gaggcggtct ctttttcctt ttccaaacct   5640
ttagtacggg taattaacgg caccctagag gaaggaggag ggggaattta gtatgctgtg   5700
cttgggtgtt ttgaagtggt acggcggtgc gcggagtccg agaaaatctg gaagagtaaa   5760
aaaggagtag agacattttg aagctatgcc ggcagatcta tttaaatggc gcgccgacgt   5820
caggtggcac ttttcgggga aatgtgcgcg gaacccctat ttgtttattt ttctaaatac   5880
attcaaatat gtatccgctc atgagacaat aaccctgata aatgcttcaa taatattgaa   5940
aaaggaagag tatgagtatt caacatttcc gtgtcgccct tattcccttt tttgcggcat   6000
```

```
tttgccttcc tgtttttgct cacccagaaa cgctggtgaa agtaaaagat gctgaagatc   6060

agttgggtgc acgagtgggt tacatcgaac tggatctcaa cagcggtaag atccttgaga   6120

gttttcgccc cgaagaacgt tttccaatga tgagcacttt taaagttctg ctatgtggcg   6180

cggtattatc ccgtattgac gccgggcaag agcaactcgg tcgccgcata cactattctc   6240

agaatgactt ggttgagtac tcaccagtca cagaaaagca tcttacggat ggcatgacag   6300

taagagaatt atgcagtgct gccataacca tgagtgataa cactgcggcc aacttacttc   6360

tgacaacgat cggaggaccg aaggagctaa ccgctttttt gcacaacatg ggggatcatg   6420

taactcgcct tgatcgttgg gaaccggagc tgaatgaagc cataccaaac gacgagcgtg   6480

acaccacgat gcctgtagca atggcaacaa cgttgcgcaa actattaact ggcgaactac   6540

ttactctagc ttcccggcaa caattaatag actggatgga ggcggataaa gttgcaggac   6600

cacttctgcg ctcggccctt ccggctggct ggtttattgc tgataaatct ggagccggtg   6660

agcgtgggtc tcgcggtatc attgcagcac tggggccaga tggtaagccc tcccgtatcg   6720

tagttatcta cacgacgggg agtcaggcaa ctatggatga acgaaataga cagatcgctg   6780

agataggtgc ctcactgatt aagcattggt aactgtcaga ccaagtttac tcatatatac   6840

tttagattga tttaaaactt catttttaat ttaaaaggat ctaggtgaag atcctttttg   6900

ataatctcat gaccaaaatc ccttaacgtg agttttcgtt ccactgagcg tcagaccccg   6960

tagaaaagat caaaggatct tcttgagatc cttttttct gcgcgtaatc tgctgcttgc    7020

aaacaaaaaa accaccgcta ccagcggtgg tttgtttgcc ggatcaagag ctaccaactc   7080

tttttccgaa ggtaactggc ttcagcagag cgcagatacc aaatactgtt cttctagtgt   7140

agccgtagtt aggccaccac ttcaagaact ctgtagcacc gcctacatac ctcgctctgc   7200

taatcctgtt accagtggct gctgccagtg gcgataagtc gtgtcttacc gggttggact   7260

caagacgata gttaccggat aaggcgcagc ggtcgggctg aacggggggt tcgtgcacac   7320

agcccagctt ggagcgaacg acctacaccg aactgagata cctacagcgt gagctatgag   7380

aaagcgccac gcttcccgaa gggagaaagg cggacaggta tccggtaagc ggcagggtcg   7440

gaacaggaga gcgcacgagg gagcttccag ggggaaacgc ctggtatctt tatagtcctg   7500

tcgggtttcg ccacctctga cttgagcgtc gatttttgtg atgctcgtca ggggggcgga   7560

gcctatggaa aaacgccagc aacgcggcct ttttacggtt cctggccttt tgctggcctt   7620

ttgctcacat gttctttcct gcgttatccc ctgattctgt ggataaccgt attaccgcct   7680

ttgagtgagc tgataccgct cgccgcagcc gaacgaccga gcgcagcgag tcagtgagcg   7740

aggaagcgga agagcgccca atacgcaaac cgcctctccc cgcgcgttgg ccgattcatt   7800

aatgcagctg gcacgacagg tttcccgact ggaaagcggg cagtgagcgc aacgcaatta   7860

atgtgagtta gctcactcat taggcacccc aggctttaca ctttatgctt ccggctcgta   7920

tgttgtgtgg aattgtgagc ggataacaat ttcacacagg aaacagctat gaccatgatt   7980

acgccaagct tttctttcc aattttttt ttttcgtcat tataaaaatc attacgaccg     8040

agattcccgg gtaataactg atataattaa attgaagctc taatttgtga gtttagtata   8100

catgcattta cttataatac agttttttag ttttgctggc cgcatcttct caaatatgct   8160

tcccagcctg cttttctgta acgttcaccc tctaccttag catcccttcc ctttgcaaat   8220

agtcctcttc caacaataat aatgtcagat cctgtagaga ccacatcatc cacggttcta   8280

tactgttgac ccaatgcgtc tcccttgtca tctaaaccca caccgggtgt cataatcaac   8340
```

```
caatcgtaac cttcatctct tccacccatg tctctttgag caataaagcc gataacaaaa   8400
tctttgtcgc tcttcgcaat gtcaacagta cccttagtat attctccagt agatagggag   8460
cccttgcatg acaattctgc taacatcaaa aggcctctag gttcctttgt tacttcttct   8520
gccgcctgct tcaaaccgct aacaatacct gggcccacca caccgtgtgc attcgtaatg   8580
tctgcccatt ctgctattct gtatacaccc gcagagtact gcaatttgac tgtattacca   8640
atgtcagcaa attttctgtc ttcgaagagt aaaaaattgt acttggcgga taatgccttt   8700
agcggcttaa ctgtgccctc catggaaaaa tcagtcaaga tatccacatg tgtttttagt   8760
aaacaaattt tgggacctaa tgcttcaact aactccagta attccttggt ggtacgaaca   8820
tccaatgaag cacacaagtt tgtttgcttt tcgtgcatga tattaaatag cttggcagca   8880
acaggactag gatgagtagc agcacgttcc ttatatgtag ctttcgacat gatttatctt   8940
cgtttcctgc aggtttttgt tctgtgcagt tgggttaaga atactgggca atttcatgtt   9000
tcttcaacac tacatatgcg tatatatacc aatctaagtc tgtgctcctt ccttcgttct   9060
tccttctgtt cggagattac cgaatcaaaa aaatttcaag gaaaccgaaa tcaaaaaaaa   9120
gaataaaaaa aaaatgatga attgaaaagc ttgcatgcct gcaggtcgac tctagtatac   9180
tccgtctact gtacgataca cttccgctca ggtccttgtc ctttaacgag gccttaccac   9240
tcttttgtta ctctattgat ccagctcagc aaaggcagtg tgatctaaga ttctatcttc   9300
gcgatgtagt aaaactagct agaccgagaa agagactaga aatgcaaaag gcacttctac   9360
aatggctgcc atcattatta tccgatgtga cgctgcattt tttttttttt tttttttttt   9420
tttttttttt tttttttttt tttttttttg tacaaatatc ataaaaaaag agaatctttt   9480
taagcaagga ttttcttaac ttcttcggcg acagcatcac cgacttcggt ggtactgttg   9540
gaaccaccta aatcaccagt tctgatacct gcatccaaaa cctttttaac tgcatcttca   9600
atggctttac cttcttcagg caagttcaat gacaatttca acatcattgc agcagacaag   9660
atagtggcga tagggttgac cttattcttt ggcaaatctg gagcggaacc atggcatggt   9720
tcgtacaaac caaatgcggt gttcttgtct ggcaaagagg ccaaggacgc agatggcaac   9780
aaacccaagg agcctgggat aacggaggct tcatcggaga tgatatcacc aaacatgttg   9840
ctggtgatta taataccatt taggtgggtt gggttcttaa ctaggatcat ggcggcagaa   9900
tcaatcaatt gatgttgaac tttcaatgta gggaattcgt tcttgatggt ttcctccaca   9960
gtttttctcc ataatcttga agaggccaaa acattagctt tatccaagga ccaaataggc  10020
aatggtggct catgttgtag ggccatgaaa gcggccattc ttgtgattct ttgcacttct  10080
ggaacggtgt attgttcact atcccaagcg acaccatcac catcgtcttc ctttctctta  10140
ccaaagtaaa tacctcccac taattctcta acaacaacga agtcagtacc tttagcaaat  10200
tgtggcttga ttggagataa gtctaaaaga gagtcggatg caaagttaca tggtcttaag  10260
ttggcgtaca attgaagttc tttacggatt tttagtaaac cttgttcagg tctaacacta  10320
ccggtacccc atttaggacc acccacagca cctaacaaaa cggcatcagc cttcttggag  10380
gcttccagcg cctcatctgg aagtggaaca cctgtagcat cgatagcagc accaccaatt  10440
aaatgatttt cgaaatcgaa cttgacattg gaacgaacat cagaaatagc tttaagaacc  10500
ttaatggctt cggctgtgat ttcttgacca acgtggtcac ctggcaaaac gacgatcttc  10560
ttaggggcag acattacaat ggtatatcct tgaaatatat ataaaaaaaa aaaaaaaaaa  10620
aaaaaaaaaa aatgcagctt ctcaatgata ttcgaatacg ctttgaggag atacagccta  10680
atatccgaca aactgtttta cagatttacg atcgtacttg ttacccatca ttgaattttg  10740
```

```
aacatccgaa cctgggagtt ttccctgaaa cagatagtat atttgaacct gtataataat  10800

atatagtcta gcgctttacg gaagacaatg tatgtatttc ggttcctgga gaaactattg  10860

catctattgc ataggtaatc ttgcacgtcg catccccggt tcattttctg cgtttccatc  10920

ttgcacttca atagcatatc tttgttaacg aagcatctgt gcttcatttt gtagaacaaa  10980

aatgcaacgc gagagcgcta atttttcaaa caaagaatct gagctgcatt tttacagaac  11040

agaaatgcaa cgcgaaagcg ctattttacc aacgaagaat ctgtgcttca tttttgtaaa  11100

acaaaaatgc aacgcgagag cgctaatttt tcaaacaaag aatctgagct gcatttttac  11160

agaacagaaa tgcaacgcga gagcgctatt ttaccaacaa agaatctata cttctttttt  11220

gttctacaaa aatgcatccc gagagcgcta tttttctaac aaagcatctt agattacttt  11280

ttttctcctt tgtgcgctct ataatgcagt ctcttgataa ctttttgcac tgtaggtccg  11340

ttaaggttag aagaaggcta ctttggtgtc tattttctct tccataaaaa aagcctgact  11400

ccacttcccg cgtttactga ttactagcga agctgcgggt gcattttttc aagataaagg  11460

catccccgat tatattctat accgatgtgg attgcgcata ctttgtgaac agaaagtgat  11520

agcgttgatg attcttcatt ggtcagaaaa ttatgaacgg tttcttctat tttgtctcta  11580

tatactacgt ataggaaatg tttacatttt cgtattgttt tcgattcact ctatgaatag  11640

ttcttactac aatttttttg tctaaagagt aatactagag ataaacataa aaaatgtaga  11700

ggtcgagttt agatgcaagt tcaaggagcg aaaggtggat gggtaggtta tatagggata  11760

tagcacagag atatatagca aagagatact tttgagcaat gtttgtggaa gcggtattcg  11820

caatatttta gtagctcgtt acagtccggt gcgtttttgg tttttgaaa gtgcgtcttc  11880

agagcgcttt tggttttcaa aagcgctctg aagttcctat actttctaga gaataggaac  11940

ttcggaatag gaacttcaaa gcgtttccga aaacgagcgc ttccgaaaat gcaacgcgag  12000

ctgcgcacat acagctcact gttcacgtcg cacctatatc tgcgtgttgc ctgtatatat  12060

atatacatga gaagaacggc atagtgcgtg tttatgctta aatgcgtact tatatgcgtc  12120

tatttatgta ggatgaaagg tagtctagta cctcctgtga tattatccca ttccatgcgg  12180

ggtatcgtat gcttccttca gcactaccct ttagctgttc tatatgctgc cactcctcaa  12240

ttggattagt ctcatccttc aatgctatca tttcctttga tattggatca tatgcatagt  12300

accgagaaac tagaggatc                                              12319
```

```
<210> SEQ ID NO 109
<211> LENGTH: 11013
<212> TYPE: DNA
<213> ORGANISM: Artificial Sequence
<220> FEATURE:
<223> OTHER INFORMATION: pRS413 BiADH kivD

<400> SEQUENCE: 109

tcgcgcgttt cggtgatgac ggtgaaaacc tctgacacat gcagctcccg gagacggtca     60

cagcttgtct gtaagcggat gccgggagca gacaagcccg tcagggcgcg tcagcgcgtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctctag tacactctat atttttttat gcctcggtaa tgattttcat    360

ttttttttt cccctagcgg atgactcttt ttttttctta gcgattggca ttatcacata    420
```

```
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
ccttttttct tttgctttt tcttttttt tctcttgaac tcgacggatc tatgcggtgt   1380
gaaataccgc acagatgcgt aaggagaaaa taccgcatca ggaaattgta aacgttaata   1440
ttttgttaaa attcgcgtta aatttttgtt aaatcagctc atttttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta aatcggaacc ctaaagggag cccccgattt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa aggggatgt gctgcaaggc   1980
gattaagttg ggtaacgcca gggttttccc agtcacgacg ttgtaaaacg acggccagtg   2040
agcgcgcgta atacgactca ctatagggcg aattgggtac cgggcccccc ctgtacgcat   2100
gtaacattat actgaaaacc ttgcttgaga aggttttggg acgctcgaag gctttaattt   2160
cctgcaggaa ttaccgtcgc tcgtgatttg tttgcaaaaa gaacaaaact gaaaaaaccc   2220
agacacgctc gacttcctgt cttcctattg attgcagctt ccaatttcgt cacacaacaa   2280
ggtcctgtcg acgcctactt ggcttcacat acgttgcata cgtcgatata gataataatg   2340
ataatgacag caggattatc gtaatacgta atagttgaaa atctcaaaaa tgtgtgggtc   2400
attacgtaaa taatgatagg aatgggattc ttctattttt cctttttcca ttctagcagc   2460
cgtcgggaaa acgtggcatc ctctctttcg ggctcaattg gagtcacgct gccgtgagca   2520
tcctctcttt ccatatctaa caactgagca cgtaaccaat ggaaaagcat gagcttagcg   2580
ttgctccaaa aaagtattgg atggttaata ccatttgtct gttctcttct gactttgact   2640
cctcaaaaaa aaaaaatcta caatcaacag atcgcttcaa ttacgccctc acaaaaactt   2700
ttttccttct tcttcgccca cgttaaattt tatccctcat gttgtctaac ggatttctgc   2760
acttgattta ttataaaaag acaaagacat aatacttctc tatcaatttc agttattgtt   2820
```

```
cttccttgcg ttattcttct gttcttcttt ttcttttgtc atatataacc ataaccaagt   2880
aatacatatt caagtttaaa catgtatacc gtaggacagt acttggtaga tagactagaa   2940
gagattggta tcgataaggt tttcggtgtg ccaggggatt acaatttgac ttttctagat   3000
tacattcaaa atcacgaagg actttcctgg caagggaata ctaatgaact aaacgcagca   3060
tatgcagcag atggctacgc ccgtgaaaga ggcgtatcag ctcttgttac tacattcgga   3120
gtgggtgaac tgtcagccat taacggaaca gctggtagtt ttgcagaaca agtccctgtc   3180
atccacatcg tgggttctcc aactatgaat gtgcaatcca acaaaaagct ggttcatcat   3240
tccttaggaa tgggtaactt tcataacttt agtgaaatgg ctaaggaagt cactgccgct   3300
acaaccatgc ttactgaaga gaatgcagct tcagagatcg acagagtatt agaaacagcc   3360
ttgttggaaa agaggccagt atacatcaat cttccaattg atatagctca taaagcaata   3420
gttaaacctg caaaagcact acaaacagag aaatcatctg gtgagagaga ggcacaactt   3480
gcagaaatca tactatcaca cttagaaaag gccgctcaac ctatcgtaat cgccggtcat   3540
gagatcgccc gtttccagat aagagaaaga tttgaaaact ggataaacca aacaaagttg   3600
ccagtaacca atttggcata tggcaaaggc tctttcaatg aagagaacga acatttcatt   3660
ggtacctatt acccagcttt ttctgacaaa aacgttctgg attacgttga caatagtgac   3720
ttcgttttac attttggtgg gaaaatcatt gacaattcta cctcctcatt ttctcaaggc   3780
tttaagactg aaaacacttt aaccgctgca aatgacatca ttatgctgcc agatgggtct   3840
acttactctg ggatttctct taacggtctt ttggcagagc tggaaaaact aaactttact   3900
tttgctgata ctgctgctaa acaagctgaa ttagctgttt tcgaaccaca ggccgaaaca   3960
ccactaaagc aagacagatt tcaccaagct gttatgaact tttgcaagc tgatgatgtg    4020
ttggtcactg agcaggggac atcatctttc ggtttgatgt tggcacctct gaaaaagggt   4080
atgaatttga tcagtcaaac attatggggc tccataggat acacattacc tgctatgatt   4140
ggttcacaaa ttgctgcccc agaaaggaga cacattctat ccatcggtga tggatctttt   4200
caactgacag cacaggaaat gtccaccatc ttcagagaga aattgacacc agtgatattc   4260
attatcaata acgatggcta tacagtcgaa agagccatcc atggagagga tgagagttac   4320
aatgatatac caacttggaa cttgcaatta gttgctgaaa catttggtgg tgatgccgaa   4380
actgtcgaca ctcacaacgt tttcacagaa acagacttcg ctaatacttt agctgctatc   4440
gatgctactc ctcaaaaagc acatgtcgtt gaagttcata tggaacaaat ggatatgcca   4500
gaatcattga gacagattgg cttagcctta tctaagcaaa actcttaacc tgcagggccg   4560
tgaatttact ttaaatcttg catttaaata aattttcttt ttatagcttt atgacttagt   4620
ttcaatttat atactatttt aatgacattt tcgattcatt gattgaaagc tttgtgtttt   4680
ttcttgatgc gctattgcat tgttcttgtc tttttcgcca catgtaatat ctgtagtaga   4740
tacctgatac attgtggatg ctgagtgaaa ttttagttaa taatggaggc gctcttaata   4800
attttgggga tattggcttt tttttttaaa gtttacaaat gaattttttc cgccaggata   4860
acgattctga agttactctt agcgttccta tcggtacagc catcaaatca tgcctataaa   4920
tcatgcctat atttgcgtgc agtcagtatc atctacatga aaaaaactcc cgcaatttct   4980
tatagaatac gttgaaaatt aaatgtacgc gccaagataa gataacatat atctagatgc   5040
agtaatatac acagattccc gcggacgtgg gaaggaaaaa attagataac aaaatctgag   5100
tgatatggaa attccgctgt atagctcata tctttcccta cctggtaaaa cctctagtgg   5160
```

```
agtagtagat gtaatcaatg aagcggaagc caaaagacca gagtagaggc ctatagaaga   5220

aactgcgata ccttttgtga tggctaaaca aacagacatc tttttatatg tttttacttc   5280

tgtatatcgt gaagtagtaa gtgataagcg aatttggcta agaacgttgt aagtgaacaa   5340

gggacctctt ttgcctttca aaaaaggatt aaatggagtt aatcattgag atttagtttt   5400

cgttagattc tgtatcccta aataactccc ttacccgacg ggaaggcaca aaagacttga   5460

ataatagcaa acggccagta gccaagacca aataatacta gagttaactg atggtcttaa   5520

acaggcatta cgtggtgaac tccaagacca atatacaaaa tatcgataag ttattcttgc   5580

ccaccaattt aaggagccta catcaggaca gtagtaccat tcctcagaga agaggtatac   5640

ataacaagaa aatcgcgtga acaccttata taacttagcc cgttattgag ctaaaaaacc   5700

ttgcaaaatt tcctatgaat aagaatactt cagacgtgat aaaaatttac tttctaactc   5760

ttctcacgct gcccctatct gttcttccgc tctaccgtga gaaataaagc atcgagtacg   5820

gcagttcgct gtcactgaac taaaacaata aggctagttc gaatgatgaa cttgcttgct   5880

gtcaaacttc tgagttgccg ctgatgtgac actgtgacaa taaattcaaa ccggttatag   5940

cggtctcctc cggtaccggt tctgccacct ccaatagagc tcccgcacgc cgaaatgcat   6000

gcaagtaacc tattcaaagt aatatctcat acatgtttca tgagggtaac aacatgcgac   6060

tgggtgagca tatgttccgc tgatgtgatg tgcaagataa acaagcaagg cagaaactaa   6120

cttcttcttc atgtaataaa cacaccccgc gtttatttac ctatctctaa acttcaacac   6180

cttatatcat aactaatatt tcttgagata agcacactgc acccatacct tccttaaaaa   6240

cgtagcttcc agtttttggt ggttccggct tccttcccga ttccgcccgc taaacgcata   6300

tttttgttgc ctggtggcat ttgcaaaatg cataacctat gcatttaaaa gattatgtat   6360

gctcttctga cttttcgtgt gatgaggctc gtggaaaaaa tgaataattt atgaatttga   6420

gaacaatttt gtgttgttac ggtattttac tatggaataa tcaatcaatt gaggatttta   6480

tgcaaatatc gtttgaatat ttttccgacc ctttgagtac ttttcttcat aattgcataa   6540

tattgtccgc tgcccctttt tctgttagac ggtgtcttga tctacttgct atcgttcaac   6600

accaccttat tttctaacta tttttttttt agctcatttg aatcagctta tggtgatggc   6660

acatttttgc ataaacctag ctgtcctcgt tgaacatagg aaaaaaaaat atataaacaa   6720

ggctctttca ctctccttgc aatcagattt gggtttgttc cctttatttt catatttctt   6780

gtcatattcc tttctcaatt attattttct actcataacc tcacgcaaaa taacacagtc   6840

aaatcaatca aaatgaaagc attagtgtat aggggcccag gccagaagtt ggtggaagag   6900

agacagaagc cagagcttaa ggaacctggt gacgctatag tgaaggtaac aaagactaca   6960

atttgcggaa ccgatctaca cattcttaaa ggtgacgttg cgacttgtaa acccggtcgt   7020

gtattagggc atgaaggagt gggggttatt gaatcagtcg gatctggggt tactgctttc   7080

caaccaggcg atagagtttt gatatcatgt atatcgagtt gcggaaagtg ctcattttgt   7140

agaagaggaa tgttcagtca ctgtacgacc gggggttgga ttctgggcaa cgaaattgat   7200

ggtacccaag cagagtacgt aagagtacca catgctgaca catccccttta tcgtattccg   7260

gcaggtgcgg atgaagaggc cttagtcatg ttatcagata ttctaccaac gggttttgag   7320

tgcggagtcc taaacggcaa agtcgcacct ggttcttcgg tggctatagt aggtgctggt   7380

cccgttggtt tggccgcctt actgacagca caattctact ccccagctga aatcataatg   7440

atcgatcttg atgataacag gctgggatta gccaaacaat ttggtgccac cagaacagta   7500

aactccacgg gtggtaacgc cgcagccgaa gtgaaagctc ttactgaagg cttaggtgtt   7560
```

```
gatactgcga ttgaagcagt tgggatacct gctacatttg aattgtgtca gaatatcgta   7620
gctcccggtg gaactatcgc taatgtcggc gttcacggta gcaaagttga tttgcatctt   7680
gaaagtttat ggtcccataa tgtcacgatt actacaaggt tggttgacac ggctaccacc   7740
ccgatgttac tgaaaactgt tcaaagtcac aagctagatc catctagatt gataacacat   7800
agattcagcc tggaccagat cttggacgca tatgaaactt ttggccaagc tgcgtctact   7860
caagcactaa aagtcatcat ttcgatggag gcttgattaa ttaagagtaa gcgaatttct   7920
tatgatttat gatttttatt attaaataag ttataaaaaa aataagtgta tacaaatttt   7980
aaagtgactc ttaggtttta aaacgaaaat tcttattctt gagtaactct ttcctgtagg   8040
tcaggttgct ttctcaggta tagcatgagg tcgctcttat tgaccacacc tctaccggca   8100
tgccgagcaa atgcctgcaa atcgctcccc atttcaccca attgtagata tgctaactcc   8160
agcaatgagt tgatgaatct cggtgtgtat tttatgtcct cagaggacaa cacctgtggt   8220
gagctccagc ttttgttccc tttagtgagg gttaattgcg cgcttggcgt aatcatggtc   8280
atagctgttt cctgtgtgaa attgttatcc gctcacaatt ccacacaaca taggagccgg   8340
aagcataaag tgtaaagcct ggggtgccta atgagtgagg taactcacat taattgcgtt   8400
gcgctcactg cccgctttcc agtcgggaaa cctgtcgtgc cagctgcatt aatgaatcgg   8460
ccaacgcgcg gggagaggcg gtttgcgtat tgggcgctct tccgcttcct cgctcactga   8520
ctcgctgcgc tcggtcgttc ggctgcggcg agcggtatca gctcactcaa aggcggtaat   8580
acggttatcc acagaatcag gggataacgc aggaaagaac atgtgagcaa aaggccagca   8640
aaaggccagg aaccgtaaaa aggccgcgtt gctggcgttt ttccataggc tccgcccccc   8700
tgacgagcat cacaaaaatc gacgctcaag tcagaggtgg cgaaacccga caggactata   8760
aagataccag gcgtttcccc ctggaagctc cctcgtgcgc tctcctgttc cgaccctgcc   8820
gcttaccgga tacctgtccg cctttctccc ttcgggaagc gtggcgcttt ctcatagctc   8880
acgctgtagg tatctcagtt cggtgtaggt cgttcgctcc aagctgggct gtgtgcacga   8940
accccccgtt cagcccgacc gctgcgcctt atccggtaac tatcgtcttg agtccaaccc   9000
ggtaagacac gacttatcgc cactggcagc agccactggt aacaggatta gcagagcgag   9060
gtatgtaggc ggtgctacag agttcttgaa gtggtggcct aactacggct acactagaag   9120
gacagtattt ggtatctgcg ctctgctgaa gccagttacc ttcggaaaaa gagttggtag   9180
ctcttgatcc ggcaaacaaa ccaccgctgg tagcggtggt ttttttgttt gcaagcagca   9240
gattacgcgc agaaaaaaag gatctcaaga agatcctttg atcttttcta cggggtctga   9300
cgctcagtgg aacgaaaact cacgttaagg gattttggtc atgagattat caaaaaggat   9360
cttcacctag atccttttaa attaaaaatg aagttttaaa tcaatctaaa gtatatatga   9420
gtaaacttgg tctgacagtt accaatgctt aatcagtgag gcacctatct cagcgatctg   9480
tctatttcgt tcatccatag ttgcctgact ccccgtcgtg tagataacta cgatacggga   9540
gggcttacca tctggcccca gtgctgcaat gataccgcga gacccacgct caccggctcc   9600
agatttatca gcaataaacc agccagccgg aagggccgag cgcagaagtg gtcctgcaac   9660
tttatccgcc tccatccagt ctattaattg ttgccgggaa gctagagtaa gtagttcgcc   9720
agttaatagt ttgcgcaacg ttgttgccat tgctacaggc atcgtggtgt cacgctcgtc   9780
gtttggtatg gcttcattca gctccggttc ccaacgatca aggcgagtta catgatcccc   9840
catgttgtgc aaaaaagcgg ttagctcctt cggtcctccg atcgttgtca gaagtaagtt   9900
```

```
ggccgcagtg ttatcactca tggttatggc agcactgcat aattctctta ctgtcatgcc   9960

atccgtaaga tgcttttctg tgactggtga gtactcaacc aagtcattct gagaatagtg  10020

tatgcggcga ccgagttgct cttgcccggc gtcaatacgg gataataccg cgccacatag  10080

cagaacttta aaagtgctca tcattggaaa acgttcttcg gggcgaaaac tctcaaggat  10140

cttaccgctg ttgagatcca gttcgatgta acccactcgt gcacccaact gatcttcagc  10200

atcttttact ttcaccagcg tttctgggtg agcaaaaaca ggaaggcaaa atgccgcaaa  10260

aaagggaata agggcgacac ggaaatgttg aatactcata ctcttccttt ttcaatatta  10320

ttgaagcatt tatcagggtt attgtctcat gagcggatac atatttgaat gtatttagaa  10380

aaataaacaa ataggggttc cgcgcacatt tccccgaaaa gtgccacctg ggtccttttc  10440

atcacgtgct ataaaaataa ttataattta aattttttaa tataaatata taaattaaaa  10500

atagaaagta aaaaaagaaa ttaaagaaaa aatagttttt gttttccgaa gatgtaaaag  10560

actctagggg gatcgccaac aaatactacc ttttatcttg ctcttcctgc tctcaggtat  10620

taatgccgaa ttgtttcatc ttgtctgtgt agaagaccac acacgaaaat cctgtgattt  10680

tacattttac ttatcgttaa tcgaatgtat atctatttaa tctgcttttc ttgtctaata  10740

aatatatatg taaagtacgc tttttgttga aattttttaa acctttgttt attttttttt  10800

cttcattccg taactcttct accttcttta tttactttct aaaatccaaa tacaaaacat  10860

aaaaataaat aaacacagag taaattccca aattattcca tcattaaaag atacgaggcg  10920

cgtgtaagtt acaggcaagc gatccgtcct aagaaaccat tattatcatg acattaacct  10980

ataaaaatag gcgtatcacg aggccctttc gtc                               11013
```

<210> SEQ ID NO 110
<211> LENGTH: 80
<212> TYPE: DNA
<213> ORGANISM: Artificial Sequence
<220> FEATURE:
<223> OTHER INFORMATION: primer 857

<400> SEQUENCE: 110

```
gcacaatatt tcaagctata ccaagcatac aatcaactat ctcatataca atgaaagcat     60

tagtgtatag gggcccaggc                                                 80
```

<210> SEQ ID NO 111
<211> LENGTH: 10934
<212> TYPE: DNA
<213> ORGANISM: Artificial sequence
<220> FEATURE:
<223> OTHER INFORMATION: pRS423::TEF(M4)-xpk1+ENO1-eutD

<400> SEQUENCE: 111

```
ggtggagctc cagcttttgt tccctttagt gagggttaat tgcgcgcttg gcgtaatcat     60

ggtcatagct gtttcctgtg tgaaattgtt atccgctcac aattccacac aacataggag    120

ccggaagcat aaagtgtaaa gcctggggtg cctaatgagt gaggtaactc acattaattg    180

cgttgcgctc actgcccgct ttccagtcgg gaaacctgtc gtgccagctg cattaatgaa    240

tcggccaacg cgcggggaga ggcggtttgc gtattgggcg ctcttccgct tcctcgctca    300

ctgactcgct gcgctcggtc gttcggctgc ggcgagcggt atcagctcac tcaaaggcgg    360

taatacggtt atccacagaa tcaggggata acgcaggaaa gaacatgtga gcaaaaggcc    420

agcaaaaggc caggaaccgt aaaaaggccg cgttgctggc gtttttccat aggctccgcc    480

cccctgacga gcatcacaaa aatcgacgct caagtcagag gtggcgaaac ccgacaggac    540
```

```
tataaagata ccaggcgttt cccctggaa gctccctcgt gcgctctcct gttccgaccc    600
tgccgcttac cggatacctg tccgcctttc tcccttcggg aagcgtggcg ctttctcata    660
gctcacgctg taggtatctc agttcggtgt aggtcgttcg ctccaagctg ggctgtgtgc    720
acgaaccccc cgttcagccc gaccgctgcg ccttatccgg taactatcgt cttgagtcca    780
acccggtaag acacgactta tcgccactgg cagcagccac tggtaacagg attagcagag    840
cgaggtatgt aggcggtgct acagagttct tgaagtggtg gcctaactac ggctacacta    900
gaaggacagt atttggtatc tgcgctctgc tgaagccagt taccttcgga aaaagagttg    960
gtagctcttg atccggcaaa caaaccaccg ctggtagcgg tggttttttt gtttgcaagc   1020
agcagattac gcgcagaaaa aaaggatctc aagaagatcc tttgatcttt tctacggggt   1080
ctgacgctca gtggaacgaa aactcacgtt aagggatttt ggtcatgaga ttatcaaaaa   1140
ggatcttcac ctagatcctt ttaaattaaa aatgaagttt taaatcaatc taaagtatat   1200
atgagtaaac ttggtctgac agttaccaat gcttaatcag tgaggcacct atctcagcga   1260
tctgtctatt tcgttcatcc atagttgcct gactccccgt cgtgtagata actacgatac   1320
gggagggctt accatctggc cccagtgctg caatgatacc gcgagaccca cgctcaccgg   1380
ctccagattt atcagcaata aaccagccag ccggaagggc cgagcgcaga agtggtcctg   1440
caactttatc cgcctccatc cagtctatta attgttgccg ggaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc ctttttcaat   2100
attattgaag catttatcag ggttattgtc tcatgagcgg atacatattt gaatgtattt   2160
agaaaaataa acaaataggg gttccgcgca catttccccg aaaagtgcca cctgaacgaa   2220
gcatctgtgc ttcattttgt agaacaaaaa tgcaacgcga gagcgctaat ttttcaaaca   2280
aagaatctga gctgcatttt tacagaacag aaatgcaacg cgaaagcgct attttaccaa   2340
cgaagaatct gtgcttcatt tttgtaaaac aaaaatgcaa cgcgagagcg ctaatttttc   2400
aaacaaagaa tctgagctgc atttttacag aacagaaatg caacgcgaga gcgctatttt   2460
accaacaaag aatctatact tcttttttgt tctacaaaaa tgcatcccga gagcgctatt   2520
tttctaacaa agcatcttag attacttttt ttctcctttg tgcgctctat aatgcagtct   2580
cttgataact ttttgcactg taggtccgtt aaggttagaa gaaggctact ttggtgtcta   2640
ttttctcttc cataaaaaaa gcctgactcc acttcccgcg tttactgatt actagcgaag   2700
ctgcgggtgc atttttcaa gataaaggca tccccgatta tattctatac cgatgtggat   2760
tgcgcatact ttgtgaacag aaagtgatag cgttgatgat tcttcattgg tcagaaaatt   2820
atgaacggtt tcttctattt tgtctctata tactacgtat aggaaatgtt tacattttcg   2880
```

```
tattgttttc gattcactct atgaatagtt cttactacaa tttttttgtc taaagagtaa   2940
tactagagat aaacataaaa aatgtagagg tcgagtttag atgcaagttc aaggagcgaa   3000
aggtggatgg gtaggttata tagggatata gcacagagat atatagcaaa gagatacttt   3060
tgagcaatgt ttgtggaagc ggtattcgca atattttagt agctcgttac agtccggtgc   3120
gtttttggtt ttttgaaagt gcgtcttcag agcgcttttg gttttcaaaa gcgctctgaa   3180
gttcctatac tttctagaga ataggaactt cggaatagga acttcaaagc gtttccgaaa   3240
acgagcgctt ccgaaaatgc aacgcgagct gcgcacatac agctcactgt tcacgtcgca   3300
cctatatctg cgtgttgcct gtatatatat atacatgaga agaacggcat agtgcgtgtt   3360
tatgcttaaa tgcgtactta tatgcgtcta tttatgtagg atgaaaggta gtctagtacc   3420
tcctgtgata ttatcccatt ccatgcgggg tatcgtatgc ttccttcagc actacccttt   3480
agctgttcta tatgctgcca ctcctcaatt ggattagtct catccttcaa tgctatcatt   3540
tcctttgata ttggatcatc taagaaacca ttattatcat gacattaacc tataaaaata   3600
ggcgtatcac gaggcccttt cgtctcgcgc gtttcggtga tgacggtgaa aacctctgac   3660
acatgcagct cccggagacg gtcacagctt gtctgtaagc ggatgccggg agcagacaag   3720
cccgtcaggg cgcgtcagcg ggtgttggcg ggtgtcgggg ctggcttaac tatgcggcat   3780
cagagcagat tgtactgaga gtgcaccata aattcccgtt ttaagagctt ggtgagcgct   3840
aggagtcact gccaggtatc gtttgaacac ggcattagtc agggaagtca taacacagtc   3900
ctttcccgca attttctttt tctattactc ttggcctcct ctagtacact ctatattttt   3960
ttatgcctcg gtaatgattt tcattttttt ttttccccta gcggatgact cttttttttt   4020
cttagcgatt ggcattatca cataatgaat tatacattat ataaagtaat gtgatttctt   4080
cgaagaatat actaaaaaat gagcaggcaa gataaacgaa ggcaaagatg acagagcaga   4140
aagccctagt aaagcgtatt acaaatgaaa ccaagattca gattgcgatc tctttaaagg   4200
gtggtcccct agcgatagag cactcgatct tcccagaaaa agaggcagaa gcagtagcag   4260
aacaggccac acaatcgcaa gtgattaacg tccacacagg tatagggttt ctggaccata   4320
tgatacatgc tctggccaag cattccggct ggtcgctaat cgttgagtgc attggtgact   4380
tacacataga cgaccatcac accactgaag actgcgggat tgctctcggt caagctttta   4440
aagaggccct actggcgcgt ggagtaaaaa ggtttggatc aggatttgcg cctttggatg   4500
aggcactttc cagagcggtg gtagatcttt cgaacaggcc gtacgcagtt gtcgaacttg   4560
gtttgcaaag ggagaaagta ggagatctct cttgcgagat gatcccgcat tttcttgaaa   4620
gctttgcaga ggctagcaga attaccctcc acgttgattg tctgcgaggc aagaatgatc   4680
atcaccgtag tgagagtgcg ttcaaggctc ttgcggttgc cataagagaa gccacctcgc   4740
ccaatggtac caacgatgtt ccctccacca aaggtgttct tatgtagtga caccgattat   4800
ttaaagctgc agcatacgat atatatacat gtgtatatat gtatacctat gaatgtcagt   4860
aagtatgtat acgaacagta tgatactgaa gatgacaagg taatgcatca ttctatacgt   4920
gtcattctga acgaggcgcg ctttcctttt ttcttttttgc tttttctttt tttttctctt   4980
gaactcgacg gatctatgcg gtgtgaaata ccgcacagat gcgtaaggag aaaataccgc   5040
atcaggaaat tgtaaacgtt aatattttgt taaaattcgc gttaaatttt tgttaaatca   5100
gctcattttt taaccaatag gccgaaatcg gcaaaatccc ttataaatca aaagaataga   5160
ccgagatagg gttgagtgtt gttccagttt ggaacaagag tccactatta aagaacgtgg   5220
actccaacgt caaagggcga aaaaccgtct atcagggcga tggcccacta cgtgaaccat   5280
```

```
caccctaatc aagtttttg gggtcgaggt gccgtaaagc actaaatcgg aaccctaaag   5340
ggagcccccg atttagagct tgacggggaa agccggcgaa cgtggcgaga aaggaaggga   5400
agaaagcgaa aggagcgggc gctagggcgc tggcaagtgt agcggtcacg ctgcgcgtaa   5460
ccaccacacc cgccgcgctt aatgcgccgc tacagggcgc gtcgcgccat tcgccattca   5520
ggctgcgcaa ctgttgggaa gggcgatcgg tgcgggcctc ttcgctatta cgccagctgg   5580
cgaaaggggg atgtgctgca aggcgattaa gttgggtaac gccagggttt tcccagtcac   5640
gacgttgtaa aacgacggcc agtgagcgcg cgtaatacga ctcactatag ggcgaattgg   5700
gtaccgggcc ccccctcgag gtcgacggta tcgataagct tgatatcgaa ttcctgcgcc   5760
cgggccacta gtcagatgcc gcgggcactt gagcacctca tgcacagcaa taacacaaca   5820
caatggttag tagcaacctg aattcggtca ttgatgcatg catgtgccgt gaagcgggac   5880
aaccagaaaa gtcgtctata aatgccggca cgtgcgatca tcgtggcggg gttttaagag   5940
tgcatatcac aaattgtcgc attaccgcgg aaccgccaga tattcattac ttgacgcaaa   6000
agcgtttgaa ataatgacga aaaagaagga agaaaaaaaa agaaaaatac cgcttctagg   6060
cgggttatct actgatccga gcttccacta ggatagcacc caaacacctg catatttgga   6120
cgacctttac ttacaccacc aaaaaccact ttcgcctctc ccgcccctga taacgtccac   6180
taattgagcg attacctgag cggtcctctt ttgtttgcag catgagactt gcatactgca   6240
aatcgtaagt agcaacgtct caaggtcaaa actgtatgga aaccttgtca cctcacttaa   6300
ttctagctag cctaccctgc aagtcaagag gtctccgtga ttcctagcca cctcaaggta   6360
tgcctctccc cggaaactgt ggccttttct ggcacacatg atctccacga tttcaacata   6420
taaatagctt ttgataatgg caatattaat caaatttatt ttacttcttt cttgtaacat   6480
ctctcttgta atcccttatt ccttctagct atttttcata aaaaaccaag caactgctta   6540
tcaacacaca aacactaaat caaagctgag gatggattta tttgagtcat tagcacaaaa   6600
aattactggt aaagatcaaa caattgtttt ccctgaagga actgaacccc gaattgtcgg   6660
tgcggcagcg cgattagctg cagacggctt ggttaagccg attgttttag gtgcaacgga   6720
caaagttcag gctgtggcta acgatttgaa tgcggattta acaggcgttc aagtccttga   6780
tcctgcgaca tacccggctg aagataagca agcaatgctt gatgccctcg ttgaacggcg   6840
gaaaggtaag aatacgccag aacaagcggc taaaatgctg gaagatgaaa actactttgg   6900
cacgatgctc gtttatatgg gcaaagcgga tgggatggtt tcaggtgcaa tccatccaac   6960
tggtgatacg gtacggccag cgttacaaat tattaagacc aagcccggtt cacaccgaat   7020
ctcgggtgca tttatcatgc aaaagggtga ggaacgctac gtctttgctg actgtgccat   7080
caatattgat cccgatgccg atacgttagc ggaaattgcc actcagagtg cggctactgc   7140
taaggtcttc gatattgacc cgaaagttgc gatgctcagc ttctcaacta agggttcggc   7200
taagggtgaa atggtcacta aagtgcaaga agcaacggcc aaggcgcaag ctgctgaacc   7260
ggaattggct atcgatggtg aacttcaatt tgacgcggcc ttcgttgaaa aagttggttt   7320
gcaaaaggct cctggttcca aagtagctgg tcatgccaat gtctttgtat ttccagagct   7380
tcagtctggt aatattggct ataagattgc gcaacgattt ggtcattttg aagcggtggg   7440
tcctgtcttg caaggcctga acaagccggt ctccgacttg tcacgtggat gcagtgaaga   7500
agacgtttat aaggttgcga ttattacagc agcccaagga ttagcttaat taattaagag   7560
taagcgaatt tcttatgatt tatgattttt attattaaat aagttataaa aaaaataagt   7620
```

```
gtatacaaat tttaaagtga ctcttaggtt ttaaaacgaa aattcttatt cttgagtaac   7680
tctttcctgt aggtcaggtt gctttctcag gtatagcatg aggtcgctct tattgaccac   7740
acctctaccg gcatgccgag caaatgcctg caaatcgctc cccatttcac ccaattgtag   7800
atatgctaac tccagcaatg agttgatgaa tctcggtgtg tattttatgt cctcagagga   7860
caacacctgt ggtactagtt ctagagcggc cgcccgcaaa ttaaagcctt cgagcgtccc   7920
aaaaccttct caagcaaggt tttcagtata atgttacatg cgtacacgcg tttgtacaga   7980
aaaaaaagaa aaatttgaaa tataaataac gttcttaata ctaacataac tattaaaaaa   8040
aataaatagg gacctagact tcaggttgtc taactccttc cttttcggtt agagcggatg   8100
tgggaggagg gcgtgaatgt aagcgtgaca taactaatta catgattaat taattatttt   8160
aaacccttcc attgccaatc attaacttct ggcaagtcag ttccggcatc ccggatatag   8220
gcattgtgtt tagcaagcat attatccatg gattgaacga aggccgcacc agtgttttcc   8280
attgctggtt gcgccgcaat tgccgactta gctaagtcga agcggtccat ctggttcatg   8340
acccgtacgt cgaatggtgt ggtaatatca ccattttcac ggtaaccgtg gacgtataag   8400
ttatggttgt gacgatcaaa gaagatgtca cgaactaagt cttcgtaacc gtggaaagca   8460
aagaccactg gtttgtcctt agtaaagtaa tggtcaaact cagcatctga caagccccgc   8520
ggatcctttt caggactacg taacttcaag atgtcgacca cgttcacgaa acgaatcttc   8580
atctctggga aactgtcgtg tagtaattgg atggcagcca acgtttcaag cgttggttcc   8640
gtcccagcag ctgcaaagac aatgtctggt tcgctacctt ggtccgtact tgcccaatca   8700
atgataccaa gaccattgtc aactaattgc ttagcttctt caatgctgaa ccattgttga   8760
cgtgggtgtt ttgacgtaac cacgtagttg atcttttctt ggctccggaa aatgacgtca   8820
ccgacagcta ataacgtgtt ggcatcggct ggtaaatatt cacgaatgta ttctggtttc   8880
ttttcggcca aatgagttaa tgcacctgga tcttggtggg tataaccatt atggtcttgt   8940
tggaatacag ttgaagccgc gataatgtta agtgatgggt actttttacg ccaatcaagt   9000
tcattggctt tacgtaacca cttgaagtgt tgcgtcaaca ttgagtccac aacgcgtagg   9060
aaggcttcat aactggcaaa taacccatga cgtccagtta agacgtaacc ttctaaccaa   9120
ccttcagctt ggtgttcaga taactgagca tctaagaccc ggccagctgg tgcttcatat   9180
tggtcactat ctggatgaat gtcttccatc cattgacgat tagtggtttc gaagacacca   9240
tataaacggt tagacatggt ttcatcaggt ccgaacaacc ggaagttatc aggatttttc   9300
ttgatgacat cccgcaaata gtctgaccaa acgatcatat cttgcttaac attcgcgcct   9360
tctttggacg tatcgaccgc ataatcacgg aagtttggta agttcaaggc tttcggatcg   9420
accccaccat tggtgattgg gttagcagcc atccgactgt ccccagtagg aataatttct   9480
ttaatatcat ccttcaaaga gccatcttca ttgaagagtt cttttggttg atatgattcg   9540
agccaatcaa ctaaagcatc cgcatgttcc atgtcatttt gatcaacagg aatcggaatt   9600
tgatgagcac ggaatgaacc ttcgatctta tcaccgtccc atgacttcgg accagtccag   9660
cccttaggtg cgcggaagac gatcattggc catactggca atgttgcatc gttattttcg   9720
cgagcatgct tctggattgc cttgatcttt tcaacggctt catccatggc cttagctaag   9780
gctgggtgaa ccttttcagg atcgtcacct tcaacgaaga ttggttccca attcatgctt   9840
tcgaagtatt ccttaatctt agcatcagaa gtccgaccaa aaatcgttgg attagaaatc   9900
ttaaaaccat ttaagttcaa gattggtaaa acagccccgt cgttgattgg gttaatgaac   9960
ttcgttgatt gccatgaagt tgctaatgga cccgtttcgg attccccatc accaacaaca  10020
```

```
accgcggcga tttcgtcagg attgtcaaga attgccccaa ccccgtgtga aattgagtaa  10080

ccaagttcgc caccttcgtg gattgaaccg ggtgtttcag gtgccgcatg ggaagcaacc  10140

ccacctggga atgagaattg cttgaagagc ttttgcatcc cttcaacatc ctgcgtaatt  10200

tctggataaa tatcggtgta agtaccgtca aggtaagagt ttgaaaccat cacttgacca  10260

ccatgacctg gaccttcaac gtagaacatc ttcaaaccgt acttgttgat gacccggtta  10320

agatgagcat agataaagtt ttgaccggca atcgtccccc agtgaccaat tggatgaacc  10380

ttaacgtcac tggccttcaa tggccgttgt aatagtggat tatcttttaa ataaagttga  10440

ccaactgata agtagttggc agcacgccag tacttatcaa ctttttgcaa atatgctggt  10500

gatgagtaat ctgttgtcat cctcagctgg aacttagatt agattgctat gctttctctc  10560

taacgagcaa gaagtaaaaa aagttgtaat agaacaagaa aaatgaaact gaagcttgag  10620

aaattgaaga ccgtttatta gcttaaatat caatgggagg tcatcgaaag agaaaaaaat  10680

caagaaagaa actctcaaga aaaagaaacg tgataaaaat ttttattgcc tctctcgacg  10740

aagagaaaga aacgaggcgg tcccttttt cttttccaaa cctttagtac gggtaattag  10800

cgacacccta gaggaagaaa gaggggaaat ttagtatgct gtgcttgggt gtcttgaagt  10860

ggtacggcga tgcgcggagt ccgagaaaat ctggaagagt aaaaaggggg tagaagcgtt  10920

ttgaagctat ccgc                                                    10934
```

<210> SEQ ID NO 112
<211> LENGTH: 80
<212> TYPE: DNA
<213> ORGANISM: Artificial sequence
<220> FEATURE:
<223> OTHER INFORMATION: N1341

<400> SEQUENCE: 112

```
gttgcaagaa atgcattatg caattttttg attatgacaa tctctcgaaa atagcttcaa     60

aacgcttcta cccccttttt                                                 80
```

<210> SEQ ID NO 113
<211> LENGTH: 80
<212> TYPE: DNA
<213> ORGANISM: Artificial sequence
<220> FEATURE:
<223> OTHER INFORMATION: N1338

<400> SEQUENCE: 113

```
catacattat acgaacggta ctgaacatta gaatacgtaa tccgcaatgc ccgcaaatta     60

aagccttcga gcgtcccaaa                                                 80
```

<210> SEQ ID NO 114
<211> LENGTH: 30
<212> TYPE: DNA
<213> ORGANISM: Artificial sequence
<220> FEATURE:
<223> OTHER INFORMATION: N1033c

<400> SEQUENCE: 114

```
gcattgcgga ttacgtattc taatgttcag                                      30
```

<210> SEQ ID NO 115
<211> LENGTH: 81
<212> TYPE: DNA
<213> ORGANISM: Artificial sequence
<220> FEATURE:

<223> OTHER INFORMATION: N1342

<400> SEQUENCE: 115
acatatgtga aaaaaaatag ttgatatttt aaaccaaatc agaaatttat caccttggct 60
aactcgttgt atcatcactg g 81

<210> SEQ ID NO 116
<211> LENGTH: 30
<212> TYPE: DNA
<213> ORGANISM: Artificial sequence
<220> FEATURE:
<223> OTHER INFORMATION: N1364

<400> SEQUENCE: 116
atgacaacag attactcatc accagcatat 30

<210> SEQ ID NO 117
<211> LENGTH: 604
<212> TYPE: DNA
<213> ORGANISM: Artificial sequence
<220> FEATURE:
<223> OTHER INFORMATION: L8

<400> SEQUENCE: 117
gcctacttgg cttcacatac gttgcatacg acgatataga aaataatgat aatgacagca 60
ggattatcgt ataacgtaat agtcgaaaaa tctcaaaaat ctgtgggtca ttacgtaaat 120
aatgatagga atgtgattct tctatttttc ctttttccat tctggcagcc gtcgggaaaa 180
cgtggcttcc tctctttcgg gctctattgg agtaacgctg ccgtgagctt cctctctttc 240
catatctaac aactgagcac gtaaccaatg gtaaagcatg agcttagcgt tgctccaaag 300
aagtattgga aggttaatac catgtgtctg ttctcttctg actttgactc ctcaaataaa 360
aaaaaattct acaatcaaca gatcgcttca attacgctct cacaaaaact tttttccttc 420
ttcttcgccc acgttaaatt ttaaccctca tgctgtctaa cggatttctg cacttaattt 480
attataaaac gacaaagaca taatacttct ctatcaattt cagttattgt tcttcattgc 540
attactcttc tgttcttctt tttcatttgt catatacaac cataaccaaa taatacatat 600
tcaa 604

<210> SEQ ID NO 118
<211> LENGTH: 80
<212> TYPE: DNA
<213> ORGANISM: Artificial sequence
<220> FEATURE:
<223> OTHER INFORMATION: N1366

<400> SEQUENCE: 118
gttgcaagaa atgcattatg caatttttttg attatgacaa tctctcgaaa gcctacttgg 60
cttcacatac gttgcatacg 80

<210> SEQ ID NO 119
<211> LENGTH: 65
<212> TYPE: DNA
<213> ORGANISM: Artificial sequence
<220> FEATURE:
<223> OTHER INFORMATION: N1368

<400> SEQUENCE: 119
atatgctggt gatgagtaat ctgttgtcat tttgaatatg tattatttgg ttatggttgt 60
atatg 65

<210> SEQ ID NO 120
<211> LENGTH: 80
<212> TYPE: DNA
<213> ORGANISM: Artificial sequence
<220> FEATURE:
<223> OTHER INFORMATION: N1371

<400> SEQUENCE: 120
aaaaactaat acgtaaacct gcattaaggt aagattatat cagaaaatgt gttgcaagaa 60
atgcattatg caattttttg 80

<210> SEQ ID NO 121
<211> LENGTH: 85
<212> TYPE: DNA
<213> ORGANISM: Artificial sequence
<220> FEATURE:
<223> OTHER INFORMATION: N1372

<400> SEQUENCE: 121
tagaagctaa tctttaacct ggaagacagg acagaaaagt aattacaaga acatatgtga 60
aaaaaaatag ttgatatttt aaacc 85

<210> SEQ ID NO 122
<211> LENGTH: 25
<212> TYPE: DNA
<213> ORGANISM: Artificial sequence
<220> FEATURE:
<223> OTHER INFORMATION: BK93

<400> SEQUENCE: 122
aaaaattgat tctcatcgta aatgc 25

<210> SEQ ID NO 123
<211> LENGTH: 30
<212> TYPE: DNA
<213> ORGANISM: Artificial sequence
<220> FEATURE:
<223> OTHER INFORMATION: N1114

<400> SEQUENCE: 123
atatgctggt gatgagtaat ctgttgtcat 30

<210> SEQ ID NO 124
<211> LENGTH: 22
<212> TYPE: DNA
<213> ORGANISM: Artificial sequence
<220> FEATURE:
<223> OTHER INFORMATION: N160SeqF5

<400> SEQUENCE: 124
cctgaagtct aggtccctat tt 22

<210> SEQ ID NO 125
<211> LENGTH: 37
<212> TYPE: DNA
<213> ORGANISM: Artificial sequence
<220> FEATURE:
<223> OTHER INFORMATION: BK380

<400> SEQUENCE: 125
tcgacgtcga tgtaaggcct tgtaattcag tttgttc 37

<210> SEQ ID NO 126

```
<211> LENGTH: 338
<212> TYPE: PRT
<213> ORGANISM: Artificial sequence
<220> FEATURE:
<223> OTHER INFORMATION: Anaerostipes caccae KARI variant K9SB2_SH

<400> SEQUENCE: 126

Met Ala Lys Ile Tyr Tyr Gln Glu Asp Cys Asn Leu Ser Leu Leu Asp
1               5                   10                  15

Gly Lys Thr Ile Ala Val Ile Gly Tyr Gly Ser Gln Gly His Ala His
            20                  25                  30

Ala Leu Asn Ala Lys Glu Ser Gly Cys Asn Val Ile Ile Gly Leu Phe
        35                  40                  45

Glu Gly Ala Glu Glu Trp Lys Arg Ala Glu Glu Gln Gly Phe Glu Val
    50                  55                  60

Tyr Thr Ala Ala Glu Ala Ala Lys Lys Ala Asp Ile Ile Met Ile Leu
65                  70                  75                  80

Ile Pro Asp Glu Lys Gln Ala Thr Met Tyr Lys Asn Asp Ile Glu Pro
                85                  90                  95

Asn Leu Glu Ala Gly Asn Met Leu Met Phe Ala His Gly Phe Asn Ile
            100                 105                 110

His Phe Gly Cys Ile Val Pro Pro Lys Asp Val Asp Val Thr Met Ile
        115                 120                 125

Ala Pro Lys Gly Pro Gly His Thr Val Arg Ser Glu Tyr Glu Glu Gly
    130                 135                 140

Lys Gly Val Pro Cys Leu Val Ala Val Glu Gln Asp Ala Thr Gly Lys
145                 150                 155                 160

Ala Leu Asp Met Ala Leu Ala Tyr Ala Leu Ala Ile Gly Gly Ala Arg
                165                 170                 175

Ala Gly Val Leu Glu Thr Thr Phe Arg Thr Glu Thr Glu Thr Asp Leu
            180                 185                 190

Phe Gly Glu Gln Ala Val Leu Cys Gly Gly Val Cys Ala Leu Met Gln
        195                 200                 205

Ala Gly Phe Glu Thr Leu Val Glu Ala Gly Tyr Asp Pro Arg Asn Ala
    210                 215                 220

Tyr Phe Glu Cys Ile His Glu Met Lys Leu Ile Val Asp Leu Ile Tyr
225                 230                 235                 240

Gln Ser Gly Phe Ser Gly Met Arg Tyr Ser Ile Ser Asn Thr Ala Glu
                245                 250                 255

Tyr Gly Asp Tyr Ile Thr Gly Pro Lys Ile Ile Thr Glu Asp Thr Lys
            260                 265                 270

Lys Ala Met Lys Lys Ile Leu Ser Asp Ile Gln Asp Gly Thr Phe Ala
        275                 280                 285

Lys Asp Phe Leu Val Asp Met Ser Asp Ala Gly Ser Gln Val His Phe
    290                 295                 300

Lys Ala Met Arg Lys Leu Ala Ser Glu His Pro Ala Glu Val Val Gly
305                 310                 315                 320

Glu Glu Ile Arg Ser Leu Tyr Ser Trp Ser Asp Glu Asp Lys Leu Ile
                325                 330                 335

Asn Asn


<210> SEQ ID NO 127
<211> LENGTH: 578
<212> TYPE: PRT
<213> ORGANISM: Artificial sequence
<220> FEATURE:
```

<223> OTHER INFORMATION: DHAD variant L2V4

<400> SEQUENCE: 127

```
Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365

Gln Lys Val Ile Met Pro Leu Glu Asn Pro Lys Arg Glu Asp Gly Pro
    370                 375                 380

Val Ile Ile Leu His Gly Asn Leu Ala Pro Asp Gly Ala Val Ala Lys
385                 390                 395                 400
```

```
Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
            420                 425                 430

Asp Gly Asp Val Val Val Val Arg Phe Val Gly Pro Lys Gly Gly Pro
        435                 440                 445

Gly Met Pro Glu Met Leu Ser Leu Ser Ser Met Ile Val Gly Lys Gly
    450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys Cys Cys Pro Gly Cys
                565                 570                 575

Cys Gly


<210> SEQ ID NO 128
<211> LENGTH: 347
<212> TYPE: PRT
<213> ORGANISM: Beijerinkia indica

<400> SEQUENCE: 128

Met Lys Ala Leu Val Tyr Arg Gly Pro Gly Gln Lys Leu Val Glu Glu
1               5                   10                  15

Arg Gln Lys Pro Glu Leu Lys Glu Pro Gly Asp Ala Ile Val Lys Val
            20                  25                  30

Thr Lys Thr Thr Ile Cys Gly Thr Asp Leu His Ile Leu Lys Gly Asp
        35                  40                  45

Val Ala Thr Cys Lys Pro Gly Arg Val Leu Gly His Glu Gly Val Gly
    50                  55                  60

Val Ile Glu Ser Val Gly Ser Gly Val Thr Ala Phe Gln Pro Gly Asp
65                  70                  75                  80

Arg Val Leu Ile Ser Cys Ile Ser Ser Cys Gly Lys Cys Ser Phe Cys
                85                  90                  95

Arg Arg Gly Met Phe Ser His Cys Thr Thr Gly Gly Trp Ile Leu Gly
            100                 105                 110

Asn Glu Ile Asp Gly Thr Gln Ala Glu Tyr Val Arg Val Pro His Ala
        115                 120                 125

Asp Thr Ser Leu Tyr Arg Ile Pro Ala Gly Ala Asp Glu Glu Ala Leu
    130                 135                 140

Val Met Leu Ser Asp Ile Leu Pro Thr Gly Phe Glu Cys Gly Val Leu
145                 150                 155                 160

Asn Gly Lys Val Ala Pro Gly Ser Ser Val Ala Ile Val Gly Ala Gly
                165                 170                 175

Pro Val Gly Leu Ala Ala Leu Leu Thr Ala Gln Phe Tyr Ser Pro Ala
            180                 185                 190
```

```
Glu Ile Ile Met Ile Asp Leu Asp Asp Asn Arg Leu Gly Leu Ala Lys
        195                 200                 205

Gln Phe Gly Ala Thr Arg Thr Val Asn Ser Thr Gly Gly Asn Ala Ala
    210                 215                 220

Ala Glu Val Lys Ala Leu Thr Glu Gly Leu Gly Val Asp Thr Ala Ile
225                 230                 235                 240

Glu Ala Val Gly Ile Pro Ala Thr Phe Glu Leu Cys Gln Asn Ile Val
                245                 250                 255

Ala Pro Gly Gly Thr Ile Ala Asn Val Gly Val His Gly Ser Lys Val
            260                 265                 270

Asp Leu His Leu Glu Ser Leu Trp Ser His Asn Val Thr Ile Thr Thr
        275                 280                 285

Arg Leu Val Asp Thr Ala Thr Thr Pro Met Leu Leu Lys Thr Val Gln
    290                 295                 300

Ser His Lys Leu Asp Pro Ser Arg Leu Ile Thr His Arg Phe Ser Leu
305                 310                 315                 320

Asp Gln Ile Leu Asp Ala Tyr Glu Thr Phe Gly Gln Ala Ala Ser Thr
                325                 330                 335

Gln Ala Leu Lys Val Ile Ile Ser Met Glu Ala
            340                 345


<210> SEQ ID NO 129
<211> LENGTH: 548
<212> TYPE: PRT
<213> ORGANISM: Listeria grayi

<400> SEQUENCE: 129

Met Tyr Thr Val Gly Gln Tyr Leu Val Asp Arg Leu Glu Glu Ile Gly
1               5                   10                  15

Ile Asp Lys Val Phe Gly Val Pro Gly Asp Tyr Asn Leu Thr Phe Leu
            20                  25                  30

Asp Tyr Ile Gln Asn His Glu Gly Leu Ser Trp Gln Gly Asn Thr Asn
        35                  40                  45

Glu Leu Asn Ala Ala Tyr Ala Ala Asp Gly Tyr Ala Arg Glu Arg Gly
    50                  55                  60

Val Ser Ala Leu Val Thr Thr Phe Gly Val Gly Glu Leu Ser Ala Ile
65                  70                  75                  80

Asn Gly Thr Ala Gly Ser Phe Ala Glu Gln Val Pro Val Ile His Ile
                85                  90                  95

Val Gly Ser Pro Thr Met Asn Val Gln Ser Asn Lys Lys Leu Val His
            100                 105                 110

His Ser Leu Gly Met Gly Asn Phe His Asn Phe Ser Glu Met Ala Lys
        115                 120                 125

Glu Val Thr Ala Ala Thr Thr Met Leu Thr Glu Glu Asn Ala Ala Ser
    130                 135                 140

Glu Ile Asp Arg Val Leu Glu Thr Ala Leu Leu Glu Lys Arg Pro Val
145                 150                 155                 160

Tyr Ile Asn Leu Pro Ile Asp Ile Ala His Lys Ala Ile Val Lys Pro
                165                 170                 175

Ala Lys Ala Leu Gln Thr Glu Lys Ser Ser Gly Glu Arg Glu Ala Gln
            180                 185                 190

Leu Ala Glu Ile Ile Leu Ser His Leu Glu Lys Ala Ala Gln Pro Ile
        195                 200                 205

Val Ile Ala Gly His Glu Ile Ala Arg Phe Gln Ile Arg Glu Arg Phe
    210                 215                 220
```

```
Glu Asn Trp Ile Asn Gln Thr Lys Leu Pro Val Thr Asn Leu Ala Tyr
225                 230                 235                 240

Gly Lys Gly Ser Phe Asn Glu Glu Asn Glu His Phe Ile Gly Thr Tyr
                245                 250                 255

Tyr Pro Ala Phe Ser Asp Lys Asn Val Leu Asp Tyr Val Asp Asn Ser
            260                 265                 270

Asp Phe Val Leu His Phe Gly Gly Lys Ile Ile Asp Asn Ser Thr Ser
        275                 280                 285

Ser Phe Ser Gln Gly Phe Lys Thr Glu Asn Thr Leu Thr Ala Ala Asn
    290                 295                 300

Asp Ile Ile Met Leu Pro Asp Gly Ser Thr Tyr Ser Gly Ile Ser Leu
305                 310                 315                 320

Asn Gly Leu Leu Ala Glu Leu Glu Lys Leu Asn Phe Thr Phe Ala Asp
                325                 330                 335

Thr Ala Ala Lys Gln Ala Glu Leu Ala Val Phe Glu Pro Gln Ala Glu
            340                 345                 350

Thr Pro Leu Lys Gln Asp Arg Phe His Gln Ala Val Met Asn Phe Leu
        355                 360                 365

Gln Ala Asp Asp Val Leu Val Thr Glu Gln Gly Thr Ser Ser Phe Gly
    370                 375                 380

Leu Met Leu Ala Pro Leu Lys Lys Gly Met Asn Leu Ile Ser Gln Thr
385                 390                 395                 400

Leu Trp Gly Ser Ile Gly Tyr Thr Leu Pro Ala Met Ile Gly Ser Gln
                405                 410                 415

Ile Ala Ala Pro Glu Arg Arg His Ile Leu Ser Ile Gly Asp Gly Ser
            420                 425                 430

Phe Gln Leu Thr Ala Gln Glu Met Ser Thr Ile Phe Arg Glu Lys Leu
        435                 440                 445

Thr Pro Val Ile Phe Ile Ile Asn Asn Asp Gly Tyr Thr Val Glu Arg
    450                 455                 460

Ala Ile His Gly Glu Asp Glu Ser Tyr Asn Asp Ile Pro Thr Trp Asn
465                 470                 475                 480

Leu Gln Leu Val Ala Glu Thr Phe Gly Gly Asp Ala Glu Thr Val Asp
                485                 490                 495

Thr His Asn Val Phe Thr Glu Thr Asp Phe Ala Asn Thr Leu Ala Ala
            500                 505                 510

Ile Asp Ala Thr Pro Gln Lys Ala His Val Val Glu Val His Met Glu
        515                 520                 525

Gln Met Asp Met Pro Glu Ser Leu Arg Gln Ile Gly Leu Ala Leu Ser
    530                 535                 540

Lys Gln Asn Ser
545
```

<210> SEQ ID NO 130
<211> LENGTH: 343
<212> TYPE: PRT
<213> ORGANISM: Artificial sequence
<220> FEATURE:
<223> OTHER INFORMATION: Anaerostipes caccae KARI variant K9JB4P

<400> SEQUENCE: 130

```
Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30
```

```
Gln Gly His Ala His Ala Leu Asn Ala Lys Glu Ser Gly Cys Asn Val
        35                  40                  45

Ile Ile Gly Leu Tyr Glu Gly Ala Glu Glu Trp Lys Arg Ala Glu Glu
    50                  55                  60

Gln Gly Phe Glu Val Tyr Thr Ala Ala Glu Ala Ala Lys Lys Ala Asp
65                  70                  75                  80

Ile Ile Met Ile Leu Ile Pro Asp Glu Lys Gln Ala Thr Met Tyr Lys
                85                  90                  95

Asn Asp Ile Glu Pro Asn Leu Glu Ala Gly Asn Met Leu Met Phe Ala
            100                 105                 110

His Gly Phe Asn Ile His Phe Gly Cys Ile Val Pro Pro Lys Asp Val
        115                 120                 125

Asp Val Thr Met Ile Ala Pro Lys Gly Pro Gly His Thr Val Arg Ser
    130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Gly Val
        195                 200                 205

Cys Ala Leu Met Gln Ala Gly Phe Glu Thr Leu Val Glu Ala Gly Tyr
    210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
            260                 265                 270

Thr Glu Asp Thr Lys Lys Ala Met Lys Lys Ile Leu Ser Asp Ile Gln
        275                 280                 285

Asp Gly Thr Phe Ala Lys Asp Phe Leu Val Asp Met Ser Asp Ala Gly
    290                 295                 300

Ser Gln Val His Phe Lys Ala Met Arg Lys Leu Ala Ser Glu His Pro
305                 310                 315                 320

Ala Glu Val Val Gly Glu Glu Ile Arg Ser Leu Tyr Ser Trp Ser Asp
                325                 330                 335

Glu Asp Lys Leu Ile Asn Asn
            340


<210> SEQ ID NO 131
<211> LENGTH: 571
<212> TYPE: PRT
<213> ORGANISM: Streptococcus mutans

<400> SEQUENCE: 131

Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
```

```
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365

Gln Lys Val Ile Met Pro Leu Glu Asn Pro Lys Arg Glu Asp Gly Pro
    370                 375                 380

Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
            420                 425                 430

Asp Gly Asp Val Val Val Val Arg Phe Val Gly Pro Lys Gly Gly Pro
        435                 440                 445

Gly Met Pro Glu Met Leu Ser Leu Ser Ser Met Ile Val Gly Lys Gly
    450                 455                 460

Gln Gly Glu Lys Val Ala Leu Leu Thr Asp Gly Arg Phe Ser Gly Gly
465                 470                 475                 480
```

```
Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570


<210> SEQ ID NO 132
<211> LENGTH: 343
<212> TYPE: PRT
<213> ORGANISM: Artificial sequence
<220> FEATURE:
<223> OTHER INFORMATION: Anaerostipes caccae KARI variant K9G9

<400> SEQUENCE: 132

Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30

Gln Gly His Ala His Ala Leu Asn Ala Lys Glu Ser Gly Cys Asn Val
        35                  40                  45

Ile Ile Gly Leu Tyr Glu Gly Ala Lys Glu Trp Lys Arg Ala Glu Glu
    50                  55                  60

Gln Gly Phe Glu Val Tyr Thr Ala Ala Glu Ala Ala Lys Lys Ala Asp
65                  70                  75                  80

Ile Ile Met Ile Leu Ile Asn Asp Glu Lys Gln Ala Thr Met Tyr Lys
                85                  90                  95

Asn Asp Ile Glu Pro Asn Leu Glu Ala Gly Asn Met Leu Met Phe Ala
            100                 105                 110

His Gly Phe Asn Ile His Phe Gly Cys Ile Val Pro Pro Lys Asp Val
        115                 120                 125

Asp Val Thr Met Ile Ala Pro Lys Gly Pro Gly His Thr Val Arg Ser
    130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Gly Val
        195                 200                 205

Cys Ala Leu Met Gln Ala Gly Phe Glu Thr Leu Val Glu Ala Gly Tyr
    210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
            260                 265                 270
```

```
Thr Glu Asp Thr Lys Lys Ala Met Lys Lys Ile Leu Ser Asp Ile Gln
        275                 280                 285

Asp Gly Thr Phe Ala Lys Asp Phe Leu Val Asp Met Ser Asp Ala Gly
    290                 295                 300

Ser Gln Val His Phe Lys Ala Met Arg Lys Leu Ala Ser Glu His Pro
305                 310                 315                 320

Ala Glu Val Val Gly Glu Glu Ile Arg Ser Leu Tyr Ser Trp Ser Asp
                325                 330                 335

Glu Asp Lys Leu Ile Asn Asn
            340


<210> SEQ ID NO 133
<211> LENGTH: 343
<212> TYPE: PRT
<213> ORGANISM: Artificial sequence
<220> FEATURE:
<223> OTHER INFORMATION: Anaerostipes caccae KARI variant K9D3

<400> SEQUENCE: 133

Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30

Gln Gly His Ala His Ala Leu Asn Ala Lys Glu Ser Gly Cys Asn Val
        35                  40                  45

Ile Ile Gly Leu Tyr Glu Gly Ala Lys Asp Trp Lys Arg Ala Glu Glu
    50                  55                  60

Gln Gly Phe Glu Val Tyr Thr Ala Ala Glu Ala Ala Lys Lys Ala Asp
65                  70                  75                  80

Ile Ile Met Ile Leu Ile Asn Asp Glu Lys Gln Ala Thr Met Tyr Lys
                85                  90                  95

Asn Asp Ile Glu Pro Asn Leu Glu Ala Gly Asn Met Leu Met Phe Ala
            100                 105                 110

His Gly Phe Asn Ile His Phe Gly Cys Ile Val Pro Pro Lys Asp Val
        115                 120                 125

Asp Val Thr Met Ile Ala Pro Lys Gly Pro Gly His Thr Val Arg Ser
    130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Gly Val
        195                 200                 205

Cys Ala Leu Met Gln Ala Gly Phe Glu Thr Leu Val Glu Ala Gly Tyr
    210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
            260                 265                 270

Thr Glu Asp Thr Lys Lys Ala Met Lys Lys Ile Leu Ser Asp Ile Gln
        275                 280                 285
```

```
Asp Gly Thr Phe Ala Lys Asp Phe Leu Val Asp Met Ser Asp Ala Gly
    290                 295                 300

Ser Gln Val His Phe Lys Ala Met Arg Lys Leu Ala Ser Glu His Pro
305                 310                 315                 320

Ala Glu Val Val Gly Glu Glu Ile Arg Ser Leu Tyr Ser Trp Ser Asp
                325                 330                 335

Glu Asp Lys Leu Ile Asn Asn
            340
```

```
<210> SEQ ID NO 134
<211> LENGTH: 571
<212> TYPE: PRT
<213> ORGANISM: Artificial sequence
<220> FEATURE:
<223> OTHER INFORMATION: DHAD variant L2V4

<400> SEQUENCE: 134

Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
    290                 295                 300
```

```
Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365

Gln Lys Val Ile Met Pro Leu Glu Asn Pro Lys Arg Glu Asp Gly Pro
    370                 375                 380

Val Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
            420                 425                 430

Asp Gly Asp Val Val Val Val Arg Phe Val Gly Pro Lys Gly Gly Pro
        435                 440                 445

Gly Met Pro Glu Met Leu Ser Leu Ser Ser Met Ile Val Gly Lys Gly
    450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570
```